(12) United States Patent
Tian et al.

(10) Patent No.: US 9,121,024 B2
(45) Date of Patent: Sep. 1, 2015

(54) NON-NATURAL AMINO ACID REPLICATION-DEPENDENT MICROORGANISMS AND VACCINES

(75) Inventors: Feng Tian, San Diego, CA (US); Brad Hehli, San Diego, CA (US)

(73) Assignee: AMBRX, INC., La Jolla, CA (US)

( * ) Notice: Subject to any disclaimer, the term of this patent is extended or adjusted under 35 U.S.C. 154(b) by 331 days.

(21) Appl. No.: 13/120,255

(22) PCT Filed: Sep. 28, 2009

(86) PCT No.: PCT/US2009/058668
§ 371 (c)(1),
(2), (4) Date: Apr. 25, 2011

(87) PCT Pub. No.: WO2010/037062
PCT Pub. Date: Apr. 1, 2010

(65) Prior Publication Data
US 2011/0195483 A1    Aug. 11, 2011

Related U.S. Application Data

(60) Provisional application No. 61/100,688, filed on Sep. 26, 2008.

(51) Int. Cl.
*A61K 39/395* (2006.01)
*C12N 15/70* (2006.01)
*C12N 1/36* (2006.01)
*C12N 9/00* (2006.01)
*A61K 39/108* (2006.01)

(52) U.S. Cl.
CPC ............ *C12N 15/70* (2013.01); *A61K 39/0258* (2013.01); *C12N 1/36* (2013.01); *C12N 9/93* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 4,289,872 A | 9/1981 | Denkewalter et al. |
| 4,412,989 A | 11/1983 | Iwashita et al. |
| 4,414,148 A | 11/1983 | Jansen et al. |
| 4,485,045 A | 11/1984 | Regen |
| 4,511,502 A | 4/1985 | Builder et al. |
| 4,511,503 A | 4/1985 | Olson et al. |
| 4,512,922 A | 4/1985 | Jones et al. |
| 4,544,545 A | 10/1985 | Ryan et al. |
| 4,551,433 A | 11/1985 | DeBoer |
| 4,569,789 A | 2/1986 | Blattler et al. |
| 4,619,794 A | 10/1986 | Hauser |
| 4,659,839 A | 4/1987 | Nicolotti et al. |
| 4,670,417 A | 6/1987 | Iwasaki et al. |
| 4,671,958 A | 6/1987 | Rodwell et al. |
| 4,680,338 A | 7/1987 | Sundoro |
| 4,689,406 A | 8/1987 | Banks et al. |
| 4,699,784 A | 10/1987 | Shih et al. |
| 4,738,921 A | 4/1988 | Belagaje et al. |
| 4,755,465 A | 7/1988 | Gray et al. |
| 4,837,148 A | 6/1989 | Cregg |
| 4,859,600 A | 8/1989 | Gray et al. |
| 4,876,197 A | 10/1989 | Burke et al. |
| 4,880,734 A | 11/1989 | Burke et al. |
| 4,902,502 A | 2/1990 | Nitecki et al. |
| 4,904,584 A | 2/1990 | Shaw |
| 4,929,555 A | 5/1990 | Cregg et al. |
| 5,021,234 A | 6/1991 | Ehrenfeld |
| 5,089,398 A | 2/1992 | Rosenberg et al. |
| 5,122,614 A | 6/1992 | Zalipsky |
| 5,162,601 A | 11/1992 | Slightom |
| 5,219,564 A | 6/1993 | Zalipsky et al. |
| 5,229,490 A | 7/1993 | Tam |
| 5,231,178 A | 7/1993 | Holtz et al. |
| 5,252,714 A | 10/1993 | Harris et al. |
| 5,281,698 A | 1/1994 | Nitecki |
| 5,290,686 A | 3/1994 | Kendal et al. |
| 5,324,639 A | 6/1994 | Brierley et al. |
| 5,324,844 A | 6/1994 | Zalipsky |
| 5,382,657 A | 1/1995 | Karasiewicz et al. |
| 5,446,090 A | 8/1995 | Harris |
| 5,468,478 A | 11/1995 | Saifer et al. |
| 5,473,034 A | 12/1995 | Yasui et al. |
| 5,476,653 A | 12/1995 | Pitt et al. |
| 5,516,657 A | 5/1996 | Murphy et al. |
| 5,516,673 A | 5/1996 | Margel et al. |
| 5,532,142 A | 7/1996 | Johnston et al. |
| 5,559,213 A | 9/1996 | Hakimi et al. |
| 5,571,709 A | 11/1996 | Devauchelle et al. |

(Continued)

FOREIGN PATENT DOCUMENTS

DE    3218121 A1    11/1983
EP    036 676 A1    9/1981

(Continued)

OTHER PUBLICATIONS

Kalis et al. Am J Vet Res vol. 62 ,No. 2 2001.*
Holland, MJ et JP Holland., "Isolation and identification of yeast messenger ribonucleic acids coding for enolase, glyceraldehyde-3-phosphate dehydrogenase, and phosphoglycerate kinase," Biochemistry. Nov. 14, 1978; 17(23):4900-7.
Holland, MJ et al., "The primary structures of two yeast enolase genes. Homology between the 5' noncoding flanking regions of yeast enolase and glyceraldehyde-3-phosphate dehydrogenase genes," J Biol Chem. Feb. 10, 1981;256(3):1385-95.

(Continued)

*Primary Examiner* — Gary Nickol
*Assistant Examiner* — Khatol Shahnan Shah
(74) *Attorney, Agent, or Firm* — Drinker Biddle & Reath LLP

(57) ABSTRACT

Compositions and methods of producing vaccines, including methods wherein whole organism vaccines are provided with limited replication abilities, thereby increasing vaccine safety and efficacy, through the use of non-natural, unnatural, or non-naturally encoded amino acids.

8 Claims, 18 Drawing Sheets

(56) References Cited

U.S. PATENT DOCUMENTS

| | | |
|---|---|---|
| 5,580,723 A | 12/1996 | Wells et al. |
| 5,583,023 A | 12/1996 | Cerutti et al. |
| 5,602,034 A | 2/1997 | Tekamp-Olson |
| 5,605,827 A | 2/1997 | Jackwood et al. |
| 5,612,460 A | 3/1997 | Zalipsky |
| 5,629,203 A | 5/1997 | Shuster |
| 5,629,384 A | 5/1997 | Veronese et al. |
| 5,643,575 A | 7/1997 | Martinez et al. |
| 5,650,234 A | 7/1997 | Dolence et al. |
| 5,672,662 A | 9/1997 | Harris et al. |
| 5,674,706 A | 10/1997 | Shuster |
| RE35,749 E | 3/1998 | Rosenberg et al. |
| 5,736,625 A | 4/1998 | Callstrom et al. |
| 5,739,208 A | 4/1998 | Harris |
| 5,747,646 A | 5/1998 | Hakimi et al. |
| 5,750,373 A | 5/1998 | Garrard et al. |
| 5,753,220 A | 5/1998 | Suzuki et al. |
| 5,762,939 A | 6/1998 | Smith et al. |
| 5,766,885 A | 6/1998 | Carrington et al. |
| 5,808,096 A | 9/1998 | Zalipsky |
| 5,824,778 A | 10/1998 | Ishikawa et al. |
| 5,824,784 A | 10/1998 | Kinstler et al. |
| 5,834,250 A | 11/1998 | Wells et al. |
| 5,834,594 A | 11/1998 | Hakimi et al. |
| 5,843,733 A | 12/1998 | Estes |
| 5,849,860 A | 12/1998 | Hakimi et al. |
| 5,858,368 A | 1/1999 | Smith et al. |
| 5,861,279 A | 1/1999 | Zhang et al. |
| 5,871,986 A | 2/1999 | Boyce |
| 5,891,676 A | 4/1999 | Estes |
| 5,900,461 A | 5/1999 | Harris |
| 5,932,462 A | 8/1999 | Harris et al. |
| 5,939,285 A | 8/1999 | Devauchelle et al. |
| 5,965,393 A | 10/1999 | Hasnain et al. |
| 5,980,948 A | 11/1999 | Goedemoed et al. |
| 5,989,868 A | 11/1999 | Harrison et al. |
| 5,990,237 A | 11/1999 | Bentley et al. |
| 6,004,573 A | 12/1999 | Rathi et al. |
| 6,013,433 A | 1/2000 | Pellett et al. |
| 6,013,478 A | 1/2000 | Wells et al. |
| 6,017,731 A | 1/2000 | Tekamp-Olson et al. |
| 6,083,723 A | 7/2000 | Tekamp-Olson |
| 6,096,304 A | 8/2000 | McCutchen |
| 6,126,944 A | 10/2000 | Pellett et al. |
| 6,129,912 A | 10/2000 | Hortin et al. |
| 6,168,932 B1 | 1/2001 | Uckun et al. |
| 6,183,985 B1 | 2/2001 | Shuster |
| 6,183,987 B1 | 2/2001 | van de Wiel et al. |
| 6,201,072 B1 | 3/2001 | Rathi et al. |
| 6,214,966 B1 | 4/2001 | Harris |
| 6,225,060 B1 | 5/2001 | Clark et al. |
| 6,245,528 B1 | 6/2001 | Chao |
| 6,261,805 B1 | 7/2001 | Wood |
| RE37,343 E | 8/2001 | Tekamp-Olson |
| 6,281,211 B1 | 8/2001 | Cai et al. |
| 6,306,821 B1 | 10/2001 | Mikos et al. |
| 6,312,923 B1 | 11/2001 | Tekamp-Olson |
| 6,337,191 B1 | 1/2002 | Swartz et al. |
| 6,338,846 B1 | 1/2002 | Kang et al. |
| 6,342,216 B1 | 1/2002 | Fidler et al. |
| 6,361,969 B1 | 3/2002 | Galeotti |
| 6,368,825 B1 | 4/2002 | Chao |
| 6,420,339 B1 | 7/2002 | Gegg et al. |
| 6,423,685 B1 | 7/2002 | Drummond et al. |
| 6,428,954 B1 | 8/2002 | Wells et al. |
| 6,436,386 B1 | 8/2002 | Roberts et al. |
| 6,451,346 B1 | 9/2002 | Shah et al. |
| 6,451,561 B1 | 9/2002 | Wells et al. |
| 6,461,603 B2 | 10/2002 | Bentley et al. |
| 6,515,100 B2 | 2/2003 | Harris |
| 6,521,427 B1 | 2/2003 | Evans |
| 6,552,167 B1 | 4/2003 | Rose |
| 6,586,207 B2 | 7/2003 | Tirrell et al. |
| 6,602,498 B2 | 8/2003 | Shen |
| 6,608,183 B1 | 8/2003 | Cox |
| 6,610,281 B2 | 8/2003 | Harris |
| 6,646,110 B2 | 11/2003 | Nissen et al. |
| 6,927,042 B2 | 8/2005 | Schultz et al. |
| 7,045,337 B2 | 5/2006 | Schultz et al. |
| 7,083,970 B2 | 8/2006 | Schultz et al. |
| 7,297,338 B2 | 11/2007 | Fan et al. |
| 2001/0021763 A1 | 9/2001 | Harris |
| 2001/0044526 A1 | 11/2001 | Shen |
| 2001/0056171 A1 | 12/2001 | Kozlowski |
| 2002/0002250 A1 | 1/2002 | Bentley et al. |
| 2002/0037949 A1 | 3/2002 | Harris et al. |
| 2002/0040076 A1 | 4/2002 | Harris et al. |
| 2002/0042097 A1 | 4/2002 | Tirrell et al. |
| 2002/0052009 A1 | 5/2002 | Hornauer et al. |
| 2002/0052430 A1 | 5/2002 | Harris et al. |
| 2002/0055169 A1 | 5/2002 | Tekamp-Olson |
| 2002/0072573 A1 | 6/2002 | Bentley et al. |
| 2002/0081660 A1 | 6/2002 | Swartz et al. |
| 2002/0082345 A1 | 6/2002 | Kozlowski et al. |
| 2002/0086939 A1 | 7/2002 | Kozlowski |
| 2002/0099133 A1 | 7/2002 | Kozlowski |
| 2002/0156047 A1 | 10/2002 | Zhao |
| 2003/0023023 A1 | 1/2003 | Harris et al. |
| 2003/0082575 A1 | 5/2003 | Schultz et al. |
| 2003/0105224 A1 | 6/2003 | Roberts et al. |
| 2003/0105275 A1 | 6/2003 | Bentley et al. |
| 2003/0108885 A1 | 6/2003 | Schultz et al. |
| 2003/0114647 A1 | 6/2003 | Harris et al. |
| 2003/0143596 A1 | 7/2003 | Bentley et al. |
| 2003/0158333 A1 | 8/2003 | Roberts et al. |
| 2003/0162949 A1 | 8/2003 | Cox |
| 2003/0220447 A1 | 11/2003 | Harris |
| 2003/0228274 A1 | 12/2003 | Rose |
| 2004/0001838 A1 | 1/2004 | Zhao et al. |
| 2004/0013637 A1 | 1/2004 | Bentley et al. |
| 2004/0110269 A1 | 6/2004 | Vipond et al. |
| 2004/0198637 A1 | 10/2004 | Schultz et al. |
| 2005/0009049 A1 | 1/2005 | Chin et al. |
| 2005/0085619 A1 | 4/2005 | Wilson et al. |
| 2005/0170404 A1 | 8/2005 | Cho et al. |
| 2005/0220762 A1 | 10/2005 | Cho et al. |
| 2008/0125347 A1 | 5/2008 | Grabstein et al. |
| 2008/0286310 A1 | 11/2008 | Zhu et al. |
| 2012/0045475 A1 | 2/2012 | Browning et al. |

FOREIGN PATENT DOCUMENTS

| | | |
|---|---|---|
| EP | 036 776 A2 | 9/1981 |
| EP | 052 322 A2 | 5/1982 |
| EP | 058 481 A1 | 8/1982 |
| EP | 073 657 A1 | 3/1983 |
| EP | 102 324 A2 | 3/1984 |
| EP | 121 775 A1 | 10/1984 |
| EP | 127 839 A2 | 12/1984 |
| EP | 133 988 A2 | 3/1985 |
| EP | 143 949 A1 | 6/1985 |
| EP | 154 316 A2 | 9/1985 |
| EP | 155 476 A1 | 9/1985 |
| EP | 164 556 A2 | 12/1985 |
| EP | 183 503 A2 | 6/1986 |
| EP | 188 256 A2 | 7/1986 |
| EP | 229 108 B1 | 7/1987 |
| EP | 244 234 A2 | 11/1987 |
| EP | 267 851 A2 | 5/1988 |
| EP | 284 044 A1 | 9/1988 |
| EP | 324 274 A1 | 7/1989 |
| EP | 329 203 A1 | 8/1989 |
| EP | 340 986 A2 | 11/1989 |
| EP | 400 472 A2 | 12/1990 |
| EP | 402 378 B1 | 12/1990 |
| EP | 439 508 B1 | 8/1991 |
| EP | 480 480 A2 | 4/1992 |
| EP | 510 356 A1 | 10/1992 |
| EP | 605 963 A1 | 7/1994 |
| EP | 732 403 A1 | 9/1996 |
| EP | 809 996 A2 | 12/1997 |
| EP | 921 131 A1 | 6/1999 |
| EP | 946 736 B1 | 10/1999 |
| JP | 83-118008 A | 1/1985 |

(56) References Cited

FOREIGN PATENT DOCUMENTS

| | | |
|---|---|---|
| RU | 2242481 | 12/2001 |
| WO | 88/07082 A1 | 9/1988 |
| WO | 89/01037 A1 | 2/1989 |
| WO | 89/01038 A1 | 2/1989 |
| WO | 90/01556 A1 | 2/1990 |
| WO | 90/02186 A1 | 3/1990 |
| WO | 90/02586 A1 | 3/1990 |
| WO | 90/05785 A1 | 5/1990 |
| WO | 90/10078 A1 | 9/1990 |
| WO | 90/10277 A1 | 9/1990 |
| WO | 90/13540 A1 | 11/1990 |
| WO | 90/14428 A1 | 11/1990 |
| WO | 91/00357 A1 | 1/1991 |
| WO | 92/01801 A1 | 2/1992 |
| WO | 92/02628 A1 | 2/1992 |
| WO | 92/16555 A1 | 10/1992 |
| WO | 92/16619 A1 | 10/1992 |
| WO | 92/16628 | 10/1992 |
| WO | 93/03173 A1 | 2/1993 |
| WO | 93/15189 A1 | 8/1993 |
| WO | 93/21259 A1 | 10/1993 |
| WO | 94/04193 A1 | 3/1994 |
| WO | 94/09027 A1 | 4/1994 |
| WO | 94/14758 A1 | 7/1994 |
| WO | 94/15625 A1 | 7/1994 |
| WO | 94/17039 A1 | 8/1994 |
| WO | 94/18247 A1 | 8/1994 |
| WO | 94/28024 A1 | 12/1994 |
| WO | 95/00162 A1 | 1/1995 |
| WO | 95/06058 A1 | 3/1995 |
| WO | 95/11924 A1 | 5/1995 |
| WO | 95/13090 A1 | 5/1995 |
| WO | 95/13312 A1 | 5/1995 |
| WO | 95/20672 A1 | 8/1995 |
| WO | 95/33490 A1 | 12/1995 |
| WO | 96/00080 A1 | 1/1996 |
| WO | 96/06161 A1 | 2/1996 |
| WO | 96/07670 A1 | 3/1996 |
| WO | 96/21469 A1 | 7/1996 |
| WO | 96/25496 A1 | 8/1996 |
| WO | 96/29400 A1 | 9/1996 |
| WO | 96/40791 A1 | 12/1996 |
| WO | 96/41813 A2 | 12/1996 |
| WO | 97/03106 A1 | 1/1997 |
| WO | 97/18832 A1 | 5/1997 |
| WO | 97/26332 A1 | 7/1997 |
| WO | 97/32607 A2 | 9/1997 |
| WO | 98/05363 A2 | 2/1998 |
| WO | 98/26080 A1 | 6/1998 |
| WO | 98/32466 A1 | 7/1998 |
| WO | 98/37208 A1 | 8/1998 |
| WO | 98/41562 A1 | 9/1998 |
| WO | 98/48837 A1 | 11/1998 |
| WO | 99/03887 A1 | 1/1999 |
| WO | 99/05297 A1 | 2/1999 |
| WO | 99/07862 A1 | 2/1999 |
| WO | 99/09193 A1 | 2/1999 |
| WO | 99/10515 A1 | 3/1999 |
| WO | 99/31257 A2 | 6/1999 |
| WO | 99/32134 A1 | 7/1999 |
| WO | 99/32139 A1 | 7/1999 |
| WO | 99/32140 A1 | 7/1999 |
| WO | 99/45130 A1 | 9/1999 |
| WO | 99/51721 A1 | 10/1999 |
| WO | 99/65942 | 12/1999 |
| WO | 99/67291 A2 | 12/1999 |
| WO | 00/20032 A1 | 4/2000 |
| WO | 00/26354 A1 | 5/2000 |
| WO | 00/55345 A2 | 9/2000 |
| WO | 00/55353 A1 | 9/2000 |
| WO | 01/05956 A2 | 1/2001 |
| WO | 01/27301 A2 | 4/2001 |
| WO | 01/90390 A1 | 11/2001 |
| WO | 02/06305 A1 | 1/2002 |
| WO | 02/085923 A2 | 10/2002 |
| WO | 02/086075 A2 | 10/2002 |
| WO | 03/101972 A1 | 12/2003 |
| WO | 2004/035605 A2 | 4/2004 |
| WO | 2004/035743 A2 | 4/2004 |
| WO | 2004/058946 A2 | 7/2004 |
| WO | 2004/094593 A2 | 11/2004 |
| WO | 2005/007624 A2 | 1/2005 |
| WO | 2005/007870 A2 | 1/2005 |
| WO | 2005/019415 A2 | 3/2005 |
| WO | 2005/035727 A2 | 4/2005 |
| WO | 2005/074524 A2 | 8/2005 |
| WO | 2005/074546 A2 | 8/2005 |
| WO | 2005/074650 A2 | 8/2005 |
| WO | 2007/103490 | 9/2007 |
| WO | 2009/048971 A1 | 4/2009 |

OTHER PUBLICATIONS

Hsiao, CL et J Carbon, "High-frequency transformation of yeast by plasmids containing the cloned yeast ARG4 gene," Proc Natl Acad Sci U S A. Aug. 1979;76(8):3829-33.

Huisgen, R. in 1,3-Dipolar Cycloaddition Chemistry, vol. 1, 1984; Ed. Padwa A.; John Wiley and Sons, New York, p. 1-176.

Hwang, KJ et al., "Hepatic uptake and degradation of unilamellar sphingomyelin/cholesterol liposomes: a kinetic study," Proc Natl Acad Sci U S A. Jul. 1980;77(7):4030-4.

Ibba, M et al., "Substrate specificity is determined by amino acid binding pocket size in *Escherichia coli* phenylalanyl-tRNA synthetase," Biochemistry. Jun. 14, 1994;33(23):7107-12.

Ibba, M and H Hennecke, "Relaxing the substrate specificity of an aminoacyl-tRNA synthetase allows in vitro and in vivo synthesis of proteins containing unnatural amino acids," FEBS Lett. May 15, 1995;364(3):272-5.

Ito, H. et al., "Transformation of intact yeast cells treated with alkali cations," J. Bacteriol. 1983; 153(1):163-8.

Jackson, DY et al. "A designed peptide ligase for total synthesis of ribonuclease A with unnatural catalytic residues," Science. Oct. 14, 1994;266(5183):243-7.

Jakobsson, PJ et al., "Identification and characterization of a novel human microsomal glutathione S-transferase with leukotriene C4 synthase activity and significant sequence identity to 5-lipoxygenase-activating protein and leukotriene C4 synthase," J Biol Chem. Sep. 6, 1996;271(36):22203-10.

Jencks, W.P., "Studies on the Mechanism of Oxime and Semicarbazone Formation," J. Am. Chem. Soc.; 1959; 81 (2):475-481.

Joppich, M. et al. "Peptides Flanked by Two Polymer Chains, 1; Synthesis of Glycyl-L-tryptophylglycine Substituted by Poly(ethylene oxide) at both the Carboxy and the Amino End Groups," Makromol. Chem. 1979;180:1381-4.

Kaiser, ET. "Synthetic approaches to biologically active peptides and proteins including enzymes," Acc Chem Res, (1989); 22(2):47-54.

Kaiser, ET et al. "The chemical modification of enzymatic specificity," Annu Rev Biochem. 1985;54:565-95.

Kaiser, ET and DS Lawrence. "Chemical mutation of enzyme active sites," Science. Nov. 2, 1984;226(4674):505-11.

Karlin, S and SF Altschul "Applications and statistics for multiple high-scoring segments in molecular sequences," Proc Natl Acad Sci U S A. Jun. 15, 1993;90(12):5873-7.

Kayser, B., et al., "Alkyne bridged alpha-amino acids by palladium mediated coupling of alkynes with N-t-Boc-4-iodo-phenylalanine methyl ester," Tetrahedron (1997); 53(7): 2475-2484.

Kelly, JM and MJ Hynes, "Transformation of *Aspergillus niger* by the amdS gene of *Aspergillus nidulans*," EMBO J. 1985; 4(2):475-479.

Kiick, K. L. and D. A. Tirrell, "Protein Engineering by In Vivo Incorporation of Non-Natural Amino Acids: Control of Incorporation of Methionine Analogues by Methionyl-tRNA Synthetase," Tetrahedron (2000), 56:9487-9493.

Kiick, KL et al., "Incorporation of azides into recombinant proteins for chemoselective modification by the Staudinger ligation," Proc Natl Acad Sci U S A. Jan. 8, 2002;99(1):19-24. Epub Dec. 18, 2001.

Kim, DM and JR Swartz, "Regeneration of adenosine triphosphate from glycolytic intermediates for cell-free protein synthesis," Biotechnol Bioeng. Aug. 20, 2001;74(4):309-16.

(56) References Cited

OTHER PUBLICATIONS

Kim, DM and JR Swartz, "Oxalate improves protein synthesis by enhancing ATP supply in a cell-free system derived from *Escherichia coli*," Biotechnology Letters, 2000; 22:1537-1542.

Kim, DM, and JR Swartz, "Prolonging cell-free protein synthesis by selective reagent additions," Biotechnol Prog. May-Jun. 2000;16(3):385-90.

Kim, DM, and JR Swartz, "Prolonging cell-free protein synthesis with a novel ATP regeneration system," Biotechnol Bioeng. 1999;66(3):180-8.

King, F.E. & Kidd, D.A.A. "A New Synthesis of Glutamine and of gamma-Dipeptides of Glutamic Acid from Phthylated Intermediates," J. Chem. Soc. 1949; 3315-3319.

Kingsman, AJ et al., "Replication in *Saccharomyces cerevisiae* of plasmid pBR313 carrying DNA from the yeast trpl region," Gene. Oct. 1979;7(2):141-52.

Kitts, PA et al. "Linearization of baculovirus DNA enhances the recovery of recombinant virus expression vectors," Nucleic Acids Res. Oct. 11, 1990;18(19):5667-72.

Klein, TM et al., "High-velocity microprojectiles for delivering nucleic acids into living cells," Nature 1987; 327 (6117):70-73.

Kobayashi, T. et al., "Structural basis for orthogonal tRNA specificities of tyrosyl-tRNA synthetases for genetic code expansion," Nature Structural Biology (2003); 10(6):425-432.

Kogan, TP. "The synthesis of substituted methoxy-poly(ethyleneglycol) derivatives suitable for selective protein modification," Synthetic Comm. 1992; 22(16):2417-24.

Kool, ET. "Synthetically modified DNAs as substrates for polymerases," Curr Opin Chem Biol. Dec. 2000;4(6):602-8.

Koskinen, A.M.P. & Rapoport, H. "Synthesis of 4-Substituted Prolines as Conformationally Constrained Amino Acid Analogues," J. Org. Chem. (1989) 54(8):1859-1866.

Kost, TA et al., "Production of a urokinase plasminogen activator-IgG fusion protein (uPA-IgG) in the baculovirus expression system," Gene. Apr. 29, 1997;190(1):139-44.

Kramer, W et al., "The gapped duplex DNA approach to oligonucleotide-directed mutation construction," Nucleic Acids Res. Dec. 21, 1984;12(24):9441-56.

Kramer, W & Fritz HJ. "Oligonucleotide-directed construction of mutations via gapped duplex DNA" Methods Enzymol. 1987;154:350-67.

Kramer, W. et al., "Improved enzymatic in vitro reactions in the gapped duplex DNA approach to oligonucleotide-directed construction of mutations," Nucleic Acids Res. Jul. 25, 1988;16(14B):7207.

Kramer, B. et al., "Different base/base mismatches are corrected with different efficiencies by the methyl-directed DNA mismatch-repair system of *E. coli*," Cell. Oct. 1984;38(3):879-87.

Kreitman, RJ and I. Pastan "Purification and characterization of IL6-PE4E, a recombinant fusion of interleukin 6 with *Pseudomonas* exotoxin," Bioconjug Chem. Nov.-Dec. 1993;4(6):581-5.

Krieg, UC, et al. "Photocrosslinking of the signal sequence of nascent preprolactin to the 54-kilodalton polypeptide of the signal recognition particle," Proc Natl Acad Sci U S A. Nov. 1986;83(22):8604-8.

Kunitani, M. et al., "Reversed-phase chromatography of interleukin-2 muteins," J Chromatogr. May 30, 1986;359:391-402.

Kunkel, "The efficiency of oligonucleotide directed mutagenesis," in Nucleic Acids & Molecular Biology 1987; Eckstein, F. and Lilley, D.M.J. eds.; Springer Verlag, Berlin; 124-135.

Kunkel, TA "Rapid and efficient site-specific mutagenesis without phenotypic selection," Proc Natl Acad Sci U S A. Jan. 1985;82(2):488-92.

Kunkel, TA et al., "Rapid and efficient site-specific mutagenesis without phenotypic selection," Methods Enzymol. 1987; 154:367-82.

Kunze, G et al., "Transformation of the industrially important yeasts *Candida maltosa* and *Pichia guilliermondii*," J. Basic Microbiol. 1985; 25:141-4.

Kurtz et al., "Integrative transformation of *Candida albicans*, using a cloned Candida ADE2 gene," Mol Cell Biol. Jan. 1986;6(1):142-9.

Kurtzhals, P et al., "Albumin binding of insulins acylated with fatty acids: characterization of the ligand-protein interaction and correlation between binding affinity and timing of the insulin effect in vivo," Biochem J. Dec. 15, 1995;312 ( Pt 3):725-31.

Langer, R et al., "Biocompatibility of polymeric delivery systems for macromolecules," J Biomed Mater Res. Mar. 1981;15(2):267-77.

Langer, R. "Controlled release of macromolecules, " Chem. Tech. 1982; 12: 98-105.

Liebman, JM et al., "When less is more: enhanced baculovirus production of recombinant proteins at very low multiplicities of infection," Biotechniques. Jan. 1999;26(1):36-8, 40, 42.

Ling, MM et BH Robinson, "Approaches to DNA mutagenesis: an overview" Anal Biochem. Dec. 15, 1997;254 (2):157-78.

Raibaud, O et M Schwartz. "Positive control of transcription initiation in bacteria," Annu Rev Genet. 1984;18:173-206.

Reverey, H. et al., "Differential Fatty Acid Selection during Biosynthetic S-Acylation of a Transmembrane Protein (HEF) and Other Proteins in Insect Cells (Sf9) and in Mammalian Cells (CV1)," J. Biol. Chem. 1996; 271 (39):23607-10.

Rivier, J et R McClintock, "Reversed-phase high-performance liquid chromatography of insulins from different species," J Chromatogr. Sep. 23, 1983;268(1):112-9.

Roberts, et al., "Generation of an antibody with enhanced affinity and specificity for its antigen by protein engineering," Nature 1987;328:731-734.

Roberts, RW and JW Szostak, "RNA-peptide fusions for the in vitro selection of peptides and proteins," Proc Natl Acad Sci U S A. Nov. 11, 1997;94(23):12297-302.

Roggenkamp, R. et al., "Transformation of the methylotrophic yeast *Hansenula polymorpha* by autonomous replication and integration vectors," MOL. Genetics and Genomics 1986;202(2):302-8.

Romani et al. "Synthesis of unsymmetrical cystine peptides: directed disulfide pairing with the sulfenohydrazide method," in Chemistry of Peptides and Proteins 1984; eds. Voelter, W. et al.; Walter de Gruyter et al., Berlin; vol. 2:29-33.

Romanos, MA et al., "Foreign gene expression in yeast: a review," Yeast. Jun. 1992;8(6):423-88.

Rosenthal, GA. "L-canaline: a potent antimetabolite and anti-cancer agent from leguminous plants," Life Sci.1997;60(19):1635-41.

Rossolini, GM et al., "Use of deoxyinosine-containing primers vs degenerate primers for polymerase chain reaction based on ambiguous sequence information," Mol. Cell. Probes 1994; 8:91-98.

Rostovtsev, VV et al., "A stepwise huisgen cycloaddition process: copper(I)-catalyzed regioselective "ligation" of azides and terminal alkynes," Angew Chem Int Ed Engl Jul. 15, 2002;41(14):2596-9.

Rowles, J et al., "Cloning and characterization of PDK4 on 7q21.3 encoding a fourth pyruvate dehydrogenase kinase isoenzyme in human," J Biol Chem. Sep. 13, 1996;271(37):22376-82.

Sakmar, TP and Khorana HG, "Total synthesis and expression of a gene for the alpha-subunit of bovine rod outer segment guanine nucleotide-binding protein (transducin)" Nucleic Acids Res. Jul. 25, 1988;16(14A):6361-72.

Sandler and Karo, "Polyoxyalkylation of hydroxyl compounds," in Polymer Synthesis, vol. 3, 1980; Academic Press, New York, 138-161.

Sartore, L et al., "Enzyme modification by MPEG with an amino acid or peptide as spacer arms," Appl Biochem Biotechnol. Jan. 1991;27(1):45-54.

Sawhney, AS et al., "Bioerodible Hydrogels Based on Photopolymerized Poly(ethylene glycol)-co-poly(alpha-hydroxy acid) Diacrylate Macromers," Macromolecules 1993; 26(4):581-7.

Saxon, E and C. Bertozzi, "Cell Surface Engineering by a Modified Staudinger Reaction," Science (2000); 287 (5460):2007-2010.

Sayers, Jr et al., "Strand specific cleavage of phosphorothioate-containing DNA by reaction with restriction endonucleases in the presence of ethidium bromide" Nucleic Acids Res. Feb. 11, 1988;16(3):803-14.

Sayers, Jr, et al. "5'-3' exonucleases in phosphorothioate-based oligonucleotide-directed mutagenesis," Nucleic Acids Res. Feb. 11, 1988;16(3):791-802.

Schanbacher, FL et al. "Galactosyltransferase Acceptor Specificity of the Lactose Synthetase A Protein," J. Biol. Chem. 1970; 245(19):5057-5061.

(56) References Cited

OTHER PUBLICATIONS

Schmidt, M et al., "Baculovirus-mediated large-scale expression and purification of a polyhistidine-tagged rubella virus capsid protein," Protein Expr Purif. Apr. 1998;12(3):323-30.
Schneider, E., et al., "Functional Purification of a Bacterial ATP-Binding Cassette Transporter Protein (MalK) from the Cytoplasmic Fraction of an Overproducing Strain," Protein Expr. Purif. 1995; 6(1):10-14.
Schnolzer, M. and SBH Kent. "Constructing proteins by dovetailing unprotected synthetic peptides: backbone-engineered HIV protease," Science. Apr. 10, 1992;256(5054):221-5.
Scouten, WH. "A survey of enzyme coupling techniques," Methods Enzymol. 1987;135:30-65.
Shao, J and JP Tam, "Unprotected Peptides as Building Blocks for the Synthesis of Peptide Dendrimers with Oxime, Hydrazone, and Thiazolidine Linkages," J. Am. Chem. Soc. 1995; 117(14):3893-3899.
Sharma, N et al., "Efficient introduction of aryl bromide functionality into proteins in vivo," FEBS Lett. Feb. 4, 2000;467 (1):37-40.
Simatake, H et M Rosenberg, "Purified gamma regulatory protein cII positively activates promoters for lysogenic development," Nature Jul. 1981; 292:128-132.
Shine, J and L Dalgarno, "Determinant of cistron specificity in bacterial ribosomes," Nature. Mar. 6, 1975;254 (5495):34-8.
Sidman, KR et al., "Controlled release of macromolecules and pharmaceuticals from synthetic polypeptides based on glutamic acid," Biopolymers. Jan. 1983;22(1):547-56.
Sieber, V. et al., "Libraries of hybrid proteins from distantly related sequences," Nature Biotechnology, May 2001;19:456-460.
Siffert, W et al., "Association of a human G-protein beta3 subunit variant with hypertension," Nat Genet. Jan. 1998;18(1):45-8.
Sikorski, RS et al., "A System of Shuttle Vectors and Yeast Host Strains Designed for Efficient Manipulation of DNA in *Saccharomyces cerevisiae*," Genetics (1989) 122:19-27.
Sisk, WP et al., "High-level expression and purification of secreted forms of herpes simplex virus type 1 glycoprotein gD synthesized by baculovirus-infected insect cells," J Virol. Feb. 1994;68(2):766-75.
Sjolander, A et al., "The serum albumin-binding region of streptococcal protein G: a bacterial fusion partner with carrier-related properties," J Immunol Methods. Feb. 14, 1997;201(1):115-23.
Smith, M. "In vitro mutagenesis" Ann. Rev. Genet. 1985; 19:423-462.
Smith, GE et al., "Production of human beta interferon in insect cells infected with a baculovirus expression vector," Mol Cell Biol. Dec. 1983;3(12):2156-65.
Stanley, SL et al., "The serine-rich Entamoeba histolytica protein is a phosphorylated membrane protein containing O-linked terminal N-acetylglucosamine residues," J Biol Chem. Feb. 24, 1995;270(8):4121-6.
Steitz, JA et al. "Genetic signals and nucleotide sequences in messenger RNA," in Biological Regulation and Development: Gene Expression 1979; ed. R. F. Goldberger; Plenum Press, New York; 349-399.
Stemmer, WPC, "Rapid evolution of a protein in vitro by DNA shuffling," Nature 1994;370(4):389-391.
Stemmer, WP "DNA shuffling by random fragmentation and reassembly: In vitro recombination for molecular evolution," Proc Natl Acad Sci U S A. Oct. 25, 1994;91(22):10747-51.
Studier, FW et BA Moffatt, "Use of bacteriophage T7 RNA polymerase to direct selective high-level expression of cloned genes," J. Mol Biol. May 5, 1986;189(1):113-30.
Subasinghe, N. et al., "Quisqualic acid analogues: synthesis of beta-heterocyclic 2-aminopropanoic acid derivatives and their activity at a novel quisqualate-sensitized site," J Med Chem. Nov. 27, 1992;35(24):4602-7.
Switzer, C et al., "Enzymatic incorporation of a new base pair into DNA and RNA," J. Am. Chem. Soc. 1989; 111 (21):8322-8323.
Tabor, S et CC Richardson, "A bacteriophage T7 RNA polymerase/promoter system for controlled exclusive expression of specific genes," Proc Natl Acad Sci U S A. Feb. 1985;82(4):1074-8.

Tae, EL et al., "Efforts toward Expansion of the Genetic Alphabet: Replication of DNA with Three Base Pairs," J. Am. Chem. Soc. 2001; 123(30):7439-7440.
Tang, Y et al., "Fluorinated Coiled-Coil Proteins Prepared In Vivo Display Enhanced Thermal and Chemical Stability," Angew Chem Int Ed Engl. Apr. 17, 2001;40(8):1494-1496.
Taylor, JW et al., "The use of phosphorothioate-modified DNA in restriction enzyme reactions to prepare nicked DNA," Nucleic Acids Res. Dec. 20, 1985;13(24):8749-64.
Taylor, JW et al., "The rapid generation of oligonucleotide-directed mutations at high frequency using phosphorothioate-modified DNA," Nucleic Acids Res. Dec. 20, 1985;13(24):8765-85.
Tijssen, P. "Overview of principles of hybridization and the strategy of nucleic acid assays," in Laboratory Techniques in Biochemistry and Molecular Biology—Hybridization with Nucleic Probes, Part I, 1993; Elsevier Science Publishers, Amsterdam, 19-78.
Tilburn, J. et al., "Transformation by integration in *Aspergillus nidulans*," Gene. Dec. 1983;26(2-3):205-21.
Zoller, MJ & Smith M, "Oligonucleotide-directed mutagenesis: a simple method using two oligonucleotide primers and a single-stranded DNA template," Methods Enzymol. 1987;154:329-50.
Mehl, RA et al. "Generation of a bacterium with a 21 amino acid genetic code," J Am Chem Soc. Jan. 29, 2003;125 (4):935-9.
Santoro, SW et al. "An efficient system for the evolution of aminoacyl-tRNA synthetase specificity," Nat Biotechnol. Oct. 2002;20(10):1044-8. Epub Sep. 16, 2002.
Caliceti, P et FM Veronese. "Pharmacokinetic and biodistribution properties of poly(ethylene glycol)-protein conjugates," Adv Drug Deliv Rev. Sep. 26, 2003;55(10):1261-77.
Clark, EDB, "Refolding of recombinant proteins," Curr Opin Biotechnol Apr. 1, 1998;9(2):157-63.
Clark, EDB, "Protein refolding for industrial processes," Curr Opin Biotechnol Apr. 2001;12(2):202-7.
Davis, GD et al., "New fusion protein systems designed to give soluble expression in *Escherichia coli*," Biotechnol Nov. 20, 1999;65(4):382-8.
Yelton, MM et al., "Transformation of *Aspergillus nidulans* by using a trpC plasmid," Proc Natl Acad Sci U S A. Mar. 1984;81(5):1470-4.
Yelverton, E et al., "Bacterial synthesis of a novel human leukocyte interferon," Nucleic Acids Res. Feb. 11, 1981;9 (3):731-41.
Zalipsky, S et al. "Attachment of drugs to polyethylene glycols," Eur. Polymer Journal. 1983 19(12):1177-83.
Zalipsky, S. "Functionalized poly(ethylene glycol) for preparation of biologically relevant conjugates," Bioconjug Chem. Mar.-Apr. 1995;6(2):150-65.
Zhang, Z., et al. "A new strategy for the site-specific modification of proteins in vivo," Biochemistry. Jun. 10, 2003;42 (22):6735-46.
Zoller, MJ & M Smith, "Oligonucleotide-directed mutagenesis using M13-derived vectors: an efficient and general procedure for the production of point mutations in any fragment of DNA" Nucleic Acids Res. Oct. 25, 1982;10 (20):6487-500.
Zoller, MJ & M. Smith, "Oligonucleotide-directed mutagenesis of DNA fragments cloned into M13 vectors" Methods Enzymol. 1983;100:468-500.
M.H. Richmond, "The effect of amino acid analogues on growth and protein synthesis in microorganisms", Bactril. Rev. (1962), 26(4):398-420.
Molina et al., "Study on Immune response of goats vaccinated with a live strain of mycobacterium paratuberculosis", Compar.Immun. Microbio Infect. Diseases (1996) 19(1): 9-15.
Herring et al., "Conditional lethal amber mutations in essential *Escherichia coli* genes", J. Bacteriology (2004) 186(9): 2673-2681.
Wang et al., "New methods enabling efficient incorporation of unnatural amino acids in yeast", J. Am. Chem. Soc. (2008) 130(19):6066-6067.
Wang et al., "Genetic incorporation of unnatural amino acids in proteins in *Mycobacterium tuberculosis*", PLOS ONE (2010) 5(2).
Wang et al., "Expanding the genetic code of *Escherichia coli*", Science (2001) 292(5516): 498-500.
Wang et al., "Expanding the genetic code", Chem Commun. (2002) 1-11.

(56) References Cited

OTHER PUBLICATIONS

Park et al., "Immunization with a DNA vaccine cocktail induces a Th1 response and protects mice against *Mycobacterium avium* subsp. Paratuberculousis challenge", Vaccine (2008) 26(34):4329-4337.

Zhang et al., (2002) "The selective incorporation of alkenes into proteins in *Escherichia coli*" Angew Chem Int Ed Engl. 41(15):2840-2842.

Extended European Search Report mailed dated Jul. 10, 2012 in EP Application No. 09817017.8.

International Preliminary Report on Patentability mailed Apr. 7, 2011 in International Application No. PCT/US2009/058668.

International Search Report mailed Nov. 16, 2009 in International Application No. PCT/US2009/058668.

Cranwell, "Control of Johne's Disease in a Flock of Sheep by Vaccination," Veterinary Record 133 (9): 219-220, 1993 (Abstract only).

Wentink et al., "Incidence of paratuberculosis after vaccination against M. paratuberculosis in two infected dairy herds," Zentralbl Veterinarmed B. 41(7-8):517-22, 1994 (Abstract only).

Van Hest, J. C. et al., "Efficient Incorporation of Unsaturated Methionine Analogues into Proteins in Vivo," J. Am. Chem. Soc.2000 ;122 (7); 1282-1288.

Van Solingen, P. et JP van der Plaat. "Fusion of yeast spheroplasts," J Bacteriol. May 1977;130(2):946-7.

Veronese, FM et al., "Surface modification of proteins. Activation of monomethoxy-polyethylene glycols by phenylchloroformates and modification of ribonuclease and superoxide dismutase," Appl Biochem Biotechnol. Apr. 1985;11(2):141-52.

Vlak, JM et al., "Functional studies on the p10 gene of Autographa californica nuclear polyhedrosis virus using a recombinant expressing a p10-beta-galactosidase fusion gene," J Gen Virol. Apr. 1988;69 ( Pt 4):765-76.

Wang, Q., et al., "Bioconjugation by Copper(I)-Catalyzed Azide-Alkyne [3+2] Cycloaddition," J. Am. Chem. Soc. 2003; 125(11):3192-3193.

Wang, L. et al., "Addition of the keto functional group to the genetic code of *Escherichia coli*," Proc. Natl. Acad. Sci. (2003); 100(1):56-61.

Wang, L et al., "Expanding the genetic code of *Escherichia coli*," Science. Apr. 20, 2001;292(5516):498-500.

Abuchowski, A. et al. "Cancer therapy with chemically modified enzymes. I. Antitumor properties of polyethylene glycol-asparaginase conjugates," Cancer Biochem Biophys. Jun. 1984;7(2):175-86.

Altschul, SF et al. "Gapped BLAST and PSI-BLAST: a new generation of protein database search programs," Nucleic Acids Res. Sep. 1, 1997;25(17):3389-402.

Altschul, SF et al. "Basic local alignment search tool," J Mol Biol. Oct. 5, 1990;215(3):403-10.

Amann, E et al., "Vectors bearing a hybrid trp-lac promoter useful for regulated expression of cloned genes in *Escherichia coli*," Gene. Nov. 1983;25(2-3):167-78.

Anderson, JC et al., "Exploring the limits of codon and anticodon size," Chem Biol. Feb. 2002;9(2):237-44.

Andresz, H et al. Abstract of "Chemische Synthese verzweigter Polysaccharide, 5; Kopplung von Oligosacchariden und Amylose an verschiedene Träger durch Hydrazonbindung," Makromol. Chem. 1978;179:301 Abstract.

Arnold, FH. "Protein engineering for unusual environments," Curr Opin Biotechnol. Aug. 1993;4(4):450-5.

Azoulay, M., et al. "Glutamine analogues as Potential Antimalarials," Eur. J. Med. Chem. (1991); 26(2):201-5.

Bain, JD. "Biosynthetic site-specific incorporation of a non-natural amino acid into a polypeptide," J. Am Chem Soc 1989;111(20):8013-8014.

Ballance, DJ et al., "Transformation of *Aspergillus nidulans* by the orotidine-5'-phosphate decarboxylase gene of *Neurospora crassa*," Biochem Biophys Res Commun. Apr. 15, 1983;112(1):284-9.

Barany, F. et al., "Genetic disease detection and DNA amplification using cloned thermostable ligase," Proc Natl Acad Sci U S A. Jan. 1, 1991;88(1):189-93.

Barton, DHR et al., "Synthesis of Novel alpha-Amino-Acids and Derivatives Using Radical Chemistry: Synthesis of L- and D-alpha-Amino-Adipic Acids, L-alpha-aminopimetic Acid and Appropriate Unsaturated Derivatives," Tetrahedron (1987) 43:4297-4308.

Bass, S et al., "Mutant Trp repressors with new DNA-binding specificities," Science (1988) 242:240-245.

Batzer, MA et al., "Enhanced evolutionary PCR using oligonucleotides with inosine at the 3'-terminus," Nucleic Acids Res. Sep. 25, 1991;19(18):5081.

Beach, D et al., "Functionally homologous cell cycle control genes in budding and fission yeast," Nature Dec. 1982; 300:706-709.

Beauchamp, CO et al., "A new procedure for the synthesis of polyethylene glycol-protein adducts; effects on function, receptor recognition, and clearance of superoxide dismutase, lactoferrin, and alpha 2-macroglobulin," Anal Biochem. May 1983;131(1):25-33.

Bernstein, FC, et al. "The protein data bank: a computer-based archival file for macromolecular structures," J. Mol. Biol. 1977: 112:535-542.

Boissel, JP et al., "Erythropoietin structure-function relationships, Mutant proteins that test a model of tertiary structure," J Biol Chem. Jul. 25, 1993;268(21):15983-93.

Boles, JO et al. "Bio-incorporation of telluromethionine into buried residues of dihydrofolate reductase," Nat Struct Biol. May 1994;1(5):283-4.

Botstein, D et D Shortle, "Strategies and applications of in vitro mutagenesis," Science. Sep. 20, 1985;229(4719):1193-201.

Brunner, J. "New photolabeling and crosslinking methods," Annu Rev Biochem. 1993;62:483-514.

Buchner, J. et al., "A method for increasing the yield of properly folded recombinant fusion proteins: Single-chain immunotoxins from renaturation of bacterial inclusion bodies," Anal. Biochem. 1992; 205(2): 263-270.

Bückmann et al. "Functionalization of Poly(ethylene glycol) and Monomethoxy-Poly(ethylene glycol)," Makromol. Chem. 1981;182:1379-84.

Budisa, N et al. "High-level biosynthetic substitution of methionine in proteins by its analogs 2-aminohexanoic acid, selenomethionine, telluromethionine and ethionine in *Escherichia coli*," Eur J Biochem. Jun. 1, 1995;230(2):788-96.

Budisa, N et al., "Bioincorporation of telluromethionine into proteins:a promising new approach for X-ray structure analysis of proteins," J Mol Biol. Jul. 25, 1997;270(4):616-23.

Budisa, N et al., "Toward the experimental codon reassignment in vivo: protein building with an expanded amino acid repertoire," FASEB J. Jan. 1999;13(1):41-51.

Cai, X-Y et al., "Expression, Purification, and Characterization of an Activated Cytokine-Suppressive Anti-inflammatory Drug-Binding Protein 2 (CSBP2) Kinase from Baculovirus-Infected Insect Cells," Protein Expression and Purifcation 1997; 10(2):263-74.

Carbonell, LF et al., "Baculovirus-mediated expression of bacterial genes in dipteran and mammalian cells," J Virol. Oct. 1985;56(1):153-60.

Carrasco, M. and R. Brown, "A Versatile Set of Aminooxy Amino Acids for the Synthesis of Neoglycopeptides," J. Org. Chem. (2003); 68(23):8853-8858.

Carter, P. "Site-directed mutagenesis," Biochem J. Jul. 1, 1986; 237(1):1-7.

Carter, P et al. "Improved oligonucleotide site-directed mutagenesis using M13 vectors" Nucleic Acids Res. Jun. 25, 1985;13(12):4431-43.

Carter, P. "Improved oligonucleotide-directed mutagenesis using M13 vectors" Methods Enzymol. 1987;154:382-403.

Chaiken, IM. "Semisynthetic peptides and proteins," CRC Crit Rev Biochem. 1981;11(3):255-301.

Chin, JW et al., "Addition of p-azido-L-phenylalanine to the genetic code of *E. coli*," J Am Chem Soc. Aug. 7, 2002; 124(31):9026-7.

Chin, JW et al., "Addition of a photocrosslinking amino acid to the genetic code of *Escherichia coli*," Proc Natl Acad Sci U S A. Aug. 20, 2002;99(17):11020-4. Epub Aug. 1, 2002.

Chin, JW et al., "An expanded eukaryotic genetic code," Science. Aug. 15, 2003;301(5635):964-7.

(56) References Cited

OTHER PUBLICATIONS

Chin, JW & P. G. Schultz, "In vivo photocrosslinking with unnatural amino acid mutagenesis," Chembiochem. Nov. 4, 2002; 3(11): 1135-7.
Christie, B.D. & Rapoport, H. "Synthesis of Optically Pure Pipecolates from L-Asparagine. Application to the Total Synthesis of (+)-Apovincamine through Amino Acid Decarbonylation and Iminium Ion Cyclization," J. Org. Chem. 1985;50(8):1239-1246.
Clark, R et al., "Long-acting growth hormones produced by conjugation with polyethylene glycol," J Biol Chem. Sep. 6, 1996;271(36):21969-77.
Corey, D.R., Schultz, P.G. "Generation of a hybrid sequence-specific single-stranded deoxyribonuclease," Science 1987; 238(4832):1401-1403.
Cornish, VW., et al., "Site-Specific Protein Modification Using a Ketone Handle," J. Am. Chem. Soc. 1996; 118(34):8150-8151.
Cornish, VW et al., "Probing Protein Structure and Function with an Expanded Genetic Code," Angew Chem Int Ed Engl, 1995;34(6):621-33.
Craig, J.C. et al. "Absolute Configuration of the Enantiomers of 7-Chloro-4 [[4-(diethylamino)-1-methylbutyl]amino] quinoline (Chloroquine)," J. Org. Chem. 1988; 53(6):1167-1170.
Cregg, JM et al., "*Pichia pastoris* as a host system for transformations," Mol Cell Biol. Dec. 1985;5(12):3376-85.
Crick, FHC, et al. "General nature of the genetic code for proteins," Nature. Dec. 30, 1961;192:1227-32.
Dale et al., Oligonucleotide-directed random mutagenesis using the phosphorothioate method, Methods Mol. Biol. 1996;57:369-374.
Das, S et al., "Transformation of *Kluyveromyces fragilis*," J Bacteriol. Jun. 1984;158(3):1165-7.
Dawson, P. E. and S. B. H. Kent, "Synthesis of native proteins by chemical ligation," Annu. Rev. Biochem. 2000; 69:923-60.
De Boer, HA et al., "The tac promoter; a functional hybrid derived from the trp and lac promoters," Proc Natl Acad Sci U S A. Jan. 1983;80(1):21-5.
De Louvencourt, L et al., "Transformation of *Kluyveromyces lactis* by killer plasmid DNA," J Bacteriol. May 1983;154(2):737-42.
Wang, L & PG Schultz, "Expanding the genetic code," Chem Commun (Camb). Jan. 7, 2002; 1-11.
Weissmann, C. "The cloning of interferon and other mistakes," in Interferon 3 1981; ed. I. Gresser; Academic Press, London, 101-134.
Wells, JA et al., "Importance of hydrogen-bond formation in stabilizing the transition state of subtilisin," Phil. Trans. R. Soc. Lond. A 1986; 317: 415-423.
Wells, JA et al., "Cassette mutagenesis: an efficient method for generation of multiple mutations at defined sites," Gene. 1985;34(2-3):315-23.
Woghiren, C et al. "Protected thiol-polyethylene glycol: a new activated polymer for reversibile protein modification," Bioconjug Chem. Sep.-Oct. 1993;4(5):314-8.
Wong, SS et L.J Wong, "Chemical crosslinking and the stabilization of proteins and enzymes," Enzyme Microb Technol. Nov. 1992;14(11):866-74.
Wright, K. "Biotechnology: Insect virus as super-vector?," Nature (1986) 321(6072):718.
Liu, H. et al. "A Method for the Generation of Glycoprotein Mimetics," J. Am. Chem. Soc. 2003 125(7): 1702-1703.
Liu, D.R. & Schultz, P.G. "Progress toward the evolution of an organism with an expanded genetic code," Proc Natl Acad Sci U S A. Apr. 27, 1999;96(9):4780-5.
Lorimer, I. A. et I. Pastan, "Random recombination of antibody single chain Fv sequences after fragmentation with DNaseI in the presence of Mn2+," Nucleic Acids Res. Aug. 11, 1995;23(15):3067-8.
Lu, T. et al. "Probing ion permeation and gating in a K +channel with backbone mutations in the selectivity filter," Nature Neurosci. Mar. 2001;4(3):239-246.
Luckow, VA and MD Summers, "High level expression of nonfused foreign genes with *Autographa californica* nuclear polyhedrosis virus expression vectors," Virology. May 1989;170(1):31-9.

Ma, C et al., "In vitro protein engineering using synthetic tRNA(Ala) with different anticodons," Biochemistry. Aug. 10, 1993;32(31):7939-45.
Magliery, TJ et al. "Expanding the Genetic Code: Selection of Efficient Suppressors of Four-base Codons and Identification of "Shifty" Four-base Codons with a Library Approach in *Escherichia coli*," J Mol Biol. Mar. 30, 2001;307(3):755-69.
Mahal, L. K., et al., "Engineering chemical reactivity on cell surfaces through oligosaccharide biosynthesis," Science. May 16, 1997;276(5315):1125-8.
Makrides, SC et al., "Extended in vivo half-life of human soluble complement receptor type 1 fused to a serum albumin-binding receptor," J Pharmacol Exp Ther. Apr. 1996;277(1):534-42.
Mamot, C, et al., "Epidermal growth factor receptor (EGFR)-targeted immunoliposomes mediate specific and efficient drug delivery to EGFR- and EGFRvIII-overexpressing tumor cells," Cancer Res. Jun. 15, 2003;63(12):3154-61.
Mandecki, W. Oligonucleotide-directed double-strand break repair in plasmids of *Escherichia coli*: a method for site-specific mutagenesis, Proc Natl Acad Sci U S A. Oct. 1986;83(19):7177-81.
Mann, SG and LA King, "Efficient transfection of insect cells with baculovirus DNA using electroporation," J Gen Virol. Dec. 1989;70 (Pt 12):3501-5.
Matsoukas, JM et al., "Differences in backbone structure between angiotensin II agonists and type I antagonists," J Med Chem. Nov. 10, 1995;38(23):4660-9.
McMinn, DL et al., "Efforts toward Expansion of the Genetic Alphabet: DNA Polymerase Recognition of a Highly Stable, Self-Pairing Hydrophobic Base," J. Am. Chem. Soc. 1999; 121(49):11585-6.
Meggers, E et al., "A Novel Copper-Mediated DNA Base Pair," J. Am. Chem. Soc. 2000; 122(43):10714-10715.
Mehvar, R., "Modulation of the pharmacokinetics and pharmacodynamics of proteins by polyethylene glycol conjugation" J Pharm Pharm Sci. Jan.-Apr. 2000;3(1):125-36.
Mendel, D, et al. "Site-directed mutagenesis with an expanded genetic code," Annu Rev Biophys Biomol Struct. 1995;24:435-62.
Miller, LK, "Baculoviruses as gene expression vectors," Ann. Rev. Microbiol. 1988; 42:177-99.
Miller, LK. "Insect baculoviruses: powerful gene expression vectors," Bioessays Oct. 1989;11(4):91-5.
Miller, JC et al. "Flash decaging of tyrosine sidechains in an ion channel," Neuron. Apr. 1998;20(4):619-24.
Minks, C. et al., Noninvasive tracing of recombinant proteins with "fluorophenylalanine-fingers," Anal Biochem. Aug. 15, 2000;284(1):29-34.
Miyanohara, A et al., "Expression of hepatitis B surface antigen gene in yeast," Proc Natl Acad Sci U S A. Jan. 1983; 80(1):1-5.
Moore, B. et al., "Quadruplet codons: implications for code expansion and the specification of translation step size," J. Mol. Biol. 2000; 298(2):195-209.
Mosbach, K. et al., "Formation of proinsulin by immobilized *Bacillus subtilis*," Nature Apr. 1983; 302:543-545.
Nakamaye, KL & Eckstein F, "Inhibition of restriction endonuclease Nci I cleavage by phosphorothioate groups and its application to oligonucleotide-directed mutagenesis" Nucleic Acids Res. Dec. 22, 1986;14(24):9679-98.
Nakatsuka, T., et al. "Peptide segment coupling catalyzed by the semisynthetic enzyme thiosubtilisin," J Am Chem Soc, 1987; 109(12): 3808-3810.
Nambiar, KP et al., "Total synthesis and cloning of a gene coding for the ribonuclease S protein," Science (1984) 223: 1299-1301.
Needleman, SB and Wunsch CD, "A general method applicable to the search for similarities in the amino acid sequence of two proteins," J Mol Biol. Mar. 1970;48(3):443-53.
Neet, KE et al. "Properties of thiol-subtilisin. The consequences of converting the active serine residue to cysteine in a serine protease," J Biol Chem. Dec. 25, 1968;243(24):6392-401.
Nielsen, UB, et al. "Therapeutic efficacy of anti-ErbB2 immunoliposomes targeted by a phage antibody selected for cellular endocytosis," Biochim Biophys Acta. Aug. 19, 2002;1591(1-3):109-118.

(56) References Cited

OTHER PUBLICATIONS

Nomura, T. et al., "Purification, cDNA Cloning, and Expression of UDP-Gal: Glucosylceramide-1,4-Galactosyltransferase from Rat Brain," J. Biol. Chem. 1998; 273(22):13570-7.
Noren, CJ et al. "A general method for site-specific incorporation of unnatural amino acids into proteins," Science. Apr. 14, 1989;244(4901):182-8.
Nowak, MW et al., "Nicotinic receptor binding site probed with unnatural amino acid incorporation in intact cells," Science. Apr. 21, 1995;268(5209):439-42.
Ogawa, AK et al., "Efforts toward the Expansion of the Genetic Alphabet: Information Storage and Replication with Unnatural Hydrophobic Base Pairs," J. Am. Chem. Soc. 2000; 122(14):3274-3287.
Ogawa, AK et al., "Rational Design of an Unnatural Base Pair with Increased Kinetic Selectivity," J. Am. Chem. Soc. 2000; 122(36); 8803-8804.
Ohtsuka, E et al., "An alternative approach to deoxyoligonucleotides as hybridization probes by insertion of deoxyinosine at ambiguous codon positions," J Biol Chem. Mar. 10, 1985;260(5):2605-8.
Olson et al. "Preparation and Characterization of Poly(ethylene glycol)yated Human Growth Hormone Antagonist," in Poly(ethylene glycol) Chemistry & Biological Applications, 1997; Eds. JM Harris & S. Zalipsky; ACS, Washington, D.C., 170-181.
Padwa, A. "Intermolecular 1,3-Dipolar Cycloadditions," in Comprehensive Organic Synthesis, vol. 4, (1991) Ed. Trost. B. M.; Pergamon, Oxford, 1069-1109.
Palva, I et al., "Secretion of interferon by *Bacillus subtilis*," Gene. May-Jun. 1983;22(2-3):229-35.
Park, JW, et al., "Development of anti-p185HER2 immunoliposomes for cancer therapy," Proc Natl Acad Sci U S A. Feb. 28, 1995;92(5):1327-31.
Park, JW, et al., "Anti-HER2 immunoliposomes: enhanced efficacy attributable to targeted delivery," Clin Cancer Res. Apr. 2002;8(4):1172-81.
Patnaik, R. and JR Swartz, "*E. coli*-based in vitro transcription/translation: in vivo-specific synthesis rates and high yields in a batch system," Biotechniques. May 1998;24(5):862-8.
Pearson, WR and DJ Lipman, "Improved tools for biological sequence comparison," Proc Natl Acad Sci U S A. Apr. 1988;85(8):2444-8.
Pepinsky, RB., et al., "Improved pharmacokinetic properties of a polyethylene glycol-modified form of interferon-beta-1a with preserved in vitro bioactivity," J Pharmacol Exp Ther. Jun. 2001;297(3):1059-66.
Piccirilli, JA et al., "Enzymatic incorporation of a new base pair into DNA and RNA extends the genetic alphabet," Nature 1990; 343:33-37.
Pintar, A et al., "CX, an algorithm that identifies protruding atoms in proteins," Bioinformatics. Jul. 2002; 18(7):980-4.
Pitha, J et al. "Detergents linked to polysaccharides: preparation and effects on membranes and cells," Eur J Biochem. Feb. 15, 1979;94(1):11-8.
Polgar, L. and ML Bender, "A new enzyme containing a synthetically formed active site. Thiol-subtilisin." J. Am Chem Soc., 1966: 88(13): 3153-3154.
Pollack, SJ et al. "Introduction of nucleophiles and spectroscopic probes into antibody combining sites," Science. Nov. 18, 1988;242(4881):1038-40.
Preneta, AZ. "Separation on the basis of size: gel permeation chromatography," in Protein Purification Methods, a practical approach, 1989; Eds. Harris & Angal; IRL Press, Oxford; 293-306.
Lamichhane et al., 2003, A postgenomic method for predicting essential genes at subsaturation levels of mutagenesis: application to *Mycobacterium tuberculosis*, PNAS 100(12):7213-7218.
Marri et al., 2006, Comparative genomics of metabolic pathways in *Mycobacterium* species: gene duplication, gene decay and lateral gene transfer, FEMS Microbiol Rev 30:906-925.

Shane, "Reducing Pathogenic *E. coli* Infection by Vaccination," Dec. 14, 2009, Accessed Jun. 17, 2014 from http://www.worldpoultry.net/Broilers/Health/2009/12/Reducing-pathogenic-E-coli-infection-by-vaccination-WP006966W/.
Debinski, W et al. "A wide range of human cancers express interleukin 4 (IL4) receptors that can be targeted with chimeric toxin composed of IL4 and *Pseudomonas* exotoxin," J Biol Chem. Jul. 5, 1993;268(19):14065-70.
Deiters, A., et al., "Adding Amino Acids with Novel Reactivity to the Genetic Code of *Saccharomyces cerevisiae*," J. Am. Chem. Soc. 2003; 125(39):11782-11783.
Delgado, C et al., "The uses and properties of PEG-linked proteins," Crit Rev Ther Drug Carrier Syst. 1992; 9(3-4):249-304.
Dennis, MS et al., "Albumin binding as a general strategy for improving the pharmacokinetics of proteins," J Biol Chem. Sep. 20, 2002;277(38):35035-43. Epub Jul. 15, 2002.
Dolphin, CT et al., "Missense mutation in flavin-containing monooxygenase 3 gene, FMO3, underlies fish-odour syndrome," Nat Genet. Dec. 1997; 17(4):491-4.
Doring, V et al., "Enlarging the amino acid set of *Escherichia coli* by infiltration of the valine coding pathway," Science. Apr. 20, 2001;292(5516):501-4.
Dougherty, DA. "Unnatural amino acids as probes of protein structure and function," Curr Opin Chem Biol. Dec. 2000;4(6):645-52.
Duewel, H et al., "Incorporation of trifluoromethionine into a phage lysozyme: implications and a new marker for use in protein 19F NMR," Biochemistry, Mar. 16, 1997;36(11):3404-16.
Eghtedarzadeh MK & S Henikoff "Use of oligonucleotides to generate large deletions" Nucleic Acids Res. Jun. 25, 1986;14(12):5115.
Elling L et MR Kula., "Immunoaffinity partitioning: synthesis and use of polyethylene glycol-oxirane for coupling to bovine serum albumin and monoclonal antibodies," Biotechnol Appl Biochem. Jun. 1991;13(3):354-62.
Elliott, S et al., "Yeast-derived recombinant human insulin-like growth factor I: production, purification, and structural characterization," J Protein Chem. Feb. 1990;9(1):95-104.
Ellman, J.A., Mendel, D., Anthony-Cahill, S., Noren, C.J., Schultz, P.G. "Biosynthetic method for introducing unnatural amino acids site-specifically into proteins," Methods in Enz., 1992; 202:301-336.
Ellman, JA, et al. "Site-specific incorporation of novel backbone structures into proteins," Science. Jan. 10, 1992;255(5041):197-200.
England, P. M., et al., "Backbone mutations in transmembrane domains of a ligand-gated ion channel; implications for the mechanism of gating," Cell. Jan. 9, 1999;96(1):89-98.
Eppstein et al., "Biological Activity of Liposome-Encapsulated Murine Interferon is Mediated by a Cell Membrane Receptor," Proc. Natl. Acad. Sci. U.S.A.(1995); 82: 3568-3692.
Fieschko, JC et al., "Controlled expression and purification of human immune interferon from high-cell-density fermentations of *Saccharomyces cerevisiae*," Biotech. Bioeng. (1987) 29(9):1113-21.
Forster, AC et al., "Programming peptidomimetic syntheses by translating genetic codes designed de novo," Proc Natl Acad Sci U S A. May 27, 2003; 100(11):6353-7. Epub May 16, 2003.
Frankel, A et al., "Encodamers: unnatural peptide oligomers encoded in RNA," Chem Biol. Nov. 2003;10(11):1043-50.
Fraser, MJ et al., "Expression of eucaryotic genes in insect cell cultures," In Vitro Cell. Dev. Biol. 1989; 25:225-235.
Friedman, O.M. & R. Chatterrji. "Synthesis of Derivatives of Glutamine as Model Substrates for Anti-Tumor Agents," J. Am. Chem. Soc. 1959; 81(14):3750-3752.
Fritz HJ et al., "Oligonucleotide-directed construction of mutations: a gapped duplex DNA procedure without enzymatic reactions in vitro," Nucleic Acids Res. Jul. 25, 1988;16(14B):6987-99.
Fromm, M. et al., "Expression of Genes Transferred into Monocot and Dicot Plant Cells by Electroporation," Proc. Natl. Acad. Sci. USA (1985) 82:5824-8.
Furter, R. "Expansion of the genetic code: site-directed p-fluorophenylalanine incorporation in *Escherichia coli*," Protein Sci. Feb. 1998;7(2):419-26.
Gaertner, HF et al., "Construction of protein analogues by site-specific condensation of unprotected fragments," Bioconjug Chem. May-Jun. 1992;3(3):262-8.

(56) References Cited

OTHER PUBLICATIONS

Gaertner, HF et al., "Chemo-enzymic backbone engineering of proteins. Site-specific incorporation of synthetic peptides that mimic the 64-74 disulfide loop of granulocyte colony-stimulating factor," J Biol Chem. Mar. 11, 1994;269(10):7224-30.
Gallivan, JP et al., "Site-specific incorporation of biotinylated amino acids to identify surface-exposed residues in integral membrane proteins," Chem. Biol. Oct. 1997;4(10):739-49.
Gellissen, G et al., "Heterologous protein production in yeast," Antonie Van Leeuwenhoek. Aug. 1992;62(1-2):79-93.
Geoghegan, KF and JG Stroh, "Site-directed conjugation of nonpeptide groups to peptides and proteins via periodate oxidation of a 2-amino alcohol. Application to modification at N-terminal serine," Bioconjug Chem. Mar.-Apr. 1992;3(2):138-46.
Gillam, S. & M Smith, "Site-specific mutagenesis using synthetic oligodeoxyribonucleotide primers: I. Optimum conditions and minimum oligodeoxyribonucleotide length." Gene 1979: 8(1):81-97.
Gleeson, MA et al., "Transformation of the methylotrophic yeast hansenula polymorphica," J. Gen. Microbiol. (1986) 132:3459-3465.
Goeddel, DV, "Systems for heterologous gene expression," Methods Enzymol. 1990;185:3-7.
Goeddel, DV et al., "Synthesis of human fibroblast interferon by *E. coli*," Nucleic Acids Res. Sep. 25, 1980;8(18):4057-74.
Goodson RJ et NV Katre. "Site-directed pegylation of recombinant interleukin-2 at its glycosylation site," Biotechnology (N Y). Apr. 1990;8(4):343-6.
Graves, SW et al., "Expression, purification, and initial kinetic characterization of the large subunit of the human mitochondrial DNA polymerase," Biochemistry. Apr. 28, 1998;37(17):6050-8.
Griffin, BA et al., "Specific Covalent Labeling of Recombinant Protein Molecules Inside Live Cells," Science (1998) 281:269-272.
Grundström T et al., "Oligonucleotide-directed mutagenesis by microscale 'shot-gun' gene synthesis," Nucleic Acids Res. May 10, 1985;13(9):3305-16.
Guckian, KM and ET Kool, "Highly Precise Shape Mimicry by a Difluorotoluene Deoxynucleoside, a Replication-Competent Substitute for Thymidine," Angew. Chem. Int. Ed. Engl (1998) 36(24):2825-8.
Hamano-Takaku, F et al., "A mutant *Escherichia coli* tyrosyl-tRNA synthetase utilizes the unnatural amino acid azatyrosine more efficiently than tyrosine," J Biol Chem. Dec. 22, 2000;275(51):40324-8.
Hang, HC and CR Bertozzi, "Chemoselective approaches to glycoprotein assembly," Acc Chem Res. Sep. 2001;34(9):727-36.
Harris, JM et al. "Synthesis and Characterization of Poly(ethylene Glycol) Derivatives," J. Polym. Sci. Chem. Ed. 1984; 22:341-352.
Harris, JM, "Laboratory Synthesis of Polyethylene Glycol Derivatives," JMS-Rev. Macromol. Chem. Phys. 1985;C25(3):325-373.
Hendrickson, WA et al., "Selenomethionyl proteins produced by analysis by multiwavelength anomalous diffraction (MAD): a vehicle for direct determination of three-dimensional structure," EMBO J. May 1990;9(5):1665-72.
Henikoff, S and JG Henikoff "Amino Acid Substitution Matrices from Protein Blocks," Proc. Natl. Acad. Sci. USA 1992; 89:10915-9.
Hess, B. et al., "Cooperation of glycolytic enzymes," J. Adv. Enzyme Reg. (1969) 7:149-67.
Hinnen, A et al., "Transformation of yeast," Proc Natl Acad Sci U S A. Apr. 1978;75(4):1929-33.
Hirao, I et al., "An unnatural base pair for incorporating amino acid analogues into proteins," Nat Biotechnol. Feb. 2002;20(2):171-82.
Hitzeman, RA et al., "Isolation and characterization of the yeast 3-phosphoglycerokinase gene (PGK) by an immunological screening technique," J. Biol Chem. Dec. 25, 1990;255(24):12073-80.
Hofmann, K. et H. Bohn. "Studies on polypeptides. XXXVI. The effect of pyrazole-imidazole replacements on the S-protein activating potency of an S-peptide fragment," J. Am Chem, (1966); 88(24):5914-5919.
Hohsaka, T et al., "Efficient Incorporation of Nonnatural Amino Acids with Large Aromatic Groups into Streptavidin in In Vitro Protein Synthesizing Systems," J. Am. Chem. Soc. 1999; 121(1):34-40.
Hohsaka, T et al., "Incorporation of Two Different Nonnatural Amino Acids Independently into a Single Protein through Extension of the Genetic Code," J. Am. Chem. Soc. 1999; 121(51):12194-12195.
Duncan, R. "The dawning era of polymer therapeutics," Nat Rev Drug Discov May 2003;2(5):347-60.
Gaertner, HF et RE Offord. "Site-specific attachment of functionalized poly(ethylene glycol) to the amino terminus of proteins," Bioconjug Chem Jan.-Feb. 1996;7(1):38-44.
Gu, Z et al. "Chromatographic methods for the isolation of, and refolding of proteins from, *Escherichia coli* inclusion bodies," Protein Expr Purif. Jun. 2002;25(1):174-9.
Hohsaka, T et M Sisido. "Incorporation of non-natural amino acids into proteins," Curr Opin Chem Biol. Dec. 2002;6 (6):809-15.
Lilie, H et al. "Advances in refolding of proteins produced in *E. coli*," Curr Opin Biotechnol. Oct. 1998;9(5):497-501.
Tsumoto, K et al. "Practical considerations in refolding proteins from inclusion bodies," Protein Expr Purif. Mar. 2003;28(1):1-8.
Wang, W. "Instability, stabilization, and formulation of liquid protein pharmaceuticals," Int J Pharm. Aug. 20, 1999;185 (2):129-88.
Tondelli, L. et al. "Poly(ethylene Glycol) Imidazolyl Formates as Oligomeric Drug-Binding Matrices," J. Controlled Release 1985; 1(4):251-7.
Tornoe, CW et al., "Peptidotriazoles on solid phase: [1,2,3]-triazoles by regiospecific copper(i)-catalyzed 1,3-dipolar cycloadditions of terminal alkynes to azides," J Org Chem. May 3, 2002; 67(9):3057-64.
Trotter, KM and HA Wood, "Transfection techniques for producing recombinant baculoviruses," in Methods in Molecular Biology—Baculovirus Expression Protocols, vol. 39 (1995); Ed. C. D. Richardson, 97-107.
Tschumper, G. et al., "Sequence of a yeast DNA fragment containing a chromosomal replicator and the TRP1 gene," Gene 1980; 10(2):157-66.
Turcatti, G et al. "Probing the structure and function of the tachykinin neurokinin-2 receptor through biosynthetic incorporation of fluorescent amino acids at specific sites," J Biol Chem. Aug. 16, 1996; 271(33):19991-6.
Van Den Berg, JA et al., "Kluyveromyces as a host for heterologous gene expression: expression and secretion of prochymosin," Biotechnology (N Y). Feb. 1990; 8(2):135-9.
Van Hest, JC and DA Tirrell, "Efficient introdution of alkene functionality into proteins in vivo," FEBS Lett. May 22, 1998; 428(1-2):68-70.
Office Action dated May 7, 2015 for Canadian Application No. 2738033.

* cited by examiner

+artificial amino acid   -artificial amino acid

Y31- 1st Screen

Y31 MAP
LB agar
50ug/mL Amp
50ug/mL Kan
+ 2mM pAF

Y31 MAP
LB agar
50ug/mL Amp
50ug/mL Kan

N51- 1st Screen

N51 MAP
LB agar
50ug/mL Amp
50ug/mL Kan
+ 2mM pAF

N51 MAP
LB agar
50ug/mL Amp
50ug/mL Kan

NON-NATURAL AMINO ACID REPLICATION-DEPENDENT MICROORGANISMS AND VACCINES

CROSS REFERENCE TO RELATED APPLICATIONS

This application is a national phase entry in the United States under 35 U.S.C. §371 from International Application Number PCT/US09/58668 with an international filing date of Sep. 28, 2009 designating the United States of America, which is incorporated by reference herein in its entirety and claims the benefit of priority to U.S. provisional patent application Ser. No. 61/100,688, filed on Sep. 26, 2008, the specifications and disclosures of which are incorporated herein in their entirety for all purposes.

FIELD OF THE PRESENT INVENTION

The invention pertains to vaccines. In some embodiments, the present invention pertains to compositions and methods of producing vaccines, including whole organism vaccines, with limited or no replication abilities through the use of non-natural, unnatural, or non-naturally encoded amino acids.

BACKGROUND OF THE PRESENT INVENTION

Until now, there has been relatively slow technical progress and even more than 100 years after Louis Pasteur passed away, his "III" (Isolation, Inactivation, Injection) protocol continues to be applicable. With the advent of molecular biology and recombinant protein technology, however, people have started to develop subunit vaccines and genetically engineered whole-organism-like vaccines. More recently, advances in immunology have made several classes of immunopotentiators available, including Toll-Like Receptor(TLR) ligands. Generally, newer generation vaccines and their adjuvants have been becoming more and more well defined chemically and genetically.

The development of therapeutics and in particular vaccines directed against pathogens such as viruses, bacteria, protozoans, fungi is ongoing. Such research has proved invaluable in preventing the spread of disease in animals including humans. In fact, in modern medicine, immunotherapy including vaccination has eradicated smallpox and virtually eradicated diseases such as polio, tetanus, tuberculosis, chicken pox, and measles.

Generally, ideal vaccines have a long shelf life, are capable of inducing long lasting immunity against a pre-selected pathogen and all of the phenotypic variants, are incapable of causing the disease to which the vaccine is directed against, are effective therapeutically and prophylactically, are easily prepared using economical standard methodologies and can be administered easily in the field.

There are four major classes of commercially available vaccines. They include non-living whole organism vaccines, live attenuated vaccines, vector vaccines, and subunit vaccines. Vaccination with non-live materials such as proteins generally leads to an antibody response or CD4+ helper T cell response while, vaccination with live materials (e.g. infectious viruses) generally leads to a CD8+ cytotoxic T-lymphocyte (CTL) response. A CTL response is crucial for protection against pathogens like infectious viruses and bacteria. This poses a practical problem, for the only certain way to achieve a CTL response is to use live agents that are themselves pathogenic. The problem is generally circumvented by using attenuated viral and bacterial strains or by killing whole cells that can be used for vaccination. These strategies have worked well but the use of attenuated strains always carries the risk that the attenuated agent may recombine genetically in the host and turn into a virulent strain. Thus, there is need for therapeutics and methods that can lead to CD8+ CTL response by vaccination with non-live materials such as proteins in a specific manner.

Subunit vaccines have provided one means for dealing with some of these problems. Such vaccines generally comprise a sub-cellular component derived from a pathogen of interest. A subunit component can be either produced from a defined sub-cellular fraction of the pathogen, be a purified protein, nucleic acid or a polysaccharide. All of these elements have an antigenic determinant capable of stimulating an immune response against the pathogen of interest. Generally, the sub-cellular component of the subunit vaccine is obtained either by purifying a preparation of disrupted pathogen or synthesised using well-known procedures.

There are, however, several limitations associated with subunit vaccines. First, a requirement for the production of such a vaccine is that the antigenic determinant(s) must be characterised and identified. This imposes limitations on their use, particularly against highly variable antigenic determinants. Second, subunit vaccines are generally ineffective in stimulating cytotoxic T cell responses. Third, the immunity conferred by subunit vaccines is often short lived and therefore requires continual booster injections. Very few recombinant expressed subunit vaccines have been shown to induce strong and long lasting immunity in vaccinated animals (including man). One notable exception is the recombinant surface antigen Hepatitis B vaccine used in man. One of the problems associated with the use of such vaccines appears to be in correctly presenting the antigens to the immune system such that strong humoral immunity and strong cell-mediated immunity are induced. In particular, existing recombinant (subunit) vaccines do not appear to result in strong 'memory' responses such that vaccinated animals react very quickly when they are exposed to natural infections caused by a pathogen.

By way of example only, deficiencies in current subunit vaccines prepared from pestiviruses like bovine viral diarrhea virus (BVDV) have been extensively reported. These studies have shown that even though large amounts of recombinant protein were used in the vaccines, there were poor protection rates seen showing that the vaccines failed to protect from challenge with live BVDV isolates (either homologous protection or heterologous protection).

There are many infectious diseases for which an effective vaccine has not yet been developed, and many of the currently available vaccines provide only partial protection against disease. Further, there are gaps in the vaccine field. Live vaccines produce stronger, broader, and more durable immunity than other types of vaccines. There is a need for a safer live vaccine vehicle, which will be unable to cause disease even in immunosuppressed individuals. There is also a need for vaccines that induce cell-mediated immunity and not just antibody-based immunity. And, there is a need to induce protective immune responses directly at the mucosal surfaces of the body, where most pathogens gain entry. Thus, there is a need for improved vaccines. The present invention seeks to provide an improved therapeutic vaccine which ameliorates at least some of the disadvantages over existing prior art.

SUMMARY OF THE PRESENT INVENTION

The present invention provides chemically-modulated replication-dependent whole organisms. In some embodiments, the present invention provides a chemically-modulated whole organism with a modification whereby its ability to replicate is dependent on the presence of a non-natural amino acid. In some embodiments, the present invention provides a whole organism with one or more modifications whereby the ability of the organism to replicate depends upon its being cultured in the presence of a non-natural amino acid. In some embodiments the present invention provides a whole organism with one or more modifications whereby the ability of the organism to replicate depends upon its being cultured in the presence of one or more non-natural amino acid(s). In some embodiments the present invention provides a whole organism with two or more modifications whereby the ability of the organism to replicate depends upon its being cultured in the presence of one or more non-natural amino acid(s). In some embodiments of the present invention, the whole organism is a mitigated vaccine—a vaccine modulated by one or more site-specifically incorporated non-natural amino acids, wherein the replication or expression of the immunizing agent is modulated by the presence or absence of a non-natural amino acid.

In some embodiments of the present invention, the replication or expression of a whole organism is modulated by the presence or absence of a non-natural amino acid through a single genetic modification. In some embodiments of the present invention, the replication or expression of a whole organism is modulated by the presence or absence of a non-natural amino acid through one or more genetic modifications. In some embodiments of the present invention, the replication or expression of a whole organism is modulated by the presence or absence of a non-natural amino acid through two genetic modifications. In some embodiments of the present invention, the replication or expression of a whole organism is modulated by the presence or absence of a non-natural amino acid through three genetic modifications. In some embodiments of the present invention, the replication or expression of a whole organism is modulated by the presence or absence of a non-natural amino acid through four genetic modifications. In some embodiments of the present invention, the replication or expression of a whole organism is modulated by the presence or absence of a non-natural amino acid through five genetic modifications. In some embodiments of the present invention, the replication or expression of a whole organism is modulated by the presence or absence of a non-natural amino acid through four or more genetic modifications.

The ability to selectively induce an immune response against organisms, antigens, proteins, or self-proteins or to increase the immunogenicity of specific epitopes of foreign antigens, is significant in the production of vaccines for a number of disease states (including, but not limited to, cancer and protein folding diseases) and infectious diseases (e.g., bacterial or viral infections). The current invention utilizes the incorporation of non-natural amino acids into organisms to produce replication-dependent and/or replication-deficient immunogens to be used in whole organism vaccinations or to produce antibodies to be used in passive immunization. The current invention also utilizes the incorporation of non-natural amino acids into proteins, antigens, and/or polypeptides to produce immunogens to be used in vaccinations or to produce antibodies to be used in passive immunization. In the invention, the immunogens to which the non-natural amino acids are added correspond to target moieties (e.g., disease related moieties) within the subject to be vaccinated/immunized or correspond to target moieties (e.g., disease related moieties) that are capable of being within the subject. In embodiments where the immunogen with the non-natural amino acid is administered to a subject, the presence of the non-natural amino acid elicits an immunological response against the immunogen which is cross reactive against the target (e.g., disease related) moiety.

In a first aspect, the invention provides methods of producing or enhancing an immunological response, e.g., a B-cell mediated response and/or a T-cell mediated response, in a subject against a target moiety, e.g., a polypeptide, a carbohydrate, or a combination of both, that is in the subject or that is capable of being within the subject. The methods include providing a genetically modified non-natural amino acid-dependent organism and administering the organism to the subject. The methods also include providing a genetically modified non-natural immunogen that comprises one or more unnatural amino acids, and administering the non-natural immunogen to the subject. The subject (e.g., a human, a monkey, a mouse, a rat, a livestock animal, a pig, a cow, a chicken, a cage bird, an aviary bird, a household pet, a dog, a cat, a reptile, and/or an amphibian) produces one or more antibodies against the unnatural immunogen, which antibodies are cross-reactive against the target moiety (thus producing or enhancing the immunogenic response against the target).

In certain embodiments, the genetically-modified whole organism can be any whole organism against which it is desirable to immunize the subject e.g., a bacterium, a virus, a fungus, a *Mycoplasma*, a protozoan, a helminth, or a prion. A whole organism vaccine can optionally include one or more of: a bacterial antigen, a viral antigen, a fungal antigen, a mycoplasmal antigen, a protozoan antigen, a helminth antigen, a prion antigen, an HIV antigen, HIVgp120, HIV gp41, HIV gag, HIV pol, HIV env, HTV tat, HIV nef, HIV rev, a calicivirus capsid antigen, a hepatitis B core antigen, a hepatitis B surface antigen, hepatitis delta agent, a herpes simplex virus glycoprotein, a varicella zoster virus glycoprotein, an influenza virus hemagglutinin, an influenza virus neuraminidase, an influenza virus nucleoprotein, a HPV capsid protein, a parainfluenza virus hemagglutinin/neuraminidase, a poliovirus capsid polypeptide, a Hep A antigen, a vaccinia virus polypeptide, a rabies virus glycoprotein G, *B. burgdorferi* OspA, *H. influenzae* type b outer membrane protein, *Mycobacterium* lipoarabinomannan, *mycobacterium* mAPG, *S. pyogenes* M protein, *S. pneumoniae* capsular polysaccharide, *Y. pestis* F1, *Y. pestis* V antigen, *P. falciparum* circumsporozoite (PfCSP), *P. falciparum* sporozoite surface protein 2 (PfSSP2), *P. falciparum* carboxyl terminus of liver state antigen 1 (PfLSA1 c-term), *P. falciparum* exported protein 1 (PfExp-1), Pfs 48/45, Pfs 28, Pfs 25, or Pfs 230.

The genetically-modified non-natural amino acid-replication dependent organism can be one or more of: a bacterium, a virus, a fungus, a *Mycoplasma*, a protozoan, a helminth, a prion, an *Actinomyces*, a *Bacillus*, a *Bacteroides*, a *Bordetella*, a *Bartonella*, a *Borrelia*, a *Brucella*, a *Campylobacter*, a *Capnocytophaga*, a *Chlamydia*, a *Clostridium*, a *Corynebacterium*, a *Coxiella*, a *Dermatophilus*, a *Enterococcus*, a Ehrlichia, a *Escherichia*, a *Francisella*, a *Fusobacterium*, a Haemobartonella, a *Haemophilus*, a *Helicobacter*, a *Klebsiella*, an L-form bacteria, a *Leptospira*, a *Listeria*, a *Mycobacterium*, a *Mycoplasma*, a *Neisseria*, a *Neorickettsia*, a *Nocardia*, a *Pasteurella*, a *Peptococcus*, a *Peptostreptococcus*, a Pneumococcus, a *Proteus*, a *Pseudomonas*, a *Rickettsia*, a *Rochalimaea*, a *Salmonella*, a *Shigella*, a *Staphylococcus*, a *Streptococcus*, a *Treponema*, a *Yersinia*, an adenovirus, an alphavirus, a calicivirus, a coronavirus, a CMV, a distemper virus, an Ebola virus, an enterovirus, an EBV, a flavivirus, a Hep C, a hepadnavirus, a Hep B, a hepititus delta agent, a Hep E or F virus, a GBV-C, a herpesvirus, a herpes simplex virus, a varicella zoster virus, an immunodeficiency virus, an HIV, an infectious peritonitis virus, an influenza virus, an influenza A virus, a leukemia virus, a Marburg virus, a orthomyxovirus, a papilloma virus, an HPV, a parainfluenza virus, a paramyxovirus, an RSV, a parvovirus, a pestivirus, a picorna virus, a poliovirus, a pox virus, a vaccinia virus, a rabies virus, a reovirus, a retrovirus, a rotavirus, an *Absidia*, an *Acremonium*, an *Alternaria*, an *Aspergillus*, a *Basidiobolus*, a *Bipolaris*, a *Blastomyces*, a *Candida*, a *Coccidioides*, a *Conidiobolus*, a *Cryptococcus*, a *Curvalaria*, an *Epidermophyton*, an Exophiala, a *Geotrichum*, a *Histoplasma*, a *Madurella*, a *Malassezia*, a *Microsporum*, a *Moniliella*, a *Mortierella*, a *Mucor*, a *Paecilomyces*, a *Penicillium*, a *Phialemonium*, a *Phialophora*, a *Prototheca*, a *Pseudallescheria*, a *Pseudomicrodochium*, a *Pythium*, a *Rhinosporidium*, a *Rhizopus*, a *Scolecobasidium*, a *Sporothrix*, a *Stemphylium*, a *Trichophyton*, a *Trichosporon*, a *Xylohypha*, a *Babesia*, a *Balantidium*, a *Besnoitia*, a *Cryptosporidium*, an *Eimeria*, an *Encephalitozoon*, an *Entamoeba*, a *Giardia*, a *Hammondia*, a *Hepatozoon*, an *Isospora*, a *Leishmania*, a *Microsporidia*, a *Neospora*, a *Nosema*, a *Pentatrichomonas*, a *Plasmodium*, a *P. falciparum*, a *Pneumocystis*, a *Sarcocystis*, a *Schistosoma*, a *Theileria*, a *Toxoplasma*, a *Trypanosoma*, an *Acanthocheilonema*, an *Aelurostrongylus*, an *Ancylostoma*, an *Angiostrongylus*, an *Ascaris*, a *Brugia*, a *Bunostomum*, a *Capillaria*, a *Chabertia*, a *Cooperia*, a *Crenosoma*, a *Dictyocaulus*, a *Dioctophyme*, a *Dipetalonema*, a *Diphyllobothrium*, a *Diplydium*, a *Dirofilaria*, a *Dracunculus*, an *Enterobius*, a *Filaroides*, a *Haemonchus*, a *Lagochilascaris*, a Loa polypeptide, a *Mansonella*, a *Muellerius*, a *Nanophyetus*, a *Necator*, a *Nematodirus*, an *Oesophagostomum*, an *Onchocerca*, an *Opisthorchis*, an *Ostertagia*, a *Parafilaria*, a *Paragonimus*, a *Parascaris*, a *Physaloptera*, a *Protostrongylus*, a *Setaria*, a *Spirocerca*, a *Spirometra*, a *Stephanofilaria*, a *Strongyloides*, a *Strongylus*, a *Thelazia*, a *Toxascaris*, a *Toxocara*, a *Trichinella*, a *Trichostrongylus*, a *Trichuris*, an *Uncinaria*, or a *Wuchereria*.

In another aspect, the invention provides methods of prophylactically or therapeutically treating a disease state in a subject, e.g., by producing a B-cell mediated response and/or a T-cell mediated response in the subject. In various embodiments, the disease state can be, but is not limited to, one or more of: a bacterial infection, a viral infection, a fungal infection, a *Mycoplasma* infection, a prion infection, a protozoan infection, or a helminth infection. One set of methods of the aspect includes administering to a subject, e.g., a human, a monkey, a mouse, a rat, a pig, a cow, a chicken, a cage bird, an aviary bird, a reptile, or an amphibian a genetically modified whole organism. The genetically modified whole organism thus stimulates production of antibodies within the subject. In a second set of methods, of this aspect, the invention comprises prophyllactically or therapeutically treating a disease state in a subject by producing an antibody against one or more diseases, conditions, or organisms that involves producing an antibody response and isolating the antibody or antibodies thath are then administered to a subject.

With the ultimate protein engineering tool, Ambrx' technology, site-specific incorporation of non-natural amino acids, presents a great opportunity in vaccine development. It can create chemically well-defined nanostructures by combining antigens with immunopotentiators. These nanostructures, which can be used for subunit vaccine development, possess antigen information and immunopotentiation functionality.

In addition, Ambrx technology can also be used to create novel attenuated whole-organism-like vaccines wherein the non-natural amino acids will serve as switches for the expression of essential genes in pathogenic organisms, instead of vehicles to introduce non-natural functional groups into protein. The resultant organisms will emulate the wild type organism, but will only be capable of replication in the presence of Ambrx non-natural amino acids, which do not exist in nature.

Subunit Vaccine:

Due to the low efficacy of subunit vaccines, adjuvants are required to stimulate an immune response. Traditionally, adjuvants are formulated as mixtures with antigens. Upon administration, antigens will be taken up by dendritic cell (DC) and presented to T cells. Adjuvants will stimulate dendritic cells for cytokine release, enhanced antigen presentation and dendritic cell maturation. An effective antigen-specific immune response will be achieved when these two independent processes, antigen presentation and immunoactivation, converge on the same DC. A relatively large dosage is required. However, the large dosage of adjuvant will evoke antigen-independent immune activation, an unwanted side effect. Therefore, intrinsically this approach is not ideal and confers upon the vaccine a low efficacy and high toxicity.

Unlike traditional adjuvants, such as alum, many newly discovered adjuvants are molecularly well defined. With its unique site-specific non-natural amino acid incorporation and its site-specific conjugation capabilities, Ambrx technology equips us with the necessary tools to create next generation vaccines with high potency and low toxicity. The key feature of Ambrx subunit vaccines will be the combination of antigen and immunopotentiator into one chemically defined nanostructure. When it is taken up by a DC the two processes, antigen presentation and immune activation, converge on the same DC.

Site-specific incorporation of non-natural amino acids is a technology that allows us to incorporate non-natural amino acids with highly immunogenic moieties such as mononitrophenyl, dinitrophenyl, directly into protein antigens. Recently, small molecule immunopotentiators, such as Toll-Like-Receptor 7 (TLR7) ligand imidazoquinoline, are becoming available. It is feasible to design non-natural amino acids with these small molecule immunopotentiators as their side chains and to incorporate them onto a protein antigen.

Ambrx's site specific conjugation technology provides even more flexibility. It allows us to conjugate not only the aforementioned small molecules to the surface of protein antigens, but also a variety of other immunopotentiators (e.g. lipid, lipopeptide, polysaccharide, DNA, RNA and nanoparticles).

Site specific conjugation of single-stranded DNA onto protein surfaces creates another dimension of freedom for vaccine design. DNAs with unmethylated CpG are TLR-9 ligands, which interestingly are present not on the cell surface but inside the cells. DNA conjugated to the antigen can serve not only as immunopotentiator, but also as a building block to create one to three dimensions and multi-antigen valent nanostructures through sequence specific hybridization processes. This general scheme can also be used to combine antigens with other elements, such as APC targeting reagents and other TLR ligands. It has been shown that APC targeting (antibody or peptide) can enhance vaccine efficiency and promote cross presentation. Combination of two different TLR ligands will have greater synergistic effect.

Ambrx site-specific conjugation allows the precise design and optimization of vaccines. Without Ambrx technology, a non-specific conjugation process has limited or no control on the modification sites on the protein antigen. The non-specific conjugation could alter the T and B epitopes. It could also modify the 3D conformation of the antigen that is critical for antibody recognition. Furthermore, some modifications could hamper the antigen processing. All these factors render the non-specifically conjugated vaccine less effective.

Whole Organism Vaccine:

Vaccinology started with whole-organism vaccines and still today these are the most successful vaccines, classified as either live attenuated or killed. The essence of whole-organism vaccines is that the vaccine should be as close as possible to the pathogenic organism itself in order to provoke a protective immune response but with very limited or no replication capabilities in the host.

So, if limited or no replication is desirable, is it possible to use small molecules to control the life cycle of microorganisms to create better and safer vaccines? The answer, using Ambrx technology, is now yes. If the non-natural amino acid is incorporated into a gene in a bacterium, virus or even parasite that is essential to the microorganism's replication, the life of these organisms will be dependent on the presence of the non-natural amino acid. Because the incorporated non-natural amino acid does not exist in nature, the result will be organisms, such as viruses and bacteria, having nearly exact viral and cell components and structures, without the ability to replicate in the host. In addition, Ambrx technology-modified virus or bacterium can serve not only as the vaccine itself, but also as vectors for gene and antigen delivery.

Ambrx subunit vaccine platform has a wide variety of applications in both infectious disease and therapeutic cancer vaccine areas. Current cancer vaccines are generally ineffective. Approaches of systemic T cell activation and negative regulatory pathway inhibition have been proposed and some of them are in clinical trials. The decoupling of T cell activation and antigen recognition can cause serious side effects. The ineffectiveness of cancer vaccines is due to the lack of technology to induce strong tumor-specific immune responses without causing serious side effects. Ambrx provides the technology to create nanostructures that can invoke strong cancer-specific immune responses, including T cell and B cell responses, and by doing so opens a new world of advantageous possibilities, both therapeutic and preventative.

The whole organism vaccine platform can find countless applications in the infectious disease area. Virus, bacterium, or even parasite that can be cultured and has a genome capable of mutation are good candidates. Vaccines of the present invention will improve the risk management in vaccine development and the vaccines are more well defined, both chemically and genetically, and provide unprecedented efficacies.

To expand the genetic code, the invention provides compositions of and methods of producing orthogonal tRNA's. Aminoacyl-tRNA synthetases aminoacylate tRNA's of the present invention with a non-naturally encoded amino acid. These translational components can be used to incorporate a selected amino acid in a specific position in a growing polypeptide chain (during nucleic acid translation) in response to a selector codon that is recognized by the tRNA.

Methods of producing a protein in a cell with a selected amino acid at a specified position are also a feature of the present invention. For example, a method includes growing, in an appropriate medium, a cell, where the cell comprises a nucleic acid that comprises at least one selector codon and encodes a protein; and, providing the selected amino acid. The cell further comprises: an orthogonal tRNA (O-tRNA) that functions in the cell and recognizes the selector codon; and, an orthogonal aminoacyl-tRNA synthetase (O-RS) that preferentially aminoacylates the O-tRNA with the selected amino acid. Typically, the O-tRNA comprises suppression activity in the presence of a cognate synthetase. A protein produced by this method is also a feature of the present invention.

DEFINITIONS

Figure 1:
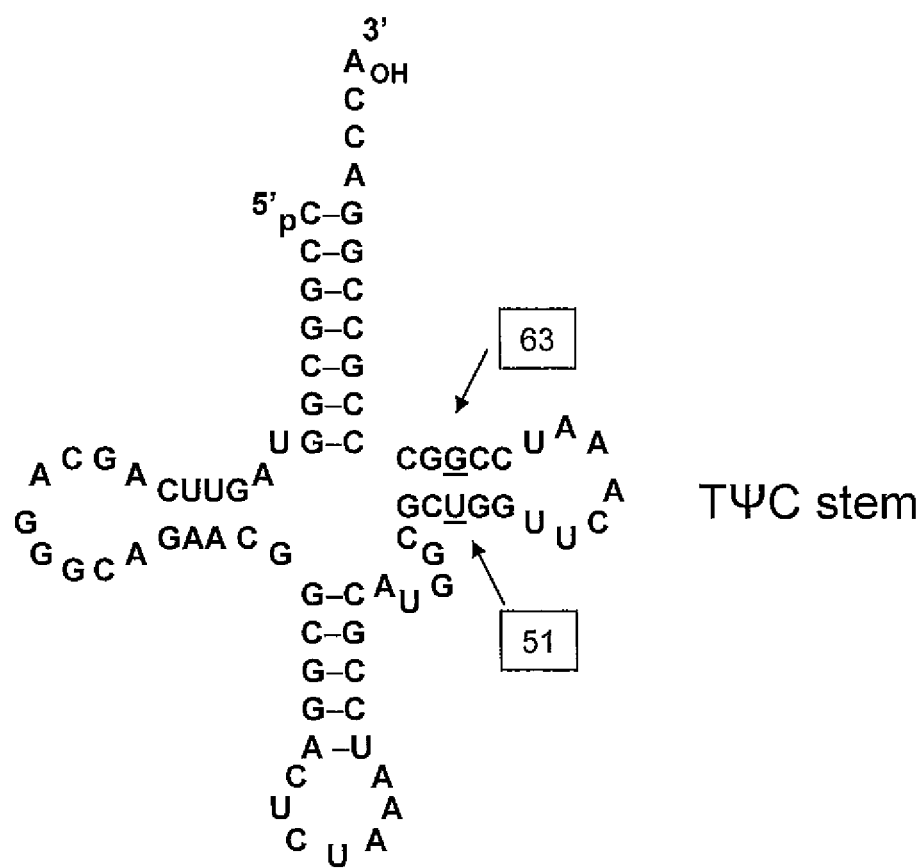
FIG. 1—The cloverleaf structure of J17 tRNA with TΨC stem mutation sites is shown.

Before describing the invention in detail, it is to be understood that this invention is not limited to particular biological systems, which can, of course, vary. It is also to be understood that the terminology used herein is for the purpose of describing particular embodiments only, and is not intended to limit the scope of the present invention, which will be limited only by the appended claims. As used herein and in the appended claims, the singular forms "a", "an" and "the" include plural referents unless the content clearly dictates otherwise. Thus, for example, reference to "a cell" includes a combination of two or more cells and includes equivalents thereof known to those of ordinary skill in the art, and so forth. Reference to "bacteria" includes mixtures of bacteria, and the like.

Unless defined herein and below in the reminder of the specification, all technical and scientific terms used herein have the same meaning as commonly understood by one of ordinary skill in the art to which the invention pertains.

All publications and patents mentioned herein are incorporated herein by reference for the purpose of describing and disclosing, for example, the constructs and methodologies that are described in the publications, which might be used in connection with the presently described invention. The publications discussed herein are provided solely for their disclosure prior to the filing date of the present application. Nothing herein is to be construed as an admission that the inventors are not entitled to antedate such disclosure by virtue of prior invention or for any other reason.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. For example, any naturally occurring nucleic acid can be modified by any available mutagenesis method to include one or more selector codon. When expressed, this mutagenized nucleic acid encodes a polypeptide comprising one or more selected amino acid, e.g. unnatural amino acid. The mutation process can, of course, additionally alter one or more standard codon, thereby changing one or more standard amino acid in the resulting mutant protein as well. The one or more standard amino acid may be changed to an unnatural amino acid or a natural amino acid. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity is routinely used to establish homology. Higher levels of sequence similarity, e.g., 30%, 35%, 40%, 45%, 50%, 55%, 60%, 65%, 70%, 75%, 80%, 85%, 90%, 91%, 92%, 93%, 94%, 95%, 96%, 97%, 98%, or 99% or more, can also be used to establish homology. Methods for determining sequence similarity percentages (e.g., BLASTP and BLASTN using default parameters) are described herein and are generally available.

As used herein, the term "orthogonal" refers to a molecule (e.g., an orthogonal tRNA (O-tRNA) and/or an orthogonal aminoacyl tRNA synthetase (O-RS)) that is used with reduced efficiency by a system of interest (e.g., a translational system, e.g., a cell). Orthogonal refers to the inability or reduced efficiency, e.g., less than 20% efficient, less than 10% efficient, less than 5% efficient, or e.g., less than 1% efficient, of an orthogonal tRNA and/or orthogonal RS to function in the translation system of interest. For example, an orthogonal tRNA in a translation system of interest is aminoacylated by any endogenous RS of a translation system of interest with reduced or even zero efficiency, when compared to aminoacylation of an endogenous tRNA by an endogenous RS. In another example, an orthogonal RS aminoacylates any endogenous tRNA in the translation system of interest with reduced or even zero efficiency, as compared to aminoacylation of the endogenous tRNA by an endogenous RS. A second orthogonal molecule can be introduced into the cell that functions with the first orthogonal molecule. For example, an orthogonal tRNA/RS pair includes introduced complementary components that function together in the cell with an efficiency (e.g., about 50% efficiency, about 60% efficiency, about 70% efficiency, about 75% efficiency, about 80% efficiency, about 85% efficiency, about 90% efficiency, about 95% efficiency, or about 99% or more efficiency) to that of a corresponding tRNA/RS endogenous pair. "Improvement in orthogonality" refers to enhanced orthogonality compared to a starting material or a naturally occurring tRNA or RS.

The term "cognate" refers to components that function together, e.g., a tRNA and an aminoacyl-tRNA synthetase. The components can also be referred to as being complementary.

The term "preferentially aminoacylates" refers to an efficiency, e.g., about 70% efficient, about 75% efficient, about 80% efficient, about 85% efficient, about 90% efficient, about 95% efficient, or about 99% or more efficient, at which an O-RS aminoacylates an O-tRNA with a selected amino acid, e.g., an unnatural amino acid, compared to the O-RS amino acylating a naturally occurring tRNA or a starting material used to generate the O-tRNA. The unnatural amino acid is then incorporated into a growing polypeptide chain with high fidelity, e.g., at greater than about 70% efficiency for a given selector codon, at greater than about 75% efficiency for a given selector codon, at greater than about 80% efficiency for a given selector codon, at greater than about 85% efficiency for a given selector codon, at greater than about 90% efficiency for a given selector codon, greater than about 95% efficiency for a given selector codon, or greater than about 99% efficiency for a given selector codon.

A "prophylactic treatment" is a treatment administered to a subject who does not display signs or symptoms of a disease, pathology, or medical disorder, or displays only early signs or symptoms of a disease, pathology, or disorder, such that treatment is administered for the purpose of diminishing, preventing, or decreasing the risk of developing the disease, pathology, or medical disorder. A prophylactic treatment functions as a preventative treatment against a disease or disorder. A "prophylactic activity" is an activity of an agent, such an unnatural immunogen and/or antibody, or composition thereof, that, when administered to a subject who does not display signs or symptoms of a pathology, disease, or disorder (or who displays only early signs or symptoms of such) diminishes, prevents, or decreases the risk of the subject developing the pathology, disease, or disorder. A "prophylactically useful" agent or compound (e.g., an unnatural immunogen and/or antibody of the invention, refers to an agent or compound that is useful in diminishing, preventing, treating, or decreasing development of a pathology, disease, or disorder.

Treatments, vaccines, and/or prophylactic treatments may be administered to a patient in need thereof. Treatments, vaccines, and/or prophylactic treatments may also be administered to a variety of animals including, but not limited to, domestic livestock, such as cows, pigs, goats, sheep, chickens, and/or other common farm animals and common household pets, e.g., cats, dogs, parrots, parakeets, etc.

The term "selector codon" refers to codons recognized by the O-tRNA in the translation process and not recognized by an endogenous tRNA. The O-tRNA anticodon loop recognizes the selector codon on the mRNA and incorporates its amino acid, e.g., a selected amino acid, such as an unnatural amino acid, at this site in the polypeptide. Selector codons can include but are not limited to, e.g., nonsense codons, such as, stop codons, including but not limited to, amber, ochre, and opal codons; four or more base codons; rare codons; codons derived from natural or unnatural base pairs and/or the like. For a given system, a selector codon can also include one of the natural three base codons, wherein the endogenous system does not use (or rarely uses) said natural three base codon. For example, this includes a system that is lacking a tRNA that recognizes the natural three base codon, and/or a system wherein the natural three base codon is a rare codon.

A suppressor tRNA is a tRNA that alters the reading of a messenger RNA (mRNA) in a given translation system, e.g., by providing a mechanism for incorporating an amino acid into a polypeptide chain in response to a selector codon. For example, a suppressor tRNA can read through a codon including but not limited to, a stop codon, a four base codon, or a rare codon.

The term "suppression activity" refers to the ability of a tRNA, e.g., a suppressor tRNA, to read through a selector codon. Activity can be expressed as a percentage of activity observed as compared to a control (e.g., lacking a cognate synthetase).

The term "translation system" refers to the components necessary to incorporate a naturally occurring amino acid into a growing polypeptide chain (protein). Components of a translation system can include, e.g., ribosomes, tRNA's, synthetases, mRNA and the like. The components of the present invention can be added to an in vitro or in vivo translation system. Examples of translation systems include but are not limited to, a non-eukaryotic cell, e.g., a bacterium (such as *E. coli*), a eukaryotic cell, e.g., a yeast cell, a mammalian cell, a plant cell, an algae cell, a fungus cell, an insect cell, a cell-free translational system e.g., a cell lysate, and/or the like.

Translation systems may be cellular or cell-free, and may be prokaryotic or eukaryotic. Cellular translation systems include, but are not limited to, whole cell preparations such as permeabilized cells or cell cultures wherein a desired nucleic acid sequence can be transcribed to mRNA and the mRNA translated. Cell-free translation systems are commercially available and many different types and systems are well-known. Examples of cell-free systems include, but are not limited to, prokaryotic lysates such as *Escherichia coli* lysates, and eukaryotic lysates such as wheat germ extracts, insect cell lysates, rabbit reticulocyte lysates, rabbit oocyte lysates and human cell lysates. Eukaryotic extracts or lysates may be preferred when the resulting protein is glycosylated, phosphorylated or otherwise modified because many such modifications are only possible in eukaryotic systems. Some of these extracts and lysates are available commercially (Promega; Madison, Wis.; Stratagene; La Jolla, Calif.; Amersham; Arlington Heights, Ill.; GIBCO/BRL; Grand Island, N.Y.). Membranous extracts, such as the canine pancreatic extracts containing microsomal membranes, are also available which are useful for translating secretory proteins.

Reconstituted translation systems may also be used. Mixtures of purified translation factors have also been used successfully to translate mRNA into protein as well as combinations of lysates or lysates supplemented with purified translation factors such as initiation factor-1 (IF-1), IF-2, IF-3 ($\alpha$ or $\beta$), elongation factor T (EF-Tu), or termination factors. Cell-free systems may also be coupled transcription/translation systems wherein DNA is introduced to the system, transcribed into mRNA and the mRNA translated as described in *Current Protocols in Molecular Biology* (F. M. Ausubel et al. editors, Wiley Interscience, 1993), which is hereby specifically incorporated by reference. RNA transcribed in eukaryotic transcription system may be in the form of heteronuclear RNA (hnRNA) or 5'-end caps (7-methyl guanosine) and 3'-end poly A tailed mature mRNA, which can be an advantage in certain translation systems. For example, capped mRNAs are translated with high efficiency in the reticulocyte lysate system.

The term "selected amino acid" refers to any desired naturally occurring amino acid or unnatural amino acid. As used herein, the term "unnatural amino acid" or "non-naturally encoded amino acid" refers to any amino acid, modified amino acid, and/or amino acid analogue that is not one of the 20 common naturally occurring amino acids or selenocysteine or pyrrolysine. Other terms that may be used synonymously with the term "non-naturally encoded amino acid" and "unnatural amino acid" are "non-natural amino acid," "non-naturally-occurring amino acid," and variously hyphenated and non-hyphenated versions thereof. The term "non-naturally encoded amino acid" also includes, but is not limited to, amino acids that occur by modification (e.g. post-translational modifications) of a naturally encoded amino acid (including but not limited to, the 20 common amino acids or pyrrolysine and selenocysteine) but are not themselves naturally incorporated into a growing polypeptide chain by the translation complex. Examples of such non-naturally-occurring amino acids include, but are not limited to, N-acetylglucosaminyl-L-serine, N-acetylglucosaminyl-L-threonine, and O-phosphotyrosine.

Non-Natural Amino Acid:

As used herein, a non-natural amino acid or an unnatural amino acid refers to any amino acid, modified amino acid, or amino acid analogue other than selenocysteine and/or pyrrolysine and the following twenty canonical genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. In various embodiments of the invention, the one or more unnatural amino acid that is incorporated into the unnatural immunogen can be any unnatural amino acid. Thus, it will be appreciated that recitation of specific unnatural amino acids herein should not necessarily be taken as limiting on the invention. A wide variety of unnatural amino acids have been incorporated into proteins by coding for them in vivo, e.g., using translation systems that comprise orthogonal elements, See, e.g., Liu, et al. (2007) "Genetic incorporation of unnatural amino acids into proteins in mammalian cells" Nat Methods 4:239-244; Wang, et al. (2006) "Expanding the genetic code" Annu Rev Biophys Biomol Struct 35:225-249; Xie & Schultz (2006) "A chemical toolkit for proteins-an expanded genetic code" Nat Rev Mol Cell Biol 7:775-782; Wang and Schultz "Expanding the Genetic Code," Angewandte Chemie Int. Ed, 44(1):34-66 (2005) and Chin, et al. (2003) "An expanded eukaryotic genetic code" Science 301:964-967 for a review.

In some embodiments of the present invention it is desirable to use non-natural amino acids that are not one of the 20 common naturally occurring amino acids or the rare naturally occurring amino acids e.g., selenocysteine or pyrrolysine. For example, the non-natural amino acids, p-nitrophenylalanine, p-sulfotyrosine, and p-carboxyphenylalanine find use in various embodiments herein. In some embodiments, the non-natural amino acid can include, but is not limited to: p-nitrophenylalanine; an o-nitrophenylalanine; an m-nitrophenylalanine; a p-boronyl phenylalanine; an o-boronylphenylalanine; an m-boronylphenylalanine; a p-aminophenylalanine; an o-aminophenylalanine; an m-aminophenylalanine; a p-acylphenylalanine; an o-acylphenylalanine; an m-acylphenylalanine; a p-OMe phenylalanine; an o-OMe phenylalanine; an m-OMe phenylalanine; a p-sulfophenylalanine; an o-sulfophenylalanine; an m-sulfophenylalanine; a 5-nitro His; a 3-nitro Tyr; a 2-nitro Tyr; a nitro substituted Len; a nitro substituted His; a nitro substituted De; a nitro substituted Trp; a 2-nitro Trp; a 4-nitro Trp; a 5-nitro Trp; a 6-nitro Trp; a 7-nitro Trp; 3-aminotyrosine, 2-aminotyrosine, O-sulfotyrosine, 2-sulfooxyphenylalanine, 3-sulfooxyphenylalanine or p-carboxyphenylalanine, o-carboxyphenyalanine, and m-carboxyphenylalanine. Again, it will be appreciated that the invention is not limited to particular non-natural amino acids.

In addition, in various embodiments of the present invention, unnatural amino acids can be incorporated into immunogens in vitro, e.g., using biosynthetic methods in which a suppressor tRNA is chemically acylated with a desired unnatural amino acid and is added to an in vitro extract capable of supporting immunogen biosynthesis. For a description of such in vitro synthetic methods, see, e.g., V. W. Cornish, D. Mendel and P. G. Schultz, Angew. Chem. Int. Ed. Engl. 1995, 34;621 (1995); C. J. Noren, S. J. Anthony-Cahill, M. C. Griffith, P. G. Schultz, "A general method for site-specific incorporation of unnatural amino acids into proteins," Science 244 182-188 (1989); and, J. D. Bain, C G. Glabe, T. A. Dix, A. R. Chamberlin, E. S. Diala, "Biosynthetic site-specific incorporation of a non-natural amino acid into a polypeptide," J. Am. Chem. Soc. II 1 8013-8014 (1989). Unnatural amino acids can also be added to naturally or synthetically produced proteins by available synthetic peptide chemistries (or natural amino acids can be converted to unnatural amino acids by such methods), or by post-translational processing. Again, however, it will be appreciated that such post-translation and chemical modifications are typically done in conjuction with, or in addition to, incorporation of one or more unnatural amino acids during synthesis of a molecule (e.g., direct incorporation such as orthogonal translation, solid-phase synthesis, etc.). Thus, post-translational addition or chemical modification of amino acids are typically done, if at all, only on molecules already having unnatural amino acids that were added during the synthesis of the molecule. Further information on non-orthogonal incorporation of unnatural amino acids into immunogens is given below.

As used herein, the term "derived from" refers to a component that is isolated from or made using information from a specified molecule or organism.

A "recombinant host cell" or "host cell" refers to a cell that includes an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome.

As used herein, the term "medium" or "media" includes any culture medium, solution, solid, semi-solid, or rigid support that may support or contain any host cell, including bacterial host cells, yeast host cells, insect host cells, plant host cells, eukaryotic host cells, mammalian host cells, CHO cells, prokaryotic host cells, *E. coli*, or *Pseudomonas* host cells, and cell contents. Thus, the term may encompass medium in which the host cell has been grown, e.g., medium into which a culture or whole organism or cell is growing, and the medium may have a non-natural amino acid included to support growth of replication deficient organisms or cells, including medium either before or after a proliferation step. The term also may encompass buffers or reagents that contain host cell lysates, such as in the case where the antigens are produced intracellularly and the host cells are lysed or disrupted to release the antigens or recombinant antigens.

"Reducing agent," as used herein with respect to protein refolding, is defined as any compound or material which maintains sulfhydryl groups in the reduced state and reduces intra- or intermolecular disulfide bonds. Suitable reducing agents include, but are not limited to, dithiothreitol (DTT), 2-mercaptoethanol, dithioerythritol, cysteine, cysteamine (2-aminoethanethiol), and reduced glutathione. It is readily apparent to those of ordinary skill in the art that a wide variety of reducing agents are suitable for use in the methods and compositions of the present invention.

"Oxidizing agent," as used hereinwith respect to protein refolding, is defined as any compound or material which is capable of removing an electron from a compound being oxidized. Suitable oxidizing agents include, but are not limited to, oxidized glutathione, cystine, cystamine, oxidized dithiothreitol, oxidized erythreitol, and oxygen. It is readily apparent to those of ordinary skill in the art that a wide variety of oxidizing agents are suitable for use in the methods of the present invention.

"Refolding," as used herein describes any process, reaction or method which transforms disulfide bond containing polypeptides from an improperly folded or unfolded state to a native or properly folded conformation with respect to disulfide bonds.

"Cofolding," as used herein, refers specifically to refolding processes, reactions, or methods which employ at least two polypeptides which interact with each other and result in the transformation of unfolded or improperly folded polypeptides to native, properly folded polypeptides.

An "amino terminus modification group" refers to any molecule that can be attached to the amino terminus of a polypeptide. Similarly, a "carboxy terminus modification group" refers to any molecule that can be attached to the carboxy terminus of a polypeptide. Terminus modification groups include, but are not limited to, various water soluble polymers, peptides or proteins such as serum albumin, or other moieties that increase serum half-life of peptides.

The terms "functional group", "active moiety", "activating group", "leaving group", "reactive site", "chemically reactive group" and "chemically reactive moiety" are used in the art and herein to refer to distinct, definable portions or units of a molecule. The terms are somewhat synonymous in the chemical arts and are used herein to indicate the portions of molecules that perform some function or activity and are reactive with other molecules.

The term "linkage" or "linker" is used herein to refer to groups or bonds that normally are formed as the result of a chemical reaction and typically are covalent linkages. Hydrolytically stable linkages means that the linkages are substantially stable in water and do not react with water at useful pH values, including but not limited to, under physiological conditions for an extended period of time, perhaps even indefinitely. Hydrolytically unstable or degradable linkages mean that the linkages are degradable in water or in aqueous solutions, including for example, blood. Enzymatically unstable or degradable linkages mean that the linkage can be degraded by one or more enzymes. As understood in the art, PEG and related polymers may include degradable linkages in the polymer backbone or in the linker group between the polymer backbone and one or more of the terminal functional groups of the polymer molecule. For example, ester linkages formed by the reaction of PEG carboxylic acids or activated PEG carboxylic acids with alcohol groups on a biologically active agent generally hydrolyze under physiological conditions to release the agent. Other hydrolytically degradable linkages include, but are not limited to, carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide.

The term "biologically active molecule", "biologically active moiety" or "biologically active agent" when used herein means any substance which can affect any physical or biochemical properties of a biological system, pathway, molecule, or interaction relating to an organism, including but not limited to, viruses, bacteria, bacteriophage, transposon, prion, insects, fungi, plants, animals, and humans. In particular, as used herein, biologically active molecules include, but are not limited to, any substance intended for diagnosis, cure, mitigation, treatment, or prevention of disease in humans or other animals, or to otherwise enhance physical or mental well-being of humans or animals. Examples of biologically active molecules include, but are not limited to, peptides, proteins, enzymes, small molecule drugs, vaccines, immunogens, hard drugs, soft drugs, carbohydrates, inorganic atoms or molecules, dyes, lipids, nucleosides, radionuclides, oligonucleotides, toxoids, toxins, prokaryotic and eukaryotic cells, viruses, polysaccharides, nucleic acids and portions thereof obtained or derived from viruses, bacteria, insects, animals or any other cell or cell type, liposomes, microparticles and micelles. Classes of biologically active agents that are suitable for use with the invention include, but are not limited to, drugs, prodrugs, radionuclides, imaging agents, polymers, antibiotics, fungicides, anti-viral agents, anti-inflammatory agents, anti-tumor agents, cardiovascular agents, anti-anxiety agents, hormones, growth factors, steroidal agents, microbially derived toxins, and the like.

The term "aryl" means, unless otherwise stated, a polyunsaturated, aromatic, hydrocarbon substituent which can be a single ring or multiple rings (including but not limited to, from 1 to 3 rings) which are fused together or linked covalently. The term "heteroaryl" refers to aryl groups (or rings) that contain from one to four hetero atoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (including but not limited to, aryloxy, arylthioxy, arylalkyl) includes both aryl and heteroaryl rings as defined above. Thus, the term "arylalkyl" is meant to include those radicals in which an aryl group is attached to an alkyl group (including but not limited to, benzyl, phenethyl, pyridylmethyl and the like) including those alkyl groups in which a carbon atom (including but not limited to, a methylene group) has been replaced by, for example, an oxygen atom (including but not limited to, phenoxymethyl, 2-pyridyloxymethyl, 3-(1-naphthyloxy)propyl, and the like).

Each of the above terms (including but not limited to, "alkyl," "heteroalkyl," "aryl" and "heteroaryl") are meant to include both substituted and unsubstituted forms of the indicated radical. Exemplary substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', —N—OR', —NR'R", —SR', -halogen, —SiR'R"R"', OC(O)R', —C(O)R', —CO$_2$R', —CONR'R", —OC(O)NR'R", —NR"C(O)R', NR' C(O)NR'R"', —NR"C(O)$_2$R', —NR—C(NR'R"R"')=NR", NR C(NR'R")=NR"', —S(O)R', —S(O)$_2$R', —S(O)$_2$NR'R', NRSO$_2$R', —CN and —NO$_2$ in a number ranging from zero to (2m'+1), where m' is the total number of carbon atoms in such a radical. R', R", R"' and R"" each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R"' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —CF$_3$ and —CH$_2$CF$_3$) and acyl (including but not limited to, —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, but are not limited to: halogen, OR', =O, =NR', =N—OR', —NR'R", —SR', -halogen, —SiR'R"R"', OC(O)R', —C(O)R', CO$_2$R', —CONR'R", —OC(O)NR'R", —NR"C(O)R', NR'C(O)NR"R"', —NR"C(O)2R', NR—C(NR'R"R"")=NR"", NR C(NR'R")=NR"', —S(O)R', —S(O)2R', —S(O)2NR'R", NRSO2R', —CN and —NO2, —R', —N3, —CH(Ph)$_2$, fluoro(C1-C4)alkoxy, and fluoro(C1-C4)alkyl, in a number ranging from zero to the total number of open valences on the aromatic ring system; and where R', R", R"' and R"" are independently selected from hydrogen, alkyl, heteroalkyl, aryl and heteroaryl. When a compound of the invention includes more than one R group, for example, each of the R groups is independently selected as are each R', R", R"' and R"" groups when more than one of these groups is present.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)).

Where substituent groups are specified by their conventional chemical formulas, written from left to right, they equally encompass the chemically identical substituents that would result from writing the structure from right to left, for example, the structure CH2O is equivalent to the structure —OCH2.

The term "substituents" includes but is not limited to "non-interfering substituents". "Non-interfering substituents" are those groups that yield stable compounds. Suitable non-interfering substituents or radicals include, but are not limited to, halo, C1-C10 alkyl, C2-C10 alkenyl, C2-C10 alkynyl, C1-C10 alkoxy, C1-C12 aralkyl, C1-C12 alkaryl, C3-C12 cycloalkyl, C3-C12 cycloalkenyl, phenyl, substituted phenyl, toluoyl, xylenyl, biphenyl, C2-C12 alkoxyalkyl, C2-C12 alkoxyaryl, C7-C12 aryloxyalkyl, C7-C12 oxyaryl, C1-C6 alkylsulfinyl, C1-C10 alkylsulfonyl, —(CH2)m—O—(C1-C10 alkyl) wherein m is from 1 to 8, aryl, substituted aryl, substituted alkoxy, fluoroalkyl, heterocyclic radical, substituted heterocyclic radical, nitroalkyl, —NO2, —CN, —NRC(O)—(C1-C10 alkyl), —C(O)—(C1-C10 alkyl), C2-C10 alkyl thioalkyl, —C(O)O—(C1-C10 alkyl), —OH, —SO2, =S, —COOH, —NR2, carbonyl, —C(O)—(C1-C10 alkyl)-CF3, —C(O)CF3, —C(O)NR2, —(C1-C10 aryl)-S—(C6-C10 aryl), —C(O)—(C1-C10 aryl), —(CH2)m-O—(—(CH2)m-O—(C1-C10 alkyl) wherein each m is from 1 to 8, —C(O)NR2, —C(S)NR2, —SO2NR2, —NRC(O)NR2, —NRC(S)NR2, salts thereof, and the like. Each R as used herein is H, alkyl or substituted alkyl, aryl or substituted aryl, aralkyl, or alkaryl.

The term "halogen" includes fluorine, chlorine, iodine, and bromine.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. C1-C10 means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups which are limited to hydrocarbon groups are termed "homoalkyl".

The term "alkylene" by itself or as part of another substituent means a divalent radical derived from an alkane, as exemplified, but not limited, by the structures —CH2CH2- and —CH2CH2CH2CH2-, and further includes those groups described below as "heteroalkylene." Typically, an alkyl (or alkylene) group will have from 1 to 24 carbon atoms, with those groups having 10 or fewer carbon atoms being a particular embodiment of the methods and compositions described herein. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH2-CH2-O—CH3, —CH2-CH2-NH—CH3, —CH2-CH2-N(CH3)-CH3, —CH2-S-CH2-CH3, —CH2-CH2, —S(O)—CH3, —CH2-CH2-S(O)2-CH3, —CH=CH—O—CH3, —Si(CH3)3, —CH2-CH=N—OCH3, and —CH=CH—N(CH3)-CH3. Up to two heteroatoms may be consecutive, such as, for example, —CH2-NH—OCH3 and —CH2-O—Si(CH3)3. Similarly, the term "heteroalkylene" by itself or as part of another substituent means a divalent radical derived from heteroalkyl, as exemplified, but not limited by, —CH2-CH2-S—CH2 CH2- and —CH2-S—CH2-CH2-NH—CH2-. For heteroalkylene groups, the same or different heteroatoms can also occupy either or both of the chain termini (including but not limited to, alkyleneoxy, alkylenedioxy, alkyleneamino, alkylenediamino, aminooxyalkylene, and the like). Still further, for alkylene and heteroalkylene linking groups, no orientation of the linking group is implied by the direction in which the formula of the linking group is written. For example, the formula —C(O)2R' represents both —C(O)2R' and —R'C(O)2.

The terms "cycloalkyl" and "heterocycloalkyl", by themselves or in combination with other terms, represent, unless otherwise stated, cyclic versions of "alkyl" and "heteroalkyl", respectively. Thus, a cycloalkyl or heterocycloalkyl include saturated, partially unsaturated and fully unsaturated ring linkages. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. Additionally, the term encompasses bicyclic and tricyclic ring structures. Similarly, the term "heterocycloalkylene" by itself or as part of another substituent means a divalent radical derived from heterocycloalkyl, and the term "cycloalkylene" by itself or as part of another substituent means a divalent radical derived from cycloalkyl.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine. Amino acid analogs refers to compounds that have the same basic chemical structure as a naturally occurring amino acid, i.e., an α carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid. Reference to an amino acid includes, for example, naturally occurring proteogenic L-amino acids; D-amino acids, chemically modified amino acids such as amino acid variants and derivatives; naturally occurring non-proteogenic amino acids such as α-alanine, ornithine, etc.; and chemically synthesized compounds having properties known in the art to be characteristic of amino acids. Examples of non-naturally occurring amino acids include, but are not limited to, α-methyl amino acids (e.g., α-methyl alanine), D-amino acids, histidine-like amino acids (e.g., 2-amino-histidine, α-hydroxy-histidine, homohistidine, α-fluoromethyl-histidine and α-methyl-histidine), amino acids having an extra methylene in the side chain ("homo" amino acids), and amino acids in which a carboxylic acid functional group in the side chain is replaced with a sulfonic acid group (e.g., cysteic acid).

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of ordinary skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of ordinary skill in the art will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the deletion of an amino acid, addition of an amino acid, or substitution of an amino acid with a chemically similar amino acid. Conservative substitution tables providing functionally similar amino acids are known to those of ordinary skill in the art. Such conservatively modified variants are in addition to and do not exclude polymorphic variants, interspecies homologs, and alleles of the invention.

Conservative substitution tables providing functionally similar amino acids are known to those of ordinary skill in the art. The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, Proteins: Structures and Molecular Properties (W H Freeman & Co.; 2nd edition (December 1993))

The terms "identical" or percent "identity," in the context of two or more nucleic acids or polypeptide sequences, refer to two or more sequences or subsequences that are the same. Sequences are "substantially identical" if they have a percentage of amino acid residues or nucleotides that are the same (i.e., about 60% identity, about 65%, about 70%, about 75%, about 80%, about 85%, about 90%, or about 95% identity over a specified region), when compared and aligned for maximum correspondence over a comparison window, or designated region as measured using one of the following sequence comparison algorithms (or other algorithms available to persons of ordinary skill in the art) or by manual alignment and visual inspection. This definition also refers to the complement of a test sequence. The identity can exist over a region that is at least about 50 amino acids or nucleotides in length, or over a region that is 75-100 amino acids or nucleotides in length, or, where not specified, across the entire sequence of a polynucleotide or polypeptide. A polynucleotide encoding a polypeptide of the present invention, including homologs from species other than human, may be obtained by a process comprising the steps of screening a library under stringent hybridization conditions with a labeled probe having a polynucleotide sequence of the invention or a fragment thereof, and isolating full-length cDNA and genomic clones containing said polynucleotide sequence. Such hybridization techniques are well known to the skilled artisan.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are known to those of ordinary skill in the art. Optimal alignment of sequences for comparison can be conducted, including but not limited to, by the local homology algorithm of Smith and Waterman (1970) Adv. Appl. Math. 2:482c, by the homology alignment algorithm of Needleman and Wunsch (1970) J. Mol. Biol. 48:443, by the search for similarity method of Pearson and Lipman (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., Current Protocols in Molecular Biology (1995 supplement)).

One example of an algorithm that is suitable for determining percent sequence identity and sequence similarity are the BLAST and BLAST 2.0 algorithms, which are described in Altschul et al. (1997) Nuc. Acids Res. 25:3389-3402, and Altschul et al. (1990) J. Mol. Biol. 215:403-410, respectively. Software for performing BLAST analyses is publicly available through the National Center for Biotechnology Information available at the World Wide Web at ncbi.nlm.nih.gov. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1992) Proc. Natl. Acad. Sci. USA 89:10915) alignments (B) of 50, expectation (E) of 10, M=5, N=−4, and a comparison of both strands. The BLAST algorithm is typically performed with the "low complexity" filter turned off.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, or less than about 0.01, or less than about 0.001.

The phrase "selectively (or specifically) hybridizes to" refers to the binding, duplexing, or hybridizing of a molecule only to a particular nucleotide sequence under stringent hybridization conditions when that sequence is present in a complex mixture (including but not limited to, total cellular or library DNA or RNA).

The phrase "stringent hybridization conditions" refers to hybridization of sequences of DNA, RNA, PNA, or other nucleic acid mimics, or combinations thereof under conditions of low ionic strength and high temperature as is known in the art. Typically, under stringent conditions a probe will hybridize to its target subsequence in a complex mixture of nucleic acid (including but not limited to, total cellular or library DNA or RNA) but does not hybridize to other sequences in the complex mixture. Stringent conditions are sequence-dependent and will be different in different circumstances. Longer sequences hybridize specifically at higher temperatures. An extensive guide to the hybridization of nucleic acids is found in Tijssen, Laboratory Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions may be those in which the salt concentration is less than about 1.0 M sodium ion, typically about 0.01 to 1.0 M sodium ion concentration (or other salts) at pH 7.0 to 8.3 and the temperature is at least about 30° C. for short probes (including but not limited to, 10 to 50 nucleotides) and at least about 60° C. for long probes (including but not limited to, greater than 50 nucleotides). Stringent conditions may also be achieved with the addition of destabilizing agents such as formamide. For selective or specific hybridization, a positive signal may be at least two times background, optionally 10 times background hybridization. Exemplary stringent hybridization conditions can be as following: 50% formamide, 5×SSC, and 1% SDS, incubating at 42° C., or 5×SSC, 1% SDS, incubating at 65° C., with wash in 0.2×SSC, and 0.1% SDS at 65° C. Such washes can be performed for 5, 15, 30, 60, 120, or more minutes.

As used herein, the term "eukaryote" refers to organisms belonging to the phylogenetic domain Eucarya such as animals (including but not limited to, mammals, insects, reptiles, birds, etc.), ciliates, plants (including but not limited to, monocots, dicots, algae, etc.), fungi, yeasts, flagellates, *microsporidia*, protists, etc.

As used herein, the term "non-eukaryote" refers to non-eukaryotic organisms. For example, a non-eukaryotic organism can belong to the Eubacteria (including but not limited to, *Escherichia coli, Thermus thermophilus, Bacillus stearothermophilus, Pseudomonas fluorescens, Pseudomonas aeruginosa, Pseudomonas putida*, etc.) phylogenetic domain, or the Archaea (including but not limited to, *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix*, etc.) phylogenetic domain.

The term "subject" as used herein, refers to an animal, in some embodiments a mammal, and in other embodiments a human, who is the object of treatment, observation or experiment. An animal may be a companion animal (e.g., dogs, cats, and the like), farm animal (e.g., cows, sheep, pigs, horses, and the like) or a laboratory animal (e.g., rats, mice, guinea pigs, and the like).

The term "effective amount" as used herein refers to that amount of the modified non-natural amino acid polypeptide being administered which will relieve to some extent one or more of the symptoms of the disease, condition or disorder being treated. Compositions containing the modified non-natural amino acid polypeptide described herein can be administered for prophylactic, enhancing, and/or therapeutic treatments.

The terms "enhance" or "enhancing" means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system. When used in a patient, amounts effective for this use will depend on the severity and course of the disease, disorder or condition, previous therapy, the patient's health status and response to the drugs, and the judgment of the treating physician.

As used herein, the term "positive selection" or "screening marker" refers to a marker that when present, e.g., expressed, activated or the like, results in identification of a cell with the positive selection marker from those without the positive selection marker.

As used herein, the term "negative selection" or "screening marker" refers to a marker that when present, e.g., expressed, activated or the like, allows identification of a cell that does not possess the desired property (e.g., as compared to a cell that does possess the desired property).

As used herein, the term "reporter" refers to a component that can be used to select target components of a system of interest. For example, a reporter can include a protein, e.g., an enzyme, that confers antibiotic resistance or sensitivity (including, but not limited to, β-lactamase, chloramphenicol acetyltransferase (CAT), and the like), a fluorescent screening marker (including, but not limited to, green fluorescent protein (e.g., GFP), YFP, EGFP, RFP, a luminescent marker (including but not limited to, a firefly luciferase protein), an affinity based screening marker, or positive or negative selectable marker genes such as lacZ, β-gal/lacZ (β-galactosidase), ADH (alcohol dehydrogenase), his3, ura3, leu2, lys2, or the like.

As used herein, the term "eukaryote" refers to organisms belonging to the phylogenetic domain Eucarya such as animals (including but not limited to, mammals, insects, reptiles, birds, etc.), ciliates, plants (including but not limited to, monocots, dicots, algae, etc.), fungi, yeasts, flagellates, *microsporidia*, protists, etc.

As used herein, the term "non-eukaryote" refers to non-eukaryotic organisms. For example, a non-eukaryotic organism can belong to the Eubacteria (including but not limited to, *Escherichia coli, Thermus thermophilus, Bacillus stearothermophilus, Pseudomonas fluorescens, Pseudomonas aeruginosa, Pseudomonas putida*, etc.) phylogenetic domain, or the Archaea (e.g., *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix*, etc.) phylogenetic domain.

Also included are the following non-limiting examples of viral envelope protein: envelope proteins from filoviruses (such as Ebola virus), orthomyxoviruses (such as influenza virus), VSV-G, alpha viruses (such as Semliki forest virus and Sindbis virus), arena viruses (such as lymphocytic choriomeningitis virus), flaviviruses (such as tick-borne encephalitis virus and Dengue virus), rhabdoviruses (such as vesicular stomatitis virus and rabies virus), Moloney leukemia virus, HSV, VZV, Mumps virus, Rhinoviruses, Measles, Rubella, Arbovirus, Enteroviruses (such as Polio, Coxsackie, Echoviruses), Polio virus, Coxsackie B, A & Echovirus, Rhinoviruses, Hepatitis viruses, Norwalk virus, Astroviruses, Togavirus, Alphaviruses, Pestiviruses, Coronavirus, Parainfluenza, Mumps virus, Measles virus, Respiratory Syncytial Virus (RSV), Bunyaviridae, Reoviridue, Reoviruses, Rotaviruses, HTLV, Polyomaviruses, Papillomaviruses, Adenoviruses, Parvoviruses, EBV, CMV, Varicella Zoster virus, herpes viruses, and Pox viruses.

Conservative Variant:

The term "conservative variant" refers to a translation component, e.g., a conservative variant O-tRNA or a conservative variant O-RS, that functionally performs like the component from which the conservative variant is based, e.g., an O-tRNA or O-RS, but has variations in the sequence. For example, an O-RS will aminoacylate a complementary O-tRNA or a conservative variant O-tRNA with a selected amino acid, e.g., an unnatural amino acid, although the O-tRNA and the conservative variant O-tRNA do not have the same sequence. Similarly, a tRNA will be aminoacylated with a selected amino acid, e.g., an unnatural amino acid, by a complementary O-RS or a conservative variant O-RS, although the O-RS and the conservative variant O-RS do not have the same sequence. The conservative variant can have, e.g., one variation, two variations, three variations, four variations, or five or more variations in sequence, as long as the conservative variant is complementary to the corresponding O-tRNA or O-RS.

Selection or Screening Agent:

As used herein, the term "selection or screening agent" refers to an agent that, when present, allows for a selection/screening of certain components from a population. For example, a selection or screening agent includes, but is not limited to, e.g., a nutrient, an antibiotic, a wavelength of light, an antibody, an expressed polynucleotide, or the like. The selection agent can be varied, e.g., by concentration, intensity, etc.

The term "not efficiently recognized" refers to an efficiency, e.g., less than about 10%, less than about 5%, or less than about 1%, at which a RS from one organism aminoacylates O-tRNA.

DETAILED DESCRIPTION

Until now, vaccines have been limited to those produced with killed or attenuated organisms. The killing of microorganism by the treatment of heat, UV, formalaldehyde results in reduced native epitopes, and attenuated viruses are typically produced through gene deletion and truncation which leads to extremely low but non-zero replication, a risk to the patient and particularly to younger patients, older patients, those with compromised immune systems.

In one embodiment the present invention provides whole organism modified vaccines. In another embodiment, the present invention provides genetically modified whole organism vaccines replication-dependent on one or more non-natural amino acids. The present invention provides vaccines that incorporate native microorganisms, which may be used with or without adjuvents. These additionally may provide a high density of native epitopes which are highly immunogenic and will trigger humoral and T cell mediated responses, thereby providing a more effective vaccine. The present invention provides vaccines incorporating one or more non-natural, unnatural, or non-naturally encoded amino acids into one or more sites on the virus or bacterium. In some embodiments of the present invention, the non-naturally encoded amino acid is included on a part of the microorganism required for replication, thereby eliminating the risks associated with attenuated viruses and eliminating the need for killing the virus/bacterium. The vaccine with incorporated non-naturally encoded amino acid(s) will provide a microorganism which structurally is extremely close to the native microorganism, however incapable of replication, or capable of only limited replication in a natural environment. The absolute controls of the replication of microorganism is realized using site-specific incorporation of amino acids, detailed below, to control the essential gene expression (function) using stop codon suppression. For viruses, a host production cell line site-specifically incorporates a normatural amino acid required for development. For bacteria, the genome is engineered to include one or more site-specifically incorporated normatural amino acid(s).

The control essential gene function can be realized at genetic and structural functional levels. For example, Table 2 At the genetic level, the full length essential gene is expressed in the presence of the non-naturally incorporated amino acid. At the structural functional level, the essential gene is engineered to be functional only in the presence of the normatural amino acid at a specific site. The incorporation of any natural amino acid at this site will result in the abolishment of its native function. The freedom of choice of normatural amino acid(s) enables one of skill in the art to modulate the immunogenicity of the desired vaccine and the freedom of excessive or over-controlled replication, where traditionally it has been necessary to balance between attenuation of replication and production, the site specific incorporation of a non-natural amino acid provides the development tools for a vaccine with zero replication abilities in the absence of the normatural amino acid.

Bacteria and viruses that vaccines can be developed for using this technology include known viruses. For non-limiting examples, this includes, viruses affecting the upper respiratory tract such as human rhinoviruses (HRV), adenovirus, coxsackievirus, influenza, parainfluenza, respiratory syncytia virus (RSV), Epstein-Barr Virus (EBV), and cytomegalovirus (CMV); viruses affecting the gastrointestinal (GI) tract such as rotavirus, Norwalk agent, hepatitis A (HAV), poliovirus and other picornaviruses; sexually transmitted viruses including, but not limited to, human immunodeficiency virus (HIV), human papilloma virus (HPV), herpes simplex virus (HSV)1, HSV-2, VZV, CMV, EBV, HHV-6, HHV-7 and HHV-8; CMV, hepatitis B virus (HBV), hepatitis C virus (HCV). Non-limiting examples of bacteria include both gram positive and gram negative bacteria, including *Staphylococcus, Streptococcus, Mycobacterium* (e.g. *Mycobacterium avium*, and *Mycobacterium avium* subspecies *paratuberculosis*), *Enterococcus, Corynebacterium, Borrelia, Bacillus, Chlamydia, Mycoplasma*, and the like.

Translation systems that are suitable for making proteins that include one or more selected amino acids, e.g., an unnatural amino acid, are described in U.S. patent application Ser. No. 10/126,931, entitled "METHODS AND COMPOSITION FOR THE PRODUCTION OF ORTHOGONAL tRNA-AMINOACYL tRNA SYNTHETASE PAIRS" and Ser. No. 10/126,927, entitled "IN VIVO INCORPORATION OF UNNATURAL AMINO ACIDS." In addition, see U.S. Ser. No. 10/825,867 entitled "EXPANDING THE EUKARYOTIC GENETIC CODE." Each of these applications is incorporated herein by reference in its entirety. Such translation systems generally comprise cells that include an orthogonal tRNA (O-tRNA), an orthogonal aminoacyl tRNA synthetase (O-RS), and a selected amino acid, e.g., an unnatural amino acid, where the O-RS aminoacylates the O-tRNA with the selected amino acid. An orthogonal pair of the present invention is composed of an O-tRNA, e.g., a suppressor tRNA, a frameshift tRNA, or the like, and an O-RS. The O-tRNA recognizes a first selector codon and has suppression activity in presence of a cognate synthetase in response to a selector codon. The cell uses the components to incorporate the selected amino acid into a growing polypeptide chain. For example, a nucleic acid that comprises a polynucleotide that encodes a polypeptide of interest can also be present, where the polynucleotide comprises a selector codon that is recognized by the O-tRNA. The translation system can also be an in vitro system. tRNA molecules of the present invention are useful in any translational system, including systems that utilize ribosomes in translation.

The translation system may also be a cell-free (in-vitro) translational system. In these systems, which can include either mRNA as a template (in-vitro translation) or DNA as a template (combined in-vitro transcription and translation), the in vitro synthesis is directed by the ribosomes. Considerable effort has been applied to the development of cell-free protein expression systems. See, e.g., Kim, D. M. and J. R. Swartz, *Biotechnology and Bioengineering*, 74:309-316

(2001); Kim, D. M. and J. R. Swartz, *Biotechnology Letters*, 22, 1537-1542, (2000); Kim, D. M., and J. R. Swartz, *Biotechnology Progress*, 16, 385-390, (2000); Kim, D. M., and J. R. Swartz, *Biotechnology and Bioengineering*, 66, 180-188, (1999); and Patnaik, R. and J. R. Swartz, *Biotechniques* 24, 862-868, (1998); U.S. Pat. No. 6,337,191; U.S. Patent Publication No. 2002/0081660; WO 00/55353; WO 90/05785, which are incorporated by reference herein. Another approach that may be applied includes the mRNA-peptide fusion technique. See, e.g., R. Roberts and J. Szostak, *Proc. Natl Acad. Sci.* (*USA*) 94:12297-12302 (1997); A. Frankel, et al., *Chemistry & Biology* 10:1043-1050 (2003). In this approach, an mRNA template linked to puromycin is translated into peptide on the ribosome. If one or more tRNA molecules have been modified, non-natural amino acids can be incorporated into the peptide as well. After the last mRNA codon has been read, puromycin captures the C-terminus of the peptide. If the resulting mRNA-peptide conjugate is found to have interesting properties in an in vitro assay, its identity can be easily revealed from the mRNA sequence. In this way, one may screen libraries of polypeptides comprising one or more non-naturally encoded amino acids to identify polypeptides having desired properties. More recently, in vitro ribosome translations with purified components have been reported that permit the synthesis of peptides substituted with non-naturally encoded amino acids. See, e.g., A. Forster et al., *Proc. Natl. Acad. Sci.* (*USA*) 100:6353 (2003).

In certain embodiments, the present invention provides a cell wherein a non-natural amino acid has been incorporated into an essential gene product. In other embodiments of the present invention, a cell has been genetically modified to include a non-natural amino acid in a gene product that is required for replication. In certain embodiments, the present invention provides a bacterium wherein a non-natural amino acid has been incorporated into an essential gene product. In other embodiments of the present invention, a bacterium has been genetically modified to include a non-natural amino acid in a gene product that is required for replication. In certain embodiments, the present invention provides a virus wherein a non-natural amino acid has been incorporated into an essential gene product. In other embodiments of the present invention, a virus has been genetically modified to include a non-natural amino acid in a gene product that is required for replication. In certain embodiments, the present invention provides a *mycobacterium avium* subspecies *paratuberculosis* cell wherein a non-natural amino acid has been incorporated into an essential gene product. In other embodiments of the present invention, a *mycobacterium avium* subspecies *paratuberculosis* cell has been genetically modified to include a non-natural amino acid in a gene product that is required for replication. In certain embodiments, the present invention provides a meningitis cell wherein a non-natural amino acid has been incorporated into an essential gene product. In other embodiments of the present invention, a meningitis cell has been genetically modified to include a non-natural amino acid in a gene product that is required for replication. In certain embodiments, the present invention provides a rabies cell wherein a non-natural amino acid has been incorporated into an essential gene product. In other embodiments of the present invention, a rabies cell has been genetically modified to include a non-natural amino acid in a gene product that is required for replication. In certain embodiments, the present invention provides an algae cell wherein a non-natural amino acid has been incorporated into an essential gene product. In other embodiments of the present invention, an algae cell has been genetically modified to include a non-natural amino acid in a gene product that is required for replication. In certain embodiments, the present invention provides a viral cell wherein a non-natural amino acid has been incorporated into an essential gene product. In other embodiments of the present invention, a viral cell has been genetically modified to include a non-natural amino acid in a gene product that is required for replication. In certain embodiments, the present invention provides a bacterial cell wherein a non-natural amino acid has been incorporated into an essential gene product. In other embodiments of the present invention, a bacterial cell has been genetically modified to include a non-natural amino acid in a gene product that is required for replication. In certain embodiments, the present invention provides a fungal cell wherein a non-natural amino acid has been incorporated into an essential gene product. In other embodiments of the present invention, a fungal cell has been genetically modified to include a non-natural amino acid in a gene product that is required for replication.

In certain embodiments, the present invention provides a polio cell wherein a non-natural amino acid has been incorporated into an essential gene product. In other embodiments of the present invention, a polio cell has been genetically modified to include a non-natural amino acid in a gene product that is required for replication. In certain embodiments, the present invention provides an *E. coli* cell wherein a non-natural amino acid has been incorporated into an essential gene product. In other embodiments of the present invention, an *E. coli* cell has been genetically modified to include a non-natural amino acid in a gene product that is required for replication. In certain embodiments, the present invention provides a mycobacterium cell wherein a non-natural amino acid has been incorporated into an essential gene product. In other embodiments of the present invention, a *mycobacterium* cell has been genetically modified to include a non-natural amino acid in a gene product that is required for replication.

In certain embodiments, genetically-modified non-natural amino acid-dependent cells of the present invention may be used to produce a vaccine. In certain embodiments, genetically-modified non-natural amino acid-dependent cells of the present invention may be used to produce antibodies that may be administered as a vaccine. In certain embodiments, genetically-modified non-natural amino acid-dependent cells of the present invention may be used in an inoculation.

In certain embodiments, an *E. coli* cell comprising the tRNA of the present invention includes such a translation system. For example, the *E. coli* cell of the present invention includes an orthogonal tRNA (O-tRNA), where the O-tRNA comprises suppression activity in presence of a cognate synthetase in response to a selector codon; an orthogonal aminoacyl-tRNA synthetase (O-RS); a selected amino acid; and, a nucleic acid that comprises a polynucleotide that encodes a polypeptide of interest, where the polynucleotide comprises a selector codon that is recognized by the O-tRNA.

The invention also features multiple O-tRNA/O-RS pairs in a cell, which allows incorporation of more than one selected amino acid. In certain embodiments, the cell can further include an additional different O-tRNA/O-RS pair and a second selected amino acid, where the O-tRNA recognizes a second selector codon and the O-RS preferentially aminoacylates the O-tRNA with the second selected amino acid. For example, a cell can further comprise, e.g., an amber suppressor tRNA-aminoacyl tRNA synthetase pair derived from the tyrosyl-tRNA synthetase of *Methanococcus jannaschii*.

The O-tRNA and/or the O-RS can be naturally occurring or can be derived by mutation of a naturally occurring tRNA and/or RS, e.g., which generates libraries of tRNA's and/or libraries of RSs, from a variety of organisms. For example, one strategy of producing an orthogonal tRNA/aminoacyl-tRNA synthetase pair involves importing a heterologous tRNA/synthetase pair from, e.g., a source other than the host cell, or multiple sources, into the host cell. The properties of the heterologous synthetase candidate include, e.g., that it does not charge any host cell tRNA, and the properties of the heterologous tRNA candidate include, e.g., that it is not aminoacylated by any host cell synthetase. In addition, the heterologous tRNA is orthogonal to all host cell synthetases.

A second strategy for generating an orthogonal pair involves generating mutant libraries from which to screen and/or select an O-tRNA or O-RS. These strategies can also be combined.

In various embodiments, the O-tRNA and O-RS are derived from at least one organism. In another embodiment, the O-tRNA is derived from a naturally occurring or mutated naturally occurring tRNA from a first organism and the O-RS is derived from naturally occurring or mutated naturally occurring RS from a second organism. In one embodiment, the first and second organisms are different. For example, an orthogonal pair may include a tRNA synthetase derived from *Methanobacterium thermoautotrophicum*, and a tRNA derived from an archael tRNA (e.g., from *Halobacterium* sp. NRC-1). Alternatively, the first and second organisms are the same. See the section entitled "Sources and Host Organisms" herein for additional information.

In certain embodiments of the present invention, an O-tRNA of the present invention comprises or is encoded by a polynucleotide sequence as set forth in SEQ ID NO.: 1, 2, or 3, or a complementary polynucleotide sequence thereof, or a conservative variation thereof. See also the section entitled "Nucleic Acid and Polypeptide Sequence and Variants" herein.

Orthogonal tRNA (O-tRNA)

An orthogonal tRNA (O-tRNA) mediates incorporation of a selected amino acid into a protein that is encoded by a polynucleotide that comprises a selector codon that is recognized by the O-tRNA, e.g., in vivo or in vitro. An O-tRNA of the present invention may be aminoacylated with a desired amino acid by any method or technique, including but not limited to, chemical or enzymatic aminoacylation. The aminoacylated O-tRNA of the present invention may be added directly to a translation system. An O-tRNA of the present invention may be aminoacylated by an RS with a selected amino acid in vitro or in vivo. In addition, the RS may be an O-RS. An O-tRNA of the present invention can be provided to the translation system (e.g., in vitro translation components, or a cell) directly, or by providing a polynucleotide that encodes an O-tRNA or a portion thereof. For example, an O-tRNA, or a portion thereof, is encoded by a polynucleotide sequence as set forth in SEQ ID NO.: 1, 2, 3, or a complementary polynucleotide sequence thereof, or a conservative variation thereof.

An O-tRNA of the present invention comprises suppression activity in the presence of a cognate synthetase in response to a selector codon. Suppression activity can be determined by any of a number of assays known in the art. For example, a β-galactosidase reporter assay can be used. A derivative of a plasmid that expresses lacZ gene under the control of promoter is used, e.g., where the Leu-25 of the peptide VVLQRRDWEN of lacZ is replaced by a selector codon, e.g., TAG, TGA, AGGA, etc. codons, or sense codons (as a control) for tyrosine, serine, leucine, etc. The derivatived lacZ plasmid is introduced into cells from an appropriate organism (e.g., an organism where the orthogonal components can be used) along with plasmid comprising an O-tRNA of the present invention. A cognate synthetase can also be introduced (either as a polypeptide or a polynucleotide that encodes the cognate synthetase when expressed). The cells are grown in media to a desired density, e.g., to an $OD_{600}$ of about 0.5, and β-galactosidase assays are performed, e.g., using the BetaFluor™ β-Galactosidase Assay Kit (Novagen). Percent suppression is calculated as the percentage of activity for a sample relative to a comparable control, e.g., the value observed from the derivativated lacZ construct, where the construct has a corresponding sense codon at desired position rather than a selector codon.

In the tRNA molecule, Thymine (T) is replaced with Uracil (U). In addition, additional modifications to the bases can be present. The invention also includes conservative variations of O-tRNA. For example, conservative variations of O-tRNA include those molecules that function like the O-tRNA and maintain the tRNA L-shaped structure, but do not have the same sequence (and are other than wild type tRNA molecules). See also the section herein entitled "Nucleic Acid and Polypeptide Sequence and Variants."

The composition comprising an O-tRNA can further include an orthogonal aminoacyl-tRNA synthetase (O-RS), where the O-RS preferentially aminoacylates the O-tRNA with a selected amino acid (e.g., an unnatural amino acid). In certain embodiments, a composition including an O-tRNA can further include a translation system (e.g., an in vitro or an in vivo translation system). A nucleic acid comprising a polynucleotide encoding a polypeptide of interest, wherein the polynucleotide comprises one or more selector codons recognized by the O-tRNA, or a combination of one or more of these, can also be present in the cell or other translation system. See also, the section herein entitled "Orthogonal Aminoacyl-tRNA Synthetases (O-RS)."

Methods of producing an orthogonal tRNA (O-tRNA), e.g., an O-tRNA, are also a feature of the present invention. A tRNA, e.g., an O-tRNA, produced by the method is also a feature of the present invention.

Methods of producing an orthogonal tRNA include mutating the anticodon loop of each of a pool of tRNA's to allow recognition of a selector codon (e.g., an amber codon, an opal codon, a four base codon, etc.), thereby providing a plurality of potential O-tRNA's; and analyzing secondary structure of a member of the plurality potential O-tRNA to identify non-canonical base pairs in the secondary structure, and optionally mutating the non-canonical base pairs (e.g., the non-canonical base pairs are mutated to canonical base pairs). The non-canonical base pairs can be located in the stem region of the secondary structure. An O-tRNA may possess an improvement of one or more characteristics or activities, such as improvement in orthogonality for a desired organism compared to the starting material, e.g., the plurality of tRNA sequences, while preserving its affinity towards a desired RS.

Alternatively, O-tRNA's may be developed by mutating a known tRNA to modulate its interaction with or binding affinity to one or more molecules that influence translation or are components of translation machinery. Such components include, but are not limited to, elongation factors. Bacterial elongation factor EF-Tu plays a key role in the elongation step in protein synthesis. Following aminoacylation of the tRNA by tRNA synthetase, EF-Tu binds the aminoacylated tRNA and brings it to the A site of the ribosome. The ester bond between the charged amino acid and the tRNA is protected from spontaneous hydrolysis due to the binding between EF-Tu and aminoacylated tRNA. Stortchevoi et al. investigated mutants of the *E. coli* initiation $tRNA^{fMet}$ U50:G64 wobble base pair in the TΨC stem, since this base pair was found to be a secondary negative determinant blocking the tRNA's activity in elongation, presumably due to a weakened interaction between the EF-Tu.GTP and aminoacylated tRNA (JBC 2003 278(20):17672-17679). Also, LaRiviere et al. described in Science 2001 Oct. 5; 294(5540):165-8 the thermodynamic contributions of the amino acid and the tRNA body to the overall binding affinity to EF-Tu. They indicated that the contributions of the tRNA body and the amino acid are independent of each other and that they compensate for one another when the tRNAs are correctly acylated. Alterations to the interaction between EF-Tu.GTP and the tRNA aminoacylated with the unnatural amino acid may affect the efficiency of the loading of the tRNA to the A site of the ribosome. Potential mutation sites may also be found by analyzing crystal structures of complexes between tRNA and other components of translational machinery such as EF-Tu. For example, Nissen et al. have indicated that EF-Tu.GTP binds directly to the phosphate backbone of the TΨC stem of yeast phenylalanyl-transfer RNA (Phe-tRNA) (Science 1995 270(5241):1464-1472).

The methods optionally include analyzing the homology of sequences of tRNA's and/or aminoacyl-tRNA synthetases to determine potential candidates for an O-tRNA, O-RS and/or pairs thereof, that appear to be orthogonal for a specific organism. Computer programs known in the art and described herein can be used for the analysis. In one example, to choose potential orthogonal translational components for use in a prokaryotic organism, a synthetase and/or a tRNA is chosen that does not display unusual homology to prokaryotic organisms.

A pool of tRNA's can also be produced by a consensus strategy. For example, the pool of tRNA's is produced by aligning a plurality of tRNA sequences; determining a consensus sequence; and generating a library of tRNA's using at least a portion, most of, or the entire consensus sequence. For example, a consensus sequence can be compiled with a computer program, e.g., the GCG program pileup. Optionally, degenerate positions determined by the program are changed to the most frequent base at those positions. A library is synthesized by techniques known in the art using the consensus sequence. For example, overlap extension of oligonucleotides in which each site of the tRNA gene can be synthesized as a doped mixture of 90% the consensus sequence and 10% a mixture of the other 3 bases can be used to provide the library based on the consensus sequence. Other mixtures can also be used, e.g., 75% the consensus sequence and 25% a mixture of the other 3 bases, 80% the consensus sequence and 20% a mixture of the other 3 bases, 95% the consensus sequence and 5% a mixture of the other 3 bases, etc.

Libraries of mutant tRNA's can be generated using various mutagenesis techniques known in the art. For example, the mutant tRNA's can be generated by site-specific mutations, random point mutations, homologous recombination, DNA shuffling or other recursive mutagenesis methods, chimeric construction or any combination thereof.

Additional mutations can be introduced at a specific position(s), e.g., at a non-conservative position(s), or at a conservative position(s), at a randomized position(s), or a combination thereof in a desired loop or region of a tRNA, e.g., an anticodon loop, the acceptor stem, D arm or loop, variable loop, PVC arm or loop, other regions of the tRNA molecule, or a combination thereof. Mutations may include matched base pairs in the stem region.

Typically, an O-tRNA is obtained by subjecting to negative selection a population of cells of a first species, where the cells comprise a member of the plurality of potential O-tRNA's. The negative selection eliminates cells that comprise a member of the plurality of potential O-tRNA's that is aminoacylated by an aminoacyl-tRNA synthetase (RS) that is endogenous to the cells. This provides a pool of tRNA's that are orthogonal to the cell of the first species.

In certain embodiments of the negative selection, a selector codon(s) is introduced into polynucleotide that encodes a negative selection marker, e.g., an enzyme that confers antibiotic resistance, e.g., β-lactamase, an enzyme that confers a detectable product, e.g., β-galactosidase, chloramphenicol acetyltransferase (CAT), e.g., a toxic product, such as barnase, at a non-essential position, etc. Screening/selection can be done by growing the population of cells in the presence of a selection agent (e.g., an antibiotic, such as ampicillin). In one embodiment, the concentration of the selection agent is varied.

For example, to measure the activity of suppressor tRNA's, a selection system is used that is based on the in vivo suppression of selector codon, e.g., nonsense or frameshift mutations introduced into a polynucleotide that encodes a negative selection marker, e.g., a gene for β-lactamase (bla). For example, polynucleotide variants, e.g., bla variants, with, e.g., TAG, AGGA, and TGA, at position a certain position, are constructed. Cells, e.g., bacteria, are transformed with these polynucleotides. In the case of an orthogonal tRNA, which cannot be efficiently charged by endogenous *E. coli* synthetases, antibiotic resistance, e.g., ampicillin resistance, should be about or less than that for a bacteria transformed with no plasmid. If the tRNA is not orthogonal, or if a heterologous synthetase capable of charging the tRNA is co-expressed in the system, a higher level of antibiotic, e.g., ampicillin, resistance is be observed. Cells, e.g., bacteria, are chosen that are unable to grow on LB agar plates with antibiotic concentrations about equal to cells transformed with no plasmids.

In the case of a toxic product (e.g., ribonuclease barnase), when a member of the plurality of potential tRNA's is aminoacylated by endogenous host, e.g., *Escherichia coli* synthetases (i.e., it is not orthogonal to the host, e.g., *Escherichia coli* synthetases), the selector codon is suppressed and the toxic polynucleotide product produced leads to cell death. Cells harboring orthogonal tRNA or non-functional tRNA's survive.

In one embodiment, the pool of tRNA's that are orthogonal to a desired organism are then subjected to a positive selection in which a selector codon is placed in a positive selection marker, e.g., encoded by a drug resistance gene, such a β-lactamase gene. The positive selection is performed on cell comprising a polynucleotide encoding or comprising a member of the pool of tRNA's, a polynucleotide encoding a positive selection marker, and a polynucleotide encoding cognate RS. These polynucleotides are expressed in the cell and the cell is grown in the presence of a selection agent, e.g., ampicillin. tRNA's are then selected for their ability to be aminoacylated by the coexpressed cognate synthetase and to insert an amino acid in response to this selector codon. Typically, these cells show an enhancement in suppression efficiency compared to cells harboring non-functional tRNA's, or tRNA's that cannot efficiently be recognized by the synthetase of interest. The cell harboring the non-functional or tRNA's that are not efficiently recognized by the synthetase of interest are sensitive to the antibiotic. Therefore, tRNA's that: (i) are not substrates for endogenous host, e.g., *Escherichia coli*, synthetases; (ii) can be aminoacylated by the synthetase of interest; and (iii) are functional in translation survive both selections.

The stringency of the selection, e.g., the positive selection, the negative selection or both the positive and negative selection, in the above described-methods, optionally may be varied. For example, because barnase is an extremely toxic protein, the stringency of the negative selection can be controlled by introducing different numbers of selector codons into the barnase gene and/or by using an inducible promoter. In another example, the concentration of the selection or screening agent is varied (e.g., ampicillin). In one aspect, the stringency is varied because the desired activity can be low during early rounds. Thus, less stringent selection criteria are applied in early rounds and more stringent criteria are applied in later rounds of selection. In certain embodiments, the negative selection, the positive selection, or both the negative and positive selection can be repeated multiple times. Multiple different negative selection markers, positive selection markers or both negative and positive selection markers can be used. In certain embodiments, the positive and negative selection marker can be the same.

Other types of selections/screening can be used in the invention for producing orthogonal translational components, e.g., an O-tRNA, an O-RS, and an O-tRNA/O-RS pair. For example, the negative selection marker, the positive selection marker or both the positive and negative selection markers can include a marker that fluoresces or catalyzes a luminescent reaction in the presence of a suitable reactant. In another embodiment, a product of the marker is detected by fluorescence-activated cell sorting (FACS) or by luminescence. Optionally, the marker includes an affinity based screening marker. See, Francisco, J. A., et al., (1993) *Production and fluorescence-activated cell sorting of Escherichia coli expressing a functional antibody fragment on the external surface. Proc Natl Acad Sci USA.* 90:10444-8.

Additional methods for producing a recombinant orthogonal tRNA can be found, e.g., in U.S. patent application Ser. No. 10/126,931, entitled "Methods and Compositions for the Production of Orthogonal tRNA-Aminoacyl tRNA Synthetase Pairs" and Ser. No. 10/126,127, entitled "In vivo Incorporation of Unnatural Amino Acids," and U.S. Ser. No. 10/825,867 entitled "EXPANDING THE EUKARYOTIC GENETIC CODE." See also, Forster et al., (2003) *Programming peptidomimetic synthetases by translating genetic codes designed de novo. PNAS* 100(11):6353-6357; and, Feng et al., (2003), *Expanding tRNA recognition of a tRNA synthetase by a single amino acid change, PNAS* 100(10): 5676-5681.

A tRNA of the present invention may be aminoacylated with a desired amino acid by any method or technique, including but not limited to, chemical or enzymatic aminoacylation.

Aminoacylation may be accomplished by aminoacyl tRNA synthetases or by other enzymatic molecules, including but not limited to, ribozymes. The term "ribozyme" is interchangeable with "catalytic RNA." Cech and coworkers (Cech, 1987, Science, 236:1532-1539; McCorkle et al., 1987, Concepts Biochem. 64:221-226) demonstrated the presence of naturally occurring RNAs that can act as catalysts (ribozymes). However, although these natural RNA catalysts have only been shown to act on ribonucleic acid substrates for cleavage and splicing, the recent development of artificial evolution of ribozymes has expanded the repertoire of catalysis to various chemical reactions. Studies have identified RNA molecules that can catalyze aminoacyl-RNA bonds on their own (2')3'-termini (Illangakekare et al., 1995 Science 267:643-647), and an RNA molecule which can transfer an amino acid from one RNA molecule to another (Lohse et al., 1996, Nature 381:442-444).

U.S. Patent Application Publication 2003/0228593, which is incorporated by reference herein, describes methods to construct ribozymes and their use in aminoacylation of tRNAs with naturally encoded and non-naturally encoded amino acids. Substrate-immobilized forms of enzymatic molecules that can aminoacylate tRNAs, including but not limited to, ribozymes, may enable efficient affinity purification of the aminoacylated products. Examples of suitable substrates include agarose, sepharose, and magnetic beads. The production and use of a substrate-immobilized form of ribozyme for aminoacylation is described in Chemistry and Biology 2003, 10; 1077-1084 and U.S. Patent Application Publication 2003/0228593, which is incorporated by reference herein.

Chemical aminoacylation methods include, but are not limited to, those introduced by Hecht and coworkers (Hecht, S. M. Acc. Chem. Res. 1992, 25, 545; Heckler, T. G.; Roesser, J. R.; Xu, C.; Chang, P.; Hecht, S. M. Biochemistry 1988, 27, 7254; Hecht, S. M.; Alford, B. L.; Kuroda, Y.; Kitano, S. J. Biol. Chem. 1978, 253, 4517) and by Schultz, Chamberlin, Dougherty and others (Cornish, V. W.; Mendel, D.; Schultz, P. G. Angew. Chem. Int. Ed. Engl. 1995, 34, 621; Robertson, S. A.; Ellman, J. A.; Schultz, P. G. J. Am. Chem. Soc. 1991, 113, 2722; Noren, C. J.; Anthony-Cahill, S. J.; Griffith, M. C.; Schultz, P. G. Science 1989, 244, 182; Bain, J. D.; Glabe, C. G.; Dix, T. A.; Chamberlin, A. R. J. Am. Chem. Soc. 1989, 111, 8013; Bain, J. D. et al. Nature 1992, 356, 537; Gallivan, J. P.; Lester, H. A.; Dougherty, D. A. Chem. Biol. 1997, 4, 740; Turcatti, et al. J. Biol. Chem. 1996, 271, 19991; Nowak, M. W. et al. Science, 1995, 268, 439; Saks, M. E. et al. J. Biol. Chem. 1996, 271, 23169; Hohsaka, T. et al. J. Am. Chem. Soc. 1999, 121, 34), to avoid the use of synthetases in aminoacylation. Such methods or other chemical aminoacylation methods may be used to aminoacylate tRNA molecules of the invention.

Biosynthetic methods that employ chemically modified aminoacyl-tRNAs have been used to incorporate several biophysical probes into proteins synthesized in vitro. See the following publications and references cited within: Brunner, J. *New Photolabeling and crosslinking methods, Annu. Rev Biochem,* 62:483-514 (1993); and, Krieg, U. C., Walter, P., Hohnson, A. E. *Photocrosslinking of the signal sequence of nascent preprolactin of the 54-kilodalton polypeptide of the signal recognition particle, Proc. Natl. Acad. Sci,* 83(22): 8604-8608 (1986).

Previously, it has been shown that unnatural amino acids can be site-specifically incorporated into proteins in vitro by the addition of chemically aminoacylated suppressor tRNAs to protein synthesis reactions programmed with a gene containing a desired amber nonsense mutation. Using these approaches, one can substitute a number of the common twenty amino acids with close structural homologues, e.g., fluorophenylalanine for phenylalanine, using strains auxotropic for a particular amino acid. See, e.g., Noren, C. J., Anthony-Cahill, Griffith, M. C., Schultz, P. G. *A general method for site-specific incorporation of unnatural amino acids into proteins, Science,* 244: 182-188 (1989); M. W. Nowak, et al., *Science* 268:439-42 (1995); Bain, J. D., Glabe, C. G., Dix, T. A., Chamberlin, A. R., Diala, E. S. *Biosynthetic site-specific Incorporation of a non-natural amino acid into a polypeptide, J. Am. Chem Soc,* 111:8013-8014 (1989); N. Budisa et al., *FASEB J.* 13:41-51 (1999); Ellman, J. A., Mendel, D., Anthony-Cahill, S., Noren, C. J., Schultz, P. G. *Biosynthetic method for introducing unnatural amino acids site-specifically into proteins, Methods in Enz.,* vol. 202, 301-336 (1992); and, Mendel, D., Cornish, V. W. & Schultz, P. G. *Site-Directed Mutagenesis with an Expanded Genetic Code, Annu Rev Biophys. Biomol Struct.* 24, 435-62 (1995).

For example, a suppressor tRNA was prepared that recognized the stop codon UAG and was chemically aminoacylated with an unnatural amino acid. Conventional site-directed mutagenesis was used to introduce the stop codon TAG, at the site of interest in the protein gene. See, e.g., Sayers, J. R., Schmidt, W. Eckstein, F. 5'-3' *Exonucleases in phosphorothioate-based olignoucleotide-directed mutagenesis, Nucleic Acids Res,* 16(3):791-802 (1988). When the acylated suppressor tRNA and the mutant gene were combined in an in vitro transcription/translation system, the unnatural amino acid was incorporated in response to the UAG codon which gave a protein containing that amino acid at the specified position. Experiments using [$^3$H]-Phe and experiments with α-hydroxy acids demonstrated that only the desired amino acid is incorporated at the position specified by the UAG codon and that this amino acid is not incorporated at any other site in the protein. See, e.g., Noren, et al, supra; Kobayashi et al., (2003) Nature Structural Biology 10(6):425-432; and, Ellman, J. A., Mendel, D., Schultz, P. G. *Site-specific incorporation of novel backbone structures into proteins, Science,* 255(5041):197-200 (1992).

Methods for generating catalytic RNA may involve generating separate pools of randomized ribozyme sequences, performing directed evolution on the pools, screening the pools for desirable amino acylation activity, and selecting sequences of those ribozymes exhibiting desired aminoacylation activity.

Ribozymes can comprise motifs and/or regions that facilitate acylation activity, such as a GGU motif and a U-rich region. For example, it has been reported that U-rich regions can facilitate recognition of an amino acid substrate, and a GGU-motif can form base pairs with the 3' termini of a tRNA. In combination, the GGU and motif and U-rich region facilitate simultaneous recognition of both the amino acid and tRNA simultaneously, and thereby facilitate amino acylation of the 3' terminus of the tRNA.

Ribozymes can be generated by in vitro selection using a partially randomized r24mini conjugated with tRNA$^{Asn}_{CCCG}$, followed by systematic engineering of a consensus sequence found in the active clones. An exemplary ribozyme obtained by this method is termed "Fx3 ribozyme" and is described in U.S. Pub. App. No. 2003/0228593, the contents of which is incorporated by reference herein, acts as a versatile catalyst for the synthesis of various aminoacyl-tRNAs charged with cognate non-natural amino acids.

Immobilization on a substrate may be used to enable efficient affinity purification of the aminoacylated tRNAs. Examples of suitable substrates include, but are not limited to, agarose, sepharose, and magnetic beads. Ribozymes can be immobilized on resins by taking advantage of the chemical structure of RNA, such as the 3'-cis-diol on the ribose of RNA can be oxidized with periodate to yield the corresponding dialdehyde to facilitate immobilization of the RNA on the resin. Various types of resins can be used including inexpensive hydrazide resins wherein reductive amination makes the interaction between the resin and the ribozyme an irreversible linkage. Synthesis of aminoacyl-tRNAs can be significantly facilitated by this on-column aminoacylation technique. Kourouklis et al. Methods 2005; 36:239-4 describe a column-based aminoacylation system.

Isolation of the aminoacylated tRNAs can be accomplished in a variety of ways. One suitable method is to elute the aminoacylated tRNAs from a column with a buffer such as a sodium acetate solution with 10 mM EDTA, a buffer containing 50 mM N-(2-hydroxyethyl)piperazine-N'-(3-propanesulfonic acid), 12.5 mM KCl, pH 7.0, 10 mM EDTA, or simply an EDTA buffered water (pH 7.0).

The aminoacylated tRNAs of the present invention can be added to translation reactions in order to incorporate the amino acid with which the tRNA was aminoacylated in a position of choice in a polypeptide made by the translation reaction. Examples of translation systems in which the aminoacylated tRNAs of the present invention may be used include, but are not limited to cell lysates. Cell lysates provide reaction components necessary for in vitro translation of a polypeptide from an input mRNA. Examples of such reaction components include but are not limited to ribosomal proteins, rRNA, amino acids, tRNAs, GTP, ATP, translation initiation and elongation factors and additional factors associated with translation. Additionally, translation systems may be batch translations or compartmentalized translation. Batch translation systems combine reaction components in a single compartment while compartmentalized translation systems separate the translation reaction components from reaction products that can inhibit the translation efficiency. Such translation systems are available commercially.

Further, a coupled transcription/translation system may be used. Coupled transcription/translation systems allow for both transcription of an input DNA into a corresponding mRNA, which is in turn translated by the reaction components. An example of a commercially available coupled transcription/translation is the Rapid Translation System (RTS, Roche Inc.). The system includes a mixture containing *E. coli* lysate for providing translational components such as ribosomes and translation factors. Additionally, an RNA polymerase is included for the transcription of the input DNA into an mRNA template for use in translation. RTS can use compartmentalization of the reaction components by way of a membrane interposed between reaction compartments, including a supply/waste compartment and a transcription/translation compartment.

Aminoacylation of tRNA may be performed by other agents, including but not limited to, transferases, polymerases, catalytic antibodies, multi-functional proteins, and the like.

Orthogonal Aminoacyl-tRNA Synthetases (O-RS)

An O-RS preferentially aminoacylates an O-tRNA of the present invention with a selected amino acid in vitro or in vivo. An O-RS of the present invention can be provided to the translation system (e.g., in vitro translation components, or a cell) by a polypeptide that includes an O-RS and/or by a polynucleotide that encodes an O-RS or a portion thereof. An O-RS, or a portion thereof, is encoded by a polynucleotide sequence or a complementary polynucleotide sequence thereof, or a conservative variation thereof. An O-tRNA of the present invention may be aminoacylated by a number of different O-RS molecules, including but not limited to, those disclosed herein.

Methods for identifying an orthogonal aminoacyl-tRNA synthetase (O-RS), e.g., an O-RS, for use with an O-tRNA, e.g., an O-tRNA, are also a feature of the present invention. For example a method includes subjecting to positive selection a population of cells of a first species, where the cells each comprise: 1) a member of a plurality of aminoacyl-tRNA synthetases (RSs), where the plurality of RSs comprise mutant RSs, RSs derived from a species other than the first species or both mutant RSs and RSs derived from a species other than the first species; 2) the orthogonal tRNA (O-tRNA) from a second species; and 3) a polynucleotide that encodes a positive selection marker and comprises at least one selector codon. Cells are selected or screened for those that show an enhancement in suppression efficiency compared to cells lacking or with a reduced amount of the member of the plurality of RSs. Cells having an enhancement in suppression efficiency comprise an active RS that aminoacylates the O-tRNA. A level of aminoacylation (in vitro or in vivo) by the active RS of a first set of tRNA's from the first species is compared to the level of aminoacylation (in vitro or in vivo) by the active RS of a second set of tRNA's from the second species. The level of aminoacylation can be determined by a detectable substance (e.g., a labeled amino acid or unnatural amino acid). The active RS that more efficiently aminoacylates the second set of tRNA's compared to the first set of tRNA's is selected, thereby providing the orthogonal aminoacyl-tRNA synthetase for use with the O-tRNA. An O-RS, e.g., an O-RS, identified by the method is also a feature of the present invention.

Any of a number of assays can be used to determine aminoacylation. These assays can be performed in vitro or in vivo. For example, in vitro aminoacylation assays are described in, e.g., Hoben, P., and Soil, D. (1985) Methods Enzymol. 113:55-59 and in U.S. Patent Application Publication No. 2003/0228593. Aminoacylation can also be determined by using a reporter along with orthogonal translation components and detecting the reporter in a cell expressing a polynucleotide comprising at least one selector codon that encodes a protein. See also, U.S. patent application Ser. No. 10/126,927, entitled "IN VIVO INCORPORATION OF UNNATURAL AMINO ACIDS;" and, U.S. Ser. No. 10/825,867 entitled "EXPANDING THE EUKARYOTIC GENETIC CODE."

An identified O-RS can be further manipulated to alter the substrate specificity of the synthetase so that only a desired unnatural amino acid, but not any of the common 20 amino acids, are charged to the O-tRNA. Methods to generate an orthogonal aminoacyl tRNA synthetases with a substrate specificity for an unnatural amino acid include mutating the synthetase, e.g., at the active site in the synthetase, at the editing mechanism site in the synthetase, at different sites by combining different domains of synthetases, or the like, and applying a selection process. A strategy is used that is based on the combination of a positive selection followed by a negative selection. In the positive selection, suppression of the selector codon introduced at a non-essential position(s) of a positive marker allows cells to survive under positive selection pressure. In the presence of both natural and unnatural amino acids, survivors thus encode active synthetases charging the orthogonal suppressor tRNA with either a natural or unnatural amino acid. In the negative selection, suppression of a selector codon introduced at a non-essential position(s) of a negative marker removes synthetases with natural amino acid specificities. Survivors of the negative and positive selection encode synthetases that aminoacylate (charge) the orthogonal suppressor tRNA with unnatural amino acids only. These synthetases can then be subjected to further mutagenesis, e.g., DNA shuffling or other recursive mutagenesis methods.

The library of mutant O-RSs can be generated using various mutagenesis techniques known in the art. For example, the mutant RSs can be generated by site-specific mutations, random point mutations, homologous recombination, DNA shuffling or other recursive mutagenesis methods, chimeric construction or any combination thereof. For example, a library of mutant RSs can be produced from two or more other, e.g., smaller, less diverse "sub-libraries." Chimeric libraries of RSs are also included in the invention. It should be noted that libraries of tRNA synthetases from various organisms (e.g., microorganisms such as eubacteria or archaebacteria) such as libraries that comprise natural diversity (see, e.g., U.S. Pat. No. 6,238,884 to Short et al; U.S. Pat. No. 5,756,316 to Schallenberger et al; U.S. Pat. No. 5,783,431 to Petersen et al; U.S. Pat. No. 5,824,485 to Thompson et al; U.S. Pat. No. 5,958,672 to Short et al), are optionally constructed and screened for orthogonal pairs.

Once the synthetases are subject to the positive and negative selection/screening strategy, these synthetases can then be subjected to further mutagenesis. For example, a nucleic acid that encodes the O-RS can be isolated; a set of polynucleotides that encode mutated O-RSs (e.g., by random mutagenesis, site-specific mutagenesis, recombination or any combination thereof) can be generated from the nucleic acid; and, these individual steps or a combination of these steps can be repeated until a mutated O-RS is obtained that preferentially aminoacylates the O-tRNA with the unnatural amino acid. In one aspect of the present invention, the steps are performed multiple times, e.g., at least two times.

Additional levels of selection/screening stringency can also be used in the methods of the present invention, for producing O-tRNA, O-RS, or pairs thereof. The selection or screening stringency can be varied on one or both steps of the method to produce an O-RS. This could include, e.g., varying the amount of selection/screening agent that is used, etc. Additional rounds of positive and/or negative selections can also be performed. Selecting or screening can also comprise one or more positive or negative selection or screening that includes, e.g., a change in amino acid permeability, a change in translation efficiency, a change in translational fidelity, etc. Typically, the one or more change is based upon a mutation in one or more gene in an organism in which an orthogonal tRNA-tRNA synthetase pair is used to produce protein.

Other types of selections can be used in the present invention for, e.g., O-RS, O-tRNA, and O-tRNA/O-RS pair. The positive selection marker can be any of a variety of molecules including, but not limited to, a product that provides a nutritional supplement for growth and the selection is performed on a medium that lacks the nutritional supplement. Examples of polynucleotides that encode positive selection markers include, but are not limited to, e.g., a reporter gene based on complementing the amino acid auxotrophy of a cell, a his3 gene (e.g., where the his3 gene encodes an imidazole glycerol phosphate dehydratase, detected by providing 3-aminotriazole (3-AT)), ura3 gene, leu2 gene, lys2 gene, lacZ gene, adh gene, etc. See, e.g., G. M. Kishore, & D. M. Shah, (1988), Amino acid biosynthesis inhibitors as herbicides, Annual Review of Biochemistry 57:627-663. In one embodiment, lacZ production is detected by ortho-nitrophenyl-β-D-galactopyranoside (ONPG) hydrolysis. See, e.g., I. G. Serebriiskii, & E. A. Golemis, (2000), Uses of lacZ to study gene function: evaluation of beta-galactosidase assays employed in the yeast two-hybrid system, Analytical Biochemistry 285:1-15. Additional positive selection markers include, e.g., luciferase, green fluorescent protein (GFP), YFP, EGFP, RFP, the product of an antibiotic resistant gene (e.g., chloramphenicol acetyltransferase (CAT)), a transcriptional modulator protein (e.g., GAL4), etc. Optionally, a polynucleotide that encodes a positive selection marker comprises a selector codon.

A polynucleotide that encodes the positive selection marker can be operably linked to a response element. An additional polynucleotide that encodes a transcriptional modulator protein that modulates transcription from the response element, and comprises at least one selector codon, can also be present. The incorporation of the unnatural amino acid into the transcriptional modulator protein by the O-tRNA aminoacylated with the unnatural amino acid results in transcription of the polynucleotide (e.g., reporter gene) encoding the positive selection marker. Optionally, the selector codon is located in or substantially near a portion of the polynucleotide that encodes a DNA binding domain of the transcriptional modulator protein.

A polynucleotide that encodes the negative selection marker can also be operably linked to a response element from which transcription is mediated by the transcriptional modulator protein. See, e.g., A. J. DeMaggio, et al., (2000), The yeast split-hybrid system, Method Enzymol. 328:128-137; H. M. Shih, et al., (1996), A positive genetic selection for disrupting protein-protein interactions: identification of CREB mutations that prevent association with the coactivator CBP, Proc. Natl. Acad. Sci. U.S.A. 93:13896-13901; M. Vidal, et al., (1996), Genetic characterization of a mammalian protein-protein interaction domain by using a yeast reverse two-hybrid system, Proc. Natl. Acad. Sci. U.S.A. 93:10321-10326; and, M. Vidal, et al., (1996), Reverse two-hybrid and one-hybrid systems to detect dissociation of protein-protein and DNA-protein interactions (Proc. Natl. Acad. Sci. U.S.A. 93:10315-10320). The incorporation of a natural amino acid into the transcriptional modulator protein by the O-tRNA aminoacylated with a natural amino acid results in transcription of the negative selection marker. Optionally, the negative selection marker comprises a selector codon. The positive selection marker and/or negative selection marker of the invention can comprise at least two selector codons, which each or both can comprise at least two different selector codons or at least two of the same selector codons.

The transcriptional modulator protein is a molecule that binds (directly or indirectly) to a nucleic acid sequence (e.g., a response element) and modulates transcription of a sequence that is operably linked to the response element. A transcriptional modulator protein can be a transcriptional activator protein (e.g., GAL4, nuclear hormone receptors, AP1, CREB, LEF/tcf family members, SMADs, VP16, SP1, etc.), a transcriptional repressor protein (e.g., nuclear hormone receptors, Groucho/tle family, Engrailed family, etc), or a protein that can have both activities depending on the environment (e.g., LEF/tcf, homobox proteins, etc.). A response element is typically a nucleic acid sequence that is recognized by the transcriptional modulator protein or an additional agent that acts in concert with the transcriptional modulator protein.

Another example of a transcriptional modulator protein is the transcriptional activator protein, GAL4. See, e.g., A. Laughon, et al., (1984), Identification of two proteins encoded by the *Saccharomyces cerevisiae* GAL4 gene, Molecular & Cellular Biology 4:268-275; A. Laughon, & R. F. Gesteland, (1984), Primary structure of the *Saccharomyces cerevisiae* GAL4 gene, Molecular & Cellular Biology 4:260-267; L. Keegan, et al., (1986), Separation of DNA binding from the transcription-activating function of a eukaryotic regulatory protein, Science 231:699-704; and, M. Ptashne, (1988), How eukaryotic transcriptional activators work, Nature 335:683-689. The N-terminal 147 amino acids of this 881 amino acid protein form a DNA binding domain (DBD) that binds DNA sequence specifically. See, e.g., M. Carey, et al., (1989), An amino-terminal fragment of GAL4 binds DNA as a dimer, J. Mol. Biol. 209:423-432; and, E. Giniger, et al., (1985), Specific DNA binding of GAL4, a positive regulatory protein of yeast, Cell 40:767-774. The DBD is linked, by an intervening protein sequence, to a C-terminal 113 amino acid activation domain (AD) that can activate transcription when bound to DNA. See, e.g., J. Ma, & M. Ptashne, (1987), Deletion analysis of GAL4 defines two transcriptional activating segments, Cell 48:847-853: and, J. Ma, & M. Ptashne, (1987), The carboxy-terminal 30 amino acids of GAL4 are recognized by GAL80, Cell 50:137-142. By placing amber codons towards, e.g., the N-terminal DBD of a single polypeptide that contains both the N-terminal DBD of GAL4 and its C-terminal AD, amber suppression by the O-tRNA/O-RS pair can be linked to transcriptional activation by GAL4. GAL4 activated reporter genes can be used to perform both positive and negative selections with the gene.

The medium used for negative selection can comprise a selecting or screening agent that is converted to a detectable substance by the negative selection marker. In one aspect of the invention, the detectable substance is a toxic substance. A polynucleotide that encodes a negative selection marker can be, e.g., an ura3 gene. For example, the URA3 reporter can be placed under control of a promoter that contains GAL4 DNA binding sites. When the negative selection marker is produced, e.g., by translation of a polynucleotide encoding the GAL4 with selector codons, GAL4 activates transcription of URA3. The negative selection is accomplished on a medium that comprises 5-flubroorotic acid (5-FOA), which is converted into a detectable substance (e.g., a toxic substance which kills the cell) by the gene product of the ura3 gene. See, e.g., J. D. Boeke, et al., (1984), A positive selection for mutants lacking orotidine-5'-phosphate decarboxylase activity in yeast: 5-fluoroorotic acid resistance, Molecular & General Genetics 197:345-346); M. Vidal, et al., (1996), Genetic characterization of a mammalian protein-protein interaction domain by using a yeast reverse two-hybrid system., Proc. Natl. Acad. Sci. U.S.A. 93:10321-10326; and, M. Vidal, et al., (1996), Reverse two-hybrid and one-hybrid systems to detect dissociation of protein-protein and DNA-protein interactions., Proc. Natl. Acad. Sci. U.S.A. 93:10315-10320.

As with the positive selection marker, the negative selection marker can also be any of a variety of molecules. The positive selection marker and/or the negative selection marker may be a polypeptide that fluoresces or catalyzes a luminescent reaction in the presence of a suitable reactant. For example, negative selection markers include, but are not limited to, e.g., luciferase, green fluorescent protein (GFP), YFP, EGFP, RFP, the product of an antibiotic resistant gene (e.g., chloramphenicol acetyltransferase (CAT)), the product of a lacZ gene, transcriptional modulator protein, etc. The positive selection marker and/or the negative selection marker may be detected by fluorescence-activated cell sorting (FACS) or by luminescence. The positive selection marker and/or negative selection marker may comprise an affinity based screening marker. The same polynucleotide can encode both the positive selection marker and the negative selection marker. For example, the positive selection step, the negative selection step or both the positive and negative selection steps and can include using a reporter, wherein the reporter is detected by fluorescence-activated cell sorting (FACS). For example, a positive selection can be done first with a positive selection marker, e.g., chloramphenicol acetyltransferase (CAT) gene, where the CAT gene comprises a selector codon, e.g., an amber stop codon, in the CAT gene, which followed by a negative selection screen, that is based on the inability to suppress a selector codon(s), e.g., two or more, at positions within a negative marker, e.g., T7 RNA polymerase gene. The positive selection marker and the negative selection marker can be found on the same vector, e.g., plasmid. Expression of the negative marker drives expression of the reporter, e.g., green fluorescent protein (GFP). The stringency of the selection and screen can be varied, e.g., the intensity of the light need to fluorescence the reporter can be varied. A positive selection can be done with a reporter as a positive selection marker, which is screened by FACS, followed by a negative selection screen, that is based on the inability to suppress a selector codon(s), e.g., two or more, at positions within a negative marker, e.g., barnase gene.

Optionally, the reporter is displayed on a cell surface, e.g., on a phage display or the like. Cell-surface display, e.g., the OmpA-based cell-surface display system, relies on the expression of a particular epitope, e.g., a poliovirus C3 peptide fused to an outer membrane porin OmpA, on the surface of the *Escherichia coli* cell. The epitope is displayed on the cell surface only when a selector codon in the protein message is suppressed during translation. The displayed peptide then contains the amino acid recognized by one of the mutant aminoacyl-tRNA synthetases in the library, and the cell containing the corresponding synthetase gene can be isolated with antibodies raised against peptides containing specific unnatural amino acids. The OmpA-based cell-surface display system was developed and optimized by Georgiou et al. as an alternative to phage display. See, Francisco, J. A., Campbell, R., Iverson, B. L. & Georgoiu, G. Production and fluorescence-activated cell sorting of *Escherichia coli* expressing a functional antibody fragment on the external surface. Proc. Natl. Acad. Sci. USA 90:10444-8 (1993).

Other embodiments of the present invention include carrying one or more of the selection steps in vitro. The selected component, e.g., synthetase and/or tRNA, can then be introduced into a cell for use in in vivo incorporation of an unnatural amino acid.

Additional details for producing O-RS, and altering the substrate specificity of the synthetase can be found in U.S. patent application Ser. No. 10/126,931 entitled "Methods and Compositions for the Production of Orthogonal tRNA-Aminoacyl tRNA Synthetase Pairs;" and, U.S. Ser. No. 10/825,867 entitled "EXPANDING THE EUKARYOTIC GENETIC CODE," which are incorporated by reference herein. Additional details for producing O-RS can be found in Hamano-Takaku et al., (2000) A mutant *Escherichia coli* Tyrosyl-tRNA Synthetase Utilizes the Unnatural Amino Acid Azatyrosine More Efficiently than Tyrosine, Journal of Biological Chemistry, 275(50:40324-40328; Kiga et al. (2002), An engineered *Escherichia coli* tyrosyl-tRNA synthetase for site-specific incorporation of an unnatural amino acid into proteins in eukaryotic translation and its application in a wheat germ cell-free system, PNAS 99(15): 9715-9723; and, Francklyn et al., (2002), Aminoacyl-tRNA synthetases: Versatile players in the changing theater of translation; RNA, 8:1363-1372, each of which are incorporated by reference herein.

Source and Host Organisms

The translational components of the present invention are typically derived from non-eukaryotic organisms. For example, the orthogonal O-tRNA can be derived from a non-eukaryotic organism, e.g., an archaebacterium, such as *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix*, or the like, or a *eubacterium*, such as *Escherichia coli, Thermus thermophilus, Bacillus stearothermphilus*, or the like, while the orthogonal O-RS can be derived from a non-eukaryotic organism, e.g., *Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix*, or the like, or a *eubacterium*, such as *Escherichia coli, Thermus thermophilus, Bacillus stearothermphilus*, or the like. In one embodiment, eukaryotic sources can also be used, including but not limited to, plants, algae, protists, fungi, yeasts, animals (e.g., mammals, insects, arthropods, etc.), or the like.

The individual components of an O-tRNA/O-RS pair can be derived from the same organism or different organisms. In one embodiment, the O-tRNA/O-RS pair is from the same organism. Alternatively, the O-tRNA and the O-RS of the O-tRNA/O-RS pair are from different organisms. For example, the O-tRNA can be derived from, e.g., a *Halobacterium* sp NRC-1, and the O-RS can be derived from, e.g., a *Methanobacterium thermoautrophicum*.

The O-tRNA, O-RS or O-tRNA/O-RS pair can be selected or screened in vivo or in vitro and/or used in a cell, e.g., a non-eukaryotic cells (such as *E. coli* cell), or a eukaryotic cell, to produce a polypeptide with a selected amino acid (e.g., an unnatural amino acid). A non-eukaryotic cell can be from a variety of sources, such as the Axchaea phylogenetic domain, including but not limited to, *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix*, or the like, or can belong to the Eubacteria phylogenetic domain (including but not limited to, *Escherichia coli, Thermus thermophilus, Bacillus stearothermophilus, Pseudomonas fluorescens, Pseudomonas aeruginosa, Pseudomonas putida*, etc.), or the like. A eukaryotic cell can be from a variety of sources, including but not limited to, a plant (e.g., complex plant such as monocots, or dicots), an algae, a protist, a fungus, a yeast (including but not limited to, *Saccharomyces cerevisiae*), an animal (including but not limited to, a mammal, an insect, an arthropod, etc.), or the like. Compositions of cells with translational components of the present invention are also a feature of the present invention. See also U.S. Ser. No. 10/825,867 entitled "Expanding the Eukaryotic Genetic Code" for screening O-tRNA and/or O-RS in one species for use in another species.

To express a polypeptide of interest with a selected amino acid in a host cell, one may subclone polynucleotides encoding a polypeptide of interest into an expression vector that contains a promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al.

Bacterial expression systems for expressing a polypeptide of interest are available in, including but not limited to, *E. coli, Bacillus* sp., *Pseudomonas fluorescens, Pseudomonas aeruginosa, Pseudomonas putida*, and *Salmonella* (Palva et al., *Gene* 22:229-235 (1983); Mosbach et al., *Nature* 302: 543-545 (1983)). Kits for such expression systems are commercially available. Eukaryotic expression systems for mammalian cells, yeast, and insect cells are well known in the art and are also commercially available.

A tRNA and/or RS of the present invention and/or a polypeptide of interest may be utilized and/or expressed in any number of suitable expression systems including, for example, yeast, insect cells, mammalian cells, and bacteria. A description of exemplary expression systems is provided below.

Yeast

As used herein, the term "yeast" includes any of the various yeasts capable of expressing a polypeptide of interest. Such yeasts include, but are not limited to, ascosporogenous yeasts (*Endomycetales*), basidiosporogenous yeasts and yeasts belonging to the Fungi imperfecti (*Blastomycetes*) group. The ascosporogenous yeasts are divided into two families, Spermophthoraceae and Saccharomycetaceae. The latter is comprised of four subfamilies, Schizosaccharomycoideae (e.g., genus *Schizosaccharomyces*), Nadsonioideae, Lipomycoideae and Saccharomycoideae (e.g., genera *Pichia, Kluyveromyces* and *Saccharomyces*). The basidiosporogenous yeasts include the genera *Leucosporidium, Rhodospo-

*ridium, Sporidiobolus, Filobasidium,* and *Filobasidiella.* Yeasts belonging to the Fungi Imperfecti (*Blastomycetes*) group are divided into two families, Sporobolomycetaceae (e.g., genera *Sporobolomyces* and *Bullera*) and Cryptococcaceae (e.g., genus *Candida*).

Of particular interest for use with the present invention are species within the genera *Pichia, Kluyveromyces, Saccharomyces, Schizosaccharomyces, Hansenula, Torulopsis,* and *Candida*, including, but not limited to, *P. pastoris, P. guillerimondii, S. cerevisiae, S. carlsbergensis, S. diastaticus, S. douglasii, S. kluyveri, S. norbensis, S. oviformis, K. lactis, K. fragilis, C. albicans, C. maltosa,* and *H. polymorpha*. Yeast are generally available from a variety of sources including, but not limited to, the Yeast Genetic Stock Center, Department of Biophysics and Medical Physics, University of California (Berkeley, Calif.), and the American Type Culture Collection ("ATCC") (Manassas, Va.).

The term "yeast host" or "yeast host cell" includes yeast that can be, or has been, used as a recipient for recombinant vectors or other transfer DNA. The term includes the progeny of the original yeast host cell that has received the recombinant vectors or other transfer DNA. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding a polypeptide of interest, are included in the progeny intended by this definition.

Expression and transformation vectors, including extrachromosomal replicons or integrating vectors, have been developed for transformation into many yeast hosts. For example, expression vectors have been developed for *S. cerevisiae* (Sikorski et al., GENETICS (1989) 122:19; Ito et al., J. BACTERIOL. (1983) 153:163; Hinnen et al., PROC. NATL. ACAD. SCI. USA (1978) 75:1929); *C. albicans* (Kurtz et al., MOL. CELL. BIOL. (1986) 6:142); *C. maltosa* (Kunze et al., J. BASIC MICROBIOL. (1985) 25:141); *H. polymorpha* (Gleeson et al., J. GEN. MICROBIOL. (1986) 132:3459; Roggenkamp et al., MOL. GENETICS AND GENOMICS (1986) 202:302); *K. fragilis* (Das et al., J. BACTERIOL, (1984) 158:1165); *K. lactis* (De Louveneourt et al., J. BACTERIOL. (1983) 154:737; Van den Berg et al., BIOTECHNOLOGY (NY) (1990) 8:135); *P. guillerimondii* (Kunze et al., J. BASIC MICROBIOL. (1985) 25:141); *P. pastoris* (U.S. Pat. Nos. 5,324,639; 4,929,555; and 4,837,148; Cregg et al., MOL. CELL. BIOL. (1985) 5:3376); *Schizosaccharomyces pombe* (Beach et al., NATURE (1982) 300:706); and *Y. lipolytica; A. nidulans* (Ballance et al., BIOCHEM. BIOPHYS. RES. COMMUN. (1983) 112:284-89; Tilburn et al., GENE (1983) 26:205-221; and Yelton et al., PROC. NATL. ACAD. SCI. USA (1984) 81:1470-74); *A. niger* (Kelly and Hynes, EMBO J. (1985) 4:475-479); *T. reesia* (EP 0 244 234); and filamentous fungi such as, e.g., *Neurospora, Tolypocladium* (WO 91/00357), each incorporated by reference herein.

Control sequences for yeast vectors are known to those of ordinary skill in the art and include, but are not limited to, promoter regions from genes such as alcohol dehydrogenase (ADH) (EP 0 284 044); enolase; glucokinase; glucose-6-phosphate isomerase; glyceraldehyde-3-phosphate-dehydrogenase (GAP or GAPDH); hexokinase; phosphofructokinase; 3-phosphoglycerate mutase; and pyruvate kinase (PyK) (EP 0 329 203). The yeast PHO5 gene, encoding acid phosphatase, also may provide useful promoter sequences (Miyanohara et al., PROC. NATL. ACAD. SCI. USA (1983) 80:1). Other suitable promoter sequences for use with yeast hosts may include the promoters for 3-phosphoglycerate kinase (Hitzeman et al., J. BIOL. CHEM. (1980) 255:12073); and other glycolytic enzymes, such as pyruvate decarboxylase, triosephosphate isomerase, and phosphoglucose isomerase (Holland et al., BIOCHEMISTRY (1978) 17:4900; Hess et al., J. ADV. ENZYME REG. (1969) 7:149). Inducible yeast promoters having the additional advantage of transcription controlled by growth conditions may include the promoter regions for alcohol dehydrogenase 2; isocytochrome C; acid phosphatase; metallothionein; glyceraldehyde-3-phosphate dehydrogenase; degradative enzymes associated with nitrogen metabolism; and enzymes responsible for maltose and galactose utilization. Suitable vectors and promoters for use in yeast expression are further described in EP 0 073 657.

Yeast enhancers also may be used with yeast promoters. In addition, synthetic promoters may also function as yeast promoters. For example, the upstream activating sequences (UAS) of a yeast promoter may be joined with the transcription activation region of another yeast promoter, creating a synthetic hybrid promoter. Examples of such hybrid promoters include the ADH regulatory sequence linked to the GAP transcription activation region. See U.S. Pat. Nos. 4,880,734 and 4,876,197, which are incorporated by reference herein. Other examples of hybrid promoters include promoters that consist of the regulatory sequences of the ADH2, GAL4, GAL10, or PHO5 genes, combined with the transcriptional activation region of a glycolytic enzyme gene such as GAP or PyK. See EP 0 164 556. Furthermore, a yeast promoter may include naturally occurring promoters of non-yeast origin that have the ability to bind yeast RNA polymerase and initiate transcription.

Other control elements that may comprise part of the yeast expression vectors include terminators, for example, from GAPDH or the enolase genes (Holland et al., J. BIOL. CHEM. (1981) 256:1385). In addition, the origin of replication from the 2µ plasmid origin is suitable for yeast. A suitable selection gene for use in yeast is the trp1 gene present in the yeast plasmid. See Tschumper et al., GENE (1980) 10:157; Kingsman et al., GENE (1979) 7:141. The trp1 gene provides a selection marker for a mutant strain of yeast lacking the ability to grow in tryptophan. Similarly, Leu2-deficient yeast strains (ATCC 20,622 or 38,626) are complemented by known plasmids bearing the Leu2 gene.

Methods of introducing exogenous DNA into yeast hosts are known to those of ordinary skill in the art, and typically include, but are not limited to, either the transformation of spheroplasts or of intact yeast host cells treated with alkali cations. For example, transformation of yeast can be carried out according to the method described in Hsiao et al., PROC. NATL. ACAD. SCI. USA (1979) 76:3829 and Van Solingen et al., J. BACT. (1977) 130:946. However, other methods for introducing DNA into cells such as by nuclear injection, electroporation, or protoplast fusion may also be used as described generally in SAMBROOK ET AL., MOLECULAR CLONING: A LAB. MANUAL (2001). Yeast host cells may then be cultured using standard techniques known to those of ordinary skill in the art.

Other methods for expressing heterologous proteins in yeast host cells are known to those of ordinary skill in the art. See generally U.S. Patent Publication No. 20020055169, U.S. Pat. Nos. 6,361,969; 6,312,923; 6,183,985; 6,083,723; 6,017,731; 5,674,706; 5,629,203; 5,602,034; and 5,089,398; U.S. Reexamined Pat. Nos. RE37,343 and RE35,749; PCT Published Patent Applications WO 99/07862; WO 98/37208; and WO 98/26080; European Patent Applications EP 0 946 736; EP 0 732 403; EP 0 480 480; WO 90/10277; EP 0 340 986; EP 0 329 203; EP 0 324 274; and EP 0 164 556. See also Gellissen et al., ANTONIE VAN LEEUWENHOEK (1992) 62(1-2):79-

93; Romanos et al., YEAST (1992) 8(6):423-488; Goeddel, METHODS IN ENZYMOLOGY (1990) 185:3-7, each incorporated by reference herein.

The yeast host strains may be grown in fermentors during the amplification stage using standard feed batch fermentation methods known to those of ordinary skill in the art. The fermentation methods may be adapted to account for differences in a particular yeast host's carbon utilization pathway or mode of expression control. For example, fermentation of a *Saccharomyces* yeast host may require a single glucose feed, complex nitrogen source (e.g., casein hydrolysates), and multiple vitamin supplementation. In contrast, the methylotrophic yeast *P. pastoris* may require glycerol, methanol, and trace mineral feeds, but only simple ammonium (nitrogen) salts for optimal growth and expression. See, e.g., U.S. Pat. No. 5,324,639; Elliott et al., J. PROTEIN CHEM. (1990) 9:95; and Fieschko et al., BIOTECH. BIOENG. (1987) 29:1113, incorporated by reference herein.

Such fermentation methods, however, may have certain common features independent of the yeast host strain employed. For example, a growth limiting nutrient, typically carbon, may be added to the fermentor during the amplification phase to allow maximal growth. In addition, fermentation methods generally employ a fermentation medium designed to contain adequate amounts of carbon, nitrogen, basal salts, phosphorus, and other minor nutrients (vitamins, trace minerals and salts, etc.). Examples of fermentation media suitable for use with *Pichia* are described in U.S. Pat. Nos. 5,324,639 and 5,231,178, which are incorporated by reference herein.

Baculovirus-Infected Insect Cells

The term "insect host" or "insect host cell" refers to a insect that can be, or has been, used as a recipient for recombinant vectors or other transfer DNA. The term includes the progeny of the original insect host cell that has been transfected. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding a polypeptide of interest, are included in the progeny intended by this definition.

The selection of suitable insect cells for expression of a polypeptide of interest is known to those of ordinary skill in the art. Several insect species are well described in the art and are commercially available including *Aedes aegypti, Bombyx mori, Drosophila melanogaster, Spodoptera frugiperda*, and *Trichoplusia ni*. In selecting insect hosts for expression, suitable hosts may include those shown to have, inter alia, good secretion capacity, low proteolytic activity, and overall robustness. Insect are generally available from a variety of sources including, but not limited to, the Insect Genetic Stock Center, Department of Biophysics and Medical Physics, University of California (Berkeley, Calif.); and the American Type Culture Collection ("ATCC") (Manassas, Va.).

Generally, the components of a baculovirus-infected insect expression system include a transfer vector, usually a bacterial plasmid, which contains both a fragment of the baculovirus genome, and a convenient restriction site for insertion of the heterologous gene to be expressed; a wild type baculovirus with sequences homologous to the baculovirus-specific fragment in the transfer vector (this allows for the homologous recombination of the heterologous gene in to the baculovirus genome); and appropriate insect host cells and growth media. The materials, methods and techniques used in constructing vectors, transfecting cells, picking plaques, growing cells in culture, and the like are known in the art and manuals are available describing these techniques.

After inserting the heterologous gene into the transfer vector, the vector and the wild type viral genome are transfected into an insect host cell where the vector and viral genome recombine. The packaged recombinant virus is expressed and recombinant plaques are identified and purified. Materials and methods for baculovirus/insect cell expression systems are commercially available in kit form from, for example, Invitrogen Corp. (Carlsbad, Calif.). These techniques are generally known to those of ordinary skill in the art and fully described in SUMMERS AND SMITH, TEXAS AGRICULTURAL EXPERIMENT STATION BULLETIN No. 1555 (1987), herein incorporated by reference. See also, RICHARDSON, 39 METHODS IN MOLECULAR BIOLOGY: BACULOVIRUS EXPRESSION PROTOCOLS (1995); AUSUBEL ET AL., CURRENT PROTOCOLS IN MOLECULAR BIOLOGY 16.9-16.11 (1994); KING AND POSSEE, THE BACULOVIRUS SYSTEM: A LABORATORY GUIDE (1992); and O'REILLY ET AL., BACULOVIRUS EXPRESSION VECTORS: A LABORATORY MANUAL (1992).

Indeed, the production of various heterologous proteins using baculovirus/insect cell expression systems is known to those of ordinary skill in the art. See, e.g., U.S. Pat. Nos. 6,368,825; 6,342,216; 6,338,846; 6,261,805; 6,245,528, 6,225,060; 6,183,987; 6,168,932; 6,126,944; 6,096,304; 6,013,433; 5,965,393; 5,939,285; 5,891,676; 5,871,986; 5,861,279; 5,858,368; 5,843,733; 5,762,939; 5,753,220; 5,605,827; 5,583,023; 5,571,709; 5,516,657; 5,290,686; WO 02/06305; WO 01/90390; WO 01/27301; WO 01/05956; WO 00/55345; WO 00/20032; WO 99/51721; WO 99/45130; WO 99/31257; WO 99/10515; WO 99/09193; WO 97/26332; WO 96/29400; WO 96/25496; WO 96/06161; WO 95/20672; WO 93/03173; WO 92/16619; WO 92/02628; WO 92/01801; WO 90/14428; WO 90/10078; WO 90/02566; WO 90/02186; WO 90/01556; WO 89/01038; WO 89/01037; WO 88/07082, which are incorporated by reference herein.

Vectors that are useful in baculovirus/insect cell expression systems are known in the art and include, for example, insect expression and transfer vectors derived from the baculovirus *Autographacaliformica* nuclear polyhedrosis virus (AcNPV), which is a helper-independent, viral expression vector. Viral expression vectors derived from this system usually use the strong viral polyhedrin gene promoter to drive expression of heterologous genes. See generally, O'Reilly ET AL., BACULOVIRUS EXPRESSION VECTORS: A LABORATORY MANUAL (1992).

Prior to inserting the foreign gene into the baculovirus genome, the above-described components, comprising a promoter, leader (if desired), coding sequence of interest, and transcription termination sequence, are typically assembled into an intermediate transplacement construct (transfer vector). Intermediate transplacement constructs are often maintained in a replicon, such as an extra chromosomal element (e.g., plasmids) capable of stable maintenance in a host, such as bacteria. The replicon will have a replication system, thus allowing it to be maintained in a suitable host for cloning and amplification. More specifically, the plasmid may contain the polyhedrin polyadenylation signal (Miller, ANN. REV. MICROBIO., (1988) 42:177) and a prokaryotic ampicillin-resistance (amp) gene and origin of replication for selection and propagation in *E. coli*.

One commonly used transfer vector for introducing foreign genes into AcNPV is pAc373. Many other vectors, known to those of skill in the art, have also been designed including, for example, pVL985, which alters the polyhedrin start codon from ATG to ATT, and which introduces a BamHI cloning site 32 base pairs downstream from the ATT. See Luckow and Summers, VIROLOGY 170:31 (1989). Other commercially available vectors include, for example, PBlue- Bac4.5/V5-His; pBlueBacHis2; pMelBac; pBlueBac4.5 (Invitrogen Corp., Carlsbad, Calif.).

After insertion of the heterologous gene, the transfer vector and wild type baculoviral genome are co-transfected into an insect cell host. Methods for introducing heterologous DNA into the desired site in the baculovirus virus are known in the art. See SUMMERS AND SMITH, TEXAS AGRICULTURAL EXPERIMENT STATION BULLETIN No. 1555 (1987); Smith et al., MOL. CELL. BIOL. (1983) 3:2156; Luckow and Summers, VIROLOGY (1989) 170:31. For example, the insertion can be into a gene such as the polyhedrin gene, by homologous double crossover recombination; insertion can also be into a restriction enzyme site engineered into the desired baculovirus gene. See Miller et al., BIOESSAYS (1989) 11(4):91.

Transfection may be accomplished by electroporation. See TROTTER AND WOOD, 39 METHODS IN MOLECULAR BIOLOGY (1995); Mann and King, J. GEN. VIROL. (1989) 70:3501. Alternatively, liposomes may be used to transfect the insect cells with the recombinant expression vector and the baculovirus. See, e.g., Liebman et al., BIOTECHNIQUES (1999) 26(1):36; Graves et al., BIOCHEMISTRY (1998) 37:6050; Nomura et al., J. BIOL. CHEM. (1998) 273 (22): 13570; Schmidt et al., PROTEIN EXPRESSION AND PURIFICATION (1998) 12:323; Siffert et al., NATURE GENETICS (1998) 18:45; TILKINS ET AL., CELL BIOLOGY: A LABORATORY HANDBOOK 145-154 (1998); Cai et al., PROTEIN EXPRESSION AND PURIFICATION (1997) 10:263; Dolphin et al., NATURE GENETICS (1997) 17:491; Kost et al., GENE (1997) 190:139; Jakobsson et al., J. BIOL. CHEM. (1996) 271:22203; Rowles et al., J. BIOL. CHEM. (1996) 271(37):22376; Reverey et al., J. BIOL. CHEM. (1996) 271(39):23607-10; Stanley et al., J. BIOL. CHEM. (1995) 270:4121; Sisk et al., J. VIROL. (1994) 68(2):766; and Peng et al., BIOTECHNIQUES (1993) 14(2):274. Commercially available liposomes include, for example, Cellfectin® and Lipofectin® (Invitrogen, Corp., Carlsbad, Calif.). In addition, calcium phosphate transfection may be used. See TROTTER AND WOOD, 39 METHODS IN MOLECULAR BIOLOGY (1995); Kitts, NAR (1990) 18(19):5667; and Mann and King, J. GEN. VIROL. (1989) 70:3501.

Baculovirus expression vectors usually contain a baculovirus promoter. A baculovirus promoter is any DNA sequence capable of binding a baculovirus RNA polymerase and initiating the downstream (3') transcription of a coding sequence (e.g., structural gene) into mRNA. A promoter will have a transcription initiation region which is usually placed proximal to the 5' end of the coding sequence. This transcription initiation region typically includes an RNA polymerase binding site and a transcription initiation site. A baculovirus promoter may also have a second domain called an enhancer, which, if present, is usually distal to the structural gene. Moreover, expression may be either regulated or constitutive.

Structural genes, abundantly transcribed at late times in the infection cycle, provide particularly useful promoter sequences. Examples include sequences derived from the gene encoding the viral polyhedron protein (FRIESEN ET AL., The Regulation of Baculovirus Gene Expression in THE MOLECULAR BIOLOGY OF BACULOVIRUSES (1986); EP 0 127 839 and 0 155 476) and the gene encoding the p10 protein (Vlak et al., J. GEN. VIROL. (1988) 69:765).

The newly formed baculovirus expression vector is packaged into an infectious recombinant baculovirus and subsequently grown plaques may be purified by techniques known to those of ordinary skill in the art. See Miller et al., BIOESSAYS (1989) 11(4):91; SUMMERS AND SMITH, TEXAS AGRICULTURAL EXPERIMENT STATION BULLETIN No. 1555 (1987).

Recombinant baculovirus expression vectors have been developed for infection into several insect cells. For example, recombinant baculoviruses have been developed for, inter alia, Aedes aegypti (ATCC No. CCL-125), Bombyx mori (ATCC No. CRL-8910), Drosophila melanogaster (ATCC No. 1963), Spodoptera frugiperda, and Trichoplusia ni. See Wright, NATURE (1986) 321:718; Carbonell et al., J. VIROL. (1985) 56:153; Smith et al., MOL. CELL. BIOL. (1983) 3:2156. See generally, Fraser et al., IN VITRO CELL. DEV. BIOL. (1989) 25:225. More specifically, the cell lines used for baculovirus expression vector systems commonly include, but are not limited to, Sf9 (Spodoptera frugiperda) (ATCC No. CRL-1711), Sf21 (Spodoptera frugiperda) (Invitrogen Corp., Cat. No. 11497-013 (Carlsbad, Calif.)), Tri-368 (Trichopulsia ni), and High-Five™ BTI-TN-5B1-4 (Trichopulsia ni).

Cells and culture media are commercially available for both direct and fusion expression of heterologous polypeptides in a baculovirus/expression, and cell culture technology is generally known to those of ordinary skill in the art.

E. coli, Pseudomonas Species, and Other Prokaryotes

Bacterial expression techniques are known to those of ordinary skill in the art. A wide variety of vectors are available for use in bacterial hosts. The vectors may be single copy or low or high multicopy vectors. Vectors may serve for cloning and/or expression. In view of the ample literature concerning vectors, commercial availability of many vectors, and even manuals describing vectors and their restriction maps and characteristics, no extensive discussion is required here. As is well-known, the vectors normally involve markers allowing for selection, which markers may provide for cytotoxic agent resistance, prototrophy or immunity. Frequently, a plurality of markers is present, which provide for different characteristics.

A bacterial promoter is any DNA sequence capable of binding bacterial RNA polymerase and initiating the downstream (3') transcription of a coding sequence (e.g. structural gene) into mRNA. A promoter will have a transcription initiation region which is usually placed proximal to the 5' end of the coding sequence. This transcription initiation region typically includes an RNA polymerase binding site and a transcription initiation site. A bacterial promoter may also have a second domain called an operator that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in Escherichia coli (E. coli) [Raibaud et al., ANNU. REV. GENET. (1984) 18:173]. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al., NATURE (1977) 198:1056], and maltose. Additional examples include promoter sequences derived from biosynthetic enzymes such as tryptophan (trp) [Goeddel et al., NUC. ACIDS RES. (1980) 8:4057; Yelverton et al., NUCL. ACIDS RES. (1981) 9:731; U.S. Pat. No. 4,738,921; EP Pub. Nos. 036 776 and 121 775, which are incorporated by reference herein]. The β-galactosidase (bla) promoter system [Weissmann (1981) "The cloning of interferon and other mistakes." In Interferon 3 (Ed. I. Gresser)], bacteriophage lambda PL [Shimatake et al., NATURE (1981) 292:128] and T5 [U.S. Pat. No. 4,689,406, which are incorporated by reference herein] promoter systems also provide useful promoter sequences. Strong promoters, such as the T7 promoter may be used to induce the polypeptide of interest at high levels. Examples of such vectors are known to those of ordinary skill in the art and include the pET29 series from Novagen, and the pPOP vectors described in WO99/05297, which is incorporated by reference herein. Such expression systems produce high levels of polypeptide in the host without compromising host cell viability or growth parameters. pET19 (Novagen) is another vector known in the art.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551,433, which is incorporated by reference herein]. For example, the tac promoter is a hybrid tip-lac promoter comprised of both trp promoter and lac operon sequences that is regulated by the lac repressor [Amann et al., GENE (1983) 25:167; de Boer et al., PROC. NATL. ACAD. SCI. (1983) 80:21]. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system [Studier et al., J. MOL. BIOL. (1986) 189:113; Tabor et al., Proc Natl. Acad. Sci. (1985) 82:1074]. In addition, a hybrid promoter can also be comprised of a bacteriophage promoter and an *E. coli* operator region (EP Pub. No. 267 851).

In addition to a functioning promoter sequence, an efficient ribosome binding site is also useful for the expression of foreign genes in prokaryotes. In *E. coli*, the ribosome binding site is called the Shine-Dalgarno (SD) sequence and includes an initiation codon (ATG) and a sequence 3-9 nucleotides in length located 3-11 nucleotides upstream of the initiation codon [Shine et al., NATURE (1975) 254:34]. The SD sequence is thought to promote binding of mRNA to the ribosome by the pairing of bases between the SD sequence and the 3' and of *E. coli* 16S rRNA [Steitz et al. "Genetic signals and nucleotide sequences in messenger RNA", In Biological Regulation and Development: Gene Expression (Ed. R. F. Goldberger, 1979)]. To express eukaryotic genes and prokaryotic genes with weak ribosome-binding site [Sambrook et al. "Expression of cloned genes in *Escherichia coli*", Molecular Cloning: A Laboratory Manual, 1989].

The term "bacterial host" or "bacterial host cell" refers to a bacterial that can be, or has been, used as a recipient for recombinant vectors or other transfer DNA. The term includes the progeny of the original bacterial host cell that has been transfected. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding a polypeptide of interest, are included in the progeny intended by this definition.

The selection of suitable host bacteria for expression of polypeptides is known to those of ordinary skill in the art. In selecting bacterial hosts for expression, suitable hosts may include those shown to have, inter alfa, good inclusion body formation capacity, low proteolytic activity, and overall robustness. Bacterial hosts are generally available from a variety of sources including, but not limited to, the Bacterial Genetic Stock Center, Department of Biophysics and Medical Physics, University of California (Berkeley, Calif.); and the American Type Culture Collection ("ATCC") (Manassas, Va.). Industrial/pharmaceutical fermentation generally use bacterial derived from K strains (e.g. W3110) or from bacteria derived from B strains (e.g. BL21). These strains are particularly useful because their growth parameters are extremely well known and robust. In addition, these strains are non-pathogenic, which is commercially important for safety and environmental reasons. Other examples of suitable *E. coli* hosts include, but are not limited to, strains of BL21, DH10B, or derivatives thereof. In another embodiment of the methods of the present invention, the *E. coli* host is a protease minus strain including, but not limited to, OMP- and LON-. The host cell strain may be a species of *Pseudomonas*, including but not limited to, *Pseudomonas fluorescens*, *Pseudomonas aeruginosa*, and *Pseudomonas putida*. *Pseudomonas fluorescens* biovar 1, designated strain MB101, is known to be useful for recombinant production and is available for therapeutic protein production processes. Examples of a *Pseudomonas* expression system include the system available from The Dow Chemical Company as a host strain (Midland, Mich. available on the World Wide Web at dow.com). U.S. Pat. Nos. 4,755,465 and 4,859,600, which are incorporated by reference herein, describe the use of *Pseudomonas* strains as a host cell for hGH production.

Once a recombinant host cell strain has been established (i.e., the expression construct has been introduced into the host cell and host cells with the proper expression construct are isolated), the recombinant host cell strain is cultured under conditions appropriate for production of the polypeptide of interest. As will be apparent to one of skill in the art, the method of culture of the recombinant host cell strain will be dependent on the nature of the expression construct utilized and the identity of the host cell. Recombinant host strains are normally cultured using methods that are well known to the art. Recombinant host cells are typically cultured in liquid medium containing assimilatable sources of carbon, nitrogen, and inorganic salts and, optionally, containing vitamins, amino acids, growth factors, and other proteinaceous culture supplements known to those of ordinary skill in the art. Liquid media for culture of host cells may optionally contain antibiotics or anti-fungals to prevent the growth of undesirable microorganisms and/or compounds including, but not limited to, antibiotics to select for host cells containing the expression vector.

Several well-known methods of introducing target nucleic acids into cells are available, any of which can be used in the invention. These include: fusion of the recipient cells with bacterial protoplasts containing the DNA, electroporation, projectile bombardment, and infection with viral vectors (discussed further, below), etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, kits are commercially available for the purification of plasmids from bacteria, (see, e.g., EasyPrep™, FlexiPrep™, both from Pharmacia Biotech; StrataClean™ from Stratagene; and, QIAprep™ from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (including but not limited to, shuttle vectors) and selection markers for both prokaryotic and eukaryotic systems. Vectors are suitable for replication and integration in prokaryotes, eukaryotes, or both. See, Gillam & Smith, Gene 8:81 (1979); Roberts, et al., Nature, 328:731 (1987); Schneider, E., et al., Protein Expr. Purif. 6(1):10-14 (1995); Ausubel, Sambrook, Berger (all supra). A catalogue of bacteria and bacteriophages useful for cloning is provided, e.g., by the ATCC, e.g., The ATCC Catalogue of Bacteria and Bacteriophage (1992) Gherna et al. (eds) published by the ATCC. Additional basic procedures for sequencing, cloning and other aspects of molecular biology and underlying theoretical considerations are also found in Watson et al. (1992) Recombinant DNA Second Edition Scientific American Books, N.Y. In addition, essentially any nucleic acid (and virtually any labeled nucleic acid, whether standard or non-standard) can be custom or standard ordered from any of a variety of commercial sources, such as the Midland Certified Reagent Company (Midland, Tex. available on the World Wide Web at mcrc.com), The Great American Gene Company (Ramona, Calif. available on the World Wide Web at genco.com), ExpressGen Inc. (Chicago, Ill. available on the World Wide Web at expressgen.com), Operon Technologies Inc. (Alameda, Calif.) and many others.

Recombinant host cells may be cultured in batch or continuous formats, with either cell harvesting (in the case where the polypeptide of interest accumulates intracellularly) or harvesting of culture supernatant in either batch or continuous formats. For production in prokaryotic host cells, batch culture and cell harvest are preferred.

Selector Codons

Selector codons of the present invention expand the genetic codon framework of protein biosynthetic machinery. For example, a selector codon includes, e.g., a unique three base codon, a nonsense codon, such as a stop codon, including but not limited to, an amber codon (UAG), an ochre codon, or an opal codon (UGA), an unnatural codon, a four base (or more) codon, a rare codon, or the like. A number of selector codons can be introduced into a desired gene or polynucleotide, e.g., one or more, two or more, three or more, etc.

Selector codons of the invention expand the genetic codon framework of protein biosynthetic machinery. For example, a selector codon includes, but is not limited to, a unique three base codon, a nonsense codon, such as a stop codon, including but not limited to, an amber codon (UAG), an ochre codon, or an opal codon (UGA), an unnatural codon, a four or more base codon, a rare codon, or the like. It is readily apparent to those of ordinary skill in the art that there is a wide range in the number of selector codons that can be introduced into a desired gene or polynucleotide, including but not limited to, one or more, two or more, three or more, 4, 5, 6, 7, 8, 9, 10 or more in a single polynucleotide encoding the antigen or whole organism, as non-limiting examples of genetically modified whole organisms using the present invention, MAP and E. coli.

In one embodiment, the methods involve the use of a selector codon that is a stop codon for the incorporation of a selected amino acid, e.g., an unnatural amino acid, in vivo. For example, an O-tRNA is produced that recognizes the stop codon and is aminoacylated by an O-RS with a selected amino acid. This O-tRNA is not recognized by the naturally occurring host's aminoacyl-tRNA synthetases. Conventional site-directed mutagenesis can be used to introduce the stop codon at the site of interest in a polypeptide of interest. See, e.g., Sayers, J. R., et al. (1988), 5'-3' *Exonucleases in phosphorothioate-based oligonucleotide-directed mutagenesis*. *Nucleic Acids Res*, 16:791-802. When the O-RS, O-tRNA and the nucleic acid that encodes a polypeptide of interest are combined, e.g., in vivo, the selected amino acid is incorporated in response to the stop codon to give a polypeptide containing the selected amino acid, e.g., an unnatural amino acid, at the specified position. In one embodiment of the present invention, a stop codon used as a selector codon is an amber codon, UAG, and/or an opal codon, UGA. For example, see SEQ ID NO.: 6 for an example of an O-tRNA that recognizes an amber codon, and see SEQ ID NO.: 7 for an example of an O-tRNA that recognizes an opal codon. A genetic code in which UAG and UGA are both used as a selector codon can encode 22 amino acids while preserving the ochre nonsense codon, UAA, which is the most abundant termination signal.

The incorporation of selected amino acids, e.g., unnatural amino acids, in vivo can be done without significant perturbation of the host cell. For example in non-eukaryotic cells, such as *Escherichia coli*, because the suppression efficiency for the UAG codon depends upon the competition between the O-tRNA, e.g., the amber suppressor tRNA, and the release factor 1 (RF1) (which binds to the UAG codon and initiates release of the growing peptide from the ribosome), the suppression efficiency can be modulated by, e.g., either increasing the expression level of O-tRNA, e.g., the suppressor tRNA, or using an RF1 deficient strain. In eukaryotic cells, because the suppression efficiency for the UAG codon depends upon the competition between the O-tRNA, e.g., the amber suppressor tRNA, and a eukaryotic release factor (e.g., eRF) (which binds to a stop codon and initiates release of the growing peptide from the ribosome), the suppression efficiency can be modulated by, e.g., increasing the expression level of O-tRNA, e.g., the suppressor tRNA.

Unnatural amino acids can also be encoded with rare codons. For example, when the arginine concentration in an in vitro protein synthesis reaction is reduced, the rare arginine codon, AGG, has proven to be efficient for insertion of Ala by a synthetic tRNA acylated with alanine. See, e.g., Ma et al., *Biochemistry*, 32:7939 (1993). In this case, the synthetic tRNA competes with the naturally occurring tRNAArg, which exists as a minor species in *Escherichia coli*. Some organisms do not use all triplet codons. An unassigned codon AGA in *Micrococcus luteus* has been utilized for insertion of amino acids in an in vitro transcription/translation extract. See, e.g., Kowal and Oliver, *Nucl. Acid. Res.*, 25:4685 (1997). Components of the present invention can be generated to use these rare codons in vivo.

Selector codons also comprise extended codons, e.g., four or more base codons, such as, four, five, six or more base codons. Examples of four base codons include but are not limited to, AGGA, CUAG, UAGA, CCCU, and the like. Examples of five base codons include but are not limited to, AGGAC, CCCCU, CCCUC, CUAGA, CUACU, UAGGC and the like. A feature may include using extended codons based on frameshift suppression. Four or more base codons can insert, e.g., one or multiple selected amino acids, including but not limited to, unnatural amino acids, into the same protein. For example, in the presence of mutated O-tRNA's, e.g., a special frameshift suppressor tRNA's, with anticodon loops, e.g., with a $CU(X)_n$ XXXAA sequence (where n=1), the four or more base codon is read as single amino acid. For example, see SEQ ID NOs.: 6, 12 from PCT/US04/22061 for O-tRNA's that recognize a four base codon. In other embodiments, the anticodon loops can decode, e.g., at least a four-base codon, at least a five-base codon, or at least a six-base codon or more. Since there are 256 possible four-base codons, multiple unnatural amino acids can be encoded in the same cell using a four or more base codon. See, Anderson et al., (2002) *Exploring the Limits of Codon and Anticodon Size, Chemistry and Biology*, 9:237-244; Magliery, (2001) *Expanding the Genetic Code: Selection of Efficient Suppressors of Four-base Codons and Identification of "Shifty" Four-base Codons with a Library Approach in Escherichia coli, J. Mol. Biol.* 307: 755-769.

For example, four-base codons have been used to incorporate unnatural amino acids into proteins using in vitro biosynthetic methods. See, e.g., Ma et al., (1993) *Biochemistry*, 32:7939; and Hohsaka et al., (1999) *J. Am. Chem. Soc.*, 121: 34. CGGG and AGGU were used to simultaneously incorporate 2-naphthylalanine and an NBD derivative of lysine into streptavidin in vitro with two chemically acylated frameshift suppressor tRNA's. See, e.g., Hohsaka et al., (1999) *J. Am. Chem. Soc.*, 121:12194. In an in vivo study, Moore et al. examined the ability of tRNALeu derivatives with NCUA anticodons to suppress UAGN codons (N can be U, A, G, or C), and found that the quadruplet UAGA can be decoded by a tRNALeu with a UCUA anticodon with an efficiency of 13 to 26% with little decoding in the 0 or −1 frame. See, Moore et al., (2000) *J. Mol. Biol.*, 298:195. In one embodiment, extended codons based on rare codons or nonsense codons can be used in invention, which can reduce missense readthrough and frameshift suppression at other unwanted sites.

For a given system, a selector codon can also include one of the natural three base codons, where the endogenous system does not use (or rarely uses) the natural base codon. For example, this includes a system that is lacking a tRNA that recognizes the natural three base codon, and/or a system where the three base codon is a rare codon.

Selector codons optionally include unnatural base pairs. These unnatural base pairs further expand the existing genetic alphabet. One extra base pair increases the number of triplet codons from 64 to 125. Properties of third base pairs include stable and selective base pairing, efficient enzymatic incorporation into DNA with high fidelity by a polymerase, and the efficient continued primer extension after synthesis of the nascent unnatural base pair. Descriptions of unnatural base pairs which can be adapted for methods and compositions include, e.g., Hirao, et al., (2002) *An unnatural base pair for incorporating amino acid analogues into protein, Nature Biotechnology*, 20:177-182. See, also, Wu, Y., et al., (2002) *J. Am. Chem. Soc.* 124:14626-14630. Other relevant publications are listed below.

For in vivo usage, the unnatural nucleoside is membrane permeable and is phosphorylated to form the corresponding triphosphate. In addition, the increased genetic information is stable and not destroyed by cellular enzymes. Previous efforts by Benner and others took advantage of hydrogen bonding patterns that are different from those in canonical Watson-Crick pairs, the most noteworthy example of which is the iso-C:iso-G pair. See, e.g., Switzer et al., (1989) *J. Am. Chem. Soc.*, 111:8322; and Piccirilli et al., (1990) *Nature*, 343:33; Kool, (2000) *Curr. Opin. Chem. Biol.*, 4:602. These bases in general mispair to some degree with natural bases and cannot be enzymatically replicated. Kool and co-workers demonstrated that hydrophobic packing interactions between bases can replace hydrogen bonding to drive the formation of base pair. See, Kool, (2000) *Curr. Opin. Chem. Biol.*, 4:602; and Guckian and Kool, (1998) *Angew. Chem. Int. Ed. Engl.*, 36, 2825. In an effort to develop an unnatural base pair satisfying all the above requirements, Schultz, Romesberg and co-workers have systematically synthesized and studied a series of unnatural hydrophobic bases. A PICS:PICS self-pair is found to be more stable than natural base pairs, and can be efficiently incorporated into DNA by Klenow fragment of *Escherichia coli* DNA polymerase I (KF). See, e.g., McMinn et al., (1999) *J. Am. Chem. Soc.*, 121: 11585-6; and Ogawa et al., (2000) *J. Am. Chem. Soc.*, 122:3274. A 3MN:3MN self-pair can be synthesized by KF with efficiency and selectivity sufficient for biological function. See, e.g., Ogawa et al., (2000) *J. Am. Chem. Soc.*, 122:8803. However, both bases act as a chain terminator for further replication. A mutant DNA polymerase has been recently evolved that can be used to replicate the PICS self pair. In addition, a 7AI self pair can be replicated. See, e.g., Tae et al., (2001) *J. Am. Chem. Soc.*, 123:7439. A novel metallobase pair, Dipic:Py, has also been developed, which forms a stable pair upon binding Cu(II). See, Meggers et al., (2000) *J. Am. Chem. Soc.*, 122:10714. Because extended codons and unnatural codons are intrinsically orthogonal to natural codons, the methods of the present invention can take advantage of this property to generate orthogonal tRNAs for them.

A translational bypassing system can also be used to incorporate a selected amino acid, e.g., an unnatural amino acid, in a desired polypeptide. In a translational bypassing system, a large sequence is inserted into a gene but is not translated into protein. The sequence contains a structure that serves as a cue to induce the ribosome to hop over the sequence and resume translation downstream of the insertion.

Selected and Unnatural Amino Acids

As used herein, a selected amino acid refers to any desired naturally occurring amino acid or unnatural amino acid. A naturally occurring amino acid includes any one of the twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. In one embodiment, the selected amino acid is incorporated into a growing polypeptide chain with high fidelity, e.g., at greater than about 70% efficiency for given selector codon, at greater than 75% efficiency for a given selector codon, at greater than about 80% efficiency for a given selector codon, at greater than about 85% efficiency for a given selector codon, at greater than about 90% efficiency for a given selector codon, at greater than about 95% efficiency for a given selector codon, or at greater than about 99% or more efficiency for a given selector codon.

As used herein, an unnatural amino acid refers to any amino acid, modified amino acid, or amino acid analogue other than selenocysteine and/or pyrrolysine and the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. The generic structure of an alpha-amino acid is illustrated by Formula I:

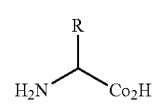

I

An unnatural amino acid is typically any structure having Formula I wherein the R group is any substituent other than one used in the twenty natural amino acids. See, e.g., *Biochemistry* by L. Stryer, 3$^{rd}$ ed. 1988, Freeman and Company, New York, for structures of the twenty natural amino acids. Note that, the unnatural amino acids of the present invention can be naturally occurring compounds other than the twenty alpha-amino acids above.

Because the unnatural amino acids of the present invention typically differ from the natural amino acids only in the structure of the side chain, the unnatural amino acids form amide bonds with other amino acids, including but not limited to, natural or unnatural, in the same manner in which they are formed in naturally occurring proteins. However, the unnatural amino acids have side chain groups that distinguish them from the natural amino acids. For example, R in Formula I may comprise an alkyl-, aryl-, acyl-, keto-, azido-, hydroxyl-, hydrazine, cyano-, halo-, hydrazide, alkenyl, alkynl, ether, thiol, seleno-, sulfonyl-, borate, boronate, phospho, phosphono, phosphine, heterocyclic, enone, imine, aldehyde, ester, thioacid, hydroxylamine, amine, and the like, or any combination thereof. Other non-naturally occurring amino acids include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, amino acids comprising biotin or a biotin analogue, glycosylated amino acids such as a sugar substituted serine, other carbohydrate modified amino acids, keto-containing amino acids, amino acids comprising polyethylene glycol or polyether, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety. See, also, U.S. Patent Application Publications 2003/0082575 and 2003/0108885, which are incorporated by reference herein. Unnatural amino acids may have a photoactivatable cross-linker that is used, e.g., to link a protein to a solid support. Unnatural amino acids may have a saccharide moiety attached to the amino acid side chain.

In addition to unnatural amino acids that contain novel side chains, unnatural amino acids also optionally comprise modified backbone structures, e.g., as illustrated by the structures of Formula II and III:

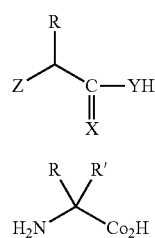

wherein Z typically comprises OH, NH$_2$, SH, NH—R', or S—R'; X and Y, which can be the same or different, typically comprise S or O, and R and R', which are optionally the same or different, are typically selected from the same list of constituents for the R group described above for the unnatural amino acids having Formula I as well as hydrogen. For example, unnatural amino acids may comprise substitutions in the amino or carboxyl group as illustrated by Formulas II and III. Unnatural amino acids of this type include, but are not limited to, α-hydroxy acids, α-thioacids, α-aminothiocarboxylates, e.g., with side chains corresponding to the common twenty natural amino acids or unnatural side chains. In addition, substitutions at the α-carbon optionally include L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3, 4, 6, 7, 8, and 9 membered ring proline analogues, β and γ amino acids such as substituted β-alanine and γ-amino butyric acid.

Many unnatural amino acids are based on natural amino acids, such as tyrosine, glutamine, phenylalanine, and the like. Tyrosine analogs include para-substituted tyrosines, ortho-substituted tyrosines, and meta substituted tyrosines, wherein the substituted tyrosine comprises a keto group (including but not limited to, an acetyl group), a benzoyl group, an amino group, a hydrazine, an hydroxyamine, a thiol group, a carboxy group, an isopropyl group, a methyl group, a C$_6$-C$_{20}$ straight chain or branched hydrocarbon, a saturated or unsaturated hydrocarbon, an O-methyl group, a polyether group, a nitro group, or the like. In addition, multiply substituted aryl rings are also contemplated. Glutamine analogs include, but are not limited to, α-hydroxy derivatives, γ-substituted derivatives, cyclic derivatives, and amide substituted glutamine derivatives. Example phenylalanine analogs include, but are not limited to, para-substituted phenylalanines, ortho-substituted phenyalanines, and meta-substituted phenylalanines, wherein the substituent comprises a hydroxy group, a methoxy group, a methyl group, an allyl group, an aldehyde, an azido, an iodo, a bromo, a keto group (including but not limited to, an acetyl group), or the like. Specific examples of unnatural amino acids include, but are not limited to, a p-acetyl-L-phenylalanine, a p-propargyl-phenylalanine, O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcfβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, and a p-propargyloxy-phenylalanine, and the like. Examples of structures of a variety of unnatural amino acids are provided in, for example, WO 2002/085923 entitled "In vivo incorporation of unnatural amino acids," which is incorporated by reference herein. See also Kiick et al., (2002) *Incorporation of azides into recombinant proteins for chemoselective modification by the Staudinger ligation*, PNAS 99:19-24, which is incorporated by reference herein, for additional methionine analogs.

A non-natural amino acid incorporated into a polypeptide at the amino terminus can be composed of an R group that is any substituent other than one used in the twenty natural amino acids and a 2$^{nd}$ reactive group different from the NH$_2$ group normally present in α-amino acids (see Formula I). A similar non-natural amino acid can be incorporated at the carboxyl terminus with a 2$^{nd}$ reactive group different from the COOH group normally present in α-amino acids (see Formula I).

The unnatural amino acids of the invention may be selected or designed to provide additional characteristics unavailable in the twenty natural amino acids. For example, unnatural amino acid may be optionally designed or selected to modify the biological properties of a protein, e.g., into which they are incorporated. For example, the following properties may be optionally modified by inclusion of an unnatural amino acid into a protein: toxicity, biodistribution, solubility, stability, e.g., thermal, hydrolytic, oxidative, resistance to enzymatic degradation, and the like, facility of purification and processing, structural properties, spectroscopic properties, chemical and/or photochemical properties, catalytic activity, redox potential, half-life, ability to react with other molecules, e.g., covalently or noncovalently, and the like.

The structures of a variety of unnatural amino acids are provided in, for example, FIGS. 16, 17, 18, 19, 26, and 29 of WO 2002/085923 entitled "In vivo incorporation of unnatural amino acids," which is incorporated by reference herein. The examples are not meant to be limiting in any way of amino acids that may be attached to a tRNA of the present invention.

One advantage of an unnatural amino acid is that it presents additional chemical moieties that can be used to add additional molecules. These modifications can be made in vivo in a eukaryotic or non-eukaryotic cell, or in vitro. Thus, in certain embodiments, the post-translational modification is through the unnatural amino acid. An unnatural amino acid in a polypeptide may be used to attach another molecule to the polypeptide, including but not limited to, a label, a dye, a polymer, a water-soluble polymer, a derivative of polyethylene glycol, a photocrosslinker, a radionuclide, a cytotoxic compound, a drug, an affinity label, a photoaffinity label, a reactive compound, a resin, a second protein or polypeptide or polypeptide analog, an antibody or antibody fragment, a metal chelator, a cofactor, a fatty acid, a carbohydrate, a polynucleotide, a DNA, a RNA, an antisense polynucleotide, a saccharide, a water-soluble dendrimer, a cyclodextrin, an inhibitory ribonucleic acid, a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a photoisomerizable moiety, biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, a small molecule, a quantum dot, a nanotransmitter, or any combination of the above or any other desirable compound or substance, comprising a second reactive group to at least one unnatural amino acid comprising a first reactive group utilizing chemistry methodology that is known to one of ordinary skill in the art to be suitable for the particular reactive groups.

For example, the post-translational modification can be through a nucleophilic-electrophilic reaction. Most reactions currently used for the selective modification of proteins involve covalent bond formation between nucleophilic and electrophilic reaction partners, including but not limited to the reaction of α-haloketones with histidine or cysteine side chains. Selectivity in these cases is determined by the number and accessibility of the nucleophilic residues in the protein. In proteins of the invention, other more selective reactions can be used such as the reaction of an unnatural keto-amino acid with hydrazides or aminooxy compounds, in vitro and in vivo. See, e.g., Cornish, et al., (1996) *J. Am. Chem. Soc.,* 118:8150-8151; Mahal, et al., (1997) *Science,* 276:1125-1128; Wang, et al., (2001) *Science* 292:498-500; Chin, et al., (2002) *J. Am. Chem. Soc.* 124:9026-9027; Chin, et al., (2002) *Proc. Natl. Acad. Sci.,* 99:11020-11024; Wang, et al., (2003) *Proc. Natl. Acad. Sci.,* 100:56-61; Zhang, et al., (2003) *Biochemistry,* 42:6735-6746; and, Chin, et al., (2003) *Science,* 301:964-7, all of which are incorporated by reference herein. This allows the selective labeling of virtually any protein with a host of reagents including fluorophores, crosslinking agents, saccharide derivatives and cytotoxic molecules. See also, U.S. Pat. No. 6,927,042 entitled "Glycoprotein synthesis," which is incorporated by reference herein. Post-translational modifications, including but not limited to, through an azido amino acid, can also made through the Staudinger ligation (including but not limited to, with triarylphosphine reagents). See, e.g., Kiick et al., (2002) *Incorporation of azides into recombinant proteins for chemoselective modification by the Staudinger ligation, PNAS* 99:19-24.

Chemical Synthesis of Unnatural Amino Acids

Many unnatural amino acids are commercially available, e.g., from Sigma-Aldrich (St. Louis, Mo., USA), Novabiochem (a division of EMD Biosciences, Darmstadt, Germany), or Peptech (Burlington, Mass., USA). Those that are not commercially available are optionally synthesized as provided herein or using standard methods known to those of ordinary skill in the art. For organic synthesis techniques, see, e.g., *Organic Chemistry* by Fessendon and Fessendon, (1982, Second Edition, Willard Grant Press, Boston Mass.); *Advanced Organic Chemistry* by March (Third Edition, 1985, Wiley and Sons, New York); and *Advanced Organic Chemistry* by Carey and Sundberg (Third Edition, Parts A and B, 1990, Plenum Press, New York). Additional publications describing the synthesis of unnatural amino acids include, e.g., WO 2002/085923 entitled "In vivo incorporation of Unnatural Amino Acids;" Matsoukas et al., (1995) *J. Med. Chem.,* 38, 4660-4669; King, F. E. & Kidd, D. A. A. (1949) *A New Synthesis of Glutamine and of γ-Dipeptides of Glutamic Acid from Phthylated Intermediates. J. Chem. Soc.,* 3315-3319; Friedman, O. M. & Chatterrji, R. (1959) *Synthesis of Derivatives of Glutamine as Model Substrates for Anti-Tumor Agents. J. Am. Chem. Soc.* 81, 3750-3752; Craig, J. C. et al. (1988) *Absolute Configuration of the Enantiomers of 7-Chloro-4[[4-(diethylamine)-1-methylbutyl]amino]quinoline (Chloroquine). J. Org. Chem.* 53, 1167-1170; Azoulay, M., Vilmont, M. & Frappier, F. (1991) *Glutamine analogues as Potential Antimalarials, Eur. J. Med. Chem.* 26, 201-5; Koskinen, A. M. P. & Rapoport, H. (1989) *Synthesis of 4-Substituted Prolines as Conformationally Constrained Amino Acid Analogues. J. Org. Chem.* 54, 1859-1866; Christie, B. D. & Rapoport, H. (1985) *Synthesis of Optically Pure Pipecolates from L-Asparagine. Application to the Total Synthesis of (+)-Apovincamine through Amino Acid Decarbonylation and Iminium Ion Cyclization. J. Org. Chem.* 50:1239-1246; Barton et al., (1987) *Synthesis of Novel alpha-Amino-Acids and Derivatives Using Radical Chemistry: Synthesis of L-and D-alpha-Amino-Adipic Acids, L-alpha-aminopimelic Acid and Appropriate Unsaturated Derivatives. Tetrahedron* 43:4297-4308; and, Subasinghe et al., (1992) *Quisqualic acid analogues: synthesis of beta-heterocyclic 2-aminopropanoic acid derivatives and their activity at a novel quisqualate-sensitized site. J. Med. Chem.* 35:4602-7. See also, U.S. Patent Publication No. US 2004/0198637 entitled "Protein Arrays," which is incorporated by reference.

Cellular Uptake of Unnatural Amino Acids

Unnatural amino acid uptake by a cell is one issue that is typically considered when designing and selecting unnatural amino acids, e.g., for incorporation into a protein. For example, the high charge density of α-amino acids suggests that these compounds are unlikely to be cell permeable. Natural amino acids are taken up into the cell via a collection of protein-based transport systems. A rapid screen can be done which assesses which unnatural amino acids, if any, are taken up by cells. See, e.g., the toxicity assays in, e.g., U.S. Patent Publication No. US 2004/0198637 entitled "Protein Arrays" which is incorporated by reference herein, and Liu, D. R. & Schultz, P. G. (1999) *Progress toward the evolution of an organism with an expanded genetic code. PNAS United States* 96:4780-4785. Although uptake is easily analyzed with various assays, an alternative to designing unnatural amino acids that are amenable to cellular uptake pathways is to provide biosynthetic pathways to create amino acids in vivo.

Biosynthesis of Unnatural Amino Acids

Many biosynthetic pathways already exist in cells for the production of amino acids and other compounds. While a biosynthetic method for a particular unnatural amino acid may not exist in nature, including but not limited to, in a cell, the invention provides such methods. For example, biosynthetic pathways for unnatural amino acids are optionally generated in host cell by adding new enzymes or modifying existing host cell pathways. Additional new enzymes are optionally naturally occurring enzymes or artificially evolved enzymes. For example, the biosynthesis of p-aminophenylalanine (as presented in an example in WO 2002/085923 entitled "In vivo incorporation of unnatural amino acids") relies on the addition of a combination of known enzymes from other organisms. The genes for these enzymes can be introduced into a cell by transforming the cell with a plasmid comprising the genes. The genes, when expressed in the cell, provide an enzymatic pathway to synthesize the desired compound. Examples of the types of enzymes that are optionally added are provided in the examples below. Additional enzymes sequences are found, for example, in Genbank. Artificially evolved enzymes are also optionally added into a cell in the same manner. In this manner, the cellular machinery and resources of a cell are manipulated to produce unnatural amino acids.

A variety of methods are available for producing novel enzymes for use in biosynthetic pathways or for evolution of existing pathways. For example, recursive recombination, e.g., as developed by Maxygen, Inc. (available on the World Wide Web at maxygen.com), is optionally used to develop novel enzymes and pathways. See, e.g., Stemmer (1994), *Rapid evolution of a protein in vitro by DNA shuffling, Nature* 370(4):389-391; and, Stemmer, (1994), *DNA shuffling by random fragmentation and reassembly: In vitro recombination for molecular evolution, Proc. Natl. Acad. Sci. USA.*, 91:10747-10751. Similarly DesignPath™, developed by Genencor (available on the World Wide Web at genencor.com) is optionally used for metabolic pathway engineering, e.g., to engineer a pathway to create O-methyl-L-tyrosine in a cell. This technology reconstructs existing pathways in host organisms using a combination of new genes, including but not limited to, those identified through functional genomics, and molecular evolution and design. Diversa Corporation (available on the World Wide Web at diversa.com) also provides technology for rapidly screening libraries of genes and gene pathways, including but not limited to, to create new pathways.

Typically, the unnatural amino acid produced with an engineered biosynthetic pathway of the present invention is produced in a concentration sufficient for efficient protein biosynthesis, e.g., a natural cellular amount, but not to such a degree as to affect the concentration of the other amino acids or exhaust cellular resources. Typical concentrations produced in vivo in this manner are about 10 mM to about 0.05 mM. Once a cell is transformed with a plasmid comprising the genes used to produce enzymes desired for a specific pathway and an unnatural amino acid is generated, in vivo selections are optionally used to further optimize the production of the unnatural amino acid for both ribosomal protein synthesis and cell growth.

Nucleic Acid and Polypeptide Sequence and Variants

As described above and below, the invention provides for nucleic acid polynucleotide sequences and polypeptide amino acid sequences, e.g., tRNA's and RSs, and, e.g., compositions and methods comprising said sequences. Examples of said sequences, e.g., tRNA's and RSs are disclosed herein. However, one of skill in the art will appreciate that the invention is not limited to those sequences disclosed herein, e.g., the Examples. One of skill will appreciate that the invention also provides many related and unrelated sequences with the functions described herein, e.g., encoding an O-tRNA or an O-RS.

The invention provides polypeptides (O-RSs) and polynucleotides, e.g., O-tRNA, polynucleotides that encode O-RSs or portions thereof, oligonucleotides used to isolate aminoacyl-tRNA synthetase clones, etc. Polynucleotides of the present invention include those that encode proteins or polypeptides of interests of the present invention with one or more selector codon. In addition, polynucleotides of the present invention include, e.g., a polynucleotide comprising a nucleotide sequence as set forth in any one of SEQ ID NO.: 1, 2, 3; a polynucleotide that is complementary to, or a conservative variation thereof. Similarly, a nucleic acid that hybridizes to a polynucleotide indicated above under highly stringent conditions over substantially the entire length of the nucleic acid is a polynucleotide of the present invention.

In certain embodiments, a vector (e.g., a plasmid, a cosmid, a phage, a bacterium, a virus, a naked polynucleotide, a conjugated polynucleotide, etc.) comprises a polynucleotide of the present invention. In one embodiment, the vector is an expression vector. In another embodiment, the expression vector includes a promoter operably linked to one or more of the polynucleotides of the present invention. In another embodiment, a cell comprises a vector that includes a polynucleotide of the present invention.

One of skill will also appreciate that many variants of the disclosed sequences are included in the invention. For example, conservative variations of the disclosed sequences that yield a functionally identical sequence are included in the invention. Variants of the nucleic acid polynucleotide sequences, wherein the variants hybridize to at least one disclosed sequence, are considered to be included in the invention. Unique subsequences of the sequences disclosed herein, as determined by, e.g., standard sequence comparison techniques, are also included in the invention.

Conservative Variations

Owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid. Similarly, "conservative amino acid substitutions," in one or a few amino acids in an amino acid sequence are substituted with different amino acids with highly similar properties, are also readily identified as being highly similar to a disclosed construct. Such conservative variations of each disclosed sequence are a feature of the present invention.

"Conservative variations" of a particular nucleic acid sequence refers to those nucleic acids which encode identical or essentially identical amino acid sequences, or, where the nucleic acid does not encode an amino acid sequence, to essentially identical sequences. One of ordinary skill in the art will recognize that individual substitutions, deletions or additions which alter, add or delete a single amino acid or a small percentage of amino acids in an encoded sequence are "conservatively modified variations" or "conservatively modified variants" where the alterations result in the deletion of an amino acid, addition of an amino acid, or substitution of an amino acid with a chemically similar amino acid. Thus, "conservative variations" of a listed polypeptide sequence of the present invention include substitutions of a small percentage, typically less than 5%, more typically less than 4%, 2% or 1%, of the amino acids of the polypeptide sequence, with a conservatively selected amino acid of the same conservative substitution group. The addition of sequences which do not alter the encoded activity of a nucleic acid molecule, such as the addition of a non-functional sequence, is a conservative variation of the basic nucleic acid.

Conservative substitution tables providing functionally similar amino acids are known to those of ordinary skill in the art. The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins: Structures and Molecular Properties* (W H Freeman & Co.; 2nd edition (December 1993))

Nucleic Acid Hybridization

Comparative hybridization can be used to identify nucleic acids of the present invention, such as SEQ ID NO.: 1-3, including conservative variations of nucleic acids of the present invention, and this comparative hybridization method is a preferred method of distinguishing nucleic acids of the present invention. In addition, target nucleic acids which hybridize to the nucleic acids represented by SEQ ID NO: 1-3 under high, ultra-high, and/or ultra-ultra high stringency conditions are a feature of the present invention. Examples of such nucleic acids include those with one or a few silent or conservative nucleic acid substitutions as compared to a given nucleic acid sequence.

A test nucleic acid is said to specifically hybridize to a probe nucleic acid when it hybridizes at least ½ as well to the probe as to the perfectly matched complementary target, i.e., with a signal to noise ratio at least ½ as high as hybridization of the probe to the target under conditions in which the perfectly matched probe binds to the perfectly matched complementary target with a signal to noise ratio that is at least about 5x-10x as high as that observed for hybridization to any of the unmatched target nucleic acids.

Nucleic acids "hybridize" when they associate, typically in solution. Nucleic acids hybridize due to a variety of well characterized physico-chemical forces, such as hydrogen bonding, solvent exclusion, base stacking and the like. The phrase "stringent hybridization conditions" refers to conditions of low ionic strength and high temperature as is known in the art. Typically, under stringent conditions a probe will hybridize to its target subsequence in a complex mixture of nucleic acid (including but not limited to, total cellular or library DNA or RNA) but does not hybridize to other sequences in the complex mixture. An extensive guide to the hybridization of nucleic acids is found in Tijssen (1993) *Laboratory Techniques in Biochemistry and Molecular Biology—Hybridization with Nucleic Acid Probes* part I chapter 2, "Overview of principles of hybridization and the strategy of nucleic acid probe assays," (Elsevier, New York), as well as in Ausubel et al., *Current Protocols in Molecular Biology* (1995). Hames and Higgins (1995) *Gene Probes* 1 IRL Press at Oxford University Press, Oxford, England, (Hames and Higgins 1) and Hames and Higgins (1995) *Gene Probes* 2 IRL Press at Oxford University Press, Oxford, England (Hames and Higgins 2) provide details on the synthesis, labeling, detection and quantification of DNA and RNA, including oligonucleotides. Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$ 50% of the probes are occupied at equilibrium). Stringent conditions may be those in which the salt concentration is less than about 1.0 M sodium ion, typically about 0.01 to 1.0 M sodium ion concentration (or other salts) at pH 7.0 to 8.3 and the temperature is at least about 30° C. for short probes (including but not limited to, 10 to 50 nucleotides) and at least about 60° C. for long probes (including but not limited to, greater than 50 nucleotides). Stringent conditions may also be achieved with the addition of destabilizing agents such as formamide. For selective or specific hybridization, a positive signal may be at least two times background, optionally 10 times background hybridization. Exemplary stringent hybridization conditions can be as following: 50% formamide, 5×SSC, and 1% SDS, incubating at 42° C., or 5×SSC, 1% SDS, incubating at 65° C., with wash in 0.2×SSC, and 0.1% SDS at 65° C. Such washes can be performed for 5, 15, 30, 60, 120, or more minutes.

An example of stringent hybridization conditions for hybridization of complementary nucleic acids which have more than 100 complementary residues on a filter in a Southern or Northern blot is 50% formalin with 1 mg of heparin at 42° C., with the hybridization being carried out overnight. An example of stringent wash conditions is a 0.2×SSC wash at 65° C. for 15 minutes (see, Sambrook et al., *Molecular Cloning, A Laboratory Manual* (3rd ed. 2001) for a description of SSC buffer). Often the high stringency wash is preceded by a low stringency wash to remove background probe signal. An example low stringency wash is 2×SSC at 40° C. for 15 minutes. In general, a signal to noise ratio of 5× (or higher) than that observed for an unrelated probe in the particular hybridization assay indicates detection of a specific hybridization.

"Stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993), supra. and in Hames and Higgins, 1 and 2, supra. Stringent hybridization and wash conditions can easily be determined empirically for any test nucleic acid. For example, in determining highly stringent hybridization and wash conditions, the hybridization and wash conditions are gradually increased (e.g., by increasing temperature, decreasing salt concentration, increasing detergent concentration and/or increasing the concentration of organic solvents such as formalin in the hybridization or wash), until a selected set of criteria are met. For example, the hybridization and wash conditions are gradually increased until a probe binds to a perfectly matched complementary target with a signal to noise ratio that is at least 5× as high as that observed for hybridization of the probe to an unmatched target.

"Very stringent" conditions are selected to be equal to the thermal melting point ($T_m$) for a particular probe. The $T_m$ is the temperature (under defined ionic strength and pH) at which 50% of the test sequence hybridizes to a perfectly matched probe. For the purposes of the present invention, generally, "highly stringent" hybridization and wash conditions are selected to be about 5° C. lower than the $T_m$ or the specific sequence at a defined ionic strength and pH.

"Ultra high-stringency" hybridization and wash conditions are those in which the stringency of hybridization and wash conditions are increased until the signal to noise ratio for binding of the probe to the perfectly matched complementary target nucleic acid is at least 10× as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-high stringency conditions.

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-ultra-high stringency conditions.

Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

Unique Subsequences

In one aspect, the invention provides a nucleic acid that comprises a unique subsequence in a nucleic acid selected from the sequences of O-tRNA's and O-RSs disclosed herein. The unique subsequence is unique as compared to a nucleic acid corresponding to any known O-tRNA or O-RS nucleic acid sequence. Alignment can be performed using, e.g., BLAST set to default parameters. Any unique subsequence is useful, e.g., as a probe to identify the nucleic acids of the present invention.

Similarly, the invention includes a polypeptide which comprises a unique subsequence in a polypeptide selected from the sequences of O-RSs disclosed herein. Here, the unique subsequence is unique as compared to a polypeptide corresponding to any of known polypeptide sequence.

The invention also provides for target nucleic acids which hybridizes under stringent conditions to a unique coding oligonucleotide which encodes a unique subsequence in a polypeptide selected from the sequences of O-RSs wherein the unique subsequence is unique as compared to a polypeptide corresponding to any of the control polypeptides (e.g., parental sequences from which synthetases of the present invention were derived, e.g., by mutation). Unique sequences are determined as noted above.

Sequence Comparison, Identity, and Homology

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence over a comparison window, or designated region, as measured using one of the sequence comparison algorithms described below (or other algorithms available to persons of ordinary skill in the art) or by manual alignment and visual inspection.

The phrase "substantially identical," in the context of two nucleic acids or polypeptides (e.g., DNAs encoding an O-tRNA or O-RS, or the amino acid sequence of an O-RS) refers to two or more sequences or subsequences that have at least about 60%, about 80%, about 90-95%, about 98%, about 99% or more nucleotide or amino acid residue identity, when compared and aligned for maximum correspondence over a comparison window, or designated region, as measured using a sequence comparison algorithm (or other algorithms available to persons of ordinary skill in the art) or by manual alignment and visual inspection. Such "substantially identical" sequences are typically considered to be "homologous," without reference to actual ancestry. "Substantial identity" may exist over a region of the sequences that is at least about 50 residues in length, a region of at least about 100 residues, or a region of at least about 150 residues, or over the full length of the two sequences to be compared.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Methods of alignment of sequences for comparison are known to those of ordinary skill in the art. Optimal alignment of sequences for comparison can be conducted, e.g., by the local homology algorithm of Smith & Waterman, *Adv. Appl. Math.* 2:482c (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see e.g., Ausubel et al., *Current Protocols in Molecular Biology* (1995 supplement)).

One example of an algorithm that is suitable for determining percent sequence identity and sequence similarity is the BLAST algorithm and BLAST 2.0 algorithms, which are described in Altschul et al. (1997) *Nuc. Acids Res.* 25:3389-3402, and Altschul et al., *J. Mol. Biol.* 215:403-410 (1990). Software for performing BLAST analyses is publicly available through the National Center for Biotechnology Information available at the World Wide Web at ncbi.nlm.nih.gov. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1992) *Proc. Natl. Acad. Sci. USA* 89:10915) alignments (B) of 50, expectation (E) of 10, M=5, N=−4, and a comparison of both strands. The BLAST algorithm is typically performed with the "low complexity" filter turned off.

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid may be considered similar to a reference sequence if the smallest sum probability in a comparison of the test nucleic acid to the reference nucleic acid is less than about 0.2, less than about 0.01, or less than about 0.001.

Mutagenesis and Other Molecular Biology Techniques

Polynucleotide and polypeptides of the present invention and used in the invention can be manipulated using molecular biological techniques. A nucleotide sequence may be conveniently modified by site-directed mutagenesis in accordance with conventional methods. Alternatively, the nucleotide sequence may be prepared by chemical synthesis, including but not limited to, by using an oligonucleotide synthesizer, wherein oligonucleotides are designed based on the amino acid sequence of the desired polypeptide, and preferably selecting those codons that are favored in the host cell in which the recombinant polypeptide will be produced. For example, several small oligonucleotides coding for portions of the desired polypeptide may be synthesized and assembled by PCR, ligation or ligation chain reaction. See, e.g., Barany, et al., *Proc. Natl. Acad. Sci.* 88: 189-193 (1991); U.S. Pat. No. 6,521,427 which are incorporated by reference herein.

This invention utilizes routine techniques in the field of recombinant genetics. Basic texts disclosing the general methods of use in this invention include Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

General texts which describe molecular biological techniques include Berger and Kimmel, *Guide to Molecular Cloning Techniques, Methods in Enzymology volume* 152 Academic Press, Inc., San Diego, Calif. (Berger); Sambrook et al., *Molecular Cloning—A Laboratory Manual* (2nd Ed.), Vol. 1-3, Cold Spring Harbor Laboratory, Cold Spring Harbor, N.Y., 1989 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 1999) ("Ausubel")). These texts describe mutagenesis, the use of vectors, promoters and many other relevant topics related to, e.g., the generation of genes or polynucleotides that include selector codons for production of proteins that include selected amino acids (e.g., unnatural amino acids), orthogonal tRNA's, orthogonal synthetases, and pairs thereof.

Various types of mutagenesis are used in the invention for a variety of purposes, including but not limited to, to produce novel synthetases or tRNAs, to mutate tRNA molecules, to produce libraries of tRNAs, to mutate RS molecules, to produce libraries of synthetases, to produce selector codons, to insert selector codons that encode a selected amino acid in a protein or polypeptide of interest. They include but are not limited to, site-directed, random point mutagenesis, homologous recombination, DNA shuffling or other recursive mutagenesis methods, chimeric construction, mutagenesis using uracil containing templates, oligonucleotide-directed mutagenesis, phosphorothioate-modified DNA mutagenesis, mutagenesis using gapped duplex DNA or the like, or any combination thereof. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, including but not limited to, involving chimeric constructs, is also included in the present invention. In one embodiment, mutagenesis can be guided by known information of the naturally occurring molecule or altered or mutated naturally occurring molecule, including but not limited to, sequence, sequence comparisons, physical properties, secondary, tertiary, or quaternary structure, crystal structure or the like.

The texts and examples found herein describe these procedures. Additional information is found in the following publications and references cited within: Ling et al., *Approaches to DNA mutagenesis: an overview, Anal Biochem.* 254(2): 157-178 (1997); Dale et al., *Oligonucleotide-directed random mutagenesis using the phosphorothioate method, Methods Mol. Biol.* 57:369-374 (1996); Smith, *In vitro mutagenesis, Ann. Rev. Genet.* 19:423-462 (1985); Botstein & Shortle, *Strategies and applications of in vitro mutagenesis, Science* 229:1193-1201 (1985); Carter, *Site-directed mutagenesis, Biochem. J.* 237:1-7 (1986); Kunkel, *The efficiency of oligonucleotide directed mutagenesis, in Nucleic Acids & Molecular Biology* (Eckstein, F. and Lilley, D. M. J. eds., Springer Verlag, Berlin) (1987); Kunkel, *Rapid and efficient site-specific mutagenesis without phenotypic selection, Proc. Natl. Acad. Sci. USA* 82:488-492 (1985); Kunkel et al., *Rapid and efficient site-specific mutagenesis without phenotypic selection, Methods in Enzymol.* 154, 367-382 (1987); Bass et al., *Mutant Trp repressors with new DNA-binding specificities, Science* 242:240-245 (1988); Zoller & Smith, *Oligonucleotide-directed mutagenesis using M13-derived vectors: an efficient and general procedure for the production of point mutations in any DNA fragment, Nucleic Acids Res.* 10:6487-6500 (1982); Zoller & Smith, *Oligonucleotide-directed mutagenesis of DNA fragments cloned into M13 vectors, Methods in Enzymol.* 100:468-500 (1983); Zoller & Smith, *Oligonucleotide-directed mutagenesis: a simple method using two oligonucleotide primers and a single-stranded DNA template, Methods in Enzymol.* 154:329-350 (1987); Taylor et al., *The use of phosphorothioate-modified DNA in restriction enzyme reactions to prepare nicked DNA, Nucl. Acids Res.* 13: 8749-8764 (1985); Taylor et al., *The rapid generation of oligonucleotide-directed mutations at high frequency using phosphorothioate-modified DNA, Nucl. Acids Res.* 13: 8765-8785 (1985); Nakamaye & Eckstein, *Inhibition of restriction endonuclease Nci I cleavage by phosphorothio-* ate groups and its application to oligonucleotide-directed mutagenesis, Nucl. Acids Res. 14: 9679-9698 (1986); Sayers et al., 5'-3' *Exonucleases in phosphorothioate-based oligonucleotide-directed mutagenesis, Nucl. Acids Res.* 16:791-802 (1988); Sayers et al., *Strand specific cleavage of phosphorothioate-containing DNA by reaction with restriction endonucleases in the presence of ethidium bromide*, (1988) *Nucl. Acids Res.* 16: 803-814; Kramer et al., *The gapped duplex DNA approach to oligonucleotide-directed mutation construction, Nucl. Acids Res.* 12: 9441-9456 (1984); Kramer & Fritz *Oligonucleotide-directed construction of mutations via gapped duplex DNA, Methods in Enzymol.* 154:350-367 (1987); Kramer et al., *Improved enzymatic in vitro reactions in the gapped duplex DNA approach to oligonucleotide-directed construction of mutations, Nucl. Acids Res.* 16: 7207 (1988); Fritz et al., *Oligonucleotide-directed construction of mutations: a gapped duplex DNA procedure without enzymatic reactions in vitro, Nucl. Acids Res.* 16: 6987-6999 (1988); Kramer et al., *Different base/base mismatches are corrected with different efficiencies by the methyl-directed DNA mismatch-repair system of E. coli, Cell* 38:879-887 (1984); Carter et al., *Improved oligonucleotide site-directed mutagenesis using M13 vectors, Nucl. Acids Res.* 13: 4431-4443 (1985); Carter, *Improved oligonucleotide-directed mutagenesis using M13 vectors, Methods in Enzymol.* 154: 382-403 (1987); Eghtedarzadeh & Henikoff, *Use of oligonucleotides to generate large deletions, Nucl. Acids Res.* 14: 5115 (1986); Wells et al., *Importance of hydrogen-bond formation in stabilizing the transition state of subtilisin, Phil. Trans. R. Soc. Lond. A* 317: 415-423 (1986); Nambiar et al., *Total synthesis and cloning of a gene coding for the ribonuclease S protein, Science* 223: 1299-1301 (1984); Sakmar and Khorana, *Total synthesis and expression of a gene for the alpha-subunit of bovine rod outer segment guanine nucleotide-binding protein (transducin), Nucl. Acids Res.* 14: 6361-6372 (1988); Wells et al., *Cassette mutagenesis: an efficient method for generation of multiple mutations at defined sites, Gene* 34:315-323 (1985); Grundström et al., *Oligonucleotide-directed mutagenesis by microscale 'shotgun' gene synthesis, Nucl. Acids Res.* 13: 3305-3316 (1985); Mandecki, *Oligonucleotide-directed double-strand break repair in plasmids of Escherichia coli: a method for site-specific mutagenesis, Proc. Natl. Acad. Sci. USA*, 83:7177-7181 (1986); Arnold, *Protein engineering for unusual environments, Current Opinion in Biotechnology* 4:450-455 (1993); Sieber, et al., *Nature Biotechnology*, 19:456-460 (2001); W. P. C. Stemmer, *Nature* 370, 389-91 (1994); and, I. A. Lorimer, I. Pastan, *Nucleic Acids Res.* 23, 3067-8 (1995). Additional details on many of the above methods can be found in *Methods in Enzymology* Volume 154, which also describes useful controls for trouble-shooting problems with various mutagenesis methods.

Oligonucleotides, e.g., for use in mutagenesis of the present invention, e.g., mutating libraries of synthetases, or altering tRNAs, are typically synthesized chemically according to the solid phase phosphoramidite triester method described by Beaucage and Caruthers, Tetrahedron Letts. 22(20):1859-1862, (1981) e.g., using an automated synthesizer, as described in Needham-VanDevanter et al., Nucleic Acids Res., 12:6159-6168 (1984).

In addition, essentially any nucleic acid can be custom or standard ordered from any of a variety of commercial sources, such as The Midland Certified Reagent Company (mcrc@oligos.com), The Great American Gene Company (www.genco.com), ExpressGen Inc. (www.expressgen.com), Operon Technologies Inc. (Alameda, Calif.) and many others.

The invention also relates to eukaryotic host cells, non-eukaryotic host cells, and organisms for the in vivo incorporation of an unnatural amino acid via orthogonal tRNA/RS pairs. Host cells are genetically engineered (including but not limited to, transformed, transduced or transfected) with the polynucleotides of the present invention or constructs which include a polynucleotide of the present invention, including but not limited to, a vector of the present invention, which can be, for example, a cloning vector or an expression vector. For example, the coding regions for the orthogonal tRNA, the orthogonal tRNA synthetase, and the protein to be derivatized are operably linked to gene expression control elements that are functional in the desired host cell. The vector can be, for example, in the form of a plasmid, a cosmid, a phage, a bacterium, a virus, a naked polynucleotide, or a conjugated polynucleotide. The vectors are introduced into cells and/or microorganisms by standard methods including electroporation (Fromm et al., *Proc. Natl. Acad. Sci. USA* 82, 5824 (1985)), infection by viral vectors, high velocity ballistic penetration by small particles with the nucleic acid either within the matrix of small beads or particles, or on the surface (Klein et al., *Nature* 327, 70-73 (1987)), and/or the like.

Several well-known methods of introducing target nucleic acids into cells are available, any of which can be used in the invention. These include: fusion of the recipient cells with bacterial protoplasts containing the DNA, electroporation, projectile bombardment, and infection with viral vectors (discussed further, below), etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, kits are commercially available for the purification of plasmids from bacteria, (see, e.g., EasyPrep™, FlexiPrep™, both from Pharmacia Biotech; StrataClean™ from Stratagene; and, QIAprep™ from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (including but not limited to, shuttle vectors) and selection markers for both prokaryotic and eukaryotic systems. Vectors are suitable for replication and/or integration in prokaryotes, eukaryotes, or both. See, Gillam & Smith, *Gene* 8:81 (1979); Roberts, et al., *Nature*, 328:731 (1987); Schneider, E., et al., *Protein Expr. Purif.* 6(1)10-14 (1995); Ausubel, Sambrook, Berger (all supra). A catalogue of bacteria and bacteriophages useful for cloning is provided, e.g., by the ATCC, e.g., *The ATCC Catalogue of Bacteria and Bacteriophage* (1992) Gherna et al. (eds) published by the ATCC. Additional basic procedures for sequencing, cloning and other aspects of molecular biology and underlying theoretical considerations are also found in Watson et al. (1992) *Recombinant DNA Second Edition Scientific American Books, N.Y.* In addition, essentially any nucleic acid (and virtually any labeled nucleic acid, whether standard or non-standard) can be custom or standard ordered from any of a variety of commercial sources, such as the Midland Certified Reagent Company (Midland, Tex. available on the World Wide Web at mcrc.com), The Great American Gene Company (Ramona, Calif. available on the World Wide Web at genco.com), ExpressGen Inc. (Chicago, Ill. available on the World Wide Web at expressgen.com), Operon Technologies Inc. (Alameda, Calif.) and many others.

The engineered host cells can be cultured in conventional nutrient media modified as appropriate for such activities as, for example, screening steps, activating promoters or selecting transformants. These cells can optionally be cultured into transgenic organisms. Other useful references, e.g. for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds.) (1995) *Plant Cell, Tissue and Organ Culture*; Fundamental Methods Springer Lab Manual, Springer-Verlag (Berlin Heidelberg New York) and Atlas and Parks (eds.) *The Handbook of Microbiological Media* (1993) CRC Press, Boca Raton, Fla.

The ability to incorporate unnatural amino acids directly into proteins in vivo offers a wide variety of advantages including but not limited to high yields of mutant proteins, technical ease, the potential to study the mutant proteins in cells or possibly in living organisms and the use of these mutant proteins in therapeutic treatments and diagnostic uses. The ability to include non-natural amino acids with various sizes, acidities, nucleophilicities, hydrophobicities, and other properties into proteins can greatly expand the ability to rationally and systematically manipulate the structures of proteins, both to probe protein function and create new proteins or organisms with novel properties.

Proteins and Polypeptides of Interest

The incorporation of an unnatural amino acid can be done for a variety of purposes, including but not limited to, tailoring changes in protein structure and/or function, changing size, acidity, nucleophilicity, hydrogen bonding, hydrophobicity, accessibility of protease target sites, targeting to a moiety (including but not limited to, for a protein array), adding a biologically active molecule, attaching a polymer, attaching a radionuclide, modulating serum half-life, modulating tissue penetration (e.g. tumors), modulating active transport, modulating tissue, cell or organ specificity or distribution, modulating immunogenicity, modulating protease resistance, etc. Proteins that include an unnatural amino acid can have enhanced or even entirely new catalytic or biophysical properties. For example, the following properties are optionally modified by inclusion of an unnatural amino acid into a protein: toxicity, biodistribution, structural properties, spectroscopic properties, chemical and/or photochemical properties, catalytic ability, half-life (including but not limited to, serum half-life), ability to react with other molecules, including but not limited to, covalently or noncovalently, and the like. The compositions including proteins that include at least one unnatural amino acid are useful for, including but not limited to, novel therapeutics, diagnostics, catalytic enzymes, industrial enzymes, binding proteins (including but not limited to, antibodies), and including but not limited to, the study of protein structure and function. See, e.g., Dougherty, (2000) *Unnatural Amino Acids as Probes of Protein Structure and Function, Current Opinion in Chemical Biology*, 4:645-652.

A protein may have at least one, including but not limited to, at least two, at least three, at least four, at least five, at least six, at least seven, at least eight, at least nine, or at least ten or more unnatural amino acids. The unnatural amino acids can be the same or different, including but not limited to, there can be 1, 2, 3, 4, 5, 6, 7, 8, 9, or 10 or more different sites in the protein that comprise 1, 2, 3, 4, 5, 6, 7, 8, 9, or 10 or more different unnatural amino acids. A protein may have at least one, but fewer than all, of a particular amino acid present in the protein is substituted with the unnatural amino acid. For a given protein with more than one unnatural amino acids, the unnatural amino acids can be identical or different (including but not limited to, the protein can include two or more different types of unnatural amino acids, or can include two of the same unnatural amino acid). For a given protein with more than two unnatural amino acids, the unnatural amino acids can be the same, different or a combination of a multiple unnatural amino acid of the same kind with at least one different unnatural amino acid.

By producing proteins or polypeptides of interest with at least one unnatural amino acid in eukaryotic cells, proteins or polypeptides will typically include eukaryotic post-translational modifications. In certain embodiments, a protein includes at least one unnatural amino acid and at least one post-translational modification that is made in vivo by a eukaryotic cell, where the post-translational modification is not made by a prokaryotic cell. For example, the post-translation modification includes, including but not limited to, acetylation, acylation, lipid-modification, palmitoylation, palmitate addition, phosphorylation, glycolipid-linkage modification, glycosylation, and the like. In yet another aspect, the post-translation modification includes proteolytic processing of precursors (including but not limited to, calcitonin precursor, calcitonin gene-related peptide precursor, preproparathyroid hormone, preproinsulin, proinsulin, prepro-opiomelanocortin, pro-opiomelanocortin and the like), assembly into a multisubunit protein or macromolecular assembly, translation to another site in the cell (including but not limited to, to organelles, such as the endoplasmic reticulum, the Golgi apparatus, the nucleus, lysosomes, peroxisomes, mitochondria, chloroplasts, vacuoles, etc., or through the secretory pathway). In certain embodiments, the protein comprises a secretion or localization sequence, an epitope tag, a FLAG tag, a polyhistidine tag, a GST fusion, or the like.

Methods of producing a protein in a cell with a selected amino acid at a specified position are also a feature of the present invention. For example, a method includes growing, in an appropriate medium, the cell, where the cell comprises a nucleic acid that comprises at least one selector codon and encodes a protein; and, providing the selected amino acid; where the cell further comprises: an orthogonal tRNA (O-tRNA) that functions in the cell and recognizes the selector codon; and, an orthogonal aminoacyl-tRNA synthetase (O-RS) that preferentially aminoacylates the O-tRNA with the selected amino acid. Typically, the O-tRNA comprises suppression activity in presence of a cognate synthetase in response to a selector codon. A protein produced by this method is also a feature of the present invention.

The compositions of the present invention and compositions made by the methods of the present invention optionally are in a cell. The O-tRNA/O-RS pairs or individual components of the present invention can then be used in a host system's translation machinery, which results in a selected amino acid, e.g., unnatural amino acid, being incorporated into a protein. Patent applications U.S. Ser. No. 10/825,867, entitled "Expanding the Eukaryotic Genetic Code;" and Ser. No. 10/126,927, entitled "IN VIVO INCORPORATION OF UNNATURAL AMINO ACIDS", describe this process and are incorporated herein by reference. For example, when an O-tRNA/O-RS pair is introduced into a host, e.g., *Escherichia coli*, the pair leads to the in vivo incorporation of selected amino acid, such as an unnatural amino acid, e.g., a synthetic amino acid, such as derivative of a leucine amino acid, which can be exogenously added to the growth medium, into a protein, in response to a selector codon. Optionally, the compositions of the present invention can be in an in vitro translation system, or in an in vivo system(s).

Any protein (or portion thereof) that includes a selected amino acid, e.g., an unnatural amino acid, (and any corresponding coding nucleic acid, e.g., which includes one or more selector codons) can be produced using the compositions and methods herein. Any polypeptide is suitable for incorporation of one or more selected amino acids. No attempt is made to identify the hundreds of thousands of known proteins, any of which can be modified to include one or more unnatural amino acid, e.g., by tailoring any available mutation methods to include one or more appropriate selector codon in a relevant translation system. Common sequence repositories for known proteins include GenBank EMBL, DDBJ and the NCBI. Other repositories can easily be identified by searching the interne.

Typically, the proteins are, e.g., at least 60%, at least 70%, at least 75%, at least 80%, at least 90%, at least 95%, or at least 99% or more identical to any available protein (e.g., a therapeutic protein, a diagnostic protein, an industrial enzyme, or portion thereof, and the like), and they comprise one or more selected amino acid. Examples of therapeutic, diagnostic, and other proteins that can be modified to comprise one or more selected amino acid, e.g., an unnatural amino acid, can be found, but not limited to, those in U.S. Ser. No. 10/825,867 entitled "Expanding the Eukaryotic Genetic Code;" and, U.S. patent application Ser. No. 10/126,927, entitled "IN VIVO INCORPORATION OF UNNATURAL AMINO ACIDS."

In certain embodiments, the protein or polypeptide of interest (or portion thereof) in the methods and/or compositions of the present invention is encoded by a nucleic acid. Typically, the nucleic acid comprises at least one selector codon, at least two selector codons, at least three selector codons, at least four selector codons, at least five selector codons, at least six selector codons, at least seven selector codons, at least eight selector codons, at least nine selector codons, ten or more selector codons.

Genes coding for proteins or polypeptides of interest can be mutagenized using methods well-known to one of skill in the art and described herein under "Mutagenesis and Other Molecular Biology Techniques" to include, e.g., one or more selector codon for the incorporation of a selected amino acid, e.g., an unnatural amino acid. For example, a nucleic acid for a protein of interest is mutagenized to include one or more selector codon, providing for the insertion of the one or more selected amino acids, e.g., unnatural amino acid. The invention includes any such variant, e.g., mutant, versions of any protein, e.g., including at least one selected amino acid. Similarly, the invention also includes corresponding nucleic acids, i.e., any nucleic acid with one or more selector codon that encodes one or more selected amino acid.

To make a protein that includes a selected amino acid, one can use host cells and organisms that are adapted for the in vivo incorporation of the selected amino acid via orthogonal tRNA/RS pairs. Host cells are genetically engineered (e.g., transformed, transduced or transfected) with one or more vectors that express the orthogonal tRNA, the orthogonal tRNA synthetase, and a vector that encodes the protein to be derivatized. Each of these components can be on the same vector, or each can be on a separate vector, two components can be on one vector and the third component on a second vector. The vector can be, for example, in the form of a plasmid, a cosmid, a phage, a bacterium, a virus, a naked polynucleotide, or a conjugated polynucleotide.

Alternate Systems

Several strategies have been employed to introduce unnatural amino acids into proteins in non-recombinant host cells, mutagenized host cells, or in cell-free systems. Derivatization of amino acids with reactive side-chains such as Lys, Cys and Tyr resulted in the conversion of lysine to $N^2$-acetyllysine. Chemical synthesis also provides a straightforward method to incorporate unnatural amino acids. With the recent development of enzymatic ligation and native chemical ligation of peptide fragments, it is possible to make larger proteins. See, e.g., P. E. Dawson and S. B. H. Kent, *Annu. Rev. Biochem*, 69:923 (2000). Chemical peptide ligation and native chemical ligation are described in U.S. Pat. No. 6,184, 344, U.S. Patent Publication No. 2004/0138412, U.S. Patent Publication No. 2003/0208046, WO 02/098902, and WO 03/042235, which are incorporated by reference herein. A general in vitro biosynthetic method in which a suppressor tRNA chemically acylated with the desired unnatural amino acid is added to an in vitro extract capable of supporting protein biosynthesis, has been used to site-specifically incorporate over 100 unnatural amino acids into a variety of proteins of virtually any size. See, e.g., V. W. Cornish, D. Mendel and P. G. Schultz, *Angew. Chem. Int. Ed. Engl.*, 1995, 34:621 (1995); C. J. Noren, S. J. Anthony-Cahill, M. C. Griffith, P. G. Schultz, A general method for site-specific incorporation of unnatural amino acids into proteins, *Science* 244:182-188 (1989); and, J. D. Bain, C. G. Glabe, T. A. Dix, A. R. Chamberlin, E. S. Diala, Biosynthetic site-specific incorporation of a non-natural amino acid into a polypeptide, *J. Am. Chem. Soc.* 111:8013-8014 (1989). A broad range of functional groups has been introduced into proteins for studies of protein stability, protein folding, enzyme mechanism, and signal transduction.

An in vivo method, termed selective pressure incorporation, was developed to exploit the promiscuity of wild-type synthetases. See, e.g., N. Budisa, C. Minks, S. Alefelder, W. Wenger, F. M. Dong, L. Moroder and R. Huber, *FASEB J.*, 13:41 (1999). An auxotrophic strain, in which the relevant metabolic pathway supplying the cell with a particular natural amino acid is switched off, is grown in minimal media containing limited concentrations of the natural amino acid, while transcription of the target gene is repressed. At the onset of a stationary growth phase, the natural amino acid is depleted and replaced with the unnatural amino acid analog. Induction of expression of the recombinant protein results in the accumulation of a protein containing the unnatural analog. For example, using this strategy, o, m and p-fluorophenylalanines have been incorporated into proteins, and exhibit two characteristic shoulders in the LTV spectrum which can be easily identified, see, e.g., C. Minks, R. Huber, L. Moroder and N. Budisa, *Anal. Biochem.*, 284:29 (2000); trifluoromethionine has been used to replace methionine in bacteriophage T4 lysozyme to study its interaction with chitooligosaccharide ligands by $^{19}F$ NMR, see, e.g., H. Duewel, E. Daub, V. Robinson and J. F. Honek, *Biochemistry*, 36:3404 (1997); and trifluoroleucine has been incorporated in place of leucine, resulting in increased thermal and chemical stability of a leucine-zipper protein. See, e.g., Y. Tang, G. Ghirlanda, W. A. Petka, T. Nakajima, W. F. DeGrado and D. A. Tirrell, *Angew. Chem. Int. Ed. Engl.*, 40:1494 (2001). Moreover, selenomethionine and telluromethionine are incorporated into various recombinant proteins to facilitate the solution of phases in X-ray crystallography. See, e.g., W. A. Hendrickson, J. R. Horton and D. M. Lemaster, *EMBO J.*, 9:1665 (1990); J. O. Boles, K. Lewinski, M. Kunkle, J. D. Odom, B. Dunlap, L. Lebioda and M. Hatada, *Nat. Struct. Biol.*, 1:283 (1994); N. Budisa, B. Steipe, P. Demange, C. Eckerskorn, J. Kellermann and R. Huber, *Eur. J. Biochem.*, 230:788 (1995); and, N.

Budisa, W. Karnbrock, S. Steinbacher, A. Humm, L. Prade, T. Neuefeind, L. Moroder and R. Huber, *J. Mol. Biol.*, 270:616 (1997). Methionine analogs with alkene or alkyne functionalities have also been incorporated efficiently, allowing for additional modification of proteins by chemical means. See, e.g., J. C. van Hest and D. A. Tirrell, *FEBS Lett.*, 428:68 (1998); J. C. van Hest, K. L. Kiick and D. A. Tirrell, *J. Am. Chem. Soc.*, 122:1282 (2000); and, K. L. Kiick and D. A. Tirrell, Tetrahedron, 56:9487 (2000); U.S. Pat. No. 6,586,207; U.S. Patent Publication 2002/0042097, which are incorporated by reference herein.

The success of this method depends on the recognition of the unnatural amino acid analogs by aminoacyl-tRNA synthetases, which, in general, require high selectivity to insure the fidelity of protein translation. One way to expand the scope of this method is to relax the substrate specificity of aminoacyl-tRNA synthetases, which has been achieved in a limited number of cases. For example, replacement of Ala$^{294}$ by Gly in *Escherichia coli* phenylalanyl-tRNA synthetase (PheRS) increases the size of substrate binding pocket, and results in the acylation of tRNAPhe by p-Cl-phenylalanine (p-Cl-Phe). See, M. Ibba, P. Kast and H. Hennecke, *Biochemistry*, 33:7107 (1994). An *Escherichia coli* strain harboring this mutant PheRS allows the incorporation of p-Cl-phenylalanine or p-Br-phenylalanine in place of phenylalanine. See, e.g., M. Ibba and H. Hennecke, *FEBS Lett.*, 364:272 (1995); and, N. Sharma, R. Furter, P. Kast and D. A. Tirrell, *FEBS Lett.*, 467:37 (2000). Similarly, a point mutation Phe130Ser near the amino acid binding site of *Escherichia coli* tyrosyl-tRNA synthetase was shown to allow azatyrosine to be incorporated more efficiently than tyrosine. See, F. Hamano-Takaku, T. Iwama, S. Saito-Yano, K. Takaku, Y. Monden, M. Kitabatake, D. Soll and S. Nishimura, *J. Biol. Chem.*, 275:40324 (2000).

Another strategy to incorporate unnatural amino acids into proteins in vivo is to modify synthetases that have proofreading mechanisms. These synthetases cannot discriminate and therefore activate amino acids that are structurally similar to the cognate natural amino acids. This error is corrected at a separate site, which deacylates the mischarged amino acid from the tRNA to maintain the fidelity of protein translation. If the proofreading activity of the synthetase is disabled, structural analogs that are misactivated may escape the editing function and be incorporated. This approach has been demonstrated recently with the valyl-tRNA synthetase (ValRS). See, V. Doring, H. D. Mootz, L. A. Nangle, T. L. Hendrickson, V. de Crecy-Lagard, P. Schimmel and P. Marliere, *Science*, 292:501 (2001). ValRS can misaminoacylate tRNAVal with Cys, Thr, or aminobutyrate (Abu); these non-cognate amino acids are subsequently hydrolyzed by the editing domain. After random mutagenesis of the *Escherichia coli* chromosome, a mutant *Escherichia coli* strain was selected that has a mutation in the editing site of ValRS. This edit-defective ValRS incorrectly charges tRNAVal with Cys. Because Abu sterically resembles Cys (—SH group of Cys is replaced with —CH3 in Abu), the mutant ValRS also incorporates Abu into proteins when this mutant *Escherichia coli* strain is grown in the presence of Abu. Mass spectrometric analysis shows that about 24% of valines are replaced by Abu at each valine position in the native protein.

Solid-phase synthesis and semisynthetic methods have also allowed for the synthesis of a number of proteins containing novel amino acids. For example, see the following publications and references cited within, which are as follows: Crick, F. H. C., Barrett, L. Brenner, S. Watts-Tobin, R. *General nature of the genetic code for proteins. Nature*, 192:1227-1232 (1961); Hofmann, K., Bohn, H. *Studies on polypeptides. XXXVI. The effect of pyrazole-imidazole replacements on the S-protein activating potency of an S-peptide fragment, J. Am. Chem*, 88(24):5914-5919 (1966); Kaiser, E. T. *Synthetic approaches to biologically active peptides and proteins including enyzmes, Acc Chem Res*, 22:47-54 (1989); Nakatsuka, T., Sasaki, T., Kaiser, E. T. *Peptide segment coupling catalyzed by the semisynthetic enzyme thiosubtilisin, J Am Chem Soc*, 109:3808-3810 (1987); Schnolzer, M., Kent, S B H. *Constructing proteins by dovetailing unprotected synthetic peptides: backbone-engineered HIV protease, Science*, 256(5054):221-225 (1992); Chaiken, I. M. *Semisynthetic peptides and proteins, CRC Crit Rev Biochem*, 11(3):255-301 (1981); Afford, R. E. *Protein engineering by chemical means? Protein Eng.*, 1(3):151-157 (1987); and, Jackson, D. Y., Burnier, J., Quan, C., Stanley, M., Tom, J., Wells, J. A. *A Designed Peptide Ligase for Total Synthesis of Ribonuclease A with Unnatural Catalytic Residues, Science*, 266(5183):243 (1994).

Chemical modification has been used to introduce a variety of unnatural side chains, including cofactors, spin labels and oligonucleotides into proteins in vitro. See, e.g., Corey, D. R., Schultz, P. G. *Generation of a hybrid sequence-specific single-stranded deoxyribonuclease, Science*, 238(4832):1401-1403 (1987); Kaiser, E. T., Lawrence D. S., Rokita, S. E. *The chemical modification of enzymatic specificity, Annu Rev Biochem*, 54:565-595 (1985); Kaiser, E. T., Lawrence, D. S. *Chemical mutation of enyzme active sites, Science*, 226 (4674):505-511 (1984); Neet, K. E., Nanci A, Koshland, D. E. *Properties of thiol-subtilisin, J. Biol. Chem.*, 243(24):6392-6401 (1968); Polgar, L. et M. L. Bender. *A new enzyme containing a synthetically formed active site. Thiol-subtilisin. J. Am Chem Soc*, 88:3153-3154 (1966); and, Pollack, S. J., Nakayama, G. Schultz, P. G. *Introduction of nucleophiles and spectroscopic probes into antibody combining sites, Science*, 242(4881):1038-1040 (1988).

Defining Polypeptides by Immunoreactivity

Because the polypeptides of the present invention provide a variety of new polypeptide sequences (e.g., comprising selected amino acids (e.g., unnatural amino acids) in the case of proteins synthesized in the translation systems herein, or, e.g., in the case of the novel synthetases, novel sequences of standard amino acids), the polypeptides also provide new structural features which can be recognized, e.g., in immunological assays. The generation of antisera, which specifically bind the polypeptides of the present invention, as well as the polypeptides which are bound by such antisera, are a feature of the present invention. The term "antibody," as used herein, includes, but is not limited to a polypeptide substantially encoded by an immunoglobulin gene or immunoglobulin genes, or fragments thereof which specifically bind and recognize an analyte (antigen). Examples include polyclonal, monoclonal, chimeric, and single chain antibodies, and the like. Fragments of immunoglobulins, including Fab fragments and fragments produced by an expression library, including phage display, are also included in the term "antibody" as used herein. See, e.g., Paul, *Fundamental Immunology*, 4th Ed., 1999, Raven Press, New York, for antibody structure and terminology. Examples of the use of non-natural amino acids and immunological techniques are given in WO/2009/099672 to The Scripps Research Institute entitled Breaking Immunological Tolerance With a Genetically Encoded Unnatural Amino Acid, and is hereby incorporated by reference in its entirety.

For example, the invention includes proteins made utilizing the tRNAs and/or RSs of the present invention that specifically bind to or that are specifically immunoreactive with an antibody or antisera generated against an immunogen comprising an amino acid sequence. To eliminate cross-reactivity with other homologues, the antibody or antisera is subtracted with available protein, such as the wild-type polypeptide, e.g., the "control" polypeptides. Where the wild-type protein corresponds to a nucleic acid, a polypeptide encoded by the nucleic acid is generated and used for antibody/antisera subtraction purposes.

In one typical format, the immunoassay uses a polyclonal antiserum which was raised against one or more polypeptide or a substantial subsequence thereof (i.e., at least about 30% of the full length sequence provided). The set of potential polypeptide immunogens derived from the protein are collectively referred to below as "the immunogenic polypeptides." The resulting antisera is optionally selected to have low cross-reactivity against the control synthetase homologues and any such cross-reactivity is removed, e.g., by immunoabsorbtion, with one or more of the control homologues, prior to use of the polyclonal antiserum in the immunoassay.

In order to produce antisera for use in an immunoassay, one or more of the immunogenic polypeptides is produced and purified as described herein. For example, recombinant protein can be produced in a recombinant cell. An inbred strain of mice (used in this assay because results are more reproducible due to the virtual genetic identity of the mice) is immunized with the immunogenic protein(s) in combination with a standard adjuvant, such as Freund's adjuvant, and a standard mouse immunization protocol (see, e.g., Harlow and Lane (1988) *Antibodies, A Laboratory Manual*, Cold Spring Harbor Publications, New York, for a standard description of antibody generation, immunoassay formats and conditions that can be used to determine specific immunoreactivity.

Additional references and discussion of antibodies is also found herein and can be applied here to defining polypeptides by immunoreactivity). Alternatively, one or more synthetic or recombinant polypeptide derived from the sequences disclosed herein is conjugated to a carrier protein and used as an immunogen.

Polyclonal sera are collected and titered against the immunogenic polypeptide in an immunoassay, for example, a solid phase immunoassay with one or more of the immunogenic proteins immobilized on a solid support. Polyclonal antisera with a titer of $10^6$ or greater are selected, pooled and subtracted with the control synthetase polypeptides to produce subtracted pooled titered polyclonal antisera.

The subtracted pooled titered polyclonal antisera are tested for cross reactivity against the control homologues in a comparative immunoassay. In this comparative assay, discriminatory binding conditions are determined for the subtracted titered polyclonal antisera which result in at least about a 5-10 fold higher signal to noise ratio for binding of the titered polyclonal antisera to the immunogenic protein as compared to binding to the control synthetase homologues. That is, the stringency of the binding reaction is adjusted by the addition of non-specific competitors such as albumin or non-fat dry milk, and/or by adjusting salt conditions, temperature, and/or the like. These binding conditions are used in subsequent assays for determining whether a test polypeptide (a polypeptide being compared to the immunogenic polypeptides and/or the control polypeptides) is specifically bound by the pooled subtracted polyclonal antisera.

In another example, immunoassays in the competitive binding format are used for detection of a test polypeptide. For example, as noted, cross-reacting antibodies are removed from the pooled antisera mixture by immunoabsorbtion with the control polypeptides. The immunogenic polypeptide(s) are then immobilized to a solid support which is exposed to the subtracted pooled antisera. Test proteins are added to the assay to compete for binding to the pooled subtracted antisera. The ability of the test protein(s) to compete for binding to the pooled subtracted antisera as compared to the immobilized protein(s) is compared to the ability of the immunogenic polypeptide(s) added to the assay to compete for binding (the immunogenic polypeptides compete effectively with the immobilized immunogenic polypeptides for binding to the pooled antisera). The percent cross-reactivity for the test proteins is calculated, using standard calculations.

In a parallel assay, the ability of the control proteins to compete for binding to the pooled subtracted antisera is optionally determined as compared to the ability of the immunogenic polypeptide(s) to compete for binding to the antisera. Again, the percent cross-reactivity for the control polypeptides is calculated, using standard calculations. Where the percent cross-reactivity is at least 5-10× as high for the test polypeptides as compared to the control polypeptides and or where the binding of the test polypeptides is approximately in the range of the binding of the immunogenic polypeptides, the test polypeptides are said to specifically bind the pooled subtracted antisera.

In general, the immunoabsorbed and pooled antisera can be used in a competitive binding immunoassay as described herein to compare any test polypeptide to the immunogenic and/or control polypeptide(s). In order to make this comparison, the immunogenic, test and control polypeptides are each assayed at a wide range of concentrations and the amount of each polypeptide required to inhibit 50% of the binding of the subtracted antisera to, e.g., an immobilized control, test or immunogenic protein is determined using standard techniques. If the amount of the test polypeptide required for binding in the competitive assay is less than twice the amount of the immunogenic polypeptide that is required, then the test polypeptide is said to specifically bind to an antibody generated to the immunogenic protein, provided the amount is at least about 5-10× as high as for the control polypeptide.

As an additional determination of specificity, the pooled antisera is optionally fully immunosorbed with the immunogenic polypeptide(s) (rather than the control polypeptides) until little or no binding of the resulting immunogenic polypeptide subtracted pooled antisera to the immunogenic polypeptide(s) used in the immunosorbtion is detectable. This fully immunosorbed antisera is then tested for reactivity with the test polypeptide. If little or no reactivity is observed (i.e., no more than 2× the signal to noise ratio observed for binding of the fully immunosorbed antisera to the immunogenic polypeptide), then the test polypeptide is specifically bound by the antisera elicited by the immunogenic protein.

Additional details on proteins, antibodies, antisera, etc. can be found in U.S. Ser. No. 10/825,867 entitled "Expanding the Eukaryotic Genetic Code;" WO 2002/085923, entitled "IN VIVO INCORPORATION OF UNNATURAL AMINO ACIDS;" U.S. Pat. No. 6,927,042 entitled "Glycoprotein synthesis"; and U.S. Patent Publication No. US 2004/0198637 entitled "Protein Arrays," which is incorporated by reference.

KITS

Kits are also a feature of the present invention. For example, a kit for producing a protein that comprises at least one selected amino acid, e.g., an unnatural amino acid, in a cell is provided, where the kit includes a container containing a polynucleotide sequence encoding an O-tRNA, and/or an O-tRNA, and/or a polynucleotide sequence encoding an O-RS, and/or an O-RS. In one embodiment, the kit further includes at least selected amino acid. In another embodiment, the kit includes an aminoacylated tRNA of the invention. In another embodiment, the kit further comprises instructional materials for producing the protein.

An additional example is a kit for producing a protein that comprises at least one selected amino acid, e.g., an unnatural amino acid, in a cell-free translation system, where the kit includes a container containing a polynucleotide sequence encoding an O-tRNA, and/or an O-tRNA, and/or a polynucleotide sequence encoding an O-RS, and/or an O-RS. In one embodiment, the kit further includes a selected amino acid. In another embodiment, the kit includes an aminoacylated tRNA of the invention. In another embodiment, the kit further comprises instructional materials for producing the protein.

EXAMPLES

The following examples are offered to illustrate, but not to limit the claimed invention. One of skill will recognize a variety of non-critical parameters that may be altered without departing from the scope of the claimed invention.

Example 1

Aminoacyl-tRNA Synthetase Selection against Para-Acetyl Phenylalanine

Two DNA libraries were screened for aminoacyl-tRNA synthetases against para-acetyl phenylalanine, a non-naturally encoded amino acid. These libraries consisted of six mutations in the tyrosyl tRNA synthetase gene from *Methanococcous janneschii* in the pBK plasmid.

The selection procedure was preformed which consisted of five alternating rounds of selection, three positive, two negative. The libraries were combined in a 1:1 ratio and electroporated into the positive selection cell line (GeneHog with positive selection plasmid, pREP) and plated on minimal media plates (GMML) with appropriate antibiotics and the non-naturally encoded amino acid para-acetyl phenylalanine (pAF). The plates were incubated at 37° C. for about 40 hours at which point the cells were harvested by scraping. The DNA was extracted using a Qiagen Mini-Prep procedure, and then was agarose gel purified to isolate the library plasmid DNA.

This DNA was then electroporated into the negative selection cell line (GeneHog with negative selection plasmid pBAD derivative). These transformants were plated on LB plates with appropriate antibiotic without the non-naturally encoded amino acid (pAF). After about 17 hours these cells were harvested by scraping and the plasmid DNA was purified using the Qiagen Mini-Prep procedure and agarose gel purification.

The subsequent rounds of selection were done utilizing the same method of electroporation, plating, harvesting, and DNA purification. In the last (fifth) round of selection, serial dilutions were made of the transformed positive selection cells which were plated on minimal media plates. Individual colonies were then picked and grown in a 96 well block overnight. This block was then replica plated on minimal media plates with varying concentrations of choloramphenicol (the positive selection antibiotic) with and without unnatural amino acid pAF. After about 40 hours of growth at 37° C., the plates were visually compared to determine which colonies grew on the highest chloroamphenicol concentration but did not grow or grew poorly in the absence of the non-naturally encoded amino acid pAF. The colonies which met these criteria were grown overnight. The DNA was isolated from the cultures by Mini-Prep and agarose gel purification and were sequenced.

From this selection for pAF, 13 clones were found to have unique amino acid sequences and were subjected to further characterization to determine the fidelity and processivity of the pAF-tRNA synthetase.

To characterize these synthetases, small scale amber suppressions were performed to show that the non-naturally encoded amino acid pAF was incorporated into a polypeptide, and the results were visualized by SDS-PAGE. A single colony was picked and grown overnight in LB broth, which was then used to inoculate 50 mL of LB. The cells were grown to an OD of 0.3-0.4, at which point 1.5 mL aliquots were taken as pre-induction points and the culture was split into two flasks. 1 mM pAF was added to one split and both were grown for 30 minutes. Following the 30 minute growth, both cultures (+/− pAF) were induced with 0.2% L-Arabinose and grown 4.5 hours and the $OD_{600}$ was recorded. 1.5 mL aliquots were then taken of the +/−pAF flasks for SDS-PAGE analysis.

The 1.5 mL aliquots (Preinduction, +pAF, −pAF) were centrifuged at 10,000×g for 10 minutes to pellet the cells. The cells were then suspended in proportional Bacterial Protein Extraction Reagent (BPER, Pierce) amounts relative to their $OD_{600}$ at the time of harvest. DNase I was added to the lysed cells and incubated at 4° C. for 20 minutes. The samples were then combined with a reducing agent and loading dye and run on a 4-12% Bis-TRIS gel in MES buffer for 30 minutes. The gel was washed in DI $H_2O$ twice for 10 minutes and stained with coommassie blue dye. The +/−pAF bands were compared for the fidelity of the pAF-tRNA RS to result in incorporation of pAF, and the +pAF band was compared to the previously selected pAF-tRNA RS.

To check for the processivity of the RSs the same procedure was performed with a plasmid containing C-H6 S4am myoglobin (S4am-Myo). The S4am Myo was then purified by IMAC and sent for protein sequencing to determine the amount of pAF incorporation.

Of the pAF-tRNA RSs identified from this selection, one synthetase (E9) was found to incorporate pAF efficiently, with greater than 95% efficiency of incorporation of pAF into S4am-Myo. The incorporation was determined by amino acid sequencing while the processivity was shown by comparing protein bands on a SDS-PAGE gels. The nucleotide sequence for E9 is shown in SEQ ID NO: 4, and the amino acid sequence of E9 is shown in SEQ ID NO: 5.

An additional mutant with similar activity to E9 was identified, and has the amino acid sequence shown in SEQ ID NO: 17.

Example 2 tRNA Mutagenesis

Three mutants were generated of tRNA J17. The DNA sequence of wild-type J17 is shown as SEQ ID NO: 8 and in U.S. Patent Publication Nos. 2003/0108885 as SEQ ID NO: 1 and US 2003/0082575 as SEQ ID NO: 1 (U.S. patent application Ser. Nos. 10/126,931 and 10/126,927, respectively), both of which are incorporated by reference herein. J17 tRNA has a U51:G63 wobble pair in the TΨC stem as shown in FIG. 1.

Three J17 mutants (F12, F13, and F14) were generated to produce Watson-Crick base pairs at positions 51 and 63 of the FΨC stem. Mutagenesis was performed by overlapping PCR, and the final constructs were cloned into EcoRI and NdeI sites in a pET19 plasmid comprising the polynucleotide sequence encoding the aminoacyl tRNA synthetase E9 (SEQ ID NO: 4) and the polynucleotide sequence encoding human growth hormone (hGH) with an amber codon substitution (SEQ ID NO: 16). The expression of hGH was under the control of the T7 promoter.

Two fragments were generated for overlapping PCR. The first fragment was obtained by primer extension. The sequence of the forward primer used to generate each of the three mutants was:

```
                                      (FTam11; SEQ ID NO: 9)
GTAACGCTGAATTCCCGGCGGTAGTTCAGCAGGGCAGAACGG

CGGACTCTAAATCCGCATGGCGC.
```

To generate the F12 mutant (51C:63G), the following reverse primer was used:

```
                                     (FTam12; SEQ ID NO: 10)
GATCTGCAGTGGTCCGGCGGGCCGGATTTGAACCGGCGCCAT

GCGGATTTAGAGTCCGCCGTTCTGC.
```

To generate the F13 mutant (51U:63A), the following reverse primer was used:

```
                                     (FTam13; SEQ ID NO: 11)
GATCTGCAGTGGTCCGGCGGGCTGGATTTGAACCAGCGCCAT

GCGGATTTAGAGTCCGCCGTTCTGC.
```

To generate the F14 mutant (51A:63U), the following reverse primer was used:

```
                                     (FTam14; SEQ ID NO: 12)
GATCTGCAGTGGTCCGGCGGGCAGGATTTGAACCTGCGCCAT

GCGGATTTAGAGTCCGCCGTTCTGC.
```

To generate the second fragment, plasmid pET19 J17 E9 hGH comprising the polynucleotide sequence for J17 tRNA (SEQ ID NO: 8), the polynucleotide sequence encoding the tRNA synthetase E9 (SEQ ID NO: 4) and the polynucleotide sequence encoding human growth hormone with an amber codon substitution (SEQ ID NO: 16) was used as a template for amplification with the following set of primers: CGCCG-GACCACTGCAGATCCTTAGC-GAAAGCTAAGGATTTTTTTTAAGC (forward primer; FTam15; SEQ ID NO: 13) and CAAATTCGTCCATATGG-GATTCC (FTam 16; SEQ ID NO: 14). The forward primer was used to extend the sequence from the 3' end of tRNA to the Nde I site of the plasmid. The resulting product was gel purified.

The final step of overlapping PCR involved forward primer GTAACGCTGAATTCCCGGCG (FTam17, SEQ ID NO: 15), reverse primer FTam16 (SEQ ID NO: 14), the first fragment and the second fragment. The assembled products were digested with EcoR I and Nde I and ligated into the plasmid pET19 J17 E9 hGH digested with EcoR I and Nde I. The sequence of each construct was confirmed by sequencing, and the DNA sequences for each of the J17 mutant tRNAs are shown as SEQ ID NO: 1 (F12), SEQ ID NO: 2 (F13), and SEQ ID NO: 3 (F14). The tRNAs were named after their corresponding reverse primers.

Protein Expression

Plasmids encoding the tRNAs (J17, F12, F13 or F14) were each transformed into *E. coli* strain 1 and strain 2 bacterial host cells by chemical means and plated onto LB agar plates with 50 ug/ml carbenicillin. The plates were incubated at 37° C. overnight. For each tRNA, a single colony was picked to start an overnight culture at 37° C. in 1 ml 2×YT with 50 ug/ml carbenicillin. This 1 ml culture was used to inoculate two 10 ml 2×YT cultures with 50 ug/ml carbenicillin at 37° C. One 10 ml culture was supplemented with 4 mM para-acetylphenylalanine. At $OD_{600}=0.7$, the hGH expression was induced with 0.4 mM IPTG. After culturing the cells at 37° C. for 4 hours with 250 rpm, the cells were harvested by centrifugation at 5000×g for 5 minutes. The cells were lysed with B-PER Reagent (Pierce, Rockford, Ill.) supplemented with 5 ug/ml DNAse I. The total cell lysate was analyzed by 4-12% SDS PAGE.

Figure 2:
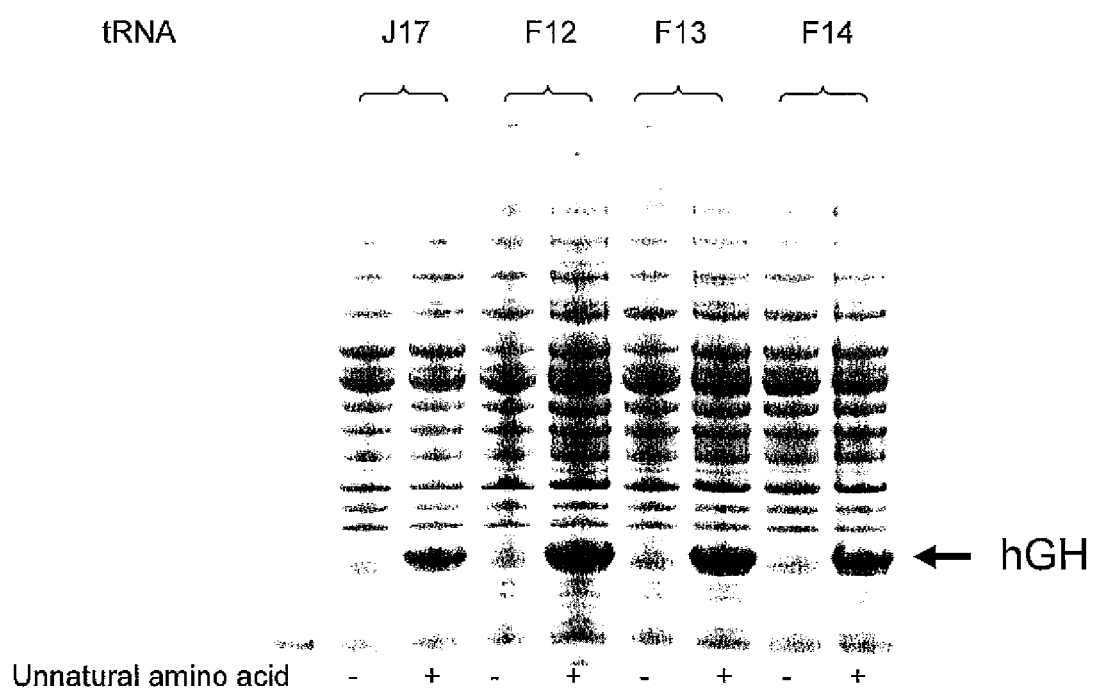
FIG. 2—Supression of an amber mutation in human growth hormone is shown using J17 or J17 mutants (F12, F13, F14). Total cell lysate for each sample was analyzed by SDS PAGE.

FIG. 2 shows an analysis of *E. coli* strain 1 total cell lysates by SDS PAGE. Supression of a selector codon in human growth hormone was performed using J17 or J17 mutant (F12, F13, F14) tRNA and the aminoacyl tRNA synthetase E9. Cells harboring J17 mutants grew slightly slower than cells harboring J17. No full length hGH product was observed by SDS-PAGE for the tRNA mutants in the absence of 4 mM para-acetylphenylalanine. In the presence of 4 mM para-acetylphenylalanine, full length product was produced with each of the tRNA mutants, demonstrating that these tRNA mutant-RS E9 pairs are orthogonal to *E. coli* machinery. Based on SDS-PAGE, the suppressed hGH yield of the J17 mutants was approximately 1.5-2 fold higher than that of J17 in *E. coli* strain 1.

Figure 3:
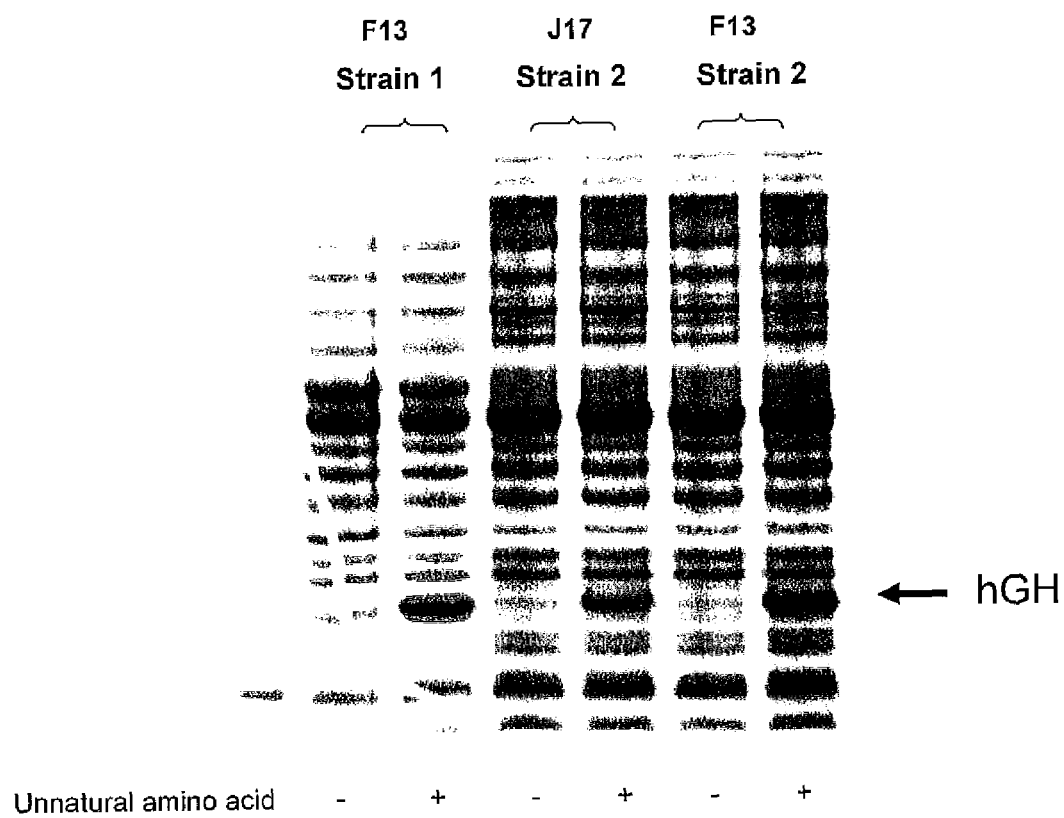
FIG. 3—Supression of an amber mutation in human growth hormone is shown in different cell lines using F13.

One J17 mutant, F13, was further tested in *E. coli* strain 2 bacterial cell line for amber suppression as shown in FIG. 3. In *E. coli* strain 2, the expression as well as amber suppression yields were reduced relative to that in *E. coli* strain 1. In the absence of para-acetylphenylalanine, no full length hGH product was observed by SDS-PAGE. In the presence 4 mM para-acetylphenylalanine, full length hGH was observed for both tRNAs. Based on SDS-PAGE, the suppressed hGH yield of F13 was about three fold higher than that of J17.

A fermentation run comparing J17 and F13 was performed with a final volume of approximately 1.5 L. The plasmid encoding the J17 tRNA and the plasmid encoding F13 tRNA were each transformed into *E. coli* strain 1. The final cell density for each was approximately 190 g wet cells/l. The hGH titer was 347 mg/L for the J17 clone and 542 mg/L for the F13 clone.

TABLE 1

| SEQ ID NO: | Label | SEQUENCE |
|---|---|---|
| 1 | F12 DNA | CCGGCGGTAGTTCAGCAGGGCAGAACGGCGGACTCTAAATCCG CATGGCGCCGGTTCAAATCCGGCCCGCCGGACCA |
| 2 | F13 DNA | CCGGCGGTAGTTCAGCAGGGCAGAACGGCGGACTCTAAATCCG CATGGCGCTGGTTCAAATCCAGCCCGCCGGACCA |
| 3 | F14 DNA | CCGGCGGTAGTTCAGCAGGGCAGAACGGCGGACTCTAAATCCG CATGGCGCAGGTTCAAATCCTGCCCGCCGGACCA |

TABLE 1-continued

| SEQ ID NO: | Label | SEQUENCE |
|---|---|---|
| 4 | E9 RS nucleic acid | ATGGACGAATTTGAAATGATAAAGAGAAACACATCTGAAATTAT CAGCGAGGAAGAGTTAAGAGAGGTTTTAAAAAAAGATGAAAAA TCTGCTGTTATAGGTTTTGAACCAAGTGGTAAATACATTTAGG GCATTATCTCCAAATAAAAAAGATGATTGATTTACAAAATGCTG GATTTGATATAATTATATATTTGGCTGATTTACACGCCTATTTAA ACCAGAAAGGAGAGTTGGATGAGATTAGAAAAATAGGAGATTA TAACAAAAAGTTTTTGAAGCAATGGGGTTAAAGGCAAAATAT GTTTATGGAAGTGAACATGGTCTTGATAAGGATTATACACTGAA TGTCTATAGATTGGCTTTAAAAACTACCTTAAAAAGAGCAAGAA GGAGTATGGAACTTATAGCAAGAGAGGATGAAAATCCAAAGGT TGCTGAAGTTATCTATCCAATAATGCAGGTTAATGGGATTCATT ATGAGGGCGTTGATGTTGCAGTTGGAGGGATGGAGCAGAGAAA AATACACATGTTAGCAAGGGAGCTTTTACCAAAAAAGGTTGTTT GTATTCACAACCCTGTCTTAACGGGTTTGGATGGAGAAGGAAAG ATGAGTTCTTCAAAAGGGAATTTTATAGCTGTTGATGACTCTCCA GAAGAGATTAGGGCTAAGATAAAGAAAGCATACTGCCCAGCTG GAGTTGTTGAAGGAAATCCAATAATGGAGATAGCTAAATACTTC CITGAATATCCTTTAACCATAAAAAGGCCAGAAAAATTTGGTGG AGATTTGACAGTTAATAGCTATGAGGAGTTAGAGAGTTTATTTA AAAATAAGGAATTGCATCCAATGGATTTAAAAAATGCTGTAGCT GAAGAACTTATAAAGATTTTAGAGCCAATTAGAAAGAGATTAAA |
| 5 | E9 RS Amino Acid | MDEFEMIKRNTSEIISEEELREVLKKDEKSAVIGFEPSGKIHLGHYLQ IKKMIDLQNAGFDIIIYLADLHAYLNQKGELDEIRKIGDYNKKVFEA MGLKAKYVYGSEHGLDKDYTLNVYRLALKTTLKRARRSMELIAR EDENPKVAEVIYPIMQVNGIHYEGVDVAVGGMEQRKIHMLARELL PKKVVCIHNPVLTGLDGEGKMSSSKGNFIAVDDSPEEIRAKIKKAY CPAGVVEGNPIMEIAKYFLEYPLTIKRPEKFGGDLTVNSYEELESLF KNKELHPMDLKNAVAEELIKILEPIRKRL |
| 6 | HL(TAG)3 tRNA DNA | CCCAGGGTAGCCAAGCTCGGCCAACGGCGACGGACTCTAAATCC GTTCTCGTAGGAGTTCGAGGGTTCGAATCCCTTCCCTGGGACCA |
| 7 | HL(TGA)1 tRNA DNA | GCGGGGGTTGCCGAGCCTGGCCAAAGGCGCCGGACTTCAAATCC GGTCCCGTAGGGGTTCCGGGGTTCAAATCCCGCCCCCGCACCA |
| 8 | J17 M. jannaschii mtRNA$_{CUA}^{Tyr}$ DNA | CCGGCGGTAGTTCAGCAGGGCAGAACGGCGGACTCTAAATCCG CATGGCGCTGGTTCAAATCCGGCCCGCCGGACCA |
| 9 | FTam11 primer | GTAACGCTGAATTCCCGGCGGTAGTTCAGCAGGGCAGAACGGC GGACTCTAAATCCGCATGGCGC |
| 10 | FTam12 primer | GATCTGCAGTGGTCCGGCGGGCCGGATTTGAACCGGCGCCATGC GGATTTAGAGTCCGCCGTTCTGC |
| 11 | FTam13 primer | GATCTGCAGTGGTCCGGCGGGCTGGATTTGAACCAGCGCCATGC GGATTTAGAGTCCGCCGTTCTGC |
| 12 | FTam14 primer | GATCTGCAGTGGTCCGGCGGGCAGGATTTGAACCTGCGCCATGC GGATTTAGAGTCCGCCGTTCTGC |
| 13 | FTam15 primer | CGCCGGACCACTGCAGATCCTTAGCGAAAGCTAAGGATTTTTTT TAAGC |
| 14 | FTam16 primer | CAAATTCGTCCATATGGGATTCC |
| 15 | FTam17 primer | GTAACGCTGAATTCCCGGCG |
| 16 | hGH (DNA) | ATGGGCCACCACCACCACCACCACTTCCCAACCATTCCCTTATCC AGGCTTTTTGACAACGCTATGCTCCGCGCCCATCGTCTGCACCA GCTGGCCTTTGACACCTACCAGGAGTTTGAAGAAGCTAGATCC CAAAGGAACAGAAGTATTCATTCCTGCAGAACCCCCAGACCTCC CTCTGTTTCTCAGAGTCTATTCCGACACCCTCCAACAGGGAGGA AACACAACAGAAATCCAACCTAGAGCTGCTCCGCATCTCCCTGC TGCTCATCCAGTCGTGGCTGGAGCCCGTGCAGTTCCTCAGGAGT GTCTTCGCCAACAGCCTGGTGTACGGCGCCTCTGACAGCAACGT CTATGACCTCCTAAAGGACCTAGAGGAAGGCATCCAAACGCTGA TGGGGAGGCTGGAAGATGGCAGCCCCCGGACTGGGCAGATCTT CAAGCAGACCTACAGCAAGTTCGACACAAACTCACACAACGAT GACGCACTACTCAAGAACTACGGGCTGCTCTACTGCTTCAGGAA |

TABLE 1-continued

| SEQ ID NO: | Label | SEQUENCE |
|---|---|---|
| | | GGACATGGACAAGGTCGAGACATTCCTGCGCATCGTGCAGTGCC GCTCTGTGGAGGGCAGCTGTGGCTTCTAA |
| 17 | D286R mutant of E9 | MDEFEMIKRN TSEIISEEEL REVLKKDEKS AVIGFEPSGK IHLGHYLQIK KMIDLQNAGF DIIIYLADLH AYLNQKGELD EIRKIGDYNK KVFEAMGLKA KYVYGSEHGL DKDYTLNVYR LALKTTLKRA RRSMELIARE DENPKVAEVI YPIMQVNGIH YEGVDVAVGG MEQRKIHMLA RELLPKKVVC IHNPVLTGLD GEGKMSSSKG NFIAVDDSPE EIRAKIKKAY CPAGVVEGNP IMEIAKYFLE YPLTIKRPEK FGGDLTVNSY EELESLFKNK ELHPMRLKNA VAEELIKILE PIRKRL |
| 18 | Y31 Primer 1 | gtattaccctgttatccctatggcgaaattcagaatgattctc |
| 19 | Y31 Primer 2 | cagaaaccgcgtgttgttcctaaacaatgtaatcattac |
| 20 | Y31 Primer 3 | gtaatgattacattgtttaggaacaacacgcggtttctg |
| 21 | Y31 Primer 4 | gagagcggtgtttgcgtactg |
| 22 | Y31 Primer 5 | attaccctgttatccctagacgctcagtggaacgaaaactcacg |
| 23 | Y31 Primer 6 | tagggataacagggtaatacaatttcaggtg |
| 24 | Y31 Primer 7 | ggtcagcttgtcgaaagtaccg |
| 25 | Y31 Primer 8 | ctacggttcgatcatctccagctagggataacagggtaat |
| 26 | N51 Primer 1 | gtattaccctgttatccctatggcgaaattcagaatgattctc |
| 27 | N51 Primer 2 | gattacattgtttaggaacaacacgcggtttctg |
| 28 | N51 Primer 3 | cagaaaccgcgtgttgttcctaaacaatgtaatc |
| 29 | NS1 Primer 4 | gagagcggtgtttgcgtactg |
| 30 | N51 Primer 5 | attaccctgttatcccta gacgctcagtggaacgaaaactcacg |
| 31 | N51 Primer 6 | tagggataacagggtaatacaatttcaggtg |
| 32 | N51 Primer 7 | ggtcagcttgtcgaaagtaccg |
| 33 | N51 Primer 8 | ctaaacaatgtaatctagggataacagggtaat |
| 34 | MAP Y31 Amber Mutant A12 | atggctatctcaatcaagaccccagaagatatcgaaaaaatgcgcgtcgctggcc gactggctgccgaagtgctggagatgatcgaaccgtaggttaaaccgggcgtcag caccggcgagctggatcgcatctgtaatgattacattgttaatgaacaacacg cggtttctgcctgcctcggctatcacggctatccgaaatccgtttgcatctctatta atgaagtggtgtgccacggtatcccggacgatgctaagctgctgaaagatggcga tatcgttaacattgatgtcaccgtaatcaaagatggtttccacggcgataccctcg aaaatgtttatcgtcggtaagccgaccatcatgggcgaacgtctgtgccgcatca cgcaagaaagcctgtacctggcgctacgcatggtaaaaccaggcattaatctgcg cgaaatcggtgcggcgattcagaaatttgtcgaagcagaaggcttctccgtcgtt cgtgaatattgcggacacggtattggtcgcggcttccatgaagaaccgcaggtgc tgcactatgactcccgtgaaaccaacgtcgtactgaaacctgggatgacgttcac catcgagccaatggtcaacgcgggtaaaaaagagatccgcaccatgaaagatggc tggacggtaaaaaccaaagatcgcagcttgtctgcacaatatgagcactattg tggtgactgataacggctgcgaaattctgacgctacgcaaggatgacaccatccc ggcgataatctcgcacgacgaataa |
| 35 | MAP N51 Amber Mutant D2 | atggctatctcaatcaagaccccagaagatatcgaaaaaatgcgcgtcgctggcc gactggctgccgaagtgctggagatgatcgaaccgtatgttaaaccgggcgtcag caccggcgagctggatcgcatctgtaatgattacattgtttaggaacaacacgcg gtttctgcctgcctcggctatcacggctatccgaaatccgtttgcatctctatta atgaagtggtgtgccacggtatcccggacgatgctaagctgctgaaagatggcga tatcgttaacattgatgtcaccgtaatcaaagatggtttccacggcgataccctcg aaaatgtttatcgtcggtaagccgaccatcatgggcgaacgtctgtgccgcatca cgcaagaaagcctgtacctggcgctacgcatggtaaaaccaggcattaatctgcg cgaaatcggtgcggcgattcagaaatttgtcgaagcagaaggcttctccgtcgtt cgtgaatattgcggacacggtattggtcgcggcttccatgaagaaccgcaggtgc tgcactatgactcccgtgaaaccaacgtcgtactgaaacctgggatgacgttcac catcgagccaatggtcaacgcgggtaaaaaagagatccgcaccatgaaagatggc tggacggtaaaaaccaaagatcgcagcttgtctgcacaatatgagcactattg tggtgactgataacggctgcgaaattctgacgctacgcaaggatgacaccatccc ggcgataatctcgcacgacgaataa |

Example 3

Live Ambrx Vaccine for *Mycobacterium avium* Subspecies *Paratuberculosis*

*Mycobacterium avium* subspecies *paratuberculosis* (MAP) is an obligate pathogenic bacteria which causes Johners disease in cattle and other ruminants. A recent study estimated that 21% of United States dairy herds are infected, resulting in considerable economic losses to the dairy industry totaling more than $200 million per annum. John's disease can only be treated with a combination of antibiotics such as Rifabutin and a macrolide such as Clarithromycin. Treatment regimes can last years. An effective MAP vaccine is critical because vaccines for *paratuberculosis* have been commercially available but unfortunately are not completely effective in preventing disease.

Connection Between MAP to Human Crohn's Disease

Crohn's disease affects between 400,000 and 600,000 people in North America. Prevalence estimates for Northern Europe have ranged from 27-48 per 100,000. It has long been suspected as a causative agent in Crohn's disease in humans; this connection is controversial. On the assumption that MAP is a causative agent in Crohn's disease, Giaconda is seeking to commercialize a combination of Rifabutin, clarithromycin, and clofazimine (Myoconda) as a potential drug therapy for Crohn's. With a clinical response of almost 95% in Phase II clinical trial. Phase Ma trial demonstrated a statistically significant improvement in achieving remission at 16 weeks compared with conventional therapy. However, Myoconda® did not achieve statistically significant results in maintaining remission after therapy was complete in this trial.

Currently, available vaccines offered are live attenuated (strain 316 F), killed whole cell based vaccines (strain 18), and there is also a subunit vaccine trial underway, however the current vaccines only delay the fecal shedding and progression to clinical disease, but do not protect against the infection (Expert Rev. Vaccines 7(6) 2008). This field is ideally looking for a rationally attenuated vaccine.

Because the complete genome sequence of MAP was published (PNAS 2005 12344-12349) and the foreign gene expression in MAP is realized, gene specific deletion and site specific mutation are now available tools for MAP (Applied and Environmental Microbiology 2008 1687-1695). The Ambrx vaccine will be a genetically modified whole organism non-natural amino acid-dependent MAP that will be administered as a vaccine to prevent MAP infection in animals. Essentail genes are selected and are then transformed to include one or more site specific amber mutations. The MAP is characterized through cell culture with and without the non-natural amino acid present in the culture media, reversion rates are characterized, and the whole organism

Example 4

Creation of Suppression Comptent/Lambda Red Cells

Figure 4:
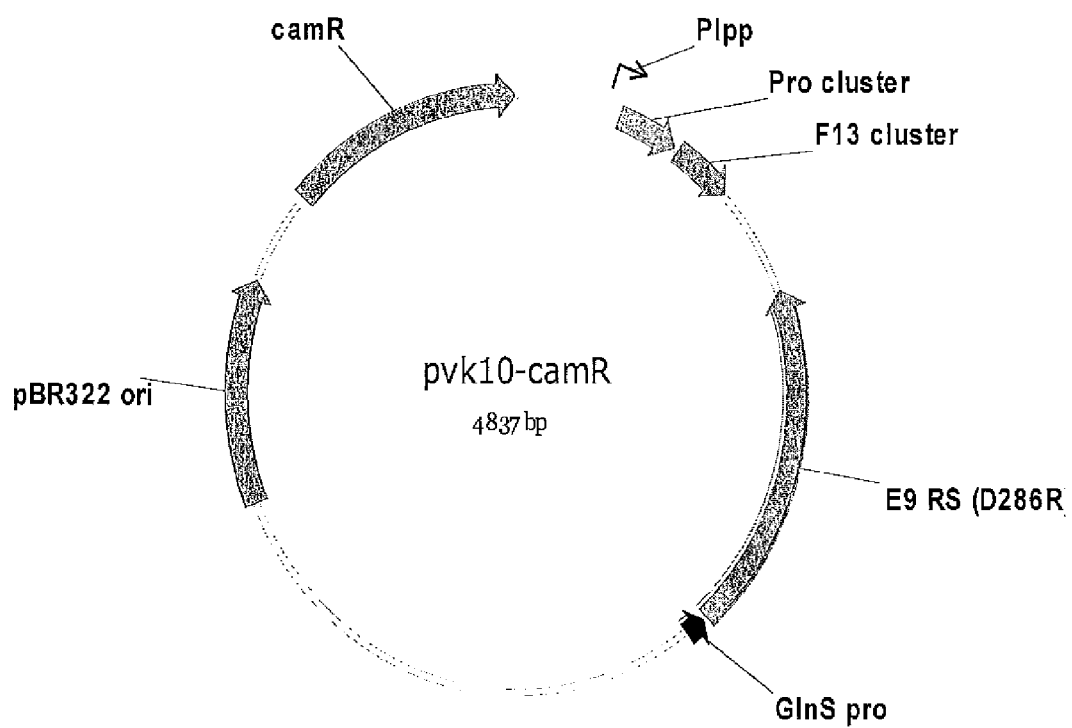
FIG. 4—Shows a diagram of the pVK10-camR vector containing the Ambrx Suppression System.
Figure 5:
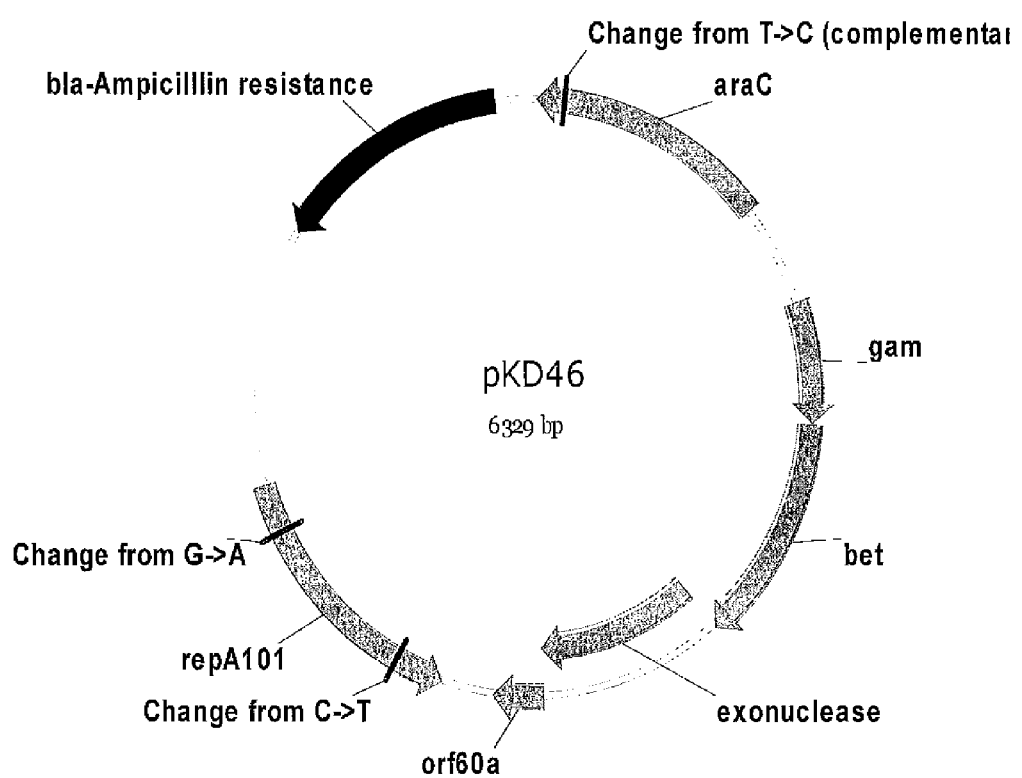
FIG. 5—Shows a diagram of the pKD46 vector containing Lambda Red components (bet, gam, exonuclease).

An *E. coli* strain was prepared. The *E. coli* strain is capable of both amber suppression and Lambda Red Recombination. W3110 *E. coli* were prepared containing pKD46n shown in FIG. 5 and were then transformed by electroporation with the plasmid pVK10/camR shown in FIG. 4. Positive transformants were selected on LB agar plates containing 50 μg/mL ampicillin and 34 μg/mL chloramphenicol grown over 48 hours at 30° C.

Electrocompetent cells containing both plasmids were prepared by growing a 500 mL culture containing both plasmid in LB media containing 50 μg/mL ampicillin, 34 μg/mL chlorampenicol, and 0.2% arabinose to a final $OD_{600}$ of 0.5. The cells were then washed three times in 10% glycerol and resuspended in 500 μL of 10% glycerol. Aliquots of 60 μl, were stored at −80° C. for future use.

Example 5

Creation of Conditonal Lethal Methione Amino Peptidase

Figure 6:
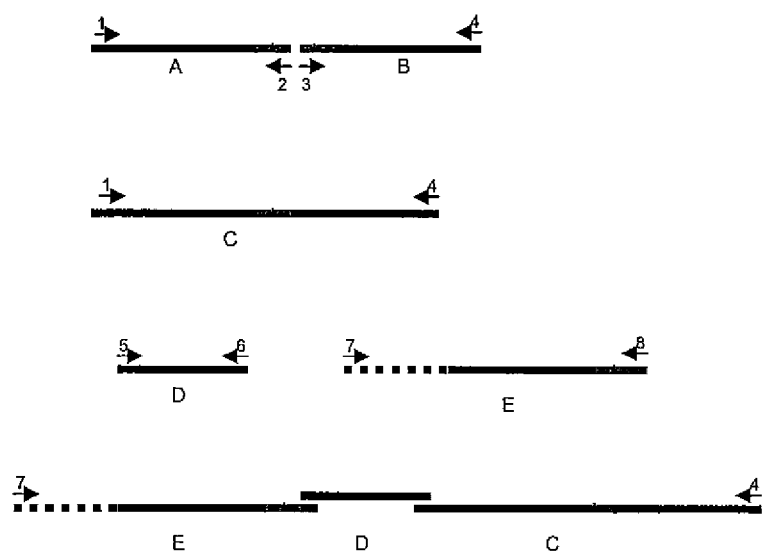
FIG. 6—Shows a scheme of overlapping primers and the methods used in Example 5. Primers are indicated by arrows and numeric identifier, and for example primer 1's for Y31 and N51 clones would be SEQ ID NO: 18 and 26, respectively; primer 2's for Y31 and N51 clones would be SEQ ID NO: 19 and 27, respectively; primer 3's for Y31 and N51 clones would be SEQ ID NO: 20 and 28, respectively; primer 4's for Y31 and N51 clones would be SEQ ID NO: 21 and 29, respectively; primer 5's for Y31 and N51 clones would be SEQ ID NO: 22 and 30, respectively; primer 6's for Y31 and N51 clones would be SEQ ID NO: 23 and 31, respectively; primer 7's for Y31 and N51 clones would be SEQ ID NO: 24 and 32, respectively; primer 8's for Y31 and N51 clones would be SEQ ID NO: 25 and 33, respectively. PCR products identified by a letter. Amber-site containing methione amino peptidase was generated by overlapping PCR over the amber mutation (A and B), making it so that it is conditionally lethal to the E. coli, as a whole organism. The mutant methione amino peptidase was then fused into a complete gene (C) and combined with a selectable marker (D) and a partial piece of mutant methione amino peptidase (E) for downstream selection.

*E. coli* strains with conditionally lethal methione amino peptidase were generated. An amber mutation was introduced at one of two sites within the methione amino peptidase gene, Y31 or N51. To integrate these mutants onto the *E. coli* chromosome, a linear piece of recombinant DNA was generated by overlapping PCR, as shown in the diagram in FIG. 6. First, using primers 1 and 2 (SEQ ID NO: 18 or 26), the 5' end of the methione amino peptidase gene was cloned (PCR product A), ending at the selected amino acid (either Y31 or N51) which was converted from the native codon to the amber codon. The 3' end of the methione amino peptidase gene was cloned, starting with the amber mutation, using primers 3 (SEQ ID NO: 20 or 28) and 4 (SEQ ID NO: 21 or 29) (PCR product B). The two reaction products overlap in the sequence flanking the amber mutation, and these products were amplified with primers 1 (SEQ ID NO: 18 or 26) and 4 (SEQ ID NO: 21 or 29) to give product C, the complete methione amino peptidase gene with an amber codon substitution at position 31 or 51.

To create the complete mutagenesis template, a Kanamycin resistance marker flanked by I-sceI homing endonuclease recognition sites was amplified using primers 5 (SEQ ID NO: 22 or 30) and 6 (SEQ ID NO: 23 or 31) on DNA from a previously generated *E. coli* strain (PCR product D). Primers 7 (SEQ ID NO: 24 or 32) and 8 (SEQ ID NO: 25 or 33) were used to amplify genomic sequence upstream of methione amino peptidase and the 5' end of methione amino peptidase, to allow for the removal of the kanamycin resistance marker and homologous recombination (PCR product E). The final DNA template for transformation was created by amplifying fragments E, D, and C using primers 7 (SEQ ID NO: 24 or 32) and 4 (SEQ ID NO: 21 or 29).

Example 7

Figure 7:
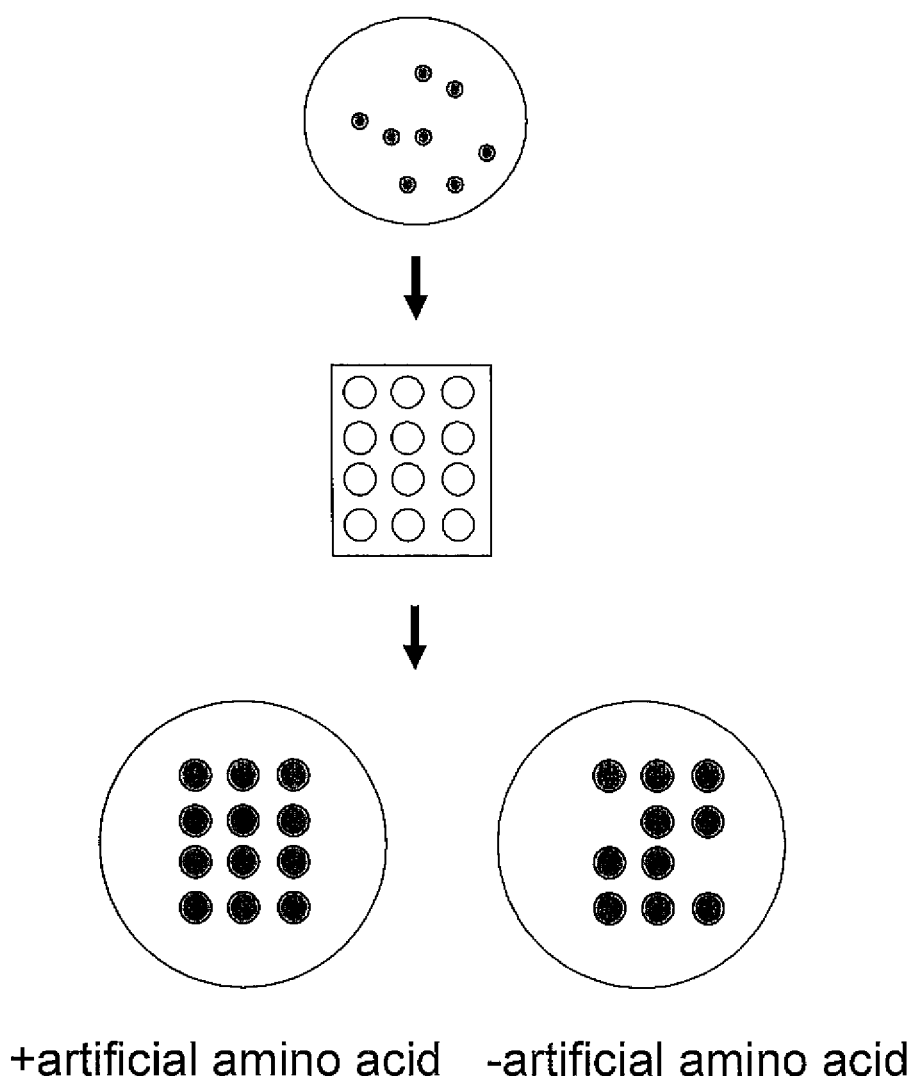
FIG. 7—Shows a schematic of screening for artificial amino acid dependence. The three steps shown are 1) picking transformants, such as KanR, AmpR positive transformants, by treating the plates; 2) culturing the survivors in KanR, AmpR, + non-natural amino acid; and 3) growing out individual colonies on plates with and without the non-natural amino acid and selecting those colonies that grow in the presence of the non-natural amino acid and die when cultured without the non-natural amino acid.
Figure 8:
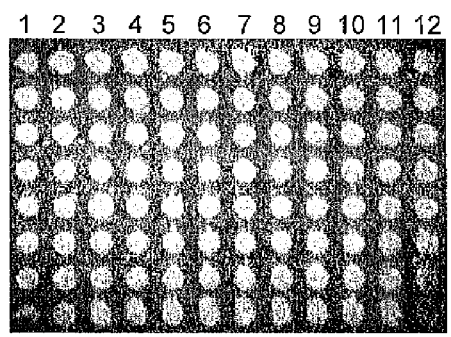
FIG. 8—Shows two cell culture plates of E. coli that are being screen for an amber mutation in the methione amino peptidase gene at Y31, each coated with LB agar and with media containing 50 μg/mL Ampicilin and 50 μg/mL Kannamycin, the plate on the left additionally containing 2 mM para-acetylphenylalanine and the plate on the right containing none. A12, C5, and E3 are examples of chemically modulated replication-dependent E. coli.
Figure 8:
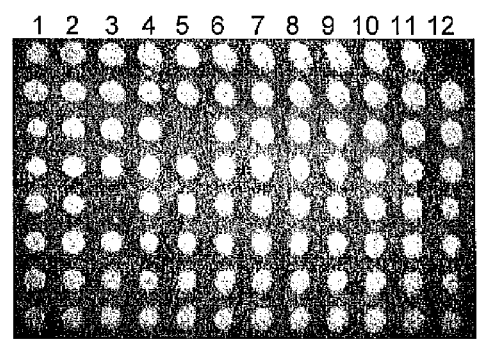
Figure 9:
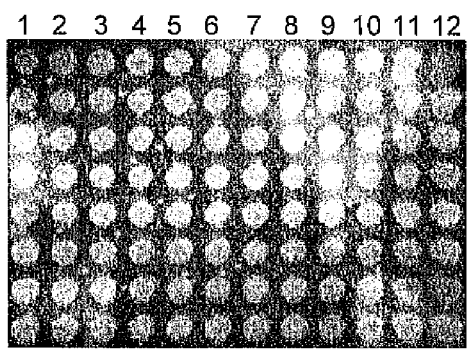
FIG. 9—Shows two cell culture plates of E. coli that are being screen for an amber mutation in the methione amino peptidase gene at N51, each coated with LB agar and with media containing 50 m/mL Ampicilin and 50 μg/mL Kannamycin, the plate on the left additionally containing 2 mM para-acetylphenylalanine and the plate on the right containing none. A12, C5, and E3 are examples of chemically modulated replication-dependent E. coli.
Figure 9:
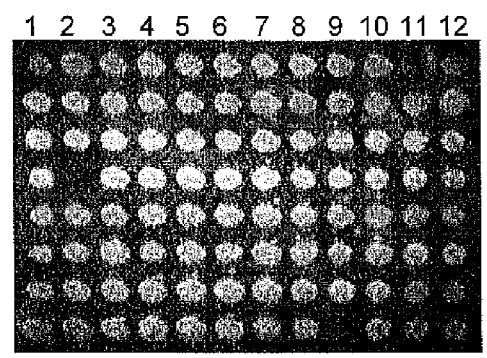
Figure 10A:
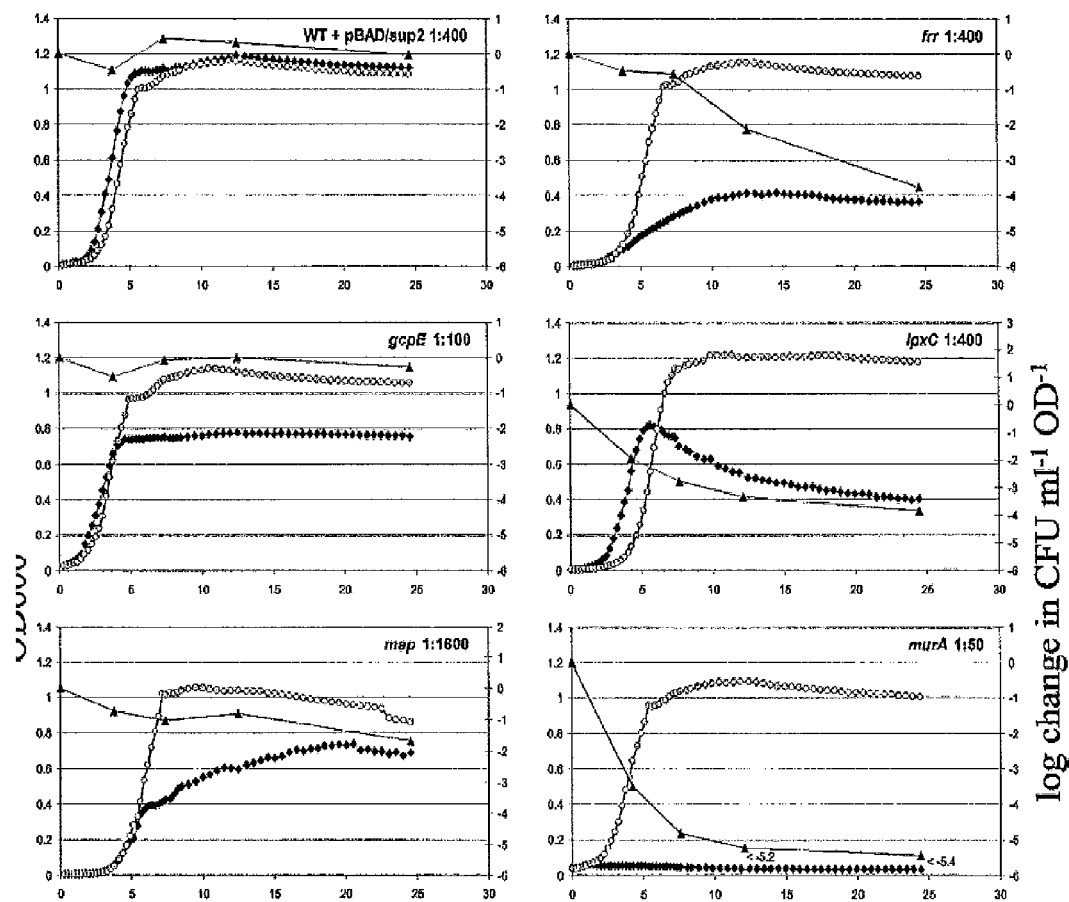
FIGS. 10A and 10B—Show growth in permissive and non-permissive media. Overnight cultures were inoculated into glucose (diamonds) or arabinose (circles) medium at the optimal dilution ratios shown in the upper right corner of each panel. OD600 was monitored in a 96-well plate in a shaking Spectramax plate reader at 37° C. with periodic removal of samples for microscopy and plating on arabinose plates. The change in viability, given on the right axis (triangles), was calculated by using the concentration of CFU normalized by dividing by the OD600. For each time point, this value was divided by the value at T=0 and the log of that value is presented here. The numbers of CFU per milliliter per OD unit at T=0 measured from the saturated inoculum and corrected for dilution were as follows: WT, $4.6 \times 10^9$; frr mutant, $3.2 \times 10^9$; gcpE mutant, $3.4 \times 10^9$; lpxC mutant, $2.2 \times 10^9$; map mutant, $2.9 \times 10^9$; murA mutant, $8.7 \times 10^8$; ppa mutant, $1.5 \times 10^9$; rpsA mutant, $1.2 \times 10^9$. OD is shown on a linear rather than on a logarithmic scale to best show the dynamics of the faltering cultures, and the scale of the right axis differs for lpxC and map to prevent the trend lines from overlapping. For the last two time points of the murA measurement, no colonies grew. From Herring and Blattner JOURNAL OF BACTERIOLOGY, 2004, p. 2673-2681, hereby incorporated by reference.
Figure 10B:
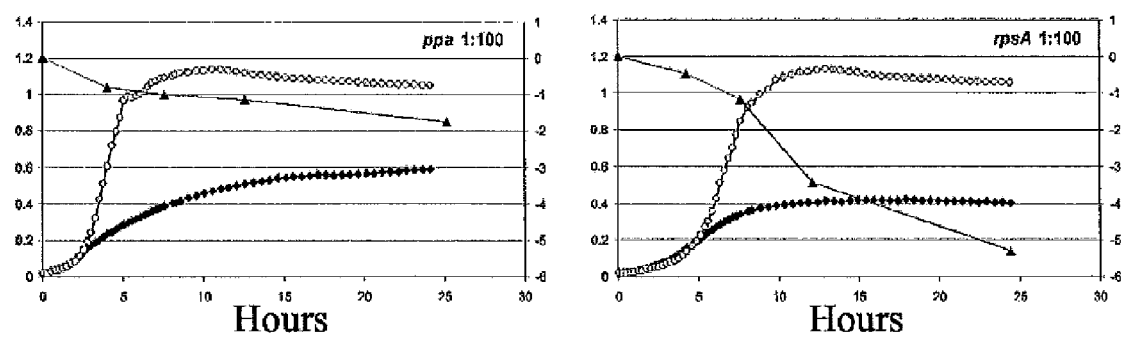

Transformation and Selection of Conditonal Lethal Methione Amino Peptidase Clones The transformation template generated by overlap PCR was used to transform electrocompetent pKD46, pVK10-camR positive cells. Positive transformants were selected by growing colonies on LB agar plates containing 50 μg/mL Ampicillin, 50 μg/mL Kanamycin, and 2 mM pAF for 48-72 hours at 30° C. To test for pAF dependent growth, 96 colonies for each site were grown in 1 mL of LB containing 50 μg/mL Ampicillin, 50 μg/mL Kanamycin, and 1 mM pAF for 72 hours at 30° C., also shown in FIG. 7, FIG. 8, and FIG. 9. These clones were then replica plated onto LB agar containing 50 μg/mL Ampicillin, 50 μg/mL Kanamycin, and 2 mM pAF and LB agar containing 50 μg/mL Ampicillin, and 50 μg/mL Kanamycin without pAF. These replica plates were grown for 72 hours at 30° C. and were then scored for growth.

Clones which exhibited growth only in the presence of 2 mM pAF were selected for further analysis.

Example 8

Clone Selection and Maturation

Clones which were positive for pAF dependence were selected for further study. These clones were Y31 A12, Y31 C5, Y31 E3, N51 D2 and N51 H9. The clones were rescreened individually and all grew only on media containing pAF, All clones were sequenced for the presence of an amber codon (tag) at the appropriate site: Y31 or N51. All five had an amber codon at the appropriate location. Clones Y31 Alt and N51 D2 were then isolated and pKD46 plasmid was removed by repeated heat treatment at 37 degrees Celsius.

Once pKD46 and ampicillin resistance was lost, cells were transformed with plasmid containing the I-SecI enzyme. After treatment with this enzyme, several clones were selected and tested for kanamycin resistance. Clones which were not resistant kanamycin were re-sequenced and frozen in 10% glycerol stocks. These clones will be the final, pAF dependent methione amino peptidase clones.

Figure 11:
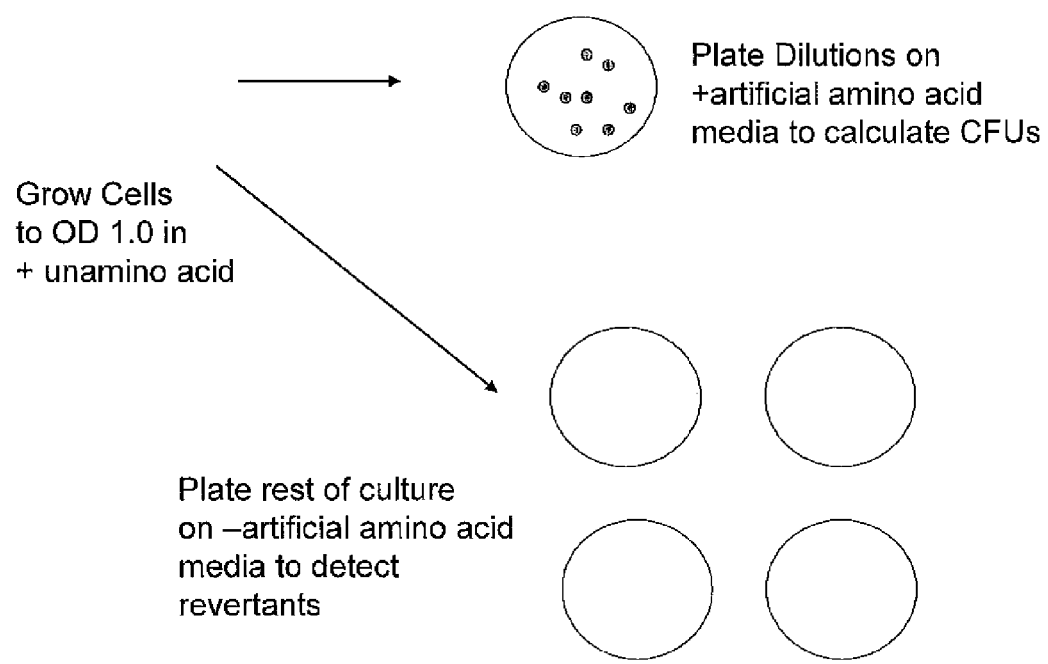
FIG. 11—Shows a schematic of the characterization of reversion rates wherein genetically modified non-natural amino acid replication dependent cells are grown to 1.0 optical density in media+non-natural amino acid, then those cells are plated in serial dilutions in media with added non-natural amino acid to calculate colony forming units and the remaining cells are cultured without the pretense of the non-natural amino acid to detect revertants.
Figure 12:
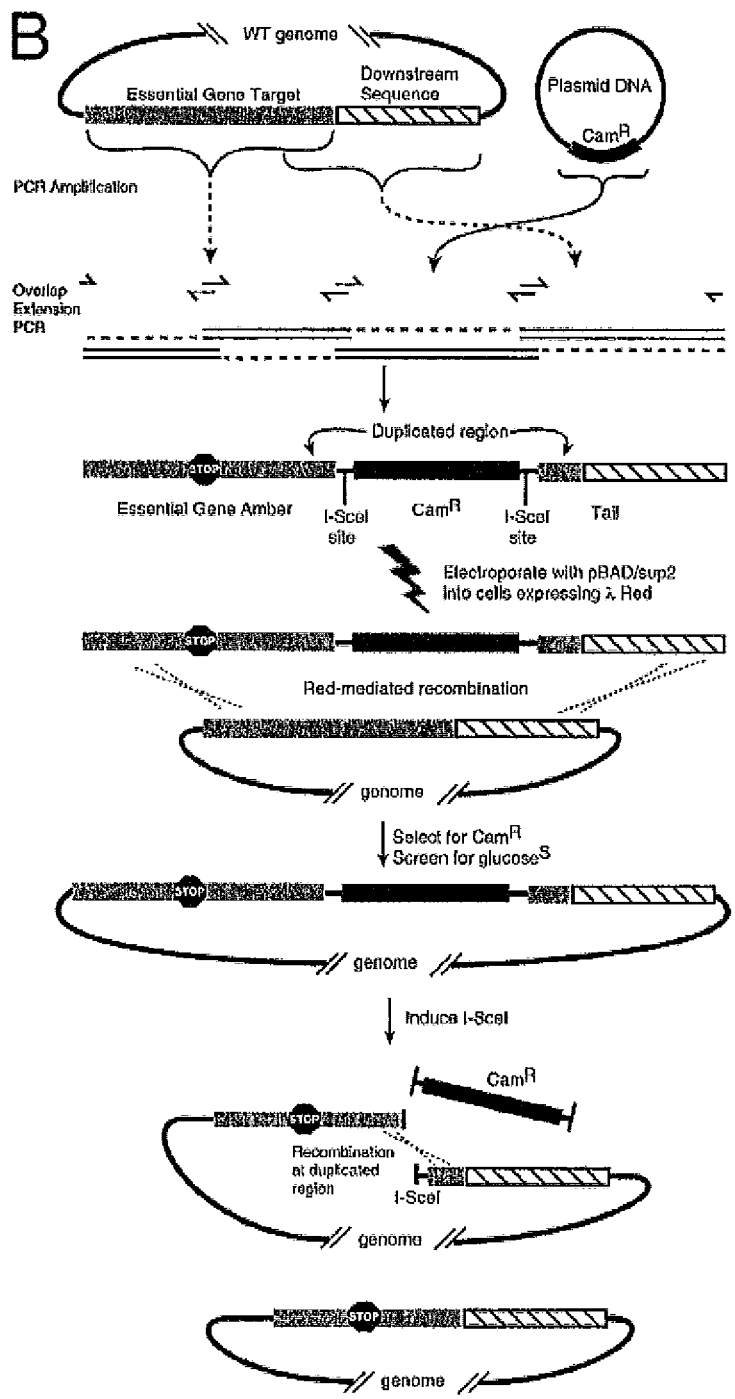
FIG. 12—Shows a schematic of a mutagenesis strategy. A linear DNA fragment is produced from WT template genomic DNA by overlap extension PCR. The positions of primers are indicated by one-sided arrows. The PCR fusion product is electroporated into cells, and integrations resulting from a doublerecombination event are selected. After identification of a clone carrying the tagalong amber stop codon, the I-SceI gene is induced, resulting in removal of the gene encoding Camr. Recombination within a short duplicated region leads to the generation of an amber mutant that is otherwise scarless.
Figure 13:
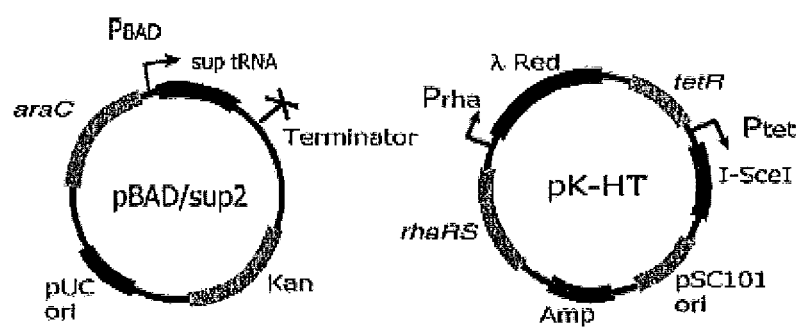
FIG. 13—Shows plasmids used in tagalong mutagenesis.
Figure 14:
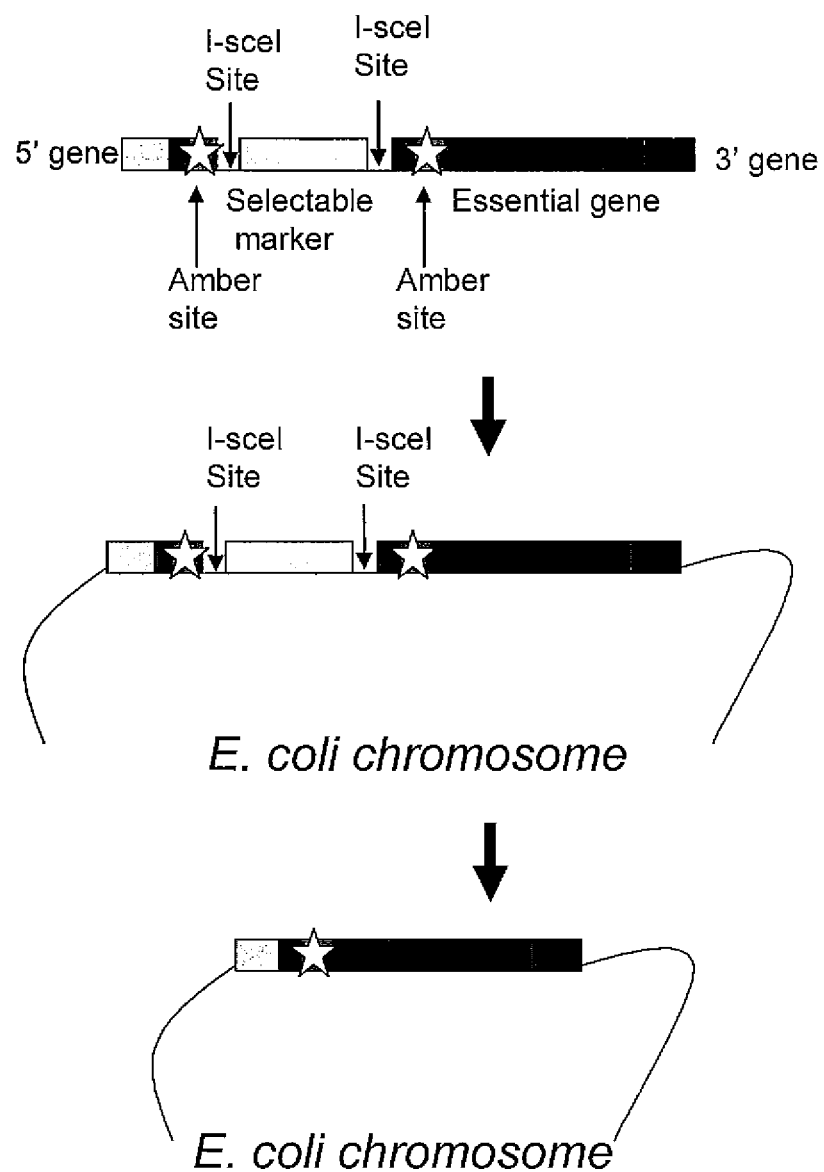
FIG. 14—Shows a schematic of the steps in creating a conditional lethal mutant in *E. coli* including, starting at the top, 1) creating a conditional mutant template; 2) transforming into lambda RED recombinant, amber suppression competent strain; and 3) inducing lambda RED recombination.
Figure 15:
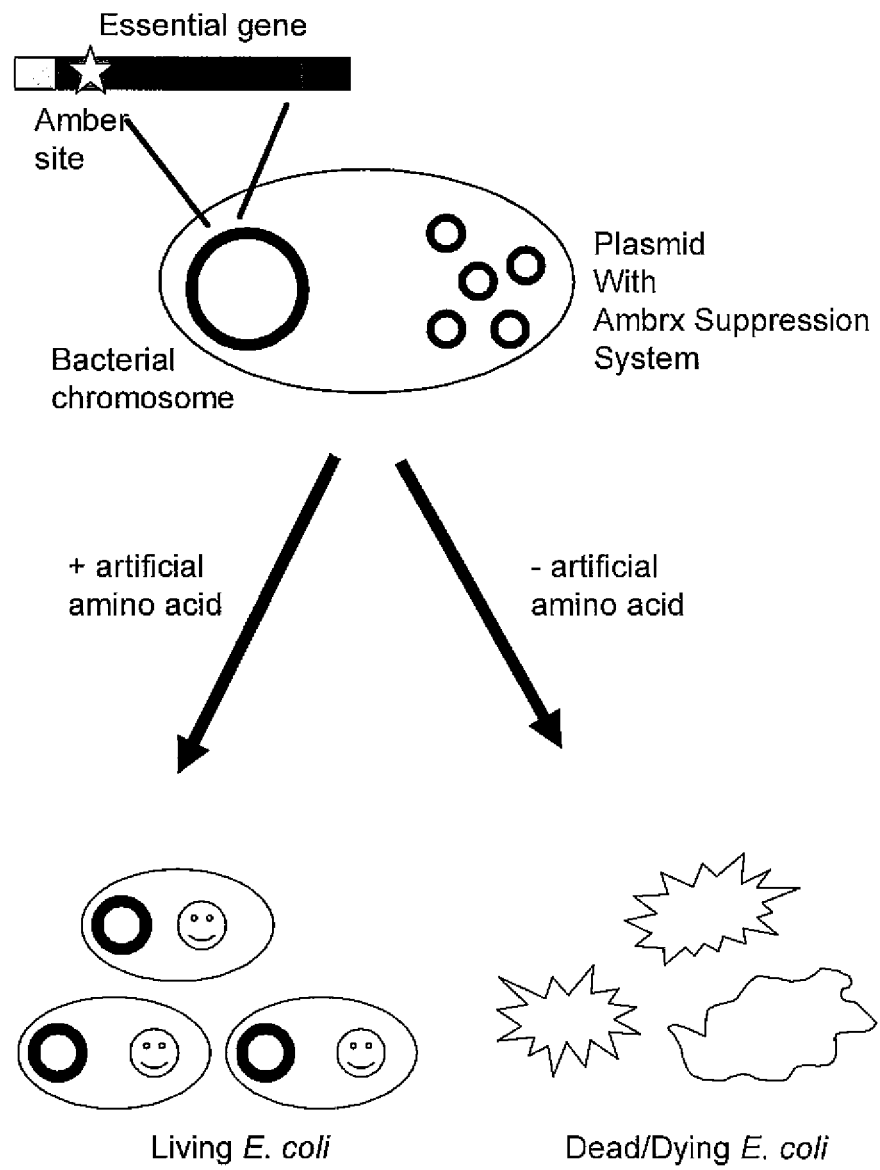
FIG. 15—Shows a schematic of the steps in characterizing a conditional lethal mutant in *E. coli* including, starting at the top, 1) characterizing growth in the presence and absence of the non-natural amino acid upon which a successfully transformed organism would be dependent; 2) characterizing mutation as bactericidal or bacteriostatic, and 3) characterizing the revertant frequency.
Figure 16:
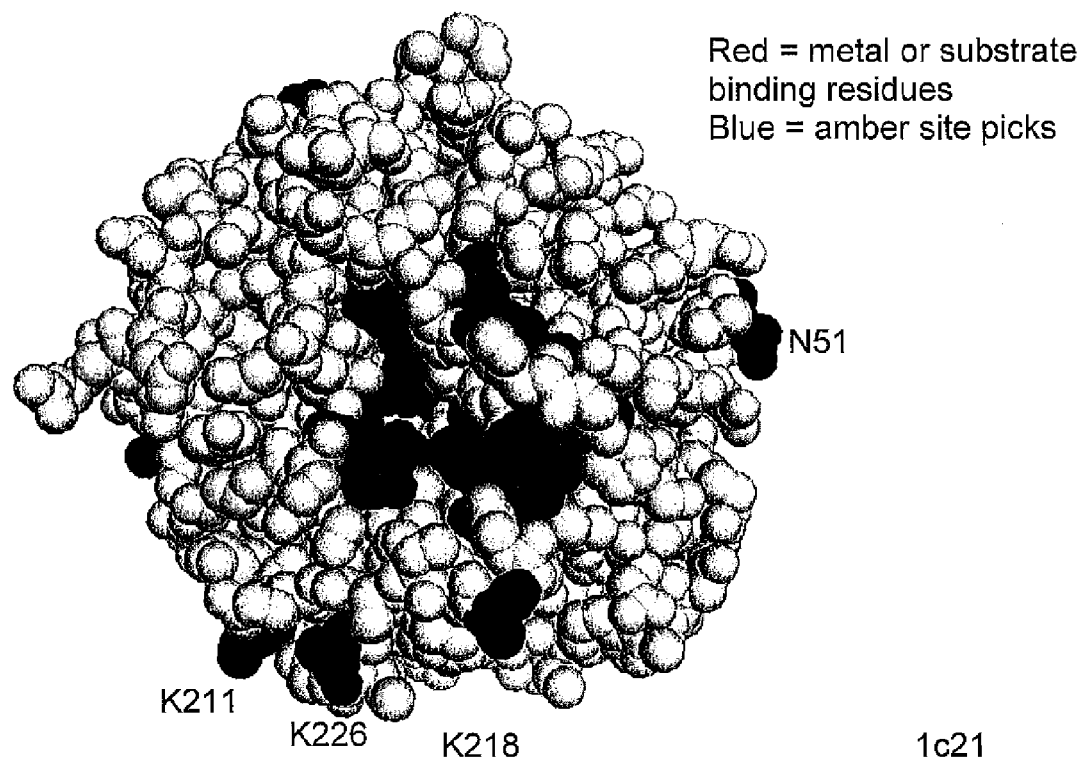
FIG. 16—Shows a structural view of the MAP residue picks.
Figure 17:
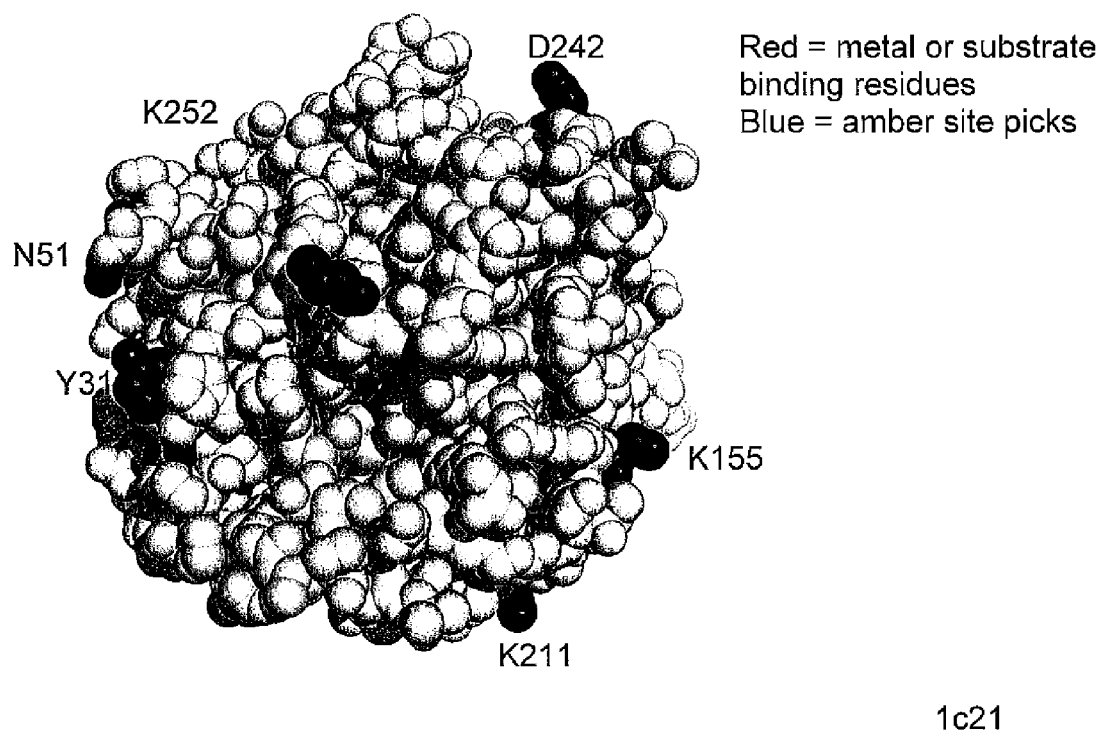
FIG. 17—Shows a structural view of the MAP residue picks.

In some embodiments of the present invention, the desired reversion rates, schematically contemplated in FIG. 11, will be less than $10^{-9}$ reverting frequency with a single switch. The Y31 and N51 clones were tested and reversion rates are shown in Table 2.

TABLE 2

| Clone | Test 1 | Test 2 |
|---|---|---|
| Y31 | $2.78 \times 10^{-8}$ | $<3 \times 10^{-8}$ (none detected) |
| N51 | $6.82 \times 10^{-8}$ | $<2 \times 10^{-8}$ (none detected) |

TABLE 3

Essential Genes in E. coli

| Alt. Symbol | Symbol | Gene Product |
|---|---|---|
| b0026 | ileS | Isoleucyl-tRNA synthetase (EC 6.1.1.5) |
| b0027 | lspA | Lipoprotein signal peptidase (EC 3.4.23.36) |
| b0029 | ispH* | IspH protein (lytB) |
| b0083 | ftsL | Cell division protein ftsL |
| b0084 | ftsI | Peptidoglycan synthetase ftsI precursor |
| b0085 | murE | UDP-N-acetylmuramoylalanyl-D-glutamate--2,6-diaminopimelate ligase (EC 6.3.2.13) |
| b0088 | murD | UDP-N-acetylmuramoylalanine--D-glutamate ligase (EC 6.3.2.9) |
| b0089 | ftsW | Cell division protein ftsW |
| b0090 | murG | UDP-N-acetylglucosamine--N-acetylmuramyl-(Pentapeptide) pyrophosphoryl-undecaprenol N-acetylglucosamine transferase (EC 2.4.1.—) |
| b0091 | murC | UDP-N-acetylmuramate--alanine ligase (EC 6.3.2.8) |
| b0093 | ftsQ | Cell division protein ftsQ |
| b0094 | ftsA | Cell division protein ftsA |
| b0095 | ftsZ | Cell division protein ftsZ |
| b0098 | secA | Preprotein translocase secA subunit |
| b0168 | map | Methionine aminopeptidase (EC 3.4.11.18) |
| b0169 | rpsB | 30S ribosomal protein S2 |
| b0171 | pyrH | Uridylate kinase (EC 2.7.4.—) |
| b0172 | frr | Ribosome recycling factor |
| b0174 | uppS | Undecaprenyl pyrophosphate synthetase (EC 2.5.1.31) |
| b0175 | cdsA | Phosphatidate cytidylyltransferase (EC 2.7.7.41) |
| b0180 | fabZ | (3R)-hydroxymyristoyl-[acyl carrier protein] dehydratase (EC 4.2.1.—) |
| b0181 | lpxA | Acyl-[acyl-carrier-protein]--UDP-N-acetylglucosamine O-acyltransferase (EC 2.3.1.129) |
| b0182 | lpxB | Lipid-A-disaccharide synthase (EC 2.4.1.182) |
| b0184 | dnaE | DNA polymerase III alpha subunit (EC 2.7.7.7) |
| b0185 | accA | Acetyl-coenzyme A carboxylase carboxyl transferase subunit alpha (EC 6.4.1.2) |
| b0194 | proS | Prolyl-tRNA synthetase (EC 6.1.1.15) |
| b0416 | nusB | N utilization substance protein B |
| b0420 | dxs | 1-deoxy-D-xylulose 5-phosphate synthase (EC 4.1.3.37) |
| b0421 | ispA | Geranyltranstransferase (EC 2.5.1.10) |
| b0470 | dnaX | DNA polymerase III subunit tau (EC 2.7.7.7) |
| b0474 | adk | Adenylate kinase (EC 2.7.4.3) |
| b0526 | cysS | Cysteinyl-tRNA synthetase (EC 6.1.1.16) |
| b0634 | mrdB | Rod shape-determining protein rodA |
| b0635 | mrdA | Penicillin-binding protein 2 |
| b0640 | holA | DNA polymerase III, delta subunit (EC 2.7.7.7) |
| b0642 | leuS | Leucyl-tRNA synthetase (EC 6.1.1.4) |
| b0680 | glnS | Glutaminyl-tRNA synthetase (EC 6.1.1.18) |
| b0893 | serS | Seryl-tRNA synthetase (EC 6.1.1.11) |
| b0914 | msbA | Probable transport ATP-binding protein msbA |
| b0918 | kdsB | 3-deoxy-manno-octulosonate cytidylyltransferase (EC 2.7.7.38) |
| b0930 | asnS | Asparaginyl-tRNA synthetase (EC 6.1.1.22) |
| b0954 | fabA | 3-hydroxydecanoyl-[acyl-carrier-protein] dehydratase (EC 4.2.1.60) |
| b1084 | rne | Ribonuclease E (EC 3.1.4.—) |
| b1092 | fabD | Malonyl CoA-acyl carrier protein transacylase (EC 2.3.1.39) |
| b1093 | fabG | 3-oxoacyl-[acyl-carrier protein] reductase (EC 1.1.1.100) |

TABLE 3-continued

Essential Genes in *E. coli*

| Alt. Symbol | Symbol | Gene Product |
|---|---|---|
| b1098 | tmk | Thymidylate kinase (EC 2.7.4.9) |
| b1099 | holB | DNA polymerase III, delta' subunit (EC 2.7.7.7) |
| b1116 | lolC | Lipoprotein releasing system transmembrane protein lolC |
| b1117 | lolD | Lipoprotein releasing system ATP-binding protein lolD |
| b1118 | lolE | Lipoprotein releasing system transmembrane protein lolE |
| b1133 | trmU | tRNA (5-methylaminomethyl-2-thiouridylate)-methyltransferase (EC 2.1.1.61) |
| b1207 | prsA | Ribose-phosphate pyrophosphokinase (EC 2.7.6.1) |
| b1274 | topA | DNA topoisomerase I (EC 5.99.1.2) |
| b1288 | fabI | Enoyl-[acyl-carrier-protein] reductase [NADH] (EC 1.3.1.9) |
| b1714 | pheS | Phenylalanyl-tRNA synthetase alpha chain (EC 6.1.1.20) |
| b1716 | rplT | 50S ribosomal protein L20 |
| b1718 | infC | Translation initiation factor IF-3 |
| b1740 | nadE | NH(3)-dependent NAD(+) synthetase (EC 6.3.5.1) |
| b1866 | aspS | Aspartyl-tRNA synthetase (EC 6.1.1.12) |
| b1876 | argS | Arginyl-tRNA synthetase (EC 6.1.1.19) |
| b2185 | rplY | 50S ribosomal protein L25 |
| b2234 | nrdA | Ribonucleoside-diphosphate reductase 1 alpha chain (EC 1.17.4.1) |
| b2235 | nrdB | Ribonucleoside-diphosphate reductase 1 beta chain (EC 1.17.4.1) |
| b2323 | fabB | 3-oxoacyl-[acyl-carrier-protein] synthase I (EC 2.3.1.41) |
| b2400 | gltX | Glutamyl-tRNA synthetase (EC 6.1.1.17) |
| b2411 | ligA | DNA ligase (EC 6.5.1.2) |
| b2412 | zipA | Cell division protein zipA |
| b2496 | yfgE | Hypothetical protein yfgE |
| b2514 | hisS | Histidyl-tRNA synthetase (EC 6.1.1.21) |
| b2563 | acpS | Holo-[acyl-carrier protein] synthase (EC 2.7.8.7) |
| b2606 | rplS | 50S ribosomal protein L19 |
| b2607 | trmD | tRNA (Guanine-N(1)-)-methyltransferase (EC 2.1.1.31) |
| b2609 | rpsP | 30S ribosomal protein S16 |
| b2610 | ffh | Signal recognition particle protein |
| b2614 | grpE | GrpE protein |
| b3018 | plsC | 1-acyl-sn-glycerol-3-phosphate acyltransferase (EC 2.3.1.51) |
| b3019 | parC | Topoisomerase IV subunit A (EC 5.99.1.—) |
| b3030 | parE | Topoisomerase IV subunit B (EC 5.99.1.—) |
| b3041 | ribB | 3,4-dihydroxy-2-butanone 4-phosphate synthase |
| b3067 | rpoD | RNA polymerase sigma factor rpoD |
| b3165 | rpsO | 30S ribosomal protein S15 |
| b3183 | yhbZ | Hypothetical GTP-binding protein yhbZ |
| b3230 | rpsI | 30S ribosomal protein S9 |
| b3231 | rplM | 50S ribosomal protein L13 |
| b3287 | def | Peptide deformylase (EC 3.5.1.88) |
| b3298 | rpsM | 30S ribosomal protein S13 |
| b3300 | secY | Preprotein translocase secY subunit |
| b3301 | rplO | 50S ribosomal protein L15 |
| b3303 | rpsE | 30S ribosomal protein S5 |
| b3304 | rplR | 50S ribosomal protein L18 |
| b3305 | rplF | 50S ribosomal protein L6 |
| b3307 | rpsN | 30S ribosomal protein S14 |
| b3309 | rplX | 50S ribosomal protein L24 |
| b3310 | rplN | 50S ribosomal protein L14 |
| b3311 | rpsQ | 30S ribosomal protein S17 |
| b3316 | rpsS | 30S ribosomal protein S19 |
| b3317 | rplB | 50S ribosomal protein L2 |
| b3318 | rplW | 50S ribosomal protein L23 |
| b3319 | rplD | 50S ribosomal protein L4 |
| b3320 | rplC | 50S ribosomal protein L3 |
| b3321 | rpsJ | 30S ribosomal protein S10 |
| b3340 | fusA | Elongation factor G |
| b3342 | rpsL | 30S ribosomal protein S12 |
| b3384 | trpS | Tryptophanyl-tRNA synthetase (EC 6.1.1.2) |
| b3464 | ftsY | Cell division protein ftsY |
| b3559 | glyS | Glycyl-tRNA synthetase beta chain (EC 6.1.1.14) |
| b3633 | kdtA | 3-deoxy-D-manno-octulosonic-acid transferase (EC 2.—.—.—) |
| b3634 | coaD | Phosphopantetheine adenylyltransferase (EC 2.7.7.3) |
| b3640 | dut | Deoxyuridine 5'-triphosphate nucleotidohydrolase (EC 3.6.1.23) |
| b3648 | gmk | Guanylate kinase (EC 2.7.4.8) |
| b3702 | dnaA | Chromosomal replication initiator protein dnaA |
| b3730 | glmU | Bifunctional glmU protein |
| b3865 | engB | Probable GTP-binding protein engB |
| b3967 | murI | Glutamate racemase (EC 5.1.1.3) |
| b3985 | rplJ | 50S ribosomal protein L10 |
| b3986 | rplL | 50S ribosomal protein L7/L12 |
| b3987 | rpoB | DNA-directed RNA polymerase beta chain (EC 2.7.7.6) |
| b3988 | rpoC | DNA-directed RNA polymerase beta' chain (EC 2.7.7,6) |
| b4052 | dnaB | Replicative DNA helicase (EC 3.6.1.—) |

TABLE 3-continued

Essential Genes in *E. coli*

| Alt. Symbol | Symbol | Gene Product |
| --- | --- | --- |
| b4142 | groS | 10 kDa chaperonin |
| b4143 | groL | 60 kDa chaperonin |
| b4147 | efp | Elongation factor P |
| b4200 | rpsF | 30S ribosomal protein S6 |
| b4226 | ppa | Inorganic pyrophosphatase (EC 3.6.1.1) |
| b4258 | valS | Valyl-tRNA synthetase (EC 6.1.1.9) |
| b4361 | dnaC | DNA replication protein dnaC |
| b4362 | dnaT | Primosomal protein I |

Example 9

Seed strain of the same type and passage as used for poliomyelitis vaccine (oral), transform to include amber mutations in more than one essential gene, and culture.

Cell Culture:

i) Different cell substrates for propagation of virus include Human diploid cell line, Monkey kidney cells, Vero cell line or any other suitable cell culture. ii) Large scale production of cells: 1. Preparation of the Manufacturer's working cell bank (MWCB): MWCB in case of primary cell cultures (cells derived from normal tissue and stored frozen at minus 70° C.) or from any other permitted continuous cell line are prepared from the cells & the cells pooled after serial subculture within the specified number of cell cultures. 2. Any of the following systems can be used which ever is suitable, for stepwise increase in the volume of cells. Roller bottles: Growth in roller bottles differs from that in stationary cultures in distribution of cells on glass surface and maximum attainable cell density. Roller bottle cultures do not deteriorate less rapidly as they can tolerate a density nearly two times higher than that of stationary cultures. Mammalian cells grown in monolayer culture will adapt best to roller bottle technique. Cell factories: These are stack of culture trays that share a common inlet and outlet port. These provide cells with a growing surface as large as inside of roller bottle, but take up less space inside incubator. These are ideal for adherent cell cultures, have low contamination, risk and are compact. Roux flasks Micro-carrier system 3. Samples for control cell cultures are incubated separately for at least two weeks and these are examined for evidence of cytopathic changes.

Propagation of Polio Virus in Cell Cultures:

i) Seed lot system: a) Passage level as followed for Oral polio Vaccine OR b) Its next passage level as derived for monovalent bulk suspension that could be used to manufacture oral polio vaccine. 1. The vaccine is manufactured on the basis of virus seed lot system. Virus seed lot is a quantity of virus processed together and of uniform composition prepared from seed lot. 2. Sub-culture of the seed virus should not be done more than 10 times counted from a seed lot used for the production of the vaccine on which original laboratory and field tests were done.

Single Harvest and Monovalent Pools:

The virus is propagated in cell cultures and harvested from cell cultures derived from a single batch of cells and processed together. This is known as single harvest. The single harvests of one type of virus suspension are processed at the same time to get crude form of monova lent pool.

Filtration or Clarification of Monovalent Pool:

Crude virus suspension of each monovalent pool is purified stepwise through filters of decreasing porosity. The purpose of filtration step is to remove particulate material and other substance that may affect inactivation process as such aggregates tend to increase on standing.

Concentration of the Monovalent Pool:

Each filtered monovalent pool is concentrated by Ultrafiltration.

Purification of the Monovalent Pool:

Chromatography with DEAE sepharose/immobilized DNA-ase column/immuno-adsorption column is employed for the purification of the monovalent pool. The purification process reduces consistently the level of cellular DNA from that of initial virus harvest by a factor of at least 108. The D-antigen concentration is determined by ELISA and display of comparable immunogenicity in rats. Accordingly the potency is adjusted. The monovalent pools of Poliovirus are blended to form the final trivalent bulk product. Formulation and Manufacturing of the Vaccine:

The purified bulk is filtered, preferably through 0.22 micron or 0.45-micron filter. The monovalent transformed viruses continue in presense of non-natural amino acid and is optionally mixed with stabilizer and/or preservative to make monovalent, bivalent, trivalent or multivalent vaccine.

Testing the Efficacy of the Vaccine:

The efficacy of the vaccine as manufactured above, as compared with established reference vaccine, is found to be similar in in-vitro and/or in-vivo method.

Various other tests based on the standard accepted methods were carried on the vaccine manufactured above such as pH determination, sterility testing, test for effective transformation (e.g. splitting and verifying death in absence of non-natural amino acid), abnormal toxicity study, volume measurement, in vitro potency determination, endotoxin test, identity test, protein nitrogen content estimation, and determination of stabilizer content and formaldehyde content to insure its effectiveness, safety and potency.

The in vitro potency of the SIPV manufactured above was determined using Sandwich ELISA. Two primary antibodies raised in different species against polio virus were utilized for the same and a second antibody conjugated with HRP is used again at the second primary antibody. The results were analyzed by comparison with reference standard.

The identity test for the vaccine was carried using, direct ELISA. Antigen was coated well in 96 ELISA plates and type specific anti polio sera is employed for determining the presence of all the three types of polio virus in the vaccine.

While the foregoing invention has been described in some detail for purposes of clarity and understanding, it will be clear to one skilled in the art from a reading of this disclosure that various changes in form and detail can be made without departing from the true scope of the present invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A non-human animal vaccine, comprising a *Mycobacterium avium* subspecies *paratuberculosis* (MAP) cell and an adjuvant, wherein the MAP cell comprises a nucleotide sequence encoding an essential gene product that is required for replication, wherein the nucleotide sequence comprises a selector codon that codes for site-specific incorporation of a non-natural amino acid into the essential gene product, such as that the MAP cell replicates only in the presence of the said non-natural amino acid, and has limited or no replication capability in the absence of said non-natural amino acid.

2. The non-human animal vaccine of claim 1, wherein said MAP cell comprises more than one selector codon in the nucleotide sequence encoding the essential gene product for replication.

3. The non-human animal vaccine of claim 1, wherein said MAP cell comprises at least a second nucleotide sequence encoding a second essential gene product required for replication, wherein the at least second nucleotide sequence comprises at least one selector codon that codes for the site-specific incorporation of a non-natural amino acid in the second essential gene product for replication.

4. The non-human animal vaccine of claim 1, wherein the non-natural amino acid is selected from the group consisting of para-acetylphenylalanine, p-nitrophenylalanine, p-sulfotyrosine p-carboxyphenylalanine, an o-nitrophenylalanine an m-nitrophenylalanine a p-boronyl phenylalanine, an o-boronylphenylalanine, an m-boronylphenylalanine a p-aminophenylalanine an o-aminophenylalaninean m-aminophenylalanine, a p-acylphenylalanine, an o-acylphenylalanine, an m-acylphenylalanine, a p-OMe phenylalanine, an o-OMe phenylalanine an m-OMe phenylalanine a p-sulfophenylalanine an o-sulfophenylalanine an m-sulfophenylalanine, a 5-nitro His, a 3-nitro Tyr a 2-nitro Tyr, a nitro substituted Leu, a nitro substituted His, a nitro substituted De, a nitro substituted Trp, a 2-nitro Trp, a 4-nitro Trp, a 5-nitro Trp a 6-nitro Trp, a 7-nitro Trp, 3-aminotyrosine, 2-aminotyrosine, O-sulfotyrosine, 2-sulfooxyphenylalanine, 3 sulfooxyphenylalanine, o-carboxyphenylalanine, m-carboxyphenylalanine, p-acetyl-L-phenylalanine a p-propargyl-phenylalanine, O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, and a p-propargyloxy-phenylalanine.

5. A method of inducing an immune response or reducing the risk of a bacterial infection, said method comprising administering to a non-human animal an effective amount of the non-human animal vaccine of claim 1.

6. The method of claim 5, wherein said bacterial infection is Johne's disease.

7. The method of claim 5, wherein said non-human animal is selected from the group consisting of: cow, pig, goat, sheep, horse, and dog.

8. A method of producing antibodies against *Mycobacterium avium* subspecies *paratuberculosis* (MAP), said method comprising administering to a non-human animal an effective amount of the non-human animal vaccine of claim 1 to produce antibodies against MAP.

* * * * *

UNITED STATES PATENT AND TRADEMARK OFFICE
CERTIFICATE OF CORRECTION

PATENT NO. : 9,121,024 B2
APPLICATION NO. : 13/120255
DATED : September 1, 2015
INVENTOR(S) : Feng Tian et al.

It is certified that error appears in the above-identified patent and that said Letters Patent is hereby corrected as shown below:

Claims

Claim 1, Column 109, lines 47-50, "such as that the MAP cell replicates only in the presence of the said non-natural amino acid, and has limited or no replication capability in the absence of said non-natural amino acid" should read -- such that the MAP cell replicates only in the presence of said non-natural amino acid, and has limited or no replication capability in the absence of said non-natural amino acid --

Claim 3, Column 109, lines 58-61, "wherein the at least second nucleotide sequence comprises at least one selector codon that codes for the site-specific incorporation of a non-natural amino acid in the second essential gene product for replication" should read -- wherein the at least second nucleotide sequence comprises at least one selector codon that codes for site-specific incorporation of a non-natural amino acid in the second essential gene product for replication --

Claim 4, Column 109, line 62 to column 110, lines 61, "4. The non-human animal vaccine of claim 1, wherein the non-natural amino acid is selected from the group consisting of para-acetylphenylalanine, p-nitrophenylalanine, p-sulfotyrosine p-carboxyphenylalanine, an o-nitrophenylalanine an m-nitrophenylalanine a p-boronyl phenylalanine, an o-boronylphenylalanine, an m-boronylphenylalanine a p-aminophenylalanine an o-aminophenylalaninean m-aminophenylalanine, a p-acylphenylalanine, an o-acylphenylalanine, an m-acylphenylalanine, a p-OMe phenylalanine, an o-OMe phenylalanine an m-OMe phenylalanine a p-sulfophenylalanine an o-sulfophenylalanine an m-sulfophenylalanine, a 5-nitro His, a 3-nitro Tyr a 2-nitro Tyr, a nitro substituted Leu, a nitro substituted His, a nitro substituted De, a nitro substituted Trp, a 2-nitro Trp, a 4-nitro Trp, a 5-nitro Trp a 6-nitro Trp, a 7-nitro Trp, 3-aminotyrosine, 2-aminotyrosine, O-sulfotyrosine, 2-sulfooxyphenylalanine, 3 sulfooxyphenylalanine, o-carboxyphenylalanine, m-carboxyphenylalanine, p-acetyl-L-phenylalanine a p-propargyl-phenylalanine, O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine an L-Dopa, a fluorinated phenylalanine, an isopropyl-L-phenylalanine, a p-azido-L-phenylalanine, a p-acyl-L-phenylalanine, a p-benzoyl-L-phenylalanine, an Signed and Sealed this
Seventh Day of June, 2016

Michelle K. Lee
*Director of the United States Patent and Trademark Office*

CERTIFICATE OF CORRECTION (continued)
U.S. Pat. No. 9,121,024 B2

L-phosphoserine, a phosphonoserine, a phosphonotyrosine, a p-iodo-phenylalanine, a p-bromophenylalanine, a p-amino-L-phenylalanine, an isopropyl-L-phenylalanine, and a p-propargyloxy-phenylalanine" should read -- 4. The non-human animal vaccine of claim 1, wherein the non-natural amino acid is selected from the group consisting of para-acetylphenylalanine, p-nitrophenylalanine, p-sulfotyrosine, p-carboxyphenylalanine, an o-nitrophenylalanine, an m-nitrophenylalanine, a p-boronyl phenylalanine, an o-boronylphenylalanine, an m-boronylphenylalanine, a p-aminophenylalanine, an o-aminophenylalanine, an m-aminophenylalanine, a p-acylphenylalanine, an o-acylphenylalanine, an m-acylphenylalanine, a p-OMe phenylalanine, an o-OMe phenylalanine, an m-OMe phenylalanine, a p-sulfophenylalanine, an o-sulfophenylalanine, an m-sulfophenylalanine, a 5-nitro His, a 3-nitro Tyr, a 2-nitro Tyr, a nitro substituted Leu, a nitro substituted His, a nitro substituted De, a nitro substituted Trp, a 2-nitro Trp, a 4-nitro Trp, a 5-nitro Trp, a 6-nitro Trp, a 7-nitro Trp, 3-aminotyrosine, 2-aminotyrosine, O-sulfotyrosine, 2-sulfooxyphenylalanine, 3-sulfooxyphenylalanine, o-carboxyphenylalanine, m-carboxyphenylalanine, p-acetyl-L-phenylalanine, a p-propargyl-phenylalanine, O-methyl-L-tyrosine, an L-3-(2-naphthyl)alanine, a 3-methylphenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, and a p-propargyloxy-phenylalanine --

```
                        SEQUENCE LISTING

<160> NUMBER OF SEQ ID NOS: 36

<210> SEQ ID NO 1
<211> LENGTH: 77
<212> TYPE: DNA
<213> ORGANISM: Artificial Sequence
<220> FEATURE:
<223> OTHER INFORMATION: Mutant tRNA derived from Methanococcus
      jannaschii tRNA

<400> SEQUENCE: 1
ccggcggtag ttcagcaggg cagaacggcg gactctaaat ccgcatggcg ccggttcaaa    60
tccggcccgc cggacca                                                   77

<210> SEQ ID NO 2
<211> LENGTH: 77
<212> TYPE: DNA
<213> ORGANISM: Artificial Sequence
<220> FEATURE:
<223> OTHER INFORMATION: Mutant tRNA derived from Methanococcus
      jannaschii tRNA

<400> SEQUENCE: 2
ccggcggtag ttcagcaggg cagaacggcg gactctaaat ccgcatggcg ctggttcaaa    60
tccagcccgc cggacca                                                   77

<210> SEQ ID NO 3
<211> LENGTH: 77
<212> TYPE: DNA
<213> ORGANISM: Artificial Sequence
<220> FEATURE:
<223> OTHER INFORMATION: Mutant tRNA derived from Methanococcus
      jannaschii tRNA

<400> SEQUENCE: 3
ccggcggtag ttcagcaggg cagaacggcg gactctaaat ccgcatggcg caggttcaaa    60
tcctgcccgc cggacca                                                   77

<210> SEQ ID NO 4
<211> LENGTH: 921
<212> TYPE: DNA
<213> ORGANISM: Artificial Sequence
<220> FEATURE:
<223> OTHER INFORMATION: Mutant synthetase derived from Methanococcus
      jannaschii synthetase

<400> SEQUENCE: 4
atggacgaat tgaaatgat aaagagaaac acatctgaaa ttatcagcga ggaagagtta     60
agagaggttt taaaaaaga tgaaaaatct gctgttatag gttttgaacc aagtggtaaa    120
atacatttag ggcattatct ccaaataaaa aagatgattg atttacaaaa tgctggattt    180
gatataatta tatatttggc tgatttacac gcctatttaa accagaaagg agagttggat    240
gagattagaa aaataggaga ttataacaaa aaagttttg aagcaatggg gttaaaggca    300
aaatatgttt atggaagtga acatggtctt gataaggatt atacactgaa tgtctataga    360
ttggctttaa aaactacctt aaaaagagca agaaggagta tggaacttat agcaagagag    420
gatgaaaatc caaaggttgc tgaagttatc tatccaataa tgcaggttaa tgggattcat    480
```

```
tatgagggcg ttgatgttgc agttggaggg atggagcaga gaaaaataca catgttagca    540
agggagcttt taccaaaaaa ggttgtttgt attcacaacc ctgtcttaac gggtttggat    600
ggagaaggaa agatgagttc ttcaaaaggg aattttatag ctgttgatga ctctccagaa    660
gagattaggg ctaagataaa gaaagcatac tgcccagctg gagttgttga aggaaatcca    720
ataatggaga tagctaaata cttccttgaa tatccttaa ccataaaaag gccagaaaaa     780
tttggtggag atttgacagt taatagctat gaggagttag agagtttatt taaaaataag    840
gaattgcatc caatggattt aaaaaatgct gtagctgaag aacttataaa gattttagag    900
ccaattagaa agagattata a                                              921

<210> SEQ ID NO 5
<211> LENGTH: 306
<212> TYPE: PRT
<213> ORGANISM: Artificial Sequence
<220> FEATURE:
<223> OTHER INFORMATION: Mutant synthetase derived from Methanococcus
      jannaschii synthetase

<400> SEQUENCE: 5
```

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Val
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
        50                  55                  60

Tyr Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser His Gly Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Gly Ile His
145                 150                 155                 160

Tyr Glu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys

```
                275                 280                 285
Asn Ala Val Ala Glu Glu Leu Ile Lys Ile Leu Glu Pro Ile Arg Lys
    290                 295                 300

Arg Leu
305

<210> SEQ ID NO 6
<211> LENGTH: 88
<212> TYPE: DNA
<213> ORGANISM: Halobacterium sp. NRC-1

<400> SEQUENCE: 6
cccagggtag ccaagctcgg ccaacggcga cggactctaa atccgttctc gtaggagttc    60
gagggttcga atcccttccc tgggacca                                      88

<210> SEQ ID NO 7
<211> LENGTH: 88
<212> TYPE: DNA
<213> ORGANISM: Artificial Sequence
<220> FEATURE:
<223> OTHER INFORMATION: Orthogonal tRNA that recognizes an opal codon

<400> SEQUENCE: 7 gcggggttg ccgagcctgg ccaaaggcgc cggacttcaa atccggtccc gtaggggttc     60
cggggttcaa atccccgccc ccgcacca                                      88

<210> SEQ ID NO 8
<211> LENGTH: 77
<212> TYPE: DNA
<213> ORGANISM: Methanococcus jannaschii

<400> SEQUENCE: 8
ccggcggtag ttcagcaggg cagaacggcg gactctaaat ccgcatggcg ctggttcaaa    60
tccggcccgc cggacca                                                  77

<210> SEQ ID NO 9
<211> LENGTH: 65
<212> TYPE: DNA
<213> ORGANISM: Artificial Sequence
<220> FEATURE:
<223> OTHER INFORMATION: Synthetic oligonucleotide primer

<400> SEQUENCE: 9
gtaacgctga attcccggcg gtagttcagc agggcagaac ggcggactct aaatccgcat    60
ggcgc                                                               65

<210> SEQ ID NO 10
<211> LENGTH: 67
<212> TYPE: DNA
<213> ORGANISM: Artificial Sequence
<220> FEATURE:
<223> OTHER INFORMATION: Synthetic oligonucleotide primer

<400> SEQUENCE: 10
gatctgcagt ggtccggcgg gccggatttg aacggcgcc atgcggattt agagtccgcc    60
gttctgc                                                             67

<210> SEQ ID NO 11
<211> LENGTH: 67
<212> TYPE: DNA
<213> ORGANISM: Artificial Sequence
```

```
<220> FEATURE:
<223> OTHER INFORMATION: Synthetic oligonucleotide primer

<400> SEQUENCE: 11
gatctgcagt ggtccggcgg gctggatttg aaccagcgcc atgcggattt agagtccgcc      60
gttctgc                                                                67

<210> SEQ ID NO 12
<211> LENGTH: 67
<212> TYPE: DNA
<213> ORGANISM: Artificial Sequence
<220> FEATURE:
<223> OTHER INFORMATION: Synthetic oligonucleotide primer

<400> SEQUENCE: 12
gatctgcagt ggtccggcgg gcaggatttg aacctgcgcc atgcggattt agagtccgcc      60
gttctgc                                                                67

<210> SEQ ID NO 13
<211> LENGTH: 49
<212> TYPE: DNA
<213> ORGANISM: Artificial Sequence
<220> FEATURE:
<223> OTHER INFORMATION: Synthetic oligonucleotide primer

<400> SEQUENCE: 13
cgccggacca ctgcagatcc ttagcgaaag ctaaggattt tttttaagc                  49

<210> SEQ ID NO 14
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 14
caaattcgtc catatgggat tcc                                              23

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 15
gtaacgctga attcccggcg                                                  20

<210> SEQ ID NO 16
<211> LENGTH: 600
<212> TYPE: DNA
<213> ORGANISM: Homo sapiens

<400> SEQUENCE: 16
atgggccacc accaccacca ccacttccca accattccct tatccaggct ttttgacaac      60
gctatgctcc gcgcccatcg tctgcaccag ctggcctttg acacctacca ggagtttgaa     120
gaagcctaga tcccaaagga acagaagtat tcattcctgc agaaccccca gacctccctc     180
tgtttctcag agtctattcc gacaccctcc aacagggagg aaacacaaca gaaatccaac     240
ctagagctgc tccgcatctc cctgctgctc atccagtcgt ggctggagcc cgtgcagttc     300
ctcaggagtg tcttcgccaa cagcctggtg tacggcgcct ctgacagcaa cgtctatgac     360
```

```
ctcctaaagg acctagagga aggcatccaa acgctgatgg ggaggctgga agatggcagc      420
ccccggactg gcagatcttc caagcagacc tacagcaagt tcgacacaaa ctcacacaac      480
gatgacgcac tactcaagaa ctacgggctg ctctactgct tcaggaagga catggacaag      540
gtcgagacat tcctgcgcat cgtgcagtgc cgctctgtgg agggcagctg tggcttctaa      600
```

<210> SEQ ID NO 17
<211> LENGTH: 306
<212> TYPE: PRT
<213> ORGANISM: Artificial Sequence
<220> FEATURE:
<223> OTHER INFORMATION: Mutant synthetase derived from Methanococcus
      jannaschii synthetase

<400> SEQUENCE: 17

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Val
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
    50                  55                  60

Tyr Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser His Gly Leu Asp Lys
            100                 105                 110

Asp Tyr Thr Leu Asn Val Tyr Arg Leu Ala Leu Lys Thr Thr Leu Lys
    115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Gly Ile His
145                 150                 155                 160

Tyr Glu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
    195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Arg Leu Lys
    275                 280                 285

Asn Ala Val Ala Glu Glu Leu Ile Lys Ile Leu Glu Pro Ile Arg Lys
290                 295                 300

Arg Leu
305
```

```
<210> SEQ ID NO 18
<211> LENGTH: 43
<212> TYPE: DNA
<213> ORGANISM: Artificial
<220> FEATURE:
<223> OTHER INFORMATION: Y31 Primer 1

<400> SEQUENCE: 18
gtattaccct gttatcccta tggcgaaatt cagaatgatt ctc                    43

<210> SEQ ID NO 19
<211> LENGTH: 39
<212> TYPE: DNA
<213> ORGANISM: Artificial
<220> FEATURE:
<223> OTHER INFORMATION: Y31 Primer 2

<400> SEQUENCE: 19
cagaaaccgc gtgttgttcc taaacaatgt aatcattac                         39

<210> SEQ ID NO 20
<211> LENGTH: 39
<212> TYPE: DNA
<213> ORGANISM: Artificial
<220> FEATURE:
<223> OTHER INFORMATION: Y31 Primer 3

<400> SEQUENCE: 20
gtaatgatta cattgtttag gaacaacacg cggtttctg                         39

<210> SEQ ID NO 21
<211> LENGTH: 21
<212> TYPE: DNA
<213> ORGANISM: Artificial
<220> FEATURE:
<223> OTHER INFORMATION: Y31 Primer 4

<400> SEQUENCE: 21
gagagcggtg tttgcgtact g                                            21

<210> SEQ ID NO 22
<211> LENGTH: 44
<212> TYPE: DNA
<213> ORGANISM: Artificial
<220> FEATURE:
<223> OTHER INFORMATION: Y31 Primer 5

<400> SEQUENCE: 22
attaccctgt tatccctaga cgctcagtgg aacgaaaact cacg                   44

<210> SEQ ID NO 23
<211> LENGTH: 31
<212> TYPE: DNA
<213> ORGANISM: Artificial
<220> FEATURE:
<223> OTHER INFORMATION: Y31 Primer 6

<400> SEQUENCE: 23
tagggataac aggtaatac aatttcaggt g                                  31

<210> SEQ ID NO 24
<211> LENGTH: 22
<212> TYPE: DNA
<213> ORGANISM: Artificial
<220> FEATURE:
<223> OTHER INFORMATION: Y31 Primer 7
```

```
<400> SEQUENCE: 24
ggtcagcttg tcgaaagtac cg                                              22

<210> SEQ ID NO 25
<211> LENGTH: 40
<212> TYPE: DNA
<213> ORGANISM: Artificial
<220> FEATURE:
<223> OTHER INFORMATION: Y31 Primer 8

<400> SEQUENCE: 25
ctacggttcg atcatctcca gctagggata acagggtaat                           40

<210> SEQ ID NO 26
<211> LENGTH: 43
<212> TYPE: DNA
<213> ORGANISM: Artificial
<220> FEATURE:
<223> OTHER INFORMATION: N51 Primer 1

<400> SEQUENCE: 26
gtattaccct gttatcccta tggcgaaatt cagaatgatt ctc                       43

<210> SEQ ID NO 27
<211> LENGTH: 34
<212> TYPE: DNA
<213> ORGANISM: Artificial
<220> FEATURE:
<223> OTHER INFORMATION: N51 Primer 2

<400> SEQUENCE: 27
gattacattg tttaggaaca acacgcggtt tctg                                 34

<210> SEQ ID NO 28
<211> LENGTH: 34
<212> TYPE: DNA
<213> ORGANISM: Artificial
<220> FEATURE:
<223> OTHER INFORMATION: N51 Primer 3

<400> SEQUENCE: 28
cagaaaccgc gtgttgttcc taaacaatgt aatc                                 34

<210> SEQ ID NO 29
<211> LENGTH: 21
<212> TYPE: DNA
<213> ORGANISM: Artificial
<220> FEATURE:
<223> OTHER INFORMATION: N51 Primer 4

<400> SEQUENCE: 29
gagagcggtg tttgcgtact g                                               21

<210> SEQ ID NO 30
<211> LENGTH: 44
<212> TYPE: DNA
<213> ORGANISM: Artificial
<220> FEATURE:
<223> OTHER INFORMATION: N51 Primer 5

<400> SEQUENCE: 30
attaccctgt tatccctaga cgctcagtgg aacgaaaact cacg                      44

<210> SEQ ID NO 31
```

```
<211> LENGTH: 31
<212> TYPE: DNA
<213> ORGANISM: Artificial
<220> FEATURE:
<223> OTHER INFORMATION: N51 Primer 6

<400> SEQUENCE: 31
tagggataac agggtaatac aatttcaggt g                              31

<210> SEQ ID NO 32
<211> LENGTH: 22
<212> TYPE: DNA
<213> ORGANISM: Artificial
<220> FEATURE:
<223> OTHER INFORMATION: N51 Primer 7

<400> SEQUENCE: 32
ggtcagcttg tcgaaagtac cg                                        22

<210> SEQ ID NO 33
<211> LENGTH: 33
<212> TYPE: DNA
<213> ORGANISM: Artificial
<220> FEATURE:
<223> OTHER INFORMATION: N51 Primer 8

<400> SEQUENCE: 33
ctaaacaatg taatctaggg ataacagggt aat                            33

<210> SEQ ID NO 34
<211> LENGTH: 795
<212> TYPE: DNA
<213> ORGANISM: Artificial
<220> FEATURE:
<223> OTHER INFORMATION: MAP Y31 Amber Mutant A12

<400> SEQUENCE: 34
atggctatct caatcaagac cccagaagat atcgaaaaaa tgcgcgtcgc tggccgactg    60
gctgccgaag tgctggagat gatcgaaccg taggttaaac cgggcgtcag caccggcgag   120
ctggatcgca tctgtaatga ttacattgtt aatgaacaac acgcggtttc tgcctgcctc   180
ggctatcacg gctatccgaa atccgttgc atctctatta tgaagtggt gtgccacggt    240
atcccggacg atgctaagct gctgaaagat ggcgatatcg ttaacattga tgtcaccgta   300
atcaaagatg gtttccacgg cgatacctcg aaaatgttta tcgtcggtaa gccgaccatc   360
atgggcgaac gtctgtgccg catcacgcaa gaaagcctgt acctggcgct acgcatggta   420
aaaccaggca ttaatctgcg cgaaatcggt gcggcgattc agaaatttgt cgaagcagaa   480
ggcttctccg tcgttcgtga atattgcgga cacggtattg gtcgcggctt ccatgaagaa   540
ccgcaggtgc tgcactatga ctcccgtgaa accaacgtcg tactgaaacc tgggatgacg   600
ttcaccatcg agccaatggt caacgcgggt aaaaaagaga tccgcaccat gaaagatggc   660
tggacggtaa aaccaaagat cgcagcttg tctgcacaat atgagcatac tattgtggtg   720
actgataacg gctgcgaaat tctgacgcta cgcaaggatg acaccatccc ggcgataatc   780
tcgcacgacg aataa                                                    795

<210> SEQ ID NO 35
<211> LENGTH: 795
<212> TYPE: DNA
<213> ORGANISM: Artificial
<220> FEATURE:
<223> OTHER INFORMATION: MAP N51 Amber Mutant D2
```

```
<400> SEQUENCE: 35
atggctatct caatcaagac cccagaagat atcgaaaaaa tgcgcgtcgc tggccgactg      60
gctgccgaag tgctggagat gatcgaaccg tatgttaaac cgggcgtcag caccggcgag     120
ctggatcgca tctgtaatga ttacattgtt taggaacaac acgcggtttc tgcctgcctc     180
ggctatcacg gctatccgaa atccgtttgc atctctatta atgaagtggt gtgccacggt     240
atcccggacg atgctaagct gctgaaagat ggcgatatcg ttaacattga tgtcaccgta     300
atcaaagatg gtttccacgg cgataccctcg aaaatgttta tcgtcggtaa gccgaccatc    360
atgggcgaac gtctgtgccg catcacgcaa gaaagcctgt acctggcgct acgcatggta     420
aaaccaggca ttaatctgcg cgaaatcggt gcggcgattc agaaatttgt cgaagcagaa     480
ggcttctccg tcgttcgtga atattgcgga cacggtattg gtcgcggctt ccatgaagaa     540
ccgcaggtgc tgcactatga ctcccgtgaa accaacgtcg tactgaaacc tgggatgacg     600
ttcaccatcg agccaatggt caacgcgggt aaaaaagaga tccgcaccat gaaagatggc     660
tggacggtaa aaaccaaaga tcgcagcttg tctgcacaat atgagcatac tattgtggtg     720
actgataacg gctgcgaaat tctgacgcta cgcaaggatg acaccatccc ggcgataatc     780
tcgcacgacg aataa                                                      795

<210> SEQ ID NO 36
<211> LENGTH: 10
<212> TYPE: PRT
<213> ORGANISM: Artificial Sequence
<220> FEATURE:
<223> OTHER INFORMATION: Peptide fragment of lacZ

<400> SEQUENCE: 36

Val Val Leu Gln Arg Arg Asp Trp Glu Asn
1               5                   10
```